US012746044B2

(12) United States Patent
Frock et al.

(10) Patent No.: US 12,746,044 B2
(45) Date of Patent: Sep. 29, 2026

(54) MEDICAL IMPLANT

(71) Applicant: Spinal Simplicity, LLC, Overland Park, KS (US)

(72) Inventors: Adam Frock, Lenexa, KS (US); Todd Moseley, Olathe, KS (US); Jeff Slover, Lee's Summit, MO (US); Melissa Frock, Lenexa, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 30 days.

(21) Appl. No.: 18/894,556

(22) Filed: Sep. 24, 2024

(65) Prior Publication Data

US 2025/0009395 A1 Jan. 9, 2025

Related U.S. Application Data

(63) Continuation of application No. 18/537,946, filed on Dec. 13, 2023, now Pat. No. 12,133,664.

(Continued)

(51) Int. Cl.

*A61B 17/70* (2006.01)
*A61B 17/00* (2006.01)

(Continued)

(52) U.S. Cl.

CPC .... *A61B 17/7065* (2013.01); *A61B 17/00234* (2013.01); *A61B 2017/00238* (2013.01);

(Continued)

(58) Field of Classification Search

CPC .......... A61B 17/7065; A61B 17/00234; A61B 2017/00238; A61B 2017/00367; A61B 2017/00982; A61B 2017/564

(Continued)

(56) References Cited

U.S. PATENT DOCUMENTS

| | | | |
|---|---|---|---|
| 2,686,520 | A | 8/1954 | Jarvis et al. |
| D287,763 | S | 1/1987 | Porat et al. |

(Continued)

FOREIGN PATENT DOCUMENTS

| | | | |
|---|---|---|---|
| EM | 0150842120001 | | 12/2024 |
| JP | 2011002997 | A | 8/2011 |

(Continued)

OTHER PUBLICATIONS

European Patent Application 23847918.2, Communication pursuant to Rules 161(1) and 162 EPC Invitation to Correct Deficiencies, issued Jul. 22, 2025.

(Continued)

*Primary Examiner* — Eduardo C Robert
*Assistant Examiner* — David C Comstock
(74) *Attorney, Agent, or Firm* — Erise IP, P.A.

(57) ABSTRACT

Systems, devices, and methods for stabilization of bones and/or joints are disclosed. A medical implant may be inserted into a treatment site, such as an interspinous process space. The implant may have an outer body, an inner body coupled to the outer body, distal wings coupled to the inner body, proximal wings coupled to the outer body, and a threaded screw coupled to the inner body and outer body. The threaded screw may be configured to couple to a driver head of an insertion tool and the outer body may be configured to couple to an attachment member of an insertion tool. Actuating the insertion tool may actuate the threaded screw to thereby transition the proximal wings and the distal wings from a closed configuration to a deployed configuration, and from a deployed configuration to a clamped configuration.

20 Claims, 61 Drawing Sheets

Related U.S. Application Data

(60) Provisional application No. 63/432,296, filed on Dec. 13, 2022.

(51) Int. Cl.
*A61B 17/88* (2006.01)
*A61B 17/56* (2006.01)

(52) U.S. Cl.
CPC ............... *A61B 2017/00367* (2013.01); *A61B 2017/00982* (2013.01); *A61B 2017/564* (2013.01)

(58) Field of Classification Search
USPC ......................... 606/248, 249, 279, 99, 86 A
See application file for complete search history.

(56) References Cited

U.S. PATENT DOCUMENTS

| | | | |
|---|---|---|---|
| D331,462 | S | 12/1992 | Kraus et al. |
| D558,337 | S | 12/2007 | Jones et al. |
| 7,585,316 | B2 | 9/2009 | Trieu |
| D606,195 | S | 12/2009 | Eisen et al. |
| D619,711 | S | 7/2010 | Lombardo et al. |
| 7,749,252 | B2 | 7/2010 | Zucherman et al. |
| 7,771,456 | B2 | 8/2010 | Hartmann et al. |
| 7,811,322 | B2 | 10/2010 | Arnin et al. |
| D627,468 | S | 11/2010 | Richter et al. |
| 7,901,432 | B2 | 3/2011 | Zucherman et al. |
| 7,918,877 | B2 | 4/2011 | Zucherman et al. |
| 8,002,802 | B2 | 8/2011 | Abdou |
| 8,097,018 | B2 | 1/2012 | Malandain et al. |
| 8,172,855 | B2 | 5/2012 | Abdou |
| 8,172,878 | B2 | 5/2012 | Yue |
| 8,187,305 | B2 | 5/2012 | Malandain et al. |
| 8,187,307 | B2 | 5/2012 | Alamin et al. |
| 8,273,108 | B2 | 9/2012 | Altarac et al. |
| 8,454,659 | B2 | 6/2013 | Zucherman et al. |
| 8,518,083 | B2 | 8/2013 | Yue |
| 8,568,460 | B2 | 10/2013 | Zucherman et al. |
| 8,690,921 | B2 | 4/2014 | Dwyer et al. |
| 8,696,709 | B2 | 4/2014 | Dinville et al. |
| 8,740,948 | B2 | 6/2014 | Reglos et al. |
| 8,795,335 | B1 | 8/2014 | Abdou et al. |
| 8,827,902 | B2 | 9/2014 | Dietze, Jr. et al. |
| 8,858,598 | B2 | 10/2014 | Seifert et al. |
| 8,900,271 | B2 | 12/2014 | Kim |
| 9,011,493 | B2 | 4/2015 | Zappacosta et al. |
| 9,023,084 | B2 | 5/2015 | Kim |
| D731,063 | S | 6/2015 | Verhage et al. |
| 9,055,981 | B2 | 6/2015 | Lamborne et al. |
| 9,084,640 | B2 | 7/2015 | Dwyer et al. |
| D741,488 | S | 10/2015 | Tohmeh et al. |
| 9,155,570 | B2 | 10/2015 | Altarac et al. |
| 9,179,944 | B2 | 11/2015 | Boyer, II et al. |
| 9,271,764 | B2 | 3/2016 | Sheffer et al. |
| 9,364,269 | B2 | 6/2016 | Seifert et al. |
| 9,393,055 | B2 | 7/2016 | Altarac et al. |
| 9,532,812 | B2 | 1/2017 | Altarac et al. |
| 9,545,267 | B2 | 1/2017 | Seifert et al. |
| 9,592,082 | B2 | 3/2017 | Ingalhalikar et al. |
| 9,662,147 | B2 | 5/2017 | Serhan et al. |
| 9,681,898 | B2 | 6/2017 | Zappacosta et al. |
| 9,730,802 | B1 | 8/2017 | Harvey |
| 9,750,544 | B2 | 9/2017 | Taber et al. |
| 9,770,271 | B2 | 9/2017 | Lamborne et al. |
| D804,026 | S | 11/2017 | Linnenschmidt |
| 9,820,865 | B2 | 11/2017 | Sharabani et al. |
| 9,913,667 | B2 | 3/2018 | Dinville et al. |
| 9,956,007 | B2 | 5/2018 | Choi et al. |
| 9,956,011 | B2 | 5/2018 | Altarac et al. |
| 10,070,898 | B2 | 9/2018 | Trautwein et al. |
| 10,070,899 | B2 | 9/2018 | Seifert et al. |
| 10,085,777 | B2 | 10/2018 | Ingalhalikar et al. |
| 10,092,330 | B2 | 10/2018 | Abdou |
| 10,149,704 | B2 | 12/2018 | Calvosa et al. |
| 10,166,047 | B2 | 1/2019 | Altarac et al. |
| D846,739 | S | 4/2019 | Baumer et al. |
| 10,258,389 | B2 | 4/2019 | Kim |
| 10,292,738 | B2 | 5/2019 | Kim |
| 10,524,772 | B2 | 1/2020 | Choi et al. |
| 10,729,476 | B2 | 8/2020 | Thommen et al. |
| 10,835,297 | B2 | 11/2020 | Altarac et al. |
| 10,945,769 | B2 | 3/2021 | Choi et al. |
| 11,298,160 | B2 | 4/2022 | Bosio et al. |
| 11,357,489 | B2 | 6/2022 | Choi et al. |
| D968,616 | S | 11/2022 | Cain |
| 11,707,302 | B2 | 7/2023 | Choi et al. |
| D1,034,971 | S | 7/2024 | Hu et al. |
| 12,035,884 | B2 | 7/2024 | Choi et al. |
| D1,083,091 | S | 7/2025 | Gray |
| 2004/0097931 | A1 | 5/2004 | Mitchell |
| 2004/0102848 | A1 | 5/2004 | Michelson |
| 2009/0005787 | A1 * | 1/2009 | Crall .................. A61B 17/7082 606/305 |
| 2009/0005819 | A1 | 1/2009 | Ben-Mokhtar et al. |
| 2012/0259416 | A1 | 10/2012 | Blackwell et al. |
| 2014/0257484 | A1 | 9/2014 | Flower et al. |
| 2016/0074172 | A1 | 3/2016 | Lee et al. |
| 2016/0113775 | A1 | 4/2016 | Willis et al. |
| 2017/0348028 | A1 | 12/2017 | Calvosa et al. |
| 2018/0200078 | A1 * | 7/2018 | Remington ............. A61F 2/447 |
| 2022/0313450 | A1 | 10/2022 | Donohoe et al. |
| 2023/0027465 | A1 | 1/2023 | Garlatti et al. |
| 2023/0240860 | A1 | 8/2023 | White et al. |
| 2024/0188996 | A1 | 6/2024 | Frock et al. |
| 2025/0107829 | A1 | 4/2025 | McQuinn et al. |
| 2025/0339191 | A1 | 11/2025 | Yadav et al. |

FOREIGN PATENT DOCUMENTS

| | | | |
|---|---|---|---|
| KR | 3009978750000 | 3/2019 | |
| KR | 3020200057069 | 4/2022 | |
| WO | WO-2008044057 A1 * | 4/2008 | ............ A61F 2/4611 |
| WO | 2015063721 A1 | 3/2015 | |

OTHER PUBLICATIONS

PCT Patent Application PCT/US2023/083725 International Preliminary Report on Patentability, issued Jun. 12, 2025.

"Aurora Spine: The Zip Procedure." Found online Jan. 20, 2026 at youtube.com. Reference dated Jul. 24, 2023. Retrieved from https://www.youtube.com/watch?v=AUxERojQktk.

"Globus Medical: Introducing the HILINE Fixation System." Found online Jan. 20, 2026 at youtube.com. Reference dated Feb. 18, 2025. Retrieved from https://www.youtube.com/watch?v=d7i R7lq240g.

"Ortho Spine News: Spinal Simplicity Announces New Real-World Fusion Study for Its Minuteman Device." Found online Jan. 20, 2026 at orthospinenews.com. Reference dated Aug. 31, 2023. Retrieved from https://orthospinenews.com/2023/08/31/spinal-simplicity-announces-new-real-world-fusion-study-for-its-minuteman-device/.

"SPINEMarketGroup: Zimmer Biomet Universal Spinal Clamp Fixation System." Found online Jan. 20, 2026 at youtube.com. X Reference dated Jul. 8, 2020. Retrieved from https://www.youtube.com/watch?v=99ypkimi47Y.

U.S. Appl. No. 29/920,758, Notice of Allowance issued Feb. 19, 2026.

U.S. Appl. No. 18/979,442, Non-Final Office Action issued Apr. 17, 2026.

Global BMD Titanium Implants, posted May 25, 2020 [online], [retrieved Feb. 18, 2026]. Retrieved from internet, https://globalbmd.com/globalbmd/Catalogs/Brochure%20GB %2028052020. pdf (Year: 2020).

PCT Patent Application PCT/US2025/57303 International Search Report and Written Opinion of the International Searching Authority issued Feb. 19, 2026.

Spinal Implants, posted Oct. 11, 2022 [online], [retrieved Feb. 18, 2026]. Retrieved from internet, https://www.youtube.com/watch?v=Ms9YWbljg NA&list= TLGGCtEsfd lkCsgxOT AyMjAyNg&t=88s (Year: 2022).

(56) References Cited

OTHER PUBLICATIONS

Spinal Simplicity Announces FDA Clearance, posted Dec. 16, 2025 [online], [retrieved Feb. 18, 2026]. Retrieved from internet, https://www.prweb.com/releases/spi nal-si m pl icity-annou nces-fda-clearance-of-minuteman-96-mis-fusion-device-302643192. html (Year: 2025).

U.S. Appl. No. 29/920,750, Non-Final Office Action issued Mar. 2, 2026.

* cited by examiner

MEDICAL IMPLANT

RELATED APPLICATIONS

This patent application is a continuation application claiming priority benefit, with regard to all common subject matter, of U.S. patent application Ser. No. 18/537,946, filed Dec. 13, 2023, and entitled "MEDICAL IMPLANT" ("the '946 Application"). The '946 Application claims priority benefit, with regard to all common subject matter, of U.S. Provisional Patent Application No. 63/432,296, filed Dec. 13, 2022, and entitled "MEDICAL IMPLANT." The above-identified applications are hereby incorporated by reference in their entirety.

This patent application shares certain subject matter in common with the following earlier-filed patents: U.S. patent application Ser. No. 12/554,922, filed Sep. 7, 2009, entitled INTERSPINOUS PROCESS IMPLANT AND FUSION CAGE SPACER, now U.S. Pat. No. 8,945,184; U.S. patent application Ser. No. 14/560,006, filed Dec. 4, 2014, entitled INTERSPINOUS PROCESS IMPLANT AND FUSION CAGE SPACER, now U.S. Pat. No. 9,314,276; U.S. patent application Ser. No. 15/085,687, filed Mar. 30, 2016, entitled INTERSPINOUS PROCESS IMPLANT AND FUSION CAGE SPACER, now U.S. Pat. No. 9,907,581; U.S. patent application Ser. No. 13/940,868, filed Jul. 12, 2013, entitled INTERSPINOUS PROCESS IMPLANT HAVING DEPLOYABLE ANCHOR BLADES, now U.S. Pat. No. 9,757,164; U.S. patent application Ser. No. 15/159,189, filed May 19, 2016, entitled INTERSPINOUS PROCESS IMPLANT HAVING A BODY WITH A REMOVABLE END PORTION, now U.S. Pat. No. 9,861,399; U.S. patent application Ser. No. 16/998,171, filed Aug. 20, 2020, entitled INTERSPINOUS PROCESS IMPLANT, now U.S. Pat. No. 11,311,388; U.S. patent application Ser. No. 17/389,418, filed Jul. 30, 2021, entitled INTERSPINOUS PROCESS IMPLANT, now U.S. Pat. No. 11,311,389; U.S. patent application Ser. No. 17/677,677, filed Feb. 22, 2022, entitled INTERSPINOUS PROCESS IMPLANT, now U.S. Pat. No. 11,534,310; U.S. patent application Ser. No. 18/072,414, filed Nov. 30, 2022, entitled INTERSPINOUS PROCESS IMPLANT; U.S. patent application Ser. No. 14/290,183, filed May 29, 2014, entitled INSTRUMENT FOR INSERTING AN INTERSPINOUS PROCESS IMPLANT, now U.S. Pat. No. 9,603,648; U.S. patent application Ser. No. 15/467,533, filed Mar. 23, 2017, entitled INSTRUMENT FOR INSERTING AN INTERSPINOUS PROCESS IMPLANT, now U.S. Pat. No. 10,285,739; U.S. patent application Ser. No. 16/376,774, filed Apr. 5, 2019, entitled INSTRUMENT FOR INSERTING AN INTERSPINOUS PROCESS IMPLANT, now U.S. Pat. No. 11,234,740; U.S. patent application Ser. No. 17/587,666, filed Jan. 28, 2022, entitled INSTRUMENT FOR INSERTING AN INTERSPINOUS PROCESS IMPLANT, now U.S. Pat. No. 11,801,075; U.S. patent application Ser. No. 17/949,648, filed Sep. 21, 2022, entitled INSTRUMENT FOR INSERTING AN INTERSPINOUS PROCESS IMPLANT, now U.S. Pat. No. 11,998,249; U.S. patent application Ser. No. 18/649,579, filed Apr. 29, 2024, entitled INSTRUMENT FOR INSERTING AN INTERSPINOUS PROCESS IMPLANT; U.S. patent application Ser. No. 15/487,087, filed Apr. 13, 2017, entitled INTERSPINOUS IMPLANT INSERTION INSTRUMENT WITH STAGGERED PATH IMPLANT DEPLOYMENT MECHANISM, now U.S. Pat. No. 10,420,591; U.S. patent application Ser. No. 16/578,604, filed Sep. 23, 2019, entitled INTERSPINOUS IMPLANT INSERTION INSTRUMENT WITH STAGGERED PATH IMPLANT DEPLOYMENT MECHANISM, now U.S. Pat. No. 11,298,161; U.S. patent application Ser. No. 17/716,813, filed Apr. 8, 2022, entitled LOCKING SYSTEM FOR INTERSPINOUS IMPLANT INSERTION INSTRUMENT, now U.S. Pat. No. 11,510,710; U.S. patent application Ser. No. 17/944,101, filed Sep. 13, 2022, entitled INTERSPINOUS IMPLANT INSERTION INSTRUMENT WITH STAGGERED PATH IMPLANT DEPLOYMENT MECHANISM; U.S. patent application Ser. No. 17/944,107, filed Sep. 13, 2022, entitled INTERSPINOUS IMPLANT INSERTION INSTRUMENT WITH WING ACTUATION TOOL, now U.S. Pat. No. 11,766,280; U.S. patent application Ser. No. 18/212,946, filed Jun. 22, 2023, entitled INTERSPINOUS IMPLANT INSERTION INSTRUMENT WITH WING ACTUATION TOOL; U.S. patent application Ser. No. 17/716,833, filed Apr. 8, 2022, entitled DISPOSABLE INTERSPINOUS IMPLANT INSERTION INSTRUMENT, now U.S. Pat. No. 11,672,572; U.S. patent application Ser. No. 18/311,048, filed May 2, 2023, entitled DISPOSABLE INTERSPINOUS IMPLANT INSERTION INSTRUMENT; U.S. patent application Ser. No. 17/077,487, filed Oct. 22, 2020, entitled COMBINED BONE RASP AND TAP, now U.S. Pat. No. 11,571,221; and U.S. patent application Ser. No. 18/163,048, filed Feb. 1, 2023, entitled COMBINED BONE TAP AND RASP.

The above-referenced patent applications are hereby incorporated by reference in their entirety into the present application.

BACKGROUND

1. Field

Embodiments of the present disclosure relate to systems, devices, and methods for medical procedures. More specifically, embodiments of the present disclosure relate to systems, devices, and methods for fusion and stabilization of various bony structures, such as the spinous processes.

2. Related Art

The spine consists of a column of twenty-four vertebrae that extend from the skull to the hips, with discs of soft tissue disposed between adjacent vertebrae. The vertebrae provide support for the head and body, while the discs act as cushions. The spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are a number of non-surgical treatments for spinal stenosis, such as non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. Surgical treatments for spinal stenosis include decompressive laminectomy, which involves removal of parts of the vertebrae. The goal of the procedure is to relieve pressure on the spinal cord and nerves by increasing the area of the spinal canal.

Interspinous process decompression (IPD) is another surgical procedure for treating spinal stenosis. IPD surgery requires little to no removal of bone or soft tissue. Instead, an implant or spacer device is positioned behind the spinal cord or nerves and between the interspinous processes protruding from the vertebrae. Examples of interspinous process implant and fusion devices are disclosed in commonly assigned U.S. Pat. Nos. 8,945,184; 9,314,276; 9,907,581; 9,757,164; 9,861,399; 11,311,388; 11,311,389; 11,534,310; U.S. patent application Ser. No. 18/072,414; the disclosures of which are incorporated by reference in their entirety.

Implants involved in surgical procedures include an implant body comprising anchors (otherwise referred to as wings or clamps) for securing the implant at the treatment site. For example, during IPD, bony or soft tissue is cleared away at the treatment site (e.g., adjacent the interspinous process space) to make a path for the implant body. The implant body is inserted into the path. The anchors of the implant body may then clamp onto nearby bony tissue or soft tissue (e.g., spinous processes) to stabilize the implant and secure the implant between the bone and/or soft tissue (e.g., between adjacent spinous processes).

The anchors are positioned proximate opposite ends of the implant body, such as near the distal end of implant body and near the proximal end of the implant body. The oppositely positioned anchors may then clamp onto opposite sides of the spinous processes to stabilize the implant. Advancing the oppositely positioned anchors toward opposite sides of the spinous processes to clamp the anchors onto nearby tissue may require multiple operations by a surgeon and/or multiple actuation steps, thereby increasing the overall complexity of the surgical procedure.

The anchors may extend outward from the implant body when the implant is inserted into the target space (e.g., interspinous process space). These outwardly extending anchors may increase the amount of soft tissue, muscle, and/or bone disrupted during surgery. This increased disruption of soft tissue, muscle, and/or bone during surgery may increase blood loss during surgery, increase recovery required after the surgery, and increase the amount of pain felt by the patient. Additionally, the outwardly extending anchors may require a larger incision be made relative to the size of the implant body for the entire implant to fit through the incision, thereby increasing the amount of blood loss. The outwardly extending anchors may require a larger sleeve and/or dilator used to deliver the implant to the treatment site in the body relative to a sleeve sized to fit the implant body, thereby requiring a larger incision be made.

During IPD, the implant body may be inserted into the interspinous process space. The anchors may then be deployed outward from the implant body. The anchors may then be advanced toward the spinous processes, such that the anchors may clamp onto nearby bony tissue or soft tissue. Inserting the implant body within the interspinous process space, deploying the anchors, and advancing the anchors toward the spinous processes may require multiple, separate actuation mechanisms within the implant body. This may increase the complexity of the implant and increase the complexity and time of the surgical procedure.

Additionally, the deployment of the anchors may clear away more soft tissue after the path has been cleared for the implant body. For example, the anchors may deploy outward from the implant body such that additional soft tissue is disturbed by the implant. Advancing the deployed anchors toward the spinous processes may clear more soft tissue away from the treatment site, relative to the soft tissue cleared away by inserting the implant body. Anchor deployment increasing the amount of tissue cleared away near the treatment site may increase the likelihood of surgical complications, by decreasing the stability near the spinous processes.

The overall profile of the implant when inserted in the treatment site may affect the safety of the surgical procedure and surgical complications. For example, a large interspinous implant may increase the size of the surgical wound resulting from surgery and may increase the amount of tissue to be cleared away. Increasing the amount of tissue to be cleared away and increasing the size of the surgical wound may increase the likelihood of surgical complications. A larger interspinous implant (e.g., long implant) may displace a larger amount of tissue and occupy a larger area nearby or at the spine, thereby decreasing the stability of the spine and at the treatment site.

The surgeon performing the surgical procedure may want to adjust the position of the implant once inserted at the treatment site or remove the implant entirely. Surgical procedures, such as IPD, may require forming an additional incision to manually close (or un-deploy) the anchors in order to remove the implant. Thus, removal of the implant may require surgical steps in addition to those performed when inserting the implant at the treatment site.

SUMMARY

Embodiments of the present disclosure solve the above-mentioned problems by providing a medical implant that may be used in various surgical procedures for treating various injuries or issues. As an example, the embodiments of a medical implant may be used in various spinal procedures, such as IPD surgery, for treating various spinal injuries or issues, such as spinal stenosis. The presently disclosed embodiments of medical implants may also be used, for example, in spinal procedures for treating degenerative disc disorder. The present disclosure describes embodiments of medical implants that can be used in joint replacement surgery for treating osteoarthritis (OA) or rheumatoid arthritis (RA) where the cartilage between bones in a joint degrades. The presently disclosed embodiments of medical implants, once inserted, would provide space to decrease the pain caused by bone-on-bone movement within a joint afflicted with OA or RA. The presently disclosed embodiments of medical implants may be used for stabilization and/or fixation of any joint and/or bone. For example, the presently disclosed embodiments of medical implants may be inserted at a sacroiliac (SI) joint space to stabilize the SI joint.

The present disclosure describes embodiments of medical implants wherein the implant advances into the treatment site (e.g., interspinous process space), the wings (otherwise referred to as anchors or clamps) deploy from the implant body, and the wings advance toward the treatment site (e.g., spinous processes), all through a single actuation mechanism. For example, the presently disclosed embodiments of medical implants may comprise an outer body, inner body, proximal wings coupled to the outer body, distal wings coupled to the inner body, and a screw operatively coupled to the outer body and inner body. Actuation of the screw pivots the proximal wings and distal wings to a deployed position, and translates the implant into the treatment site. The single actuation mechanism decreases the steps required during the surgical procedure, thereby decreasing the complexity of the implant and complexity of the surgical procedure.

The present disclosure describes embodiments of medical implants wherein the wings are housed partially or wholly inside the implant body when the implant is inserted into the patient and prior to deploying the wings to engage with bone and/or soft tissue at and/or near the treatment site. The wings may fit within the outer profile of the implant body during insertion. Housing portions of the wings and/or the entire wings inside the implant body and fitting the wings within the outer profile of the implant body decreases the overall size of the implant when inserting into the patient, thereby decreasing blood loss during surgery by decreasing the size of incision required. Housing portions of the wings or the entire wings inside the implant body also decreases the disruption of muscle, soft tissue, and/or bone in the patient during the surgery due to the smaller profile of the implant during insertion. The decreased disruption of muscle, soft tissue, and/or bone during surgery may decrease blood loss, decrease recovery time, and decrease the amount of pain felt by the patient. The implant may fit a smaller sleeve used to insert the implant up to the treatment site, due to the decreased overall profile of the implant.

The present disclosure describes embodiments of medical implants wherein the wings simultaneously form at least a portion of the path for the implant while deploying the wings into a position to engage bone or tissue near the treatment site (e.g., spinous processes) to stabilize the implant. For example, the presently disclosed embodiments of medical implants may pivot the distal wings in a first direction (e.g., pivot proximally in a proximal direction), such that the distal wings contact surfaces of the adjacent spinous processes to pull the implant at least partially through the treatment site. Simultaneously, the distal wings may pivot to a deployed position for clamping bone or tissue (e.g., spinous processes) to secure the implant at the treatment site. The medical implant embodiments may comprise an outer body, an inner body defining a rotation slot, proximal wings coupled to the outer body, distal wings coupled to the inner body and defining pins, and a screw operatively coupled to the outer body and inner body. Actuation of the screw slides the pins along the rotation slot to both pivot the distal wings in a first direction to a deployed position to engage nearby bony tissue or soft tissue and advance the distal wings within the treatment site to clear at least a portion of the path for the implant. The presently disclosed embodiments of medical implants decrease the complexity of the implant. Additionally, the presently disclosed embodiments of medical implants decrease the amount of tissue cleared away near the treatment site because the distal wings simultaneously pivot to a deployed position and advance the implant through the treatment site, thereby decreasing the likelihood of surgical complications and increasing the stability of the inserted implant near the spinous processes.

The present disclosure describes embodiments of medical implants wherein the outer body and/or implant body comprises threading on an exterior thereof. The threading may provide additional stabilization by interacting with soft tissue and/or bone at and/or near the treatment site to fix the implant within the treatment site. Additionally, the exterior threading on the body of the implant may interact with soft tissue and/or bone as the implant is inserted into the treatment site, thereby aiding the insertion process and making the insertion process easier.

The present disclosure describes embodiments of medical implants wherein the overall profile of the implant decreases after insertion of the implant at the treatment site (e.g., within interspinous process space). For example, presently disclosed embodiments of medical implants may comprise a cartridge coupled to a proximal end of a threaded body of the implant. An insertion instrument may attach to the cartridge. When the threaded body is inserted into the treatment site and the wings are deployed, the cartridge may detach from the threaded body, thereby decreasing the overall profile and size of the implant. The decreased profile of the implant may increase the stability of the spine and at the treatment site.

The present disclosure describes embodiments of medical implants that provide easier removal or repositioning of the implant after implantation, if desired. The ability of the surgeon to both selectively deploy and close the wings of the presently described medical implant embodiments allows the surgeon to remove the implant or adjust the placement of the implant, using the same small lateral incision through which the implant was originally inserted. For example, actuation of a screw comprised in presently disclosed embodiments of medical implants in a first direction may deploy distal and proximal wings and distally advance the implant body into the treatment site. Actuation of the screw in a second direction may close the distal and proximal wings and proximally move the implant body out of the treatment site. Actuation of the screw in a second direction allows a surgeon to use the same incision for inserting the implant and removing the implant. Additionally, actuation of the screw in a first direction and actuation of the screw in a second direction provides a simple removal/repositioning procedure. Additionally, actuation of the screw in a second direction allows a surgeon to easily reposition the implant at the treatment side of the patient.

In some embodiments, the techniques described herein relate to a medical implant for insertion at a treatment site, including: an outer body defining a longitudinal axis extending through a proximal end of the outer body and a distal end of the outer body; an inner body operatively coupled to the outer body; one or more proximal wings pivotally coupled to the outer body proximate the proximal end; one or more distal wings pivotally coupled to the inner body; and a threaded screw operatively coupled to the outer body and the inner body, wherein actuation of the threaded screw pivots the one or more proximal wings between a closed position and a deployed position and pivots the one or more distal wings between a closed position and a deployed position.

In some embodiments, the techniques described herein relate to a medical implant, wherein the inner body includes ramps, wherein actuation of the threaded screw causes at least a portion of each proximal wing of the one or more proximal wings to contact the ramps to thereby pivot the one or more proximal wings.

In some embodiments, the techniques described herein relate to a medical implant, wherein actuation of the threaded screw distally translates the threaded screw to contact the one or more distal wings to thereby pivot the one or more distal wings.

In some embodiments, the techniques described herein relate to a medical implant, wherein the one or more proximal wings pivot distally outward toward the distal end of the outer body to transition the one or more proximal wings from the closed position to the deployed position, wherein the one or more distal wings pivot proximally outward toward the proximal end of the outer body to transition the one or more distal wings from the closed position to the deployed position.

In some embodiments, the techniques described herein relate to a medical implant, wherein one or more inner body pieces form the inner body, wherein each inner body piece of the one or more inner body pieces includes a groove and a rotation slot, the rotation slot having a first end and second end.

In some embodiments, the techniques described herein relate to a medical implant, wherein each distal wing of the one or more distal wings includes a wing pin and the rotation slot of each inner body piece of the one or more inner body pieces receives the wing pin of each distal wing of the one or more distal wings, wherein distal translation of the threaded screw to contact the one or more distal wings causes each wing pin of each distal wing of the one or more distal wings to move between the first end and the second end of the rotation slot of each inner body piece of the one or more inner body pieces to thereby transition the one or more distal wings between the closed position and the deployed position.

In some embodiments, the techniques described herein relate to a medical implant, wherein each proximal wing of the one or more proximal wings includes a protuberance, wherein the groove of each inner body piece of the one or more inner body pieces receives the protuberance of each proximal wing of the one or more proximal wings, wherein actuation of the threaded screw moves the protuberance of each proximal wing of the one or more proximal wings along a least a portion of the groove of each inner body piece of the one or more inner body pieces.

In some embodiments, the techniques described herein relate to a medical implant, wherein the inner body includes translations surfaces, wherein, in the deployed position, the protuberance of each proximal wing of the one or more proximal wings contacts translations surfaces of the inner body to maintain each proximal wing of the one or more proximal wings in the deployed position.

In some embodiments, the techniques described herein relate to a medical implant, further including: a proximal carrier coupled to the outer body and including a carrier bore, wherein the carrier bore receives the threaded screw.

In some embodiments, the techniques described herein relate to a system configured to insert a medical implant into a treatment site, the system including: the medical implant, including: an outer body having a proximal end and a distal end; an inner body operatively coupled to the outer body; one or more proximal wings pivotally coupled to the outer body; one or more distal wings pivotally coupled to the inner body; and a threaded screw operatively coupled to the outer body and the inner body, and an insertion tool, including: an outer shaft coupled to an outer grip; a handle operatively coupled to the outer grip such that the outer shaft couples to the handle; an inner shaft, the outer shaft receiving at least a portion of the inner shaft; and an inner rod having a distal end and a proximal end, wherein the inner shaft receives at least a portion of the inner rod, wherein the distal end of the inner rod includes a driver head and the proximal end of the inner rod includes a control, wherein the threaded screw is configured to receive the driver head, wherein operation of the control rotates the driver head to actuate the threaded screw, wherein actuation of the threaded screw transitions the one or more proximal wings and the one or more distal wings between a closed position and a deployed position.

In some embodiments, the techniques described herein relate to a system, wherein the threaded screw includes a screw head and the screw head receives the driver head, wherein rotation of the driver head rotates the threaded screw to transition the one or more proximal wings and the one or more distal wings between the closed position and the deployed position.

In some embodiments, the techniques described herein relate to a system, the insertion tool further including: an attachment member coupled to the inner shaft, wherein the attachment member includes a plurality of arms configured to attach the medical implant to the insertion tool.

In some embodiments, the techniques described herein relate to a system, the medical implant further including: openings defined by the outer body, wherein the openings receive at least a portion of each arm of the plurality of arms to thereby attach the medical implant to the insertion tool and maintain the medical implant on the insertion tool.

In some embodiments, the techniques described herein relate to a system, wherein rotation of the outer grip translates the plurality of arms of the attachment member such that the openings receive the plurality of arms to thereby maintain the medical implant on the insertion tool.

In some embodiments, the techniques described herein relate to a system, the insertion tool further including: a connector coupled to the inner shaft, wherein an exterior portion of the connector includes threads, wherein a threaded bore defined by the outer grip receives the connector to threadedly couple the connector to the outer grip, wherein the connector operatively couples the outer grip to the handle.

In some embodiments, the techniques described herein relate to a system, wherein the handle defines a tunnel extending from a distal end of the handle to a proximal end of the handle, wherein the tunnel receives at least a portion of the inner rod, wherein a portion of the tunnel located at the distal end of the handle is threaded to thereby threadedly couple the handle to the connector.

In some embodiments, the techniques described herein relate to a method of inserting a medical implant into a treatment site, the method including: providing a medical implant, the medical implant including: an outer body having a proximal end and a distal end; an inner body operatively coupled to the outer body; one or more proximal wings pivotally coupled to the outer body; one or more distal wings pivotally coupled to the inner body; and a threaded screw operatively coupled to the outer body and the inner body, wherein the one or more proximal wings and the one or more distal wings are in a closed position, providing instructions including: attaching an insertion tool to the medical implant; inserting a portion of the medical implant into the treatment site; and actuating the insertion tool in a first direction to transition the medical implant from a closed configuration to a deployed configuration, wherein actuating the insertion tool in a first direction includes rotating a portion of the insertion tool in a first direction to pivot the one or more distal wings and the one or more proximal wings from the closed configuration to the deployed configuration.

In some embodiments, the techniques described herein relate to a method, wherein rotating a portion of the insertion tool in a first direction rotates the threaded screw in a first direction to thereby pivot the one or more distal wings and the one or more proximal wings from the closed configuration to the deployed configuration, wherein the one or more distal wings are configured to grip bone or tissue at the treatment site when the medical implant is transitioning from the closed configuration to the deployed configuration to pull the medical implant into the treatment site, such that the medical implant is fully inserted into the treatment site when in the deployed configuration.

In some embodiments, the techniques described herein relate to a method, wherein actuating the insertion tool transitions the medical implant from the deployed configuration to a clamped configuration, wherein, in the clamped configuration, the one or more proximal wings and the one or more distal wings engage bone or tissue at and/or near the treatment site to stabilize the medical implant within the treatment site, wherein the method further includes: detaching the insertion tool from the medical implant when the medical implant is in the clamped configuration.

In some embodiments, the techniques described herein relate to a method, further including: actuating the insertion tool in a second direction to transition the medical implant from the deployed configuration to the closed configuration, wherein actuating the insertion tool in a second direction includes rotating a portion of the insertion tool in a second direction to pivot the one or more distal wings and the one or more proximal wings from the deployed configuration to the closed configuration.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present disclosure will be apparent from the following detailed description of the embodiments and the accompanying drawing figures.

BRIEF DESCRIPTION OF THE DRAWING FIGURES

Embodiments of the present disclosure are described in detail below with reference to the attached drawing figures, wherein.

Figure 1A:
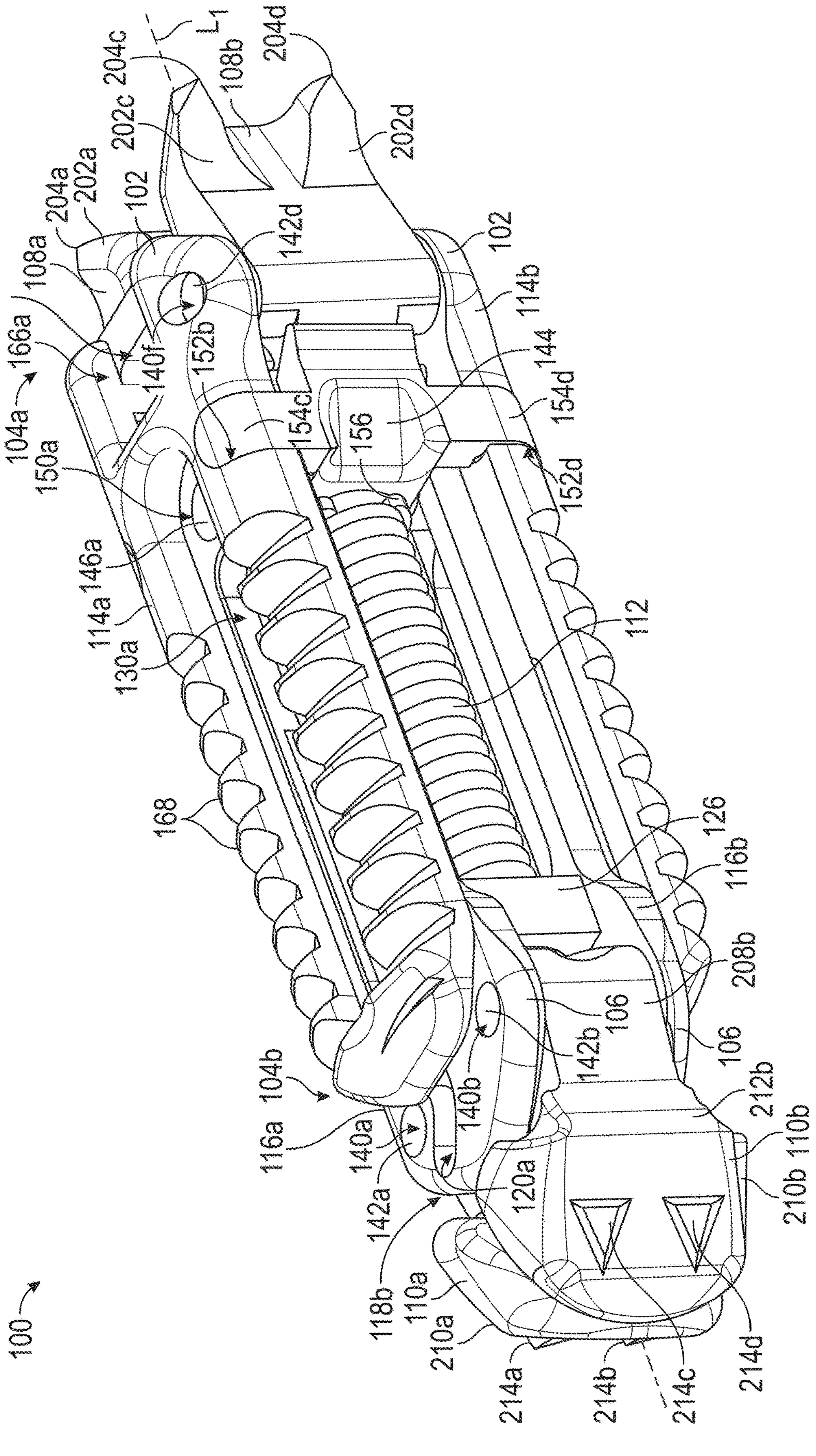
FIG. 1A illustrates a perspective view of some embodiments of an implant in a closed position.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The following detailed description references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized and changes can be made without departing from the scope of the present disclosure. The following detailed description is, therefore, not to be taken in a limiting sense. The scope of the present disclosure is defined only by the appended claims, along with the full scope of equivalents to which such claims are entitled.

In this description, references to “one embodiment,” “an embodiment,” or “embodiments” mean that the feature or features being referred to are included in at least one embodiment of the technology. Separate references to “one embodiment,” “an embodiment,” or “embodiments” in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Embodiments of the present disclosure are generally directed to systems, methods, and devices for fusion and stabilization of bony structures in a body, such as the spinous processes. In some embodiments, a medical implant is provided that includes an outer body, an inner body, distal wings operatively coupled to the inner body, proximal wings operatively coupled to the outer body, and a screw coupled to the outer body and inner body. Actuation of the screw may transition the proximal wings between a closed position and a deployed position and may transition the distal wings between a closed position and a deployed position. Actuation of the screw in a first direction may pivot the proximal wings to a deployed position and distally translate the proximal wings to engage the proximal wings with bone or tissue at the treatment site. Actuation of the screw in the first direction may pivot the distal wings to a deployed position to engage the distal wings with bone or tissue at the treatment site, such that the proximal wings deploy, the distal wings deploy, and the proximal wings distally translate through a single actuation operation. Actuation of the screw in a second direction may pivot the proximal wings and the distal wings back to a closed position to remove the wings from the bone or tissue at the treatment site, and may proximally translate the proximal wings away from the treatment site. Actuation of the screw in a second direction may remove the implant from the treatment site.

The medical implant may form part of a system, the system including an insertion tool. The system may be configured to insert a medical implant into a treatment site. The insertion tool may include an attachment member and an inner rod. A portion of the inner rod may be received by the attachment member. A screw head of the threaded screw of the medical implant may receive a portion of the inner rod when the attachment member is attached to the outer body of the medical implant. Rotation of the inner rod may actuate the threaded screw in the first direction to transition the proximal wings between the closed position and the deployed position and to transition the distal wings between the closed position and the deployed position.

A method is provided in which a medical implant is inserted at a treatment site to stabilize a joint. The method may include attaching the medical implant to the insertion tool, with the medical implant in the closed position. The implant is then placed in a patient at a desired treatment site. Rotating the inner rod of the insertion tool actuates the threaded screw of the medical implant to pivot the proximal wings to the deployed position, distally translate the proximal wings toward the treatment site, pivot the distal wings to a deployed position, and distally translate at least part of the implant into the treatment site. Pivoting the distal wings to a deployed position and distally translating the deployed proximal wings engages the proximal wings and distal wings with bony tissue and/or soft tissue at the treatment site to secure the medical implant. The insertion tool is then removed from the medical implant.

In some embodiments, the outer body of the medical implant may include a cartridge coupled to a threaded portion of the outer body. The insertion tool may attach to the cartridge of the medical implant. After inserting the medical implant at a treatment site to stabilize a joint, removing the insertion tool may detach the cartridge from the threaded portion.

First Implant Embodiment

Figure 1B:
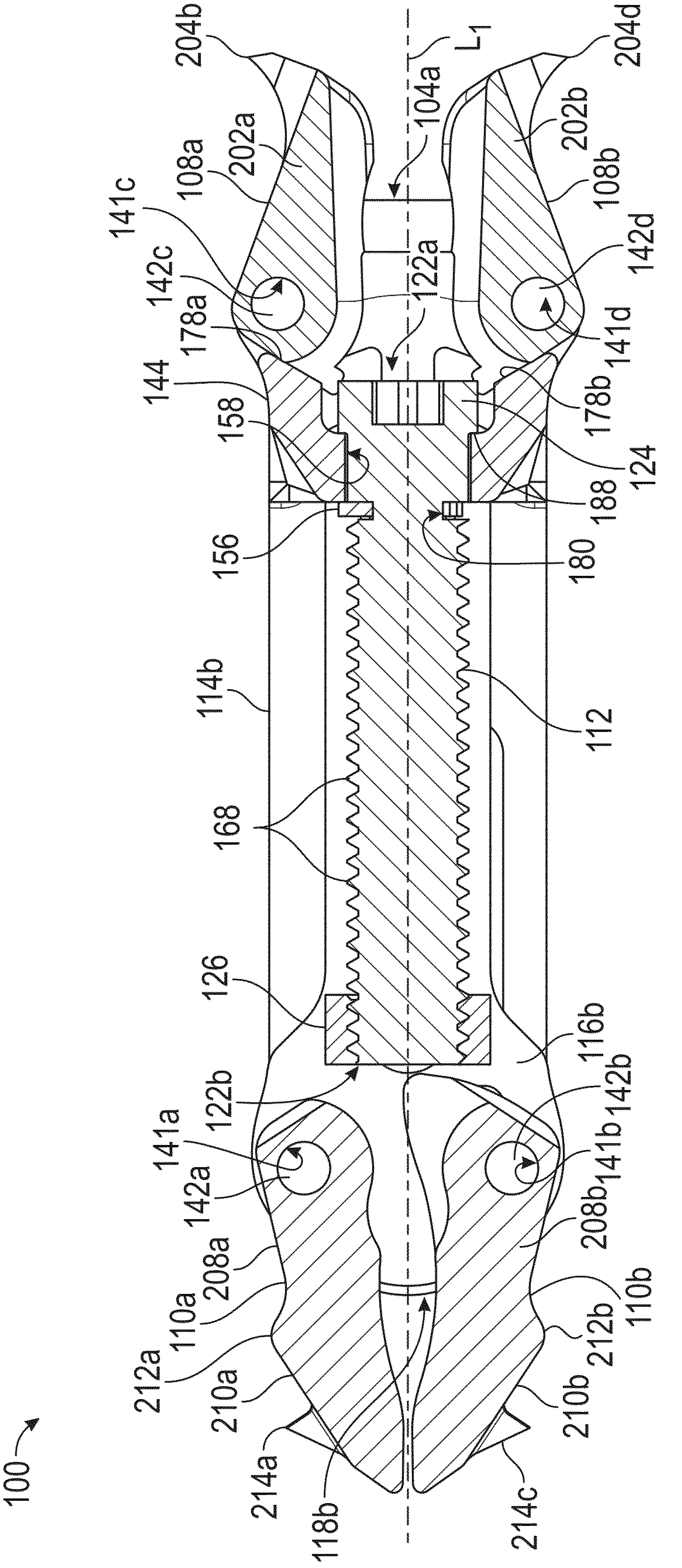
FIG. 1B illustrates a cross-sectional view of some embodiments of the implant in a closed position.

FIG. 1A illustrates a perspective view of some embodiments of an implant 100 in a closed position (also referred to as a closed configuration). FIG. 1B illustrates a top cross-sectional view of some embodiments of the implant 100 in a closed configuration. Accordingly, FIGS. 1A-1B are best viewed together. Implant 100 may be configured to be inserted within a target space between bones for fusion, fixation, and/or stabilization of bones and/or joints. Implant 100 may be inserted anywhere in a body where there is a need for fixation and/or stabilization of bones, joints, and/or soft tissue. In some embodiments, implant 100 may be configured to be inserted within an interspinous process space for fusion and stabilization of spinous processes. Implant 100 may comprise an outer body 102 defining a longitudinal axis $L_1$ extending through a proximal end 104*a* and a distal end 104*b*. Implant 100 may comprise an inner body 106 operatively coupled to outer body 102. Implant 100 may comprise proximal wings 108*a*, 108*b* (also referred to as proximal anchors) and distal wings 110*a*, 110*b* (also referred to as distal anchors). Proximal wings 108*a*, 108*b* may pivotally couple to outer body 102. Distal wings 110*a*, 110*b* may pivotally couple to inner body 106. In some embodiments, implant 100 may comprise at least one proximal wing 108*a*, 108*b* and at least one distal wing 110*a*, 110*b*. In some embodiments, implant 100 may comprise more than one proximal wing 108*a*, 108*b* and more than one distal wing 110*a*, 110*b*.

Figure 14A:
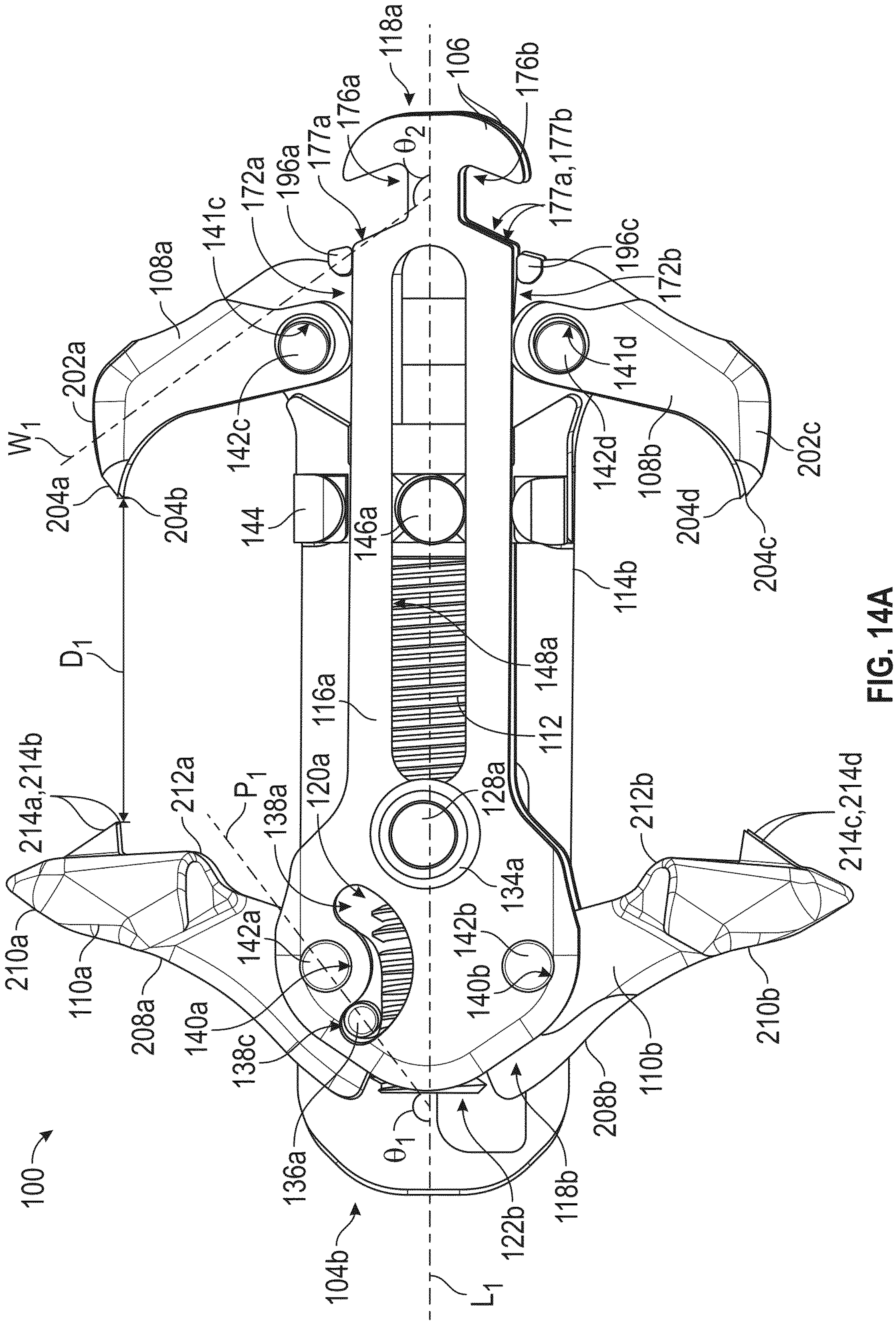
FIG. 14A illustrates a top perspective view of some embodiments of the implant in a deployed configuration with a portion of an outer body removed.
Figure 14B:
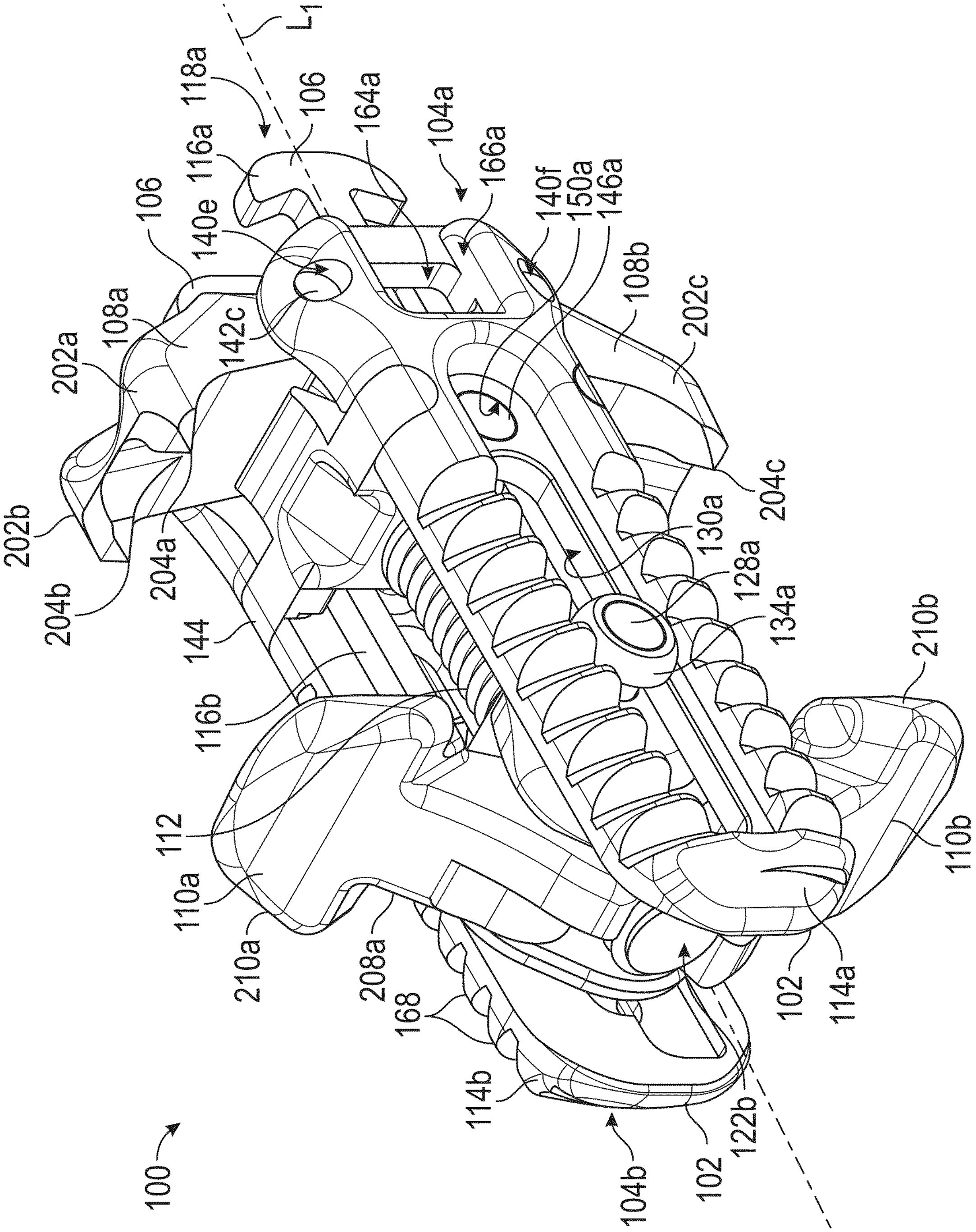
FIG. 14B illustrates a perspective view of some embodiments of the implant in a deployed configuration.
Figure 15A:
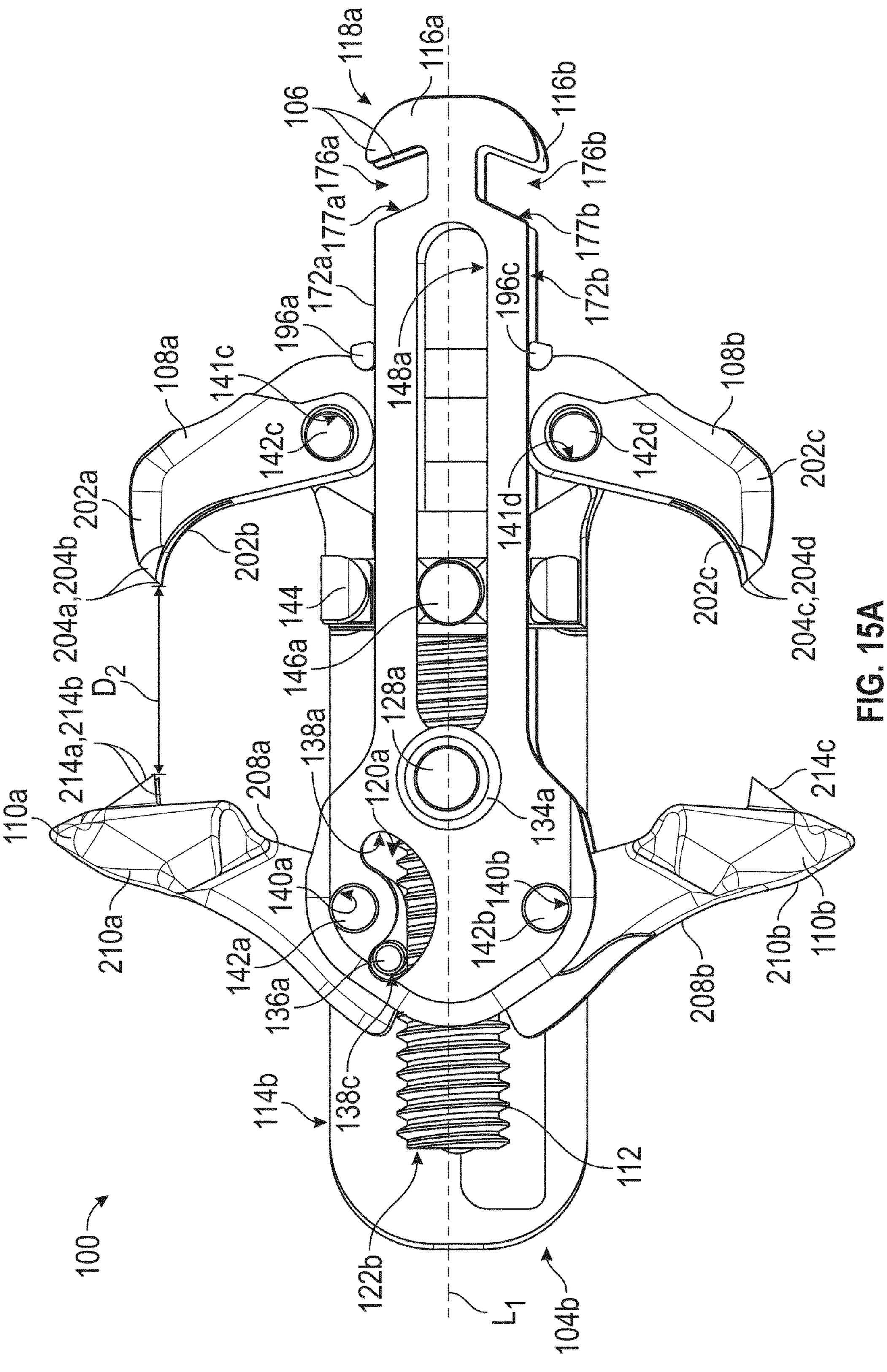
FIG. 15A illustrates a top perspective view of some embodiments of the implant in a clamped configuration with a portion of an outer body removed.
Figure 15B:
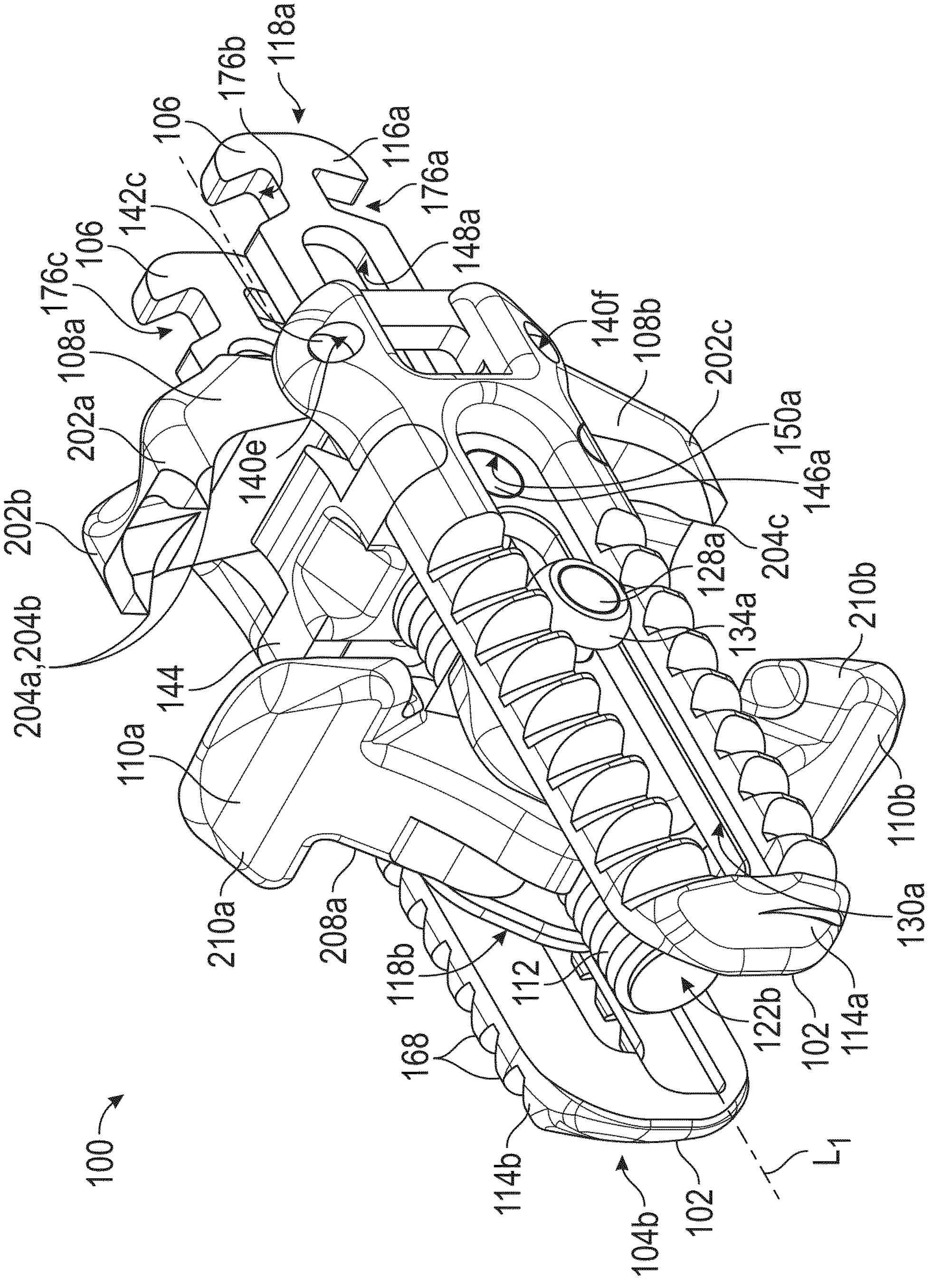
FIG. 15B illustrates a perspective view of some embodiments of the implant in a clamped configuration.
Figure 29A:
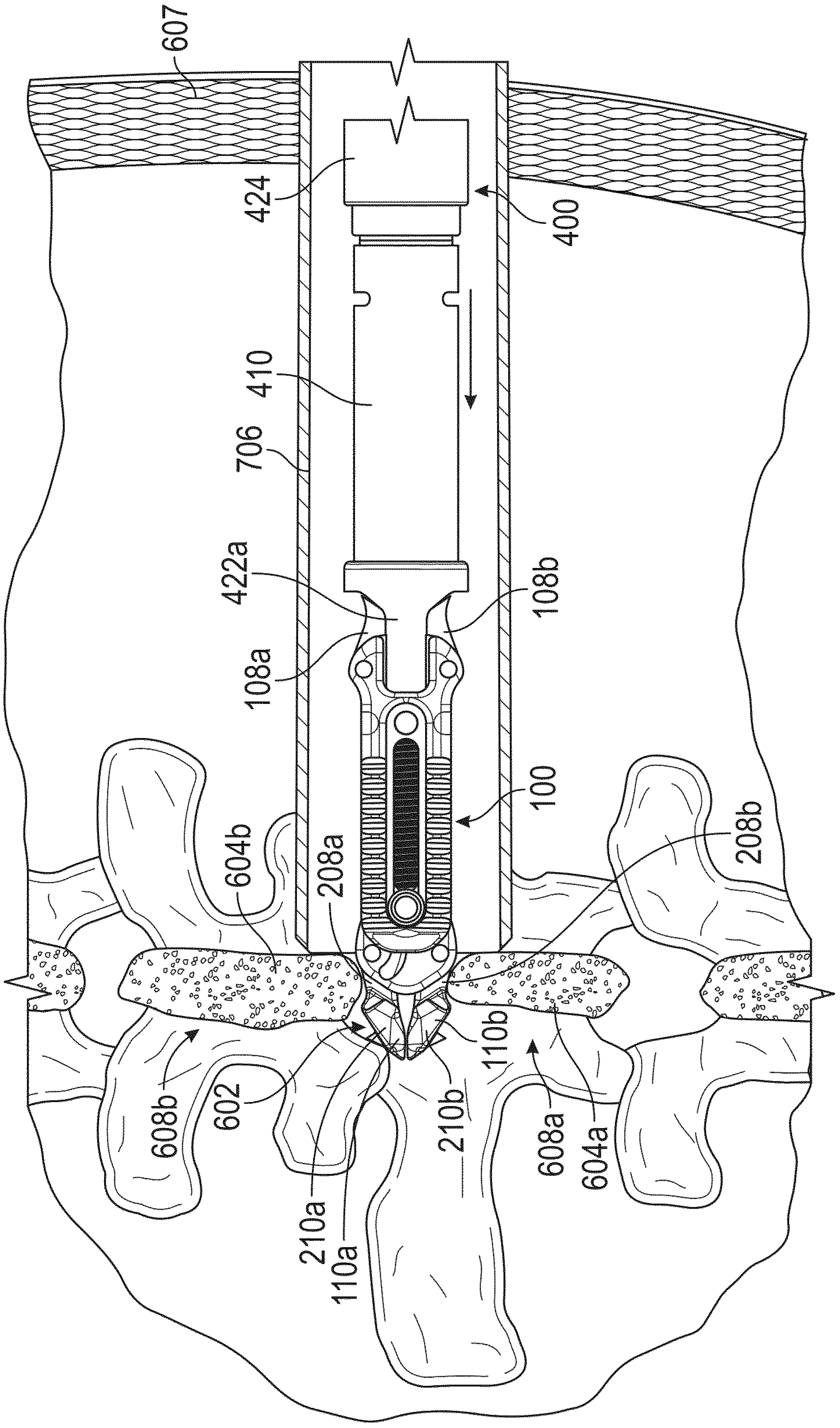
FIG. 29A illustrates a cross-sectional view of some embodiments of the implant partially inserted into a target space in the closed position, with the implant attached to the insertion tool and an outer shaft of the insertion tool removed.
Figure 29B:
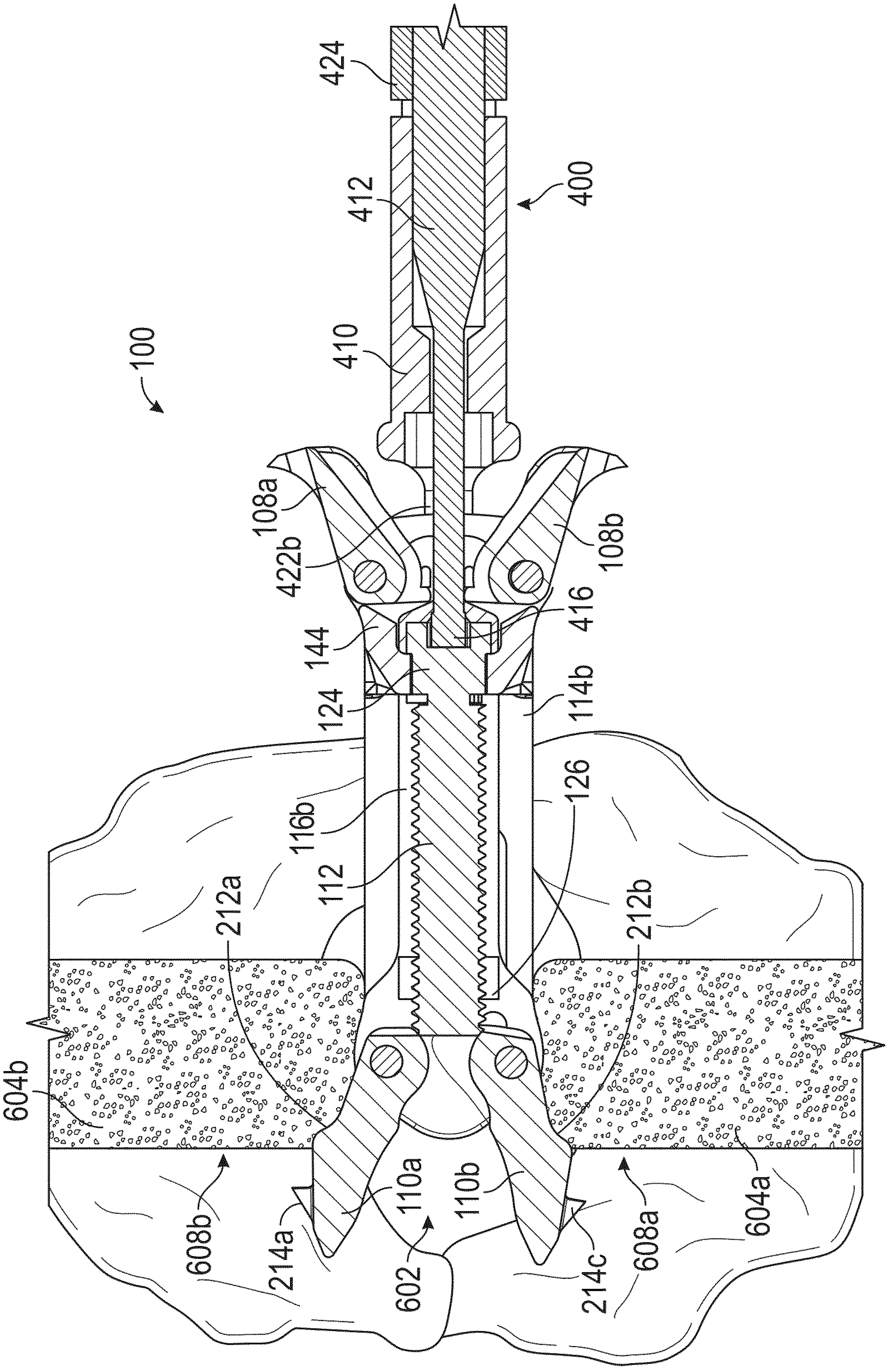
FIG. 29B illustrates a cross-sectional view of some embodiments of the implant partially inserted into a target space in an intermediate position, with the implant attached to the insertion tool and an outer shaft of the insertion tool removed.
Figure 29C:
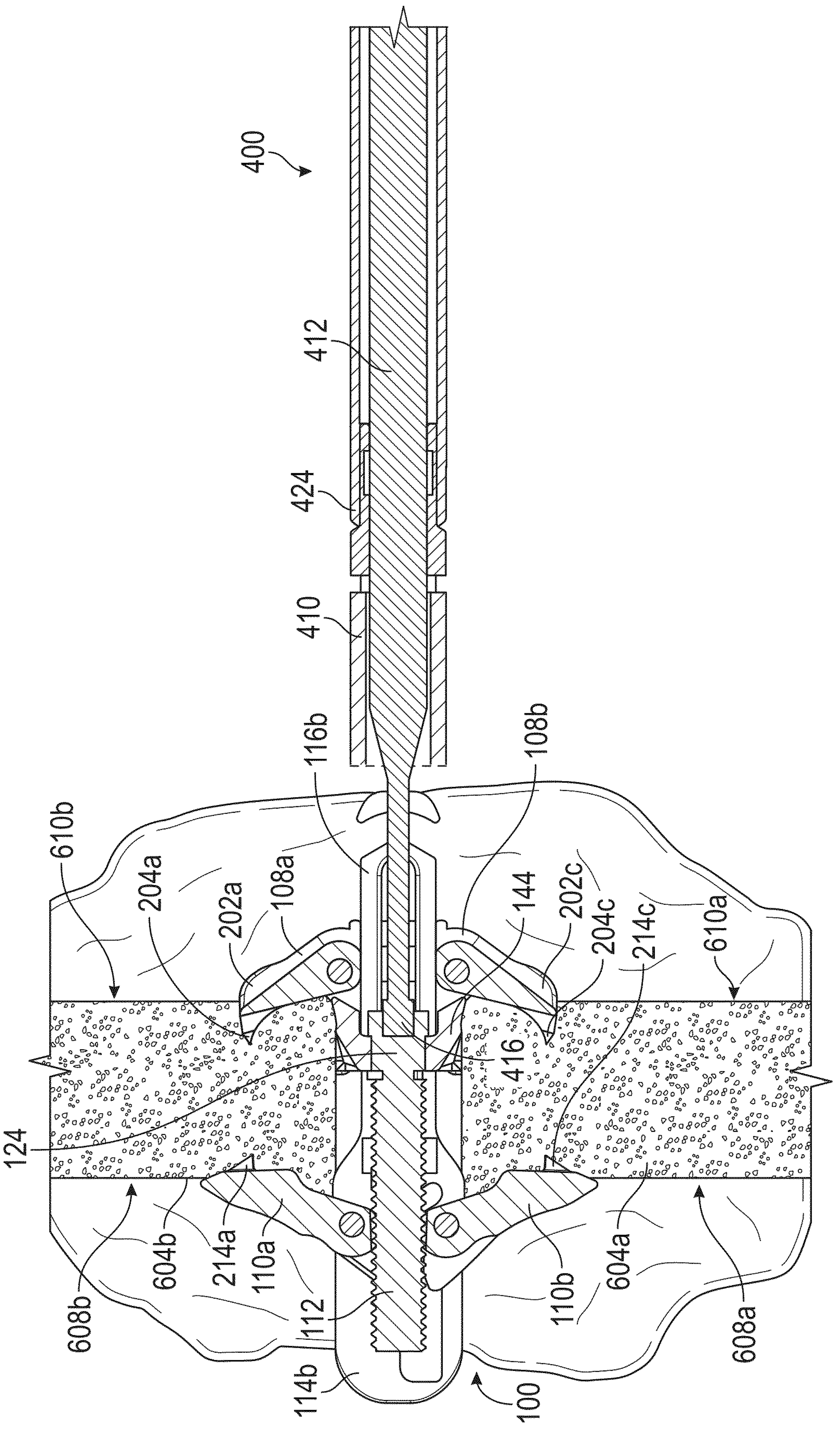
FIG. 29C illustrates a cross-sectional view of some embodiments of the implant inserted in a target space in the clamped configuration with a portion of an attachment member of the insertion tool removed and the outer shaft of the insertion tool removed.

Implant 100 may comprise a threaded screw 112 operatively coupled to the inner body 106 and outer body 102, as further discussed herein. Actuation of threaded screw 112 may transition proximal wings 108*a*, 108*b* and distal wings 110*a*, 110*b* between a closed position (as shown in FIGS. 1A-1B) and a deployed position (as shown in FIGS. 14A-14B). In some embodiments, actuation of threaded screw 112 may pivot proximal wings 108*a*, 108*b* and distal wings 110*a*, 110*b* between the closed position and the deployed position. Further actuation of threaded screw 112 may transition the implant 100 between a deployed position (as shown in FIGS. 14A-14B) and a clamped position (as shown in FIGS. 15A-15B, 29C). In some embodiments, implant 100 may comprise at least one threaded screw 112. Actuation of the at least one threaded screw 112 may pivot proximal wings 108*a*, 108*b* and distal wings 110*a*, 110*b* between the closed position and the deployed position. Further actuation of the at least one threaded screw 112 may transition the implant 100 between the deployed position and the clamped position. In some embodiments, implant 100 may comprise one or more threaded screws 112. Actuation of the one or more threaded screws 112 may pivot proximal wings 108*a*, 108*b* and distal wings 110*a*, 110*b* between the closed position and the deployed position. Further actuation of the one or more threaded screws 112 may transition the implant 100 between the deployed position and the clamped position.

Figure 11:
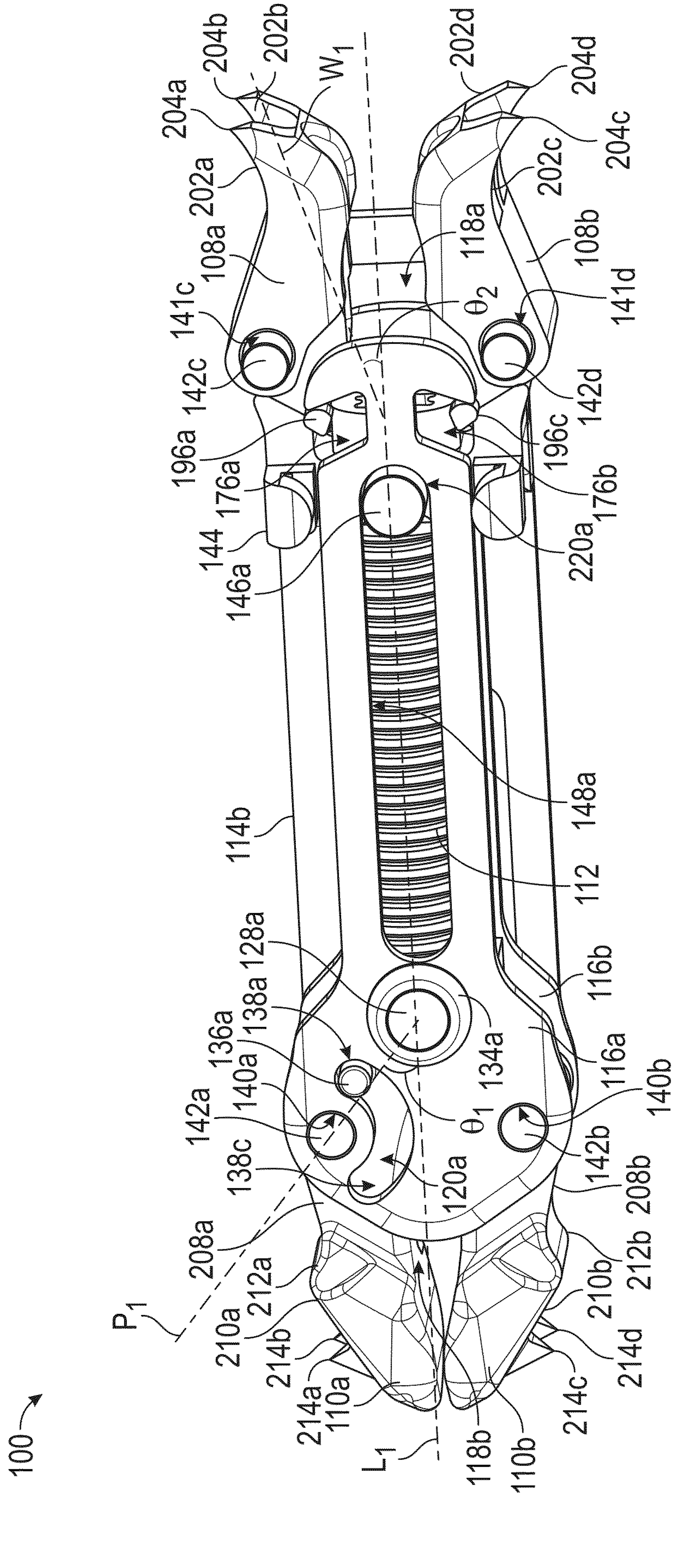
FIG. 11 illustrates a top perspective view of some embodiments of the implant in a closed configuration with a portion of an outer body removed.

A first outer body piece 114*a* and a second outer body piece 114*b* may form the outer body 102. Proximal wings 108*a*, 108*b* may pivotally couple to outer body 102 proximate the proximal end 104*a* of outer body 102. A first inner body piece 116*a* and a second inner body piece 116*b* may form the inner body 106. Inner body 106 may define a proximal end 118*a* (as shown in FIG. 11) and a distal end 118*b*, with distal wings 110*a*, 110*b* pivotally coupled to inner body 106 proximate the distal end 118*b* of inner body 106.

Inner body pieces 116*a*, 116*b* may define rotation slots 120*a*, 120*b*. Actuation of threaded screw 112 may move a portion of distal wings 110*a*, 110*b* along rotation slots 120*a*, 120*b* to pivot distal wings 110*a*, 110*b* between the closed position and the deployed position, as discussed further herein. As shown in FIG. 1B, threaded screw 112 may define a first end 122*a* comprising a screw head 124 and a second end 122_b_ proximate distal wings 110_a_, 110_b_. Screw head 124 may receive at least a portion of an insertion tool 400 for actuating threaded screw 112, as discussed further herein. In some embodiments, actuation of threaded screw 112 may advance threaded screw 112 toward distal wings 110_a_, 110_b_ to thereby pivot the distal wings 110_a_, 110_b_. For example, actuation of threaded screw 112 may distally translate threaded screw 112 toward distal wings 110_a_, 110_b_. Distal translation of threaded screw 112 may cause threaded screw 112 to contact distal wings 110_a_, 110_b_ and thereby drive distal wings 110_a_, 110_b_ to pivot about inner body 106.

As shown in FIG. 1A, outer body 102 of implant may be exterior to inner body 106, such that at least a portion of inner body 106 is positioned between outer body pieces 114_a_, 114_b_ and thereby within outer body 102. At least a portion of threaded screw 112 may be located between inner body pieces 116_a_, 116_b_ and thereby within inner body 106, such that threaded screw 112 is internal to implant 100 relative to the outer body 102. For example, outer body pieces 114_a_, 114_b_ may be exterior to threaded screw 112.

Implant 100 may further comprise a spacer 126, spacer pins 128_a_, 128_b_, outer body slots 130_a_, 130_b_, inner body through-holes 132_a_, 132_b_, caps 134_a_, 134_b_, wing pins 136_a_, 136_b_, inner body apertures 140_a_, 140_b_, 140_c_, 140_d_, pivot apertures 141_a_, 141_b_, 141_c_, 141_d_, pivot pins 142_a_, 142_b_, 142_c_, 142_d_, a proximal carrier 144, carrier pins 146_a_, 146_b_, carrier apertures 150_a_, 150_b_, recesses 152_a_, 152_b_, 152_c_, 152_d_, carrier projections 154_a_, 154_b_, 154_c_, 154_d_, walls 178_a_, 178_b_, a retaining member 156 defining a hole 180, carrier bore 158, openings 164_a_, 164_b_, depressions 166_a_, 166_b_, and threading 168, as described in further detail below. Proximal wings 108_a_, 108_b_ may comprise extensions 202_a_, 202_b_, 202_c_, 202_d_ and tips 204_a_, 204_b_, 204_c_, 204_d_, as described in further detail below. Distal wings 110_a_, 110_b_ may comprise arms 208_a_, 208_b_, clamps 210_a_, 210_b_, ridges 212_a_, 212_b_, and spikes 214_a_, 214_b_, 214_c_, 214_d_, as described in further detail below. Screw head 124 may comprise an edge 188, as described in further detail below.

Figure 2:
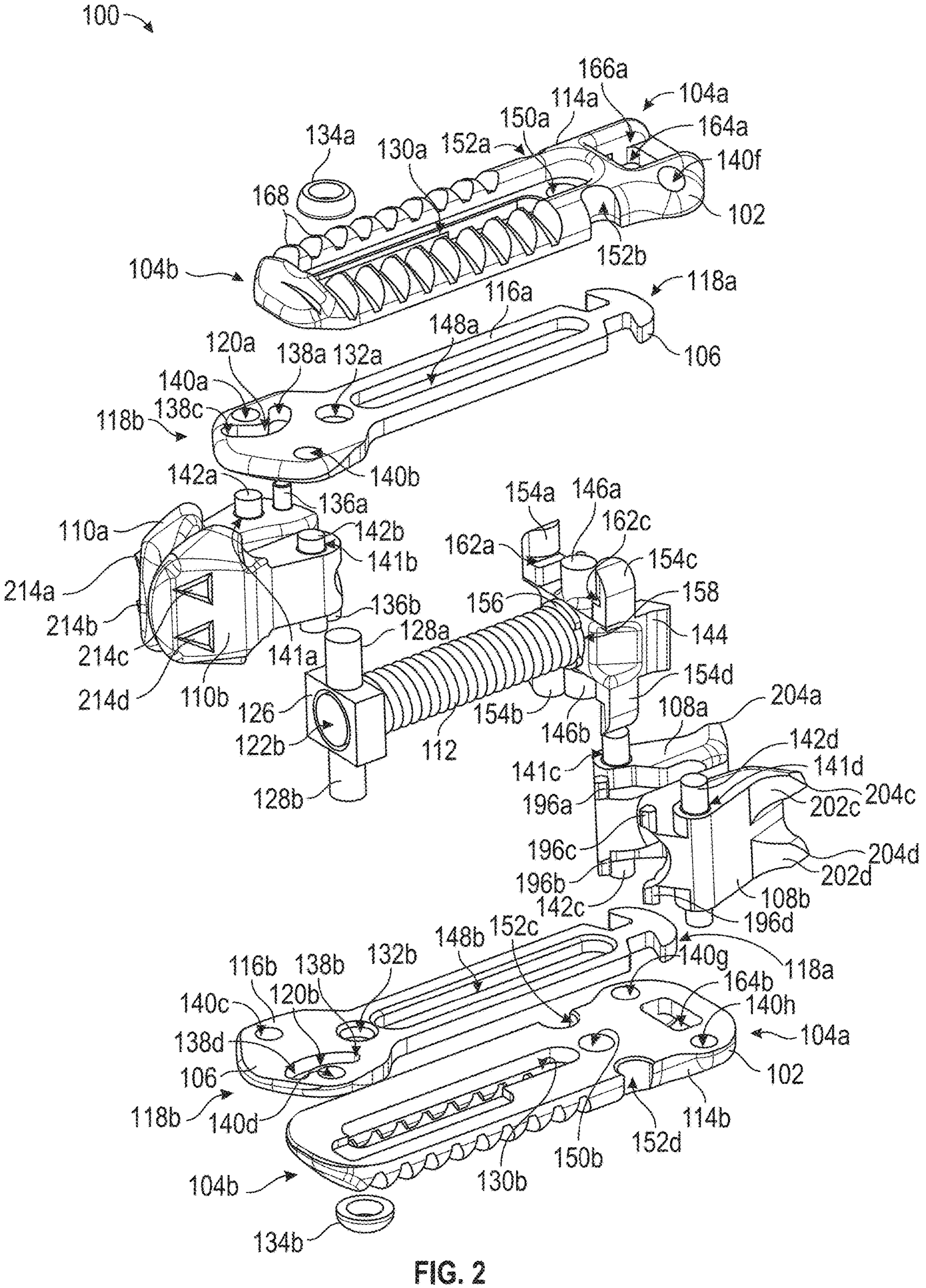
FIG. 2 illustrates an exploded view of some embodiments of the implant.

FIG. 2 illustrates an exploded view of some embodiments of implant 100.

Figure 7:
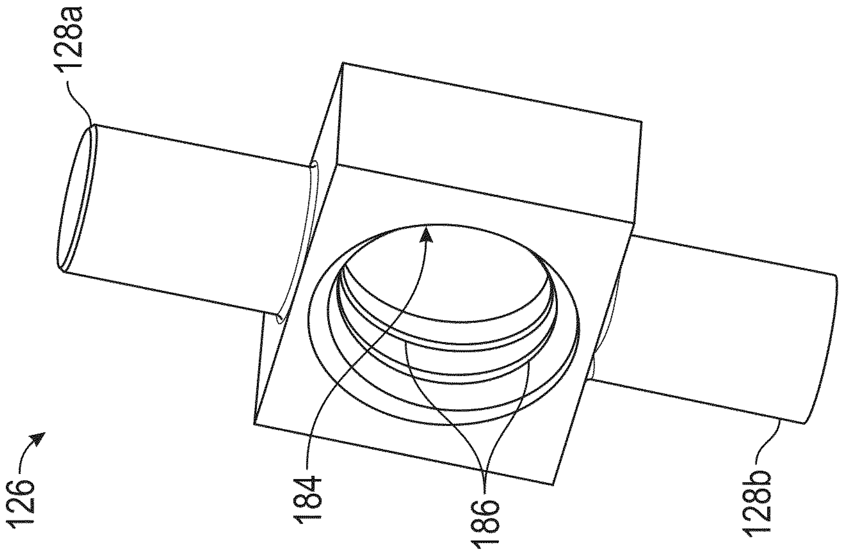
FIG. 7 illustrates a perspective view of some embodiments of a spacer of the implant.

Implant 100 may comprise a spacer 126 threadedly coupled to threaded screw 112. Spacer 126 may comprise spacer pins 128_a_, 128_b_ (as shown in FIG. 7) extending through outer body slots 130_a_, 130_b_ defined by outer body pieces 114_a_, 114_b_ and extending through inner body through-holes 132_a_, 132_b_ defined by inner body pieces 116_a_, 116_b_. Caps 134_a_, 134_b_ may receive ends of each spacer pin 128_a_, 128_b_ extending through outer body slots 130_a_, 130_b_ to an exterior of implant 100. Caps 134_a_, 134_b_ have a greater outer diameter relative to the width of outer body slots 130_a_, 130_b_, such that spacer pins 128_a_, 128_b_ are maintained in inner body through-holes 132_a_, 132_b_ and outer body slots 130_a_, 130_b_ when caps 134_a_, 134_b_ receive the ends of spacer pins 128_a_, 128_b_. The spacer pins 128_a_, 128_b_ being received by caps 134_a_, 134_b_ thereby couples the threaded screw 112 to the outer body 102 and the inner body 106. The spacer pins 128_a_, 128_b_ may slidably move within outer body slots 130_a_, 130_b_, as will be further discussed herein.

Each distal wing 110_a_, 110_b_ may comprise a wing pin 136_a_, 136_b_ extending therefrom. Rotation slots 120_a_, 120_b_ may receive wing pins 136_a_, 136_b_. In some embodiments, rotation slots 120_a_, 120_b_ may receive a portion of wing pins 136_a_, 136_b_. Wing pins 136_a_, 136_b_ may move between a first end 138_a_, 138_b_ and second end 138_c_, 138_d_ of rotation slots 120_a_, 120_b_ to pivot distal wings 110_a_, 110_b_ between the closed position and the deployed position. Distal wings 110_a_, 110_b_ may define pivot apertures 141_a_, 141_b_ for receiving pivot pins 142_a_, 142_b_. Pivot pins 142_a_, 142_b_ may insert into inner body apertures 140_a_, 140_b_, 140_c_, 140_d_ defined by inner body 106 to pivotally couple distal wings 110_a_, 110_b_ to inner body 106. In some embodiments, a first inner body piece 116_a_ may define inner body apertures 140_a_, 140_b_ and a second inner body piece 116_b_ may define inner body apertures 140_c_, 140_d_. Each pivot pin 142_a_, 142_b_ may extend from an inner body aperture 140_a_, 140_b_ of the first inner body piece 116_a_ into an inner body aperture 140_c_, 140_d_ of the second inner body piece 116_b_, to thereby pivotally couple the distal wings 110_a_, 110_b_ to the inner body 106. At least a portion of distal wings 110_a_, 110_b_ may be positioned between the inner body pieces 116_a_, 116_b_ when the implant 100 is in the closed position (as shown in FIG. 1A). The distal wings 110_a_, 110_b_ being partially housed within the inner body pieces 116_a_, 116_b_ decreases the overall profile of the implant 100 when the implant 100 is inserted in the closed position, as compared to the distal wings 110_a_, 110_b_ being deployed and positioned outside the inner body pieces 116_a_, 116_b_ during insertion. This decreases the amount of blood loss during insertion, decreases the disruption of soft tissue and/or bone during insertion, and decreases the size of the incision required to insert implant 100, thereby minimizing recovery time after the surgery and pain felt by the patient. Inner body apertures 140_a_, 140_b_, 140_c_, 140_d_ may be defined proximate the distal end 118_b_ of inner body 106, such that distal wings 110_a_, 110_b_ are pivotally coupled to inner body 106 proximate the distal end 118_b_.

Each proximal wing 108_a_, 108_b_ may define pivot apertures 141_c_, 141_d_ for receiving pivot pins 142_c_, 142_d_. Pivot pins 142_c_, 142_d_ received in proximal wings 108_a_, 108_b_ may insert into outer body apertures 140_e_, 140_f_, 140_g_, 140_h_ defined by outer body 102 to pivotally couple proximal wings 108_a_, 108_b_ to outer body 102. In some embodiments, a first outer body piece 114_a_ may define outer body apertures 140_e_, 140_f_ and a second outer body piece 114_b_ may define outer body apertures 140_g_, 140_h_. Each pivot pin 142_a_, 142_b_ received in proximal wings 108_a_, 108_b_ may extend from an outer body aperture 140_e_, 140_f_ of the first outer body piece 114_a_ into an outer body aperture 140_g_, 140_h_ of the second outer body piece 114_b_, to thereby pivotally couple the proximal wings 108_a_, 108_b_ to the outer body 102. At least a portion of proximal wings 108_a_, 108_b_ may be positioned between the outer body pieces 114_a_, 114_b_ when the implant 100 is in the closed position (as shown in FIG. 1A). The proximal wings 108_a_, 108_b_ being partially housed within the outer body pieces 114_a_, 114_b_ decreases the overall profile of the implant 100 when the implant 100 is inserted in the closed position, as compared to the proximal wings 108_a_, 108_b_ being deployed and positioned outside the outer body pieces 114_a_, 114_b_ during insertion. This decreases the amount of blood loss during insertion, decreases the disruption of soft tissue and/or bone during insertion, and decreases the size of the incision required to insert implant 100, thereby minimizing recovery time after the surgery and pain felt by the patient. Outer body apertures 140_e_, 140_f_, 140_g_, 140_h_ may be defined proximate the proximal end 104_a_ of outer body 102, such that proximal wings 108_a_, 108_b_ are pivotally coupled to outer body 102 proximate the proximal end 104_a_.

Implant 100 may comprise a proximal carrier 144 (also referred to as a translatable member). Proximal carrier 144 may comprise carrier pins 146_a_, 146_b_ extending therefrom. Translation slots 148_a_, 148_b_ defined by inner body pieces 116_a_, 116_b_ may receive carrier pins 146_a_, 146_b_, such that proximal carrier 144 slidably couples to inner body 106. For example, carrier pins 146*a*, 146*b* may slide along translation slots 148*a*, 148*b* during actuation of threaded screw 112. Carrier apertures 150*a*, 150*b* defined by outer body pieces 114*a*, 114*b* may receive carrier pins 146*a*, 146*b*, such that proximal carrier 144 couples to outer body 102. Proximal carrier 144 may couple to threaded screw 112 proximate the first end 122*a* of threaded screw 112 (as shown in FIG. 1B). In some embodiments, at least a portion of proximal carrier 144 may be positioned between outer body pieces 114*a*, 114*b*, thereby positioned within outer body 102.

Outer body 102 may comprise recesses 152*a*, 152*b*, 152*c*, 152*d* configured to receive carrier projections 154*a*, 154*b*, 154*c*, 154*d* comprised on proximal carrier 144. In some embodiments, first outer body piece 114*a* may comprise recesses 152*a*, 152*b* and second outer body piece 114*b* may comprise recesses 152*c*, 152*d*. Recesses 152*a*, 152*b* of first outer body piece 114*a* may receive carrier projections 154*a*, 154*c* and recesses 152*c*, 152*d* may receive carrier projections 154*b*, 154*d*. Recesses 152*a*, 152*b*, 152*c*, 152*d* may be configured to receive carrier projections 154*a*, 154*b*, 154*c*, 154*d* to provide additional support and stability to the connection of proximal carrier 144 and outer body 102. In some embodiments, recesses 152*a*, 152*b*, 152*c*, 152*d* receiving carrier projections 154*a*, 154*b*, 154*c*, 154*d* may provide an additional connection of proximal carrier 144 to outer body 102. In some embodiments, recesses 152*a*, 152*b*, 152*c*, 152*d* receiving carrier projections 154*a*, 154*b*, 154*c*, 154*d* may secure proximal carrier 144 to outer body 102, such that proximal carrier 144 may translate with outer body 102, as further discussed herein.

Figure 5:
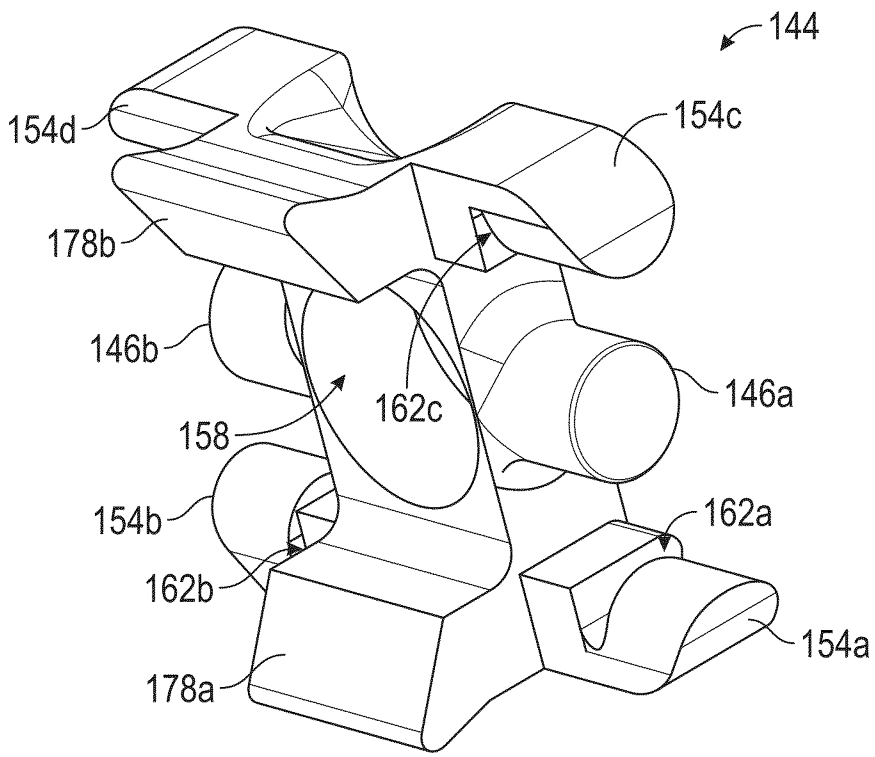
FIG. 5 illustrates a perspective view of some embodiments of a proximal carrier of the implant.

Implant 100 may comprise retaining member 156. Retaining member 156 may contact a side of proximal carrier 144. Proximal carrier 144 may comprise carrier bore 158 (as shown in FIG. 5) for receiving at least a portion of threaded screw 112. In some embodiments, retaining member 156 may contact a distal side of proximal carrier 144. Retaining member 156 may secure proximal carrier 144 to threaded screw 112, such that advancement of threaded screw 112 via actuation simultaneously advances proximal carrier 144. In some embodiments, carrier bore 158 of proximal carrier 144 may receive a portion of threaded screw 112 proximate the first end 122*a* of threaded screw 112 (as shown in FIG. 1B). Retaining member 156 may maintain proximal carrier 144 at a position proximate the first end 122*a* of threaded screw 112 when the threaded screw is actuated.

Implant 100 may further comprise carrier grooves 162*a*, 162*b*, 162*c*, 162*d*, as described further below. Proximal wings 108*a*, 108*b* may comprise protuberances 196*a*, 196*b*, 196*c*, 196*d*, as described further below.

Figure 3:
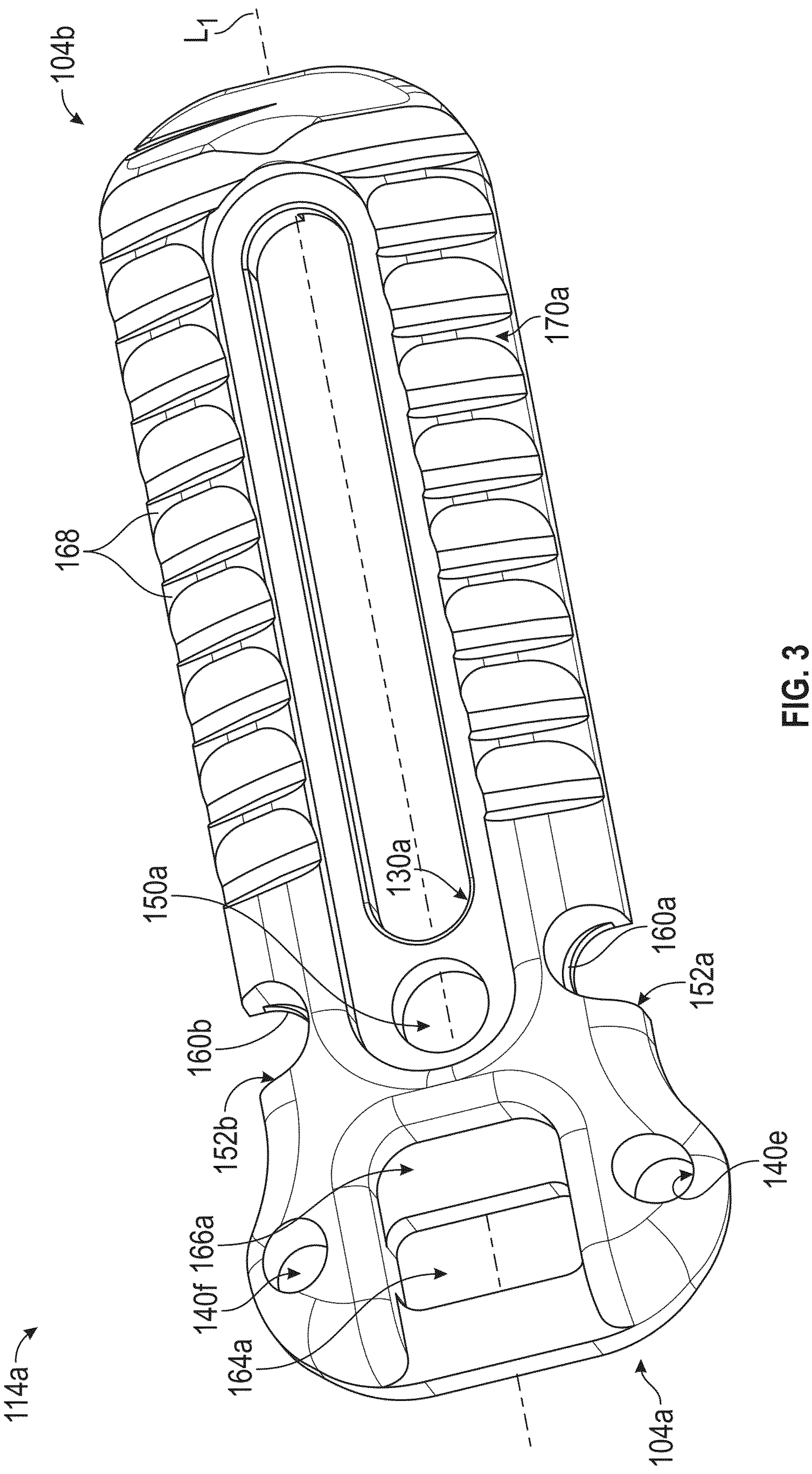
FIG. 3 illustrates a perspective view of some embodiments of an outer body piece of the implant.

FIG. 3 illustrates a perspective view of some embodiments of an outer body piece 114*a*, 114*b* of the implant 100. For example, FIG. 3 illustrates a perspective view of a first outer body piece 114*a* of implant 100. First outer body piece 114*a* may be substantially identical in shape and structure to second outer body piece 114*b*. Outer body pieces 114*a*, 114*b* forming outer body 102 may define outer body slots 130*a*, 130*b*, carrier apertures 150*a*, 150*b*, and outer body apertures 140*e*, 140*f*, 140*g*, 140*h*. For example and as shown in FIG. 3, a first outer body piece 114*a* may define outer body apertures 140*e*, 140*f* configured to receive pivot pins 142*c*, 142*d* of proximal wings 108*a*, 108*b*. First outer body piece 114*a* may define carrier aperture 150*a* configured to receive carrier pin 146*a*. First outer body piece 114*a* may define outer body slot 130*a*. Outer body slots 130*a*, 130*b* may extend along longitudinal axis $L_1$ between proximal end 104*a* and distal end 104*b* of outer body 102.

Outer body pieces 114*a*, 114*b* may comprise recesses 152*a*, 152*b*, 152*c*, 152*d*. For example and as shown in FIG. 3, first outer body piece 114*a* may comprise recesses 152*a*, 152*b* for receiving carrier projections 154*a*, 154*c* (As shown in FIG. 1A). Recesses 152*a*, 152*b*, 152*c*, 152*d* may be substantially circular. In some embodiments, recesses 152*a*, 152*b*, 152*c*, 152*d* may be shaped as semi-circles. In some embodiments, recesses 152*a*, 152*b*, 152*c*, 152*d* may be shaped substantially similar to a contour of carrier projections 154*a*, 154*b*, 154*c*, 154*d* to thereby receive carrier projections 154*a*, 154*b*, 154*c*, 154*d*. Recesses 152*a*, 152*b*, 152*c*, 152*d* may comprise segments 160*a*, 160*b*, 160*c*, 160*d*. Segments 160*a*, 160*b*, 160*c*, 160*d* may extend from a surface of recesses 152*a*, 152*b*, 152*c*, 152*d*. In some embodiments, segment 160*a*, 160*b*, 160*c*, 160*d* may be arcuately shaped. In some embodiments, segment 160*a*, 160*b*, 160*c*, 160*d* may be crescent moon shaped. Carrier grooves 162*a*, 162*b*, 162*c*, 162*d* (as shown in FIG. 2) defined by proximal carrier 144 may receive segments 160*a*, 160*b*, 160*c*, 160*d* to secure proximal carrier 144 to outer body 102 formed by outer body pieces 114*a*, 114*b*, as described further herein.

Outer body pieces 114*a*, 114*b* may define openings 164*a*, 164*b* within depressions 166*a*, 166*b*. For example, first outer body piece 114*a* may define opening 164*a* within depression 166*a*. In some embodiments, depressions 166*a*, 166*b* may define openings 164*a*, 164*b* proximate proximal ends of outer body pieces 114*a*, 114*b* such that openings 164*a*, 164*b* are defined proximate proximal end 104*a* of outer body 102 (as shown in FIG. 1A). In some embodiments, openings 164*a*, 164*b* may have a generally oblong shape. In some embodiments, openings 164*a*, 164*b* may have a generally rectangular, square, hexagonal shape, or any other shape. In some embodiments, depressions 166*a*, 166*b* may have a generally oblong shape. In some embodiments, depressions 166*a*, 166*b* may be generally rectangular, square, hexagonal, or any other shape. Outer body pieces 114*a*, 114*b* may comprise threading 168 along at least a portion of exterior surfaces 170*a*, 170*b* of outer body pieces 114*a*, 114*b*. In some embodiments, outer body pieces 114*a*, 114*b* may comprise threading 168 along the entirety of exterior surfaces 170*a*, 170*b*. Threading 168 may engage muscle, soft tissue, and/or bone at the treatment site to provide fixation of implant 100 at the treatment site. Threading 168 may engage muscle, soft tissue, and/or bone during insertion of the implant 100 up to the treatment site to aid implant insertion and make insertion easier. Threading 168 may engage muscle, soft tissue, and/or bone at the treatment site to stabilize the implant 100 at the treatment site. Exterior surface 170*a*, 170*b* of each outer body piece 114*a*, 114*b* may define depressions 166*a*, 166*b*.

Figure 4:
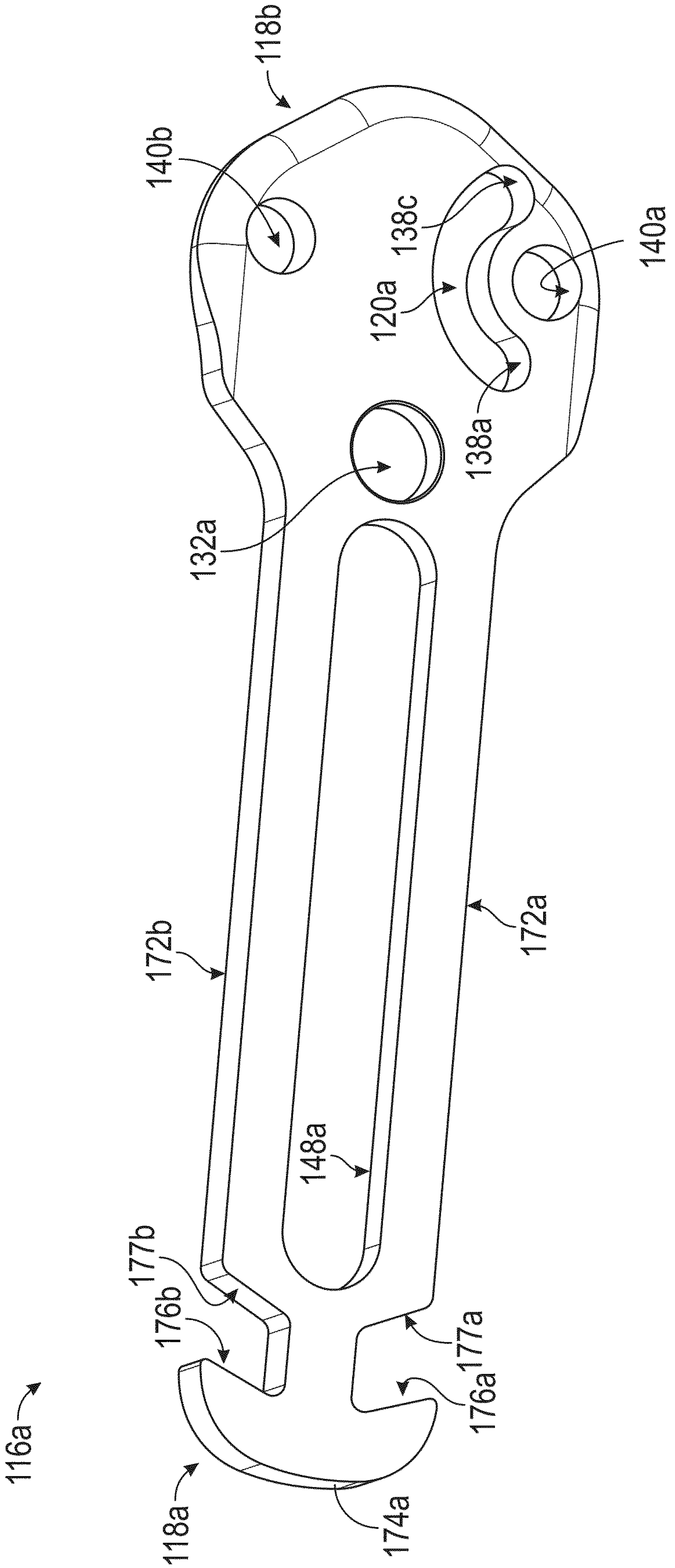
FIG. 4 illustrates a perspective view of some embodiments of an inner body piece of the implant.

FIG. 4 illustrates a perspective view of some embodiments of an inner body piece 116*a*, 116*b* of the implant 100. For example, FIG. 4 illustrates a perspective view of a first inner body piece 116*a* of implant 100. First inner body piece 116*a* may be substantially identical in shape and structure to second inner body piece 116*b*. Inner body pieces 116*a*, 116*b* may define translation slots 148*a*, 148*b*, rotation slots 120*a*, 120*b*, inner body apertures 140*a*, 140*b*, 140*c*, 140*d*, and inner body through-holes 132*a*, 132*b*. For example and as shown in FIG. 4, a first inner body piece 116*a* may define inner body apertures 140*a*, 140*b* configured to receive pivot pins 142*a*, 142*b* of distal wings 110*a*, 110*b*. First inner body piece 116*a* may define inner body through-hole 132*a* configured to receive spacer pin 128*a*. First inner body piece 116*a* may define rotation slot 120*a* having a first end 138*a* and a second end 138*c* and configured to receive wing pin

136*a* of distal wing 110*a*. Translation slots 148*a*, 148*b* may receive carrier pins 146*a*, 146*b* such that carrier pins 146*a*, 146*b* slide within translation slot 148*a*, 148*b*. Carrier pins 146*a*, 146*b* may slide along translation slots 148*a*, 148*b* during actuation of threaded screw 112. Translation slots 148*a*, 148*b* may longitudinally extend between proximal end 118*a* and distal end 118*b* of inner body 106.

In some embodiments, translation slots 148*a*, 148*b* may be generally straight and extend longitudinally, such that translation slots 148*a*, 148*b* align with threaded screw 112 (as shown in FIG. 11). Rotation slots 120*a*, 120*b* may be generally arcuately shaped or curved. Rotation slots 120*a*, 120*b* have any shape or profile that transforms linear motion of wing pins 136*a*, 136*b* received within rotation slots 120*a*, 120*b* into rotational motion to thereby pivot distal wings 110*a*, 110*b*. In some embodiments, inner body pieces 116*a*, 116*b* may define rotation slots 120*a*, 120*b* proximate distal ends of inner body pieces 116*a*, 116*b*, such that rotation slots 120*a*, 120*b* are defined proximate distal end 118*b* of inner body 106.

Inner body pieces 116*a*, 116*b* may comprise translation surfaces 172*a*, 172*b*, 172*c*, 172*d*. Translation surfaces 172*a*, 172*b*, 172*c*, 172*d* may be substantially flat and longitudinally extend along at least a portion of inner body pieces 116*a*, 116*b* between distal end 118*b* and proximal end 118*a* of inner body 106. For example, first inner body piece 116*a* may have translation surfaces 172*a*, 172*b*. Inner body pieces 116*a*, 116*b* may comprise ramps 174*a*, 174*b*. For example, first inner body piece 116*a* may comprise ramp 174*a*. At least a portion of each proximal wing 108*a*, 108*b* contacts a ramp 174*a*, 174*b* to thereby pivot proximal wings 108*a*, 108*b* from the closed position to the deployed position. Ramps 174*a*, 174*b* may be located proximate proximal ends of inner body pieces 116*a*, 116*b*, such that ramps 174*a*, 174*b* are located proximate proximal end 118*a* of inner body 106. Ramps 174*a*, 174*b* may be sloped. In some embodiments, ramps 174*a*, 174*b* may be arcuately shaped. A proximal edge of inner body pieces 116*a*, 116*b* may define ramps 174*a*, 174*b* such that at least a portion of proximal wings 108*a*, 108*b* contact a proximal edge of inner body pieces 116*a*, 116*b* to pivot proximal wings 108*a*, 108*b* from the closed position to the deployed position.

Figure 13A:
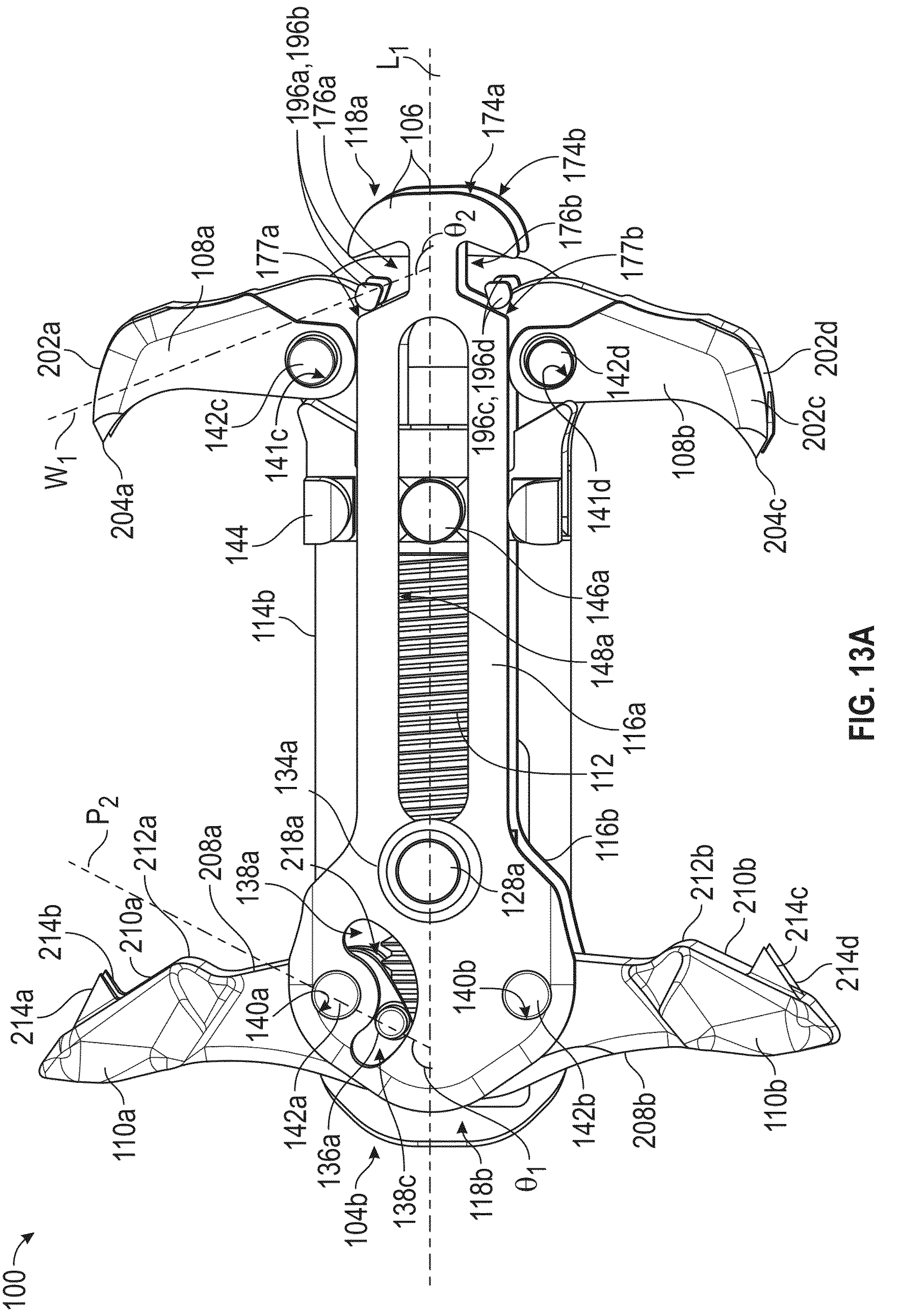
FIG. 13A illustrates a top perspective view of some embodiments of the implant in an intermediate position with a portion of an outer body removed.

Inner body pieces 116*a*, 116*b* may define inner body grooves 176*a*, 176*b*, 176*c*, 176*d* configured to interact with proximal wing protuberances 196*a*, 196*b*, 196*c*, 196*d*, as further discussed herein. Interfaces 177*a*, 177*b*, 177*c*, 177*d* may at least partially define inner body grooves 176*a*, 176*b*, 176*c*, 176*d*. Protuberances 196*a*, 196*b*, 196*c*, 196*d* may contact and move along interfaces 177*a*, 177*b*, 177*c*, 177*d* to pivot proximal wings 108*a*, 108*b* from the closed configuration to the deployed configuration (as shown in FIG. 13A). For example and as shown in FIG. 4, first inner body piece 116*a* may define inner body grooves 176*a*, 176*b*. In some embodiments, inner body grooves 176*a*, 176*b*, 176*c*, 176*d* and ramps 174*a*, 174*b* may together form a T shape. Inner body grooves 176*a*, 176*b*, 176*c*, 176*d* may be defined proximate proximal ends of inner body pieces 116*a*, 116*b*, such that inner body grooves 176*a*, 176*b*, 176*c*, 176*d* are defined proximate proximal end 118*a* of inner body 106. Inner body grooves 176*a*, 176*b*, 176*c*, 176*d* may have a generally square profile, rectangular profile, or any other shape. Interfaces 177*a*, 177*b*, 177*c*, 177*d* may be inclined such that movement of protuberances 196*a*, 196*b*, 196*c*, 196*d* along interfaces 177*a*, 177*b*, 177*c*, 177*d* causes proximal wings 108*a*, 108*b* to pivot.

FIG. 5 illustrates a perspective view of some embodiments of a proximal carrier 144 (also referred to as a translatable member) of the implant 100. Proximal carrier 144 may comprise carrier pins 146*a*, 146*b* (also referred to as translatable member pins) extending therefrom. Translation slots 148*a*, 148*b* of inner body pieces 116*a*, 116*b* may be configured to receive carrier pins 146*a*, 146*b* to slidably couple proximal carrier 144 to inner body 106 (as shown in FIG. 13A). Carrier apertures 150*a*, 150*b* (also referred to as translatable member apertures) defined by outer body pieces 114*a*, 114*b* may be configured to receive carrier pins 146*a*, 146*b* to couple proximal carrier 144 to outer body 102 (as shown in FIG. 1A). Carrier pins 146*a*, 146*b* being received in carrier apertures 150*a*, 150*b* defined by outer body pieces 114*a*, 114*b* may cause outer body 102 to translate with proximal carrier 144 as carrier pins 146*a*, 146*b* slide along translation slots 148*a*, 148*b* of inner body 106. Proximal carrier 144 may define carrier bore 158 (also referred to as translatable member bore) configured to receive at least a portion of threaded screw 112 to thereby couple proximal carrier 144 to threaded screw 112. In some embodiments, the coupling of proximal carrier 144 to threaded screw 112 causes actuation of threaded screw 112 to translate proximal carrier 144.

Proximal carrier 144 may comprise carrier projections 154*a*, 154*b*, 154*c*, 154*d* (also referred to as translatable member projections) extending therefrom. In some embodiments, carrier projections 154*a*, 154*b*, 154*c*, 154*d* may extend from corners of a generally rectangular shape of proximal carrier 144, as shown in FIG. 5. In some embodiments, proximal carrier may have a generally circular shape, square shape, or any other shape. Recesses 152*a*, 152*b*, 152*c*, 152*d* comprised in outer body 102 may receive at least a portion of each carrier projection 154*a*, 154*b*, 154*c*, 154*d*. Each recess 152*a*, 152*b*, 152*c*, 152*d* receiving at least a portion of each carrier projection 154*a*, 154*b*, 154*c*, 154*d* may cause proximal carrier 144 to translate simultaneously with outer body 102 as threaded screw 112 is actuated.

In some embodiments, carrier projections 154*a*, 154*b*, 154*c*, 154*d* may each define a carrier groove 162*a*, 162*b*, 162*c*, 162*d* (also referred to as a translatable member groove). Segments 160*a*, 160*b*, 160*c*, 160*d* of recesses 152*a*, 152*b*, 152*c*, 152*d* of outer body pieces 114*a*, 144*b* may fit within carrier grooves 162*a*, 162*b*, 162*c*, 162*d* to couple proximal carrier 144 to outer body pieces 114*a*, 114*b*, thereby securing proximal carrier 144 to outer body 102. In some embodiments, segments 160*a*, 160*b*, 160*c*, 160*d* and carrier grooves 162*a*, 162*b*, 162*c*, 162*d* may form a snap fit between recesses 152*a*, 152*b*, 152*c*, 152*d* and carrier projections 154*a*, 154*b*, 154*c*, 154*d*, to thereby secure proximal carrier 144 to outer body 102. In some embodiments, carrier grooves 162*a*, 162*b*, 162*c*, 162*d* may receive segments 160*a*, 160*b*, 160*c*, 160*d*, so as to maintain carrier projections 154*a*, 154*b*, 154*c*, 154*d* within recesses 152*a*, 152*b*, 152*c*, 152*d*.

In some embodiments, proximal carrier 144 may comprise walls 178*a*, 178*b*. At least a portion of proximal wings 108*a*, 108*b* may contact walls 178*a*, 178*b* when implant 100 is in the closed position (as shown in FIG. 1B). In some embodiments, walls 178*a*, 178*b* may be sloped. For example, as shown in FIG. 5, walls 178*a*, 178*b* may have a sloped surface. Walls 178*a*, 178*b* may extend from a proximal side of proximal carrier 144. Carrier pins 146*a*, 146*b* may extend from proximal carrier 144 between carrier projections 154*a*, 154*b*, 154*c*, 154*d*, as shown in FIG. 5. Proximal carrier 144 may define carrier bore 158 between walls 178*a*, 178*b*. In some embodiments, proximal carrier 144 may define carrier bore 158 extending through the center of proximal carrier 144.

Figure 6:
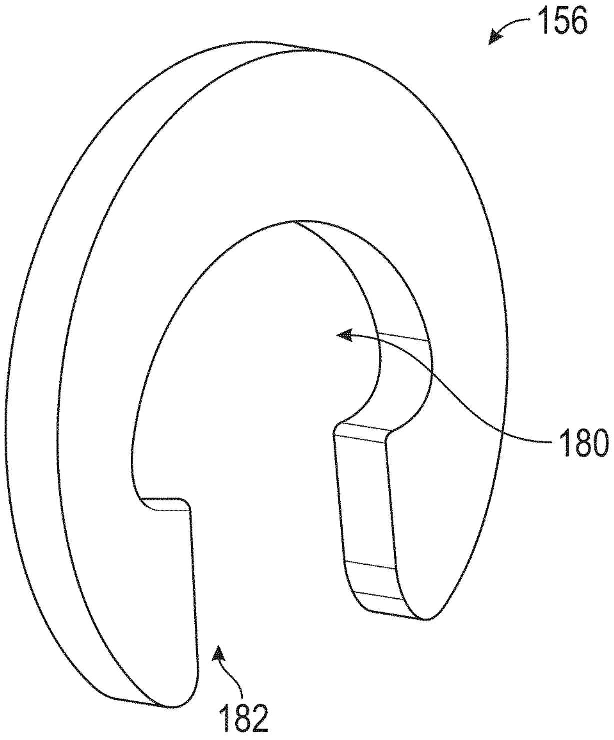
FIG. 6 illustrates a perspective view of some embodiments of a retaining member of the implant.

FIG. 6 illustrates a perspective view of some embodiments of a retaining member 156 of the implant 100. Retaining member 156 may have a generally circular outer profile. For example, in some embodiments, retaining member 156 may be shaped as a ring. In some embodiments, retaining member 156 may form a retaining ring or a snap ring known to a person of skill in the art. In some embodiments, retaining member 156 may have a C shape, as shown in FIG. 6. Retaining member 156 may define a hole 180 configured to receive at least a portion of threaded screw 112 (as shown in FIG. 1B). Retaining member 156 may comprise a gap 182 configured to provide an opening for placing retaining member 156 onto threaded screw 112.

Figure 12A:
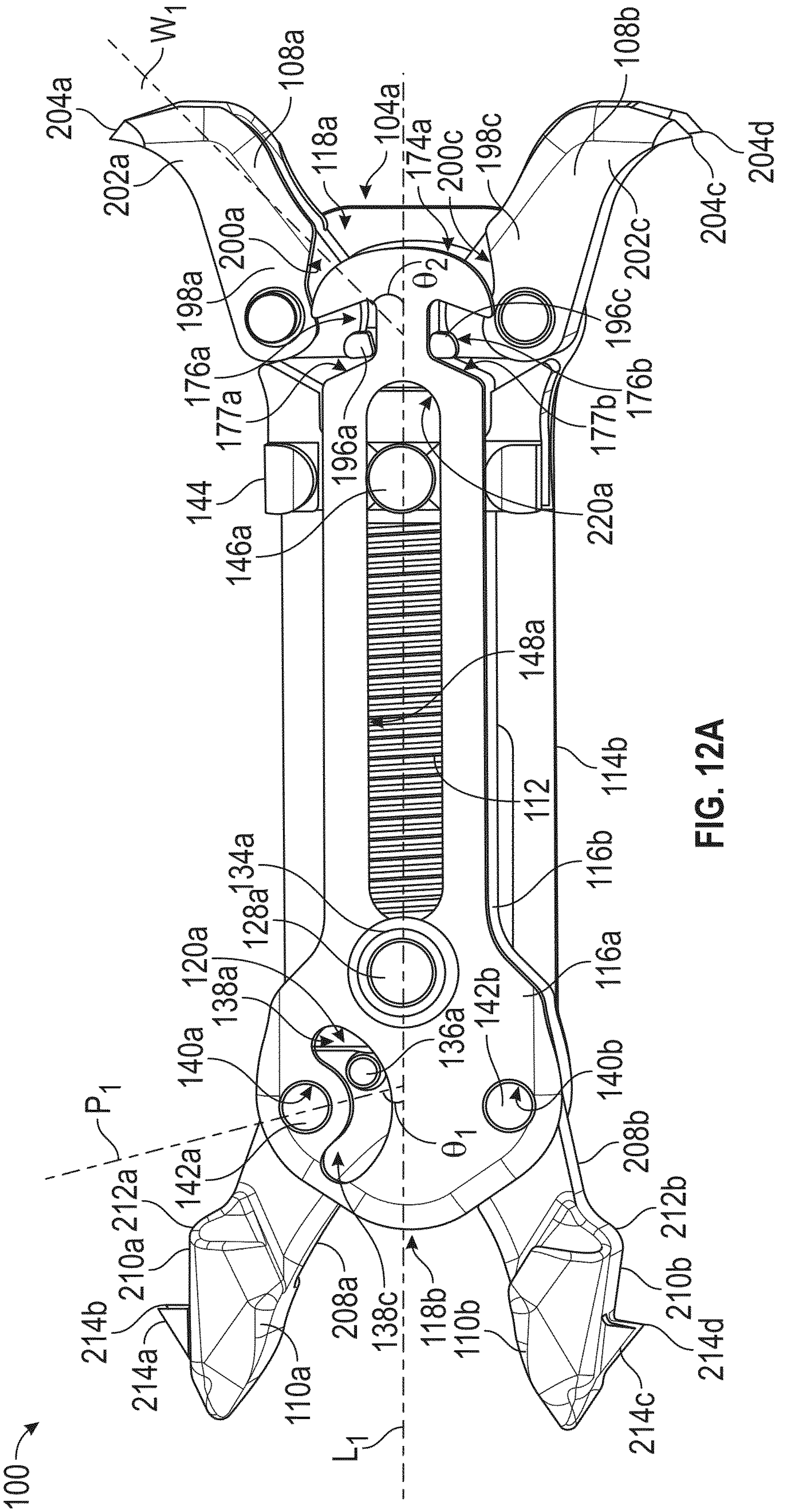
FIG. 12A illustrates a top perspective view of some embodiments of the implant in an intermediate position with a portion of an outer body removed.
Figure 12B:
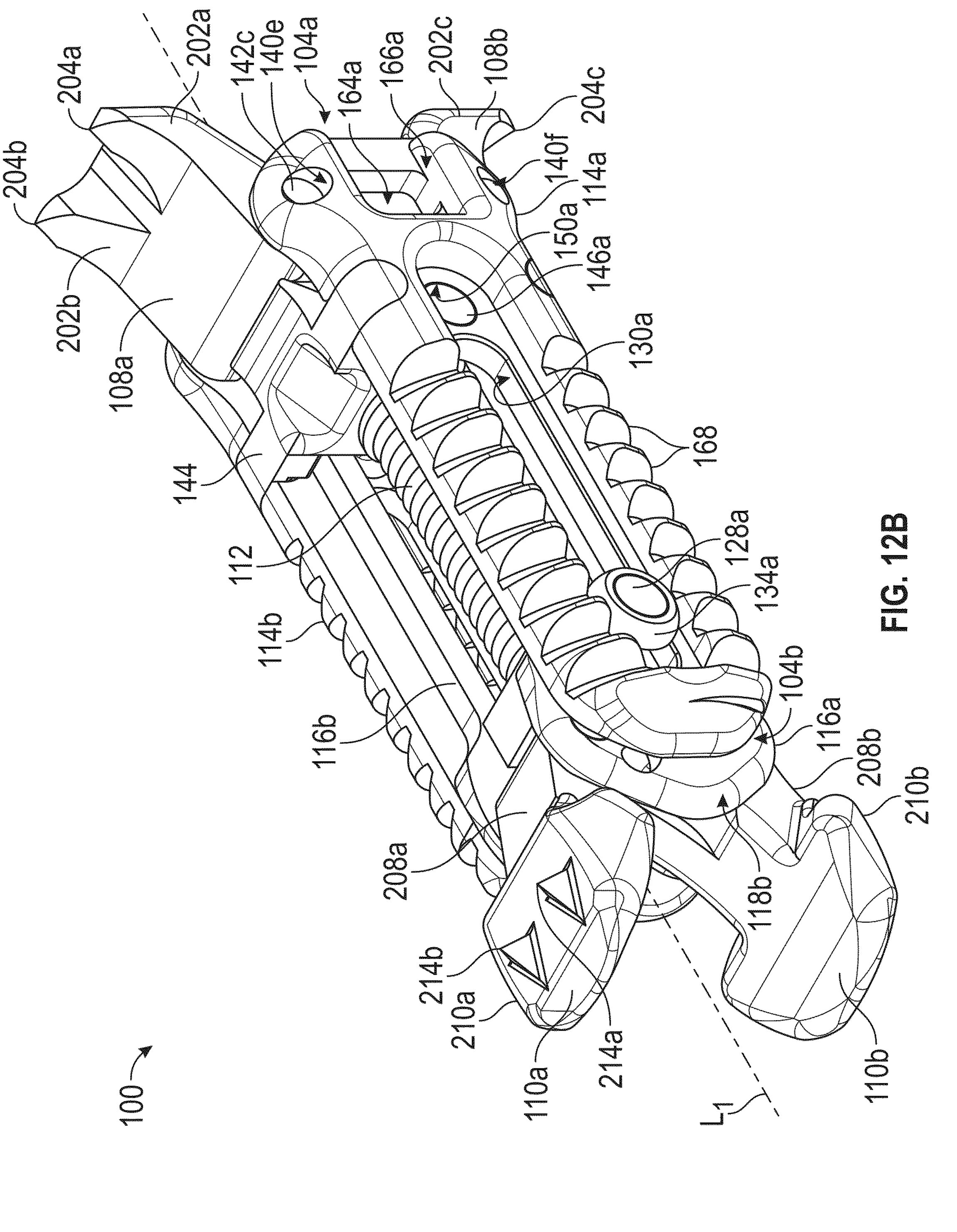
FIG. 12B illustrates a perspective view of some embodiments of the implant in an intermediate position.

FIG. 7 illustrates a perspective view of some embodiments of a spacer 126 of the implant 100. Spacer 126 may comprise spacer pins 128*a*, 128*b* extending therefrom. Outer body slots 130*a*, 130*b* and inner body through-holes 132*a*, 132*b* may receive spacer pins 128*a*, 128*b* to couple spacer 126 to inner body 106 and outer body 102. In some embodiments, ends of spacer pins 128*a*, 128*b* may receive caps 134*a*, 134*b* to secure spacer pins 128*a*, 128*b* within outer body slots 130*a*, 130*b* and inner body through-holes 132*a*, 132*b*, such that spacer 126 is coupled to outer body 102 and secured to inner body 106 (as shown in FIG. 12B). Spacer pins 128*a*, 128*b* being received in outer body slots 130*a*, 130*b* may allow outer body 102 to translate relative to spacer 126 during actuation of threaded screw 112, such that the outer body 102 moves while spacer 126 maintains a position and stays in place. Spacer 126 may define a spacer bore 184 extending through the center of spacer 126. In some embodiments, spacer 126 may comprise threads 186 on at least a portion of spacer 126. For example and as shown in FIG. 7, spacer 126 may comprise threads 186 along a portion of spacer 126 defining spacer bore 184. Threads 186 of spacer 126 may threadedly couple spacer 126 to threaded screw 112. Threads 186 may allow threaded screw 112 to move within spacer 126 during actuation of threaded screw 112. Spacer pins 128*a*, 128*b* may extend from sides of spacer 126. Spacer 126 may be generally square shaped, rectangular shaped, circular, or any other shape.

Figure 8A:
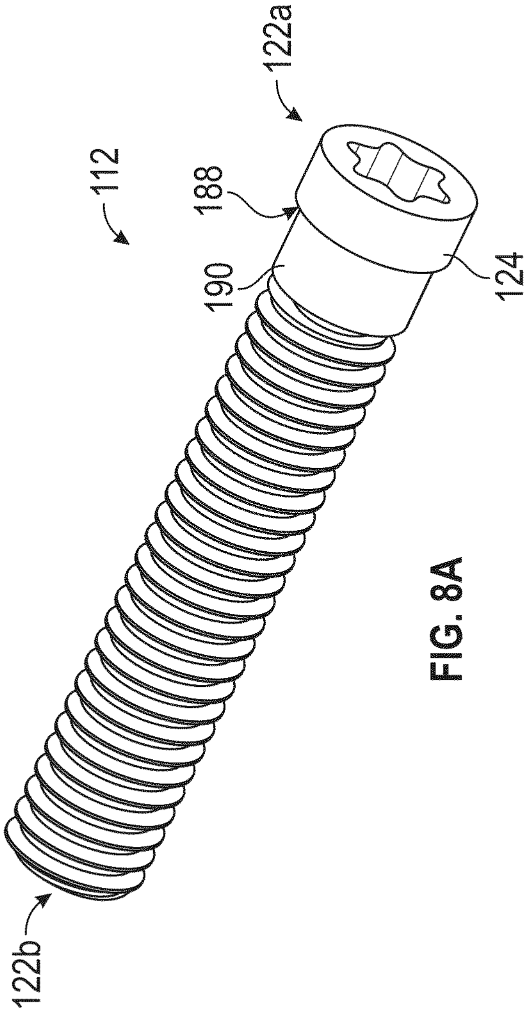
FIG. 8A illustrates a perspective view of some embodiments of a threaded screw of the implant.
Figure 8B:
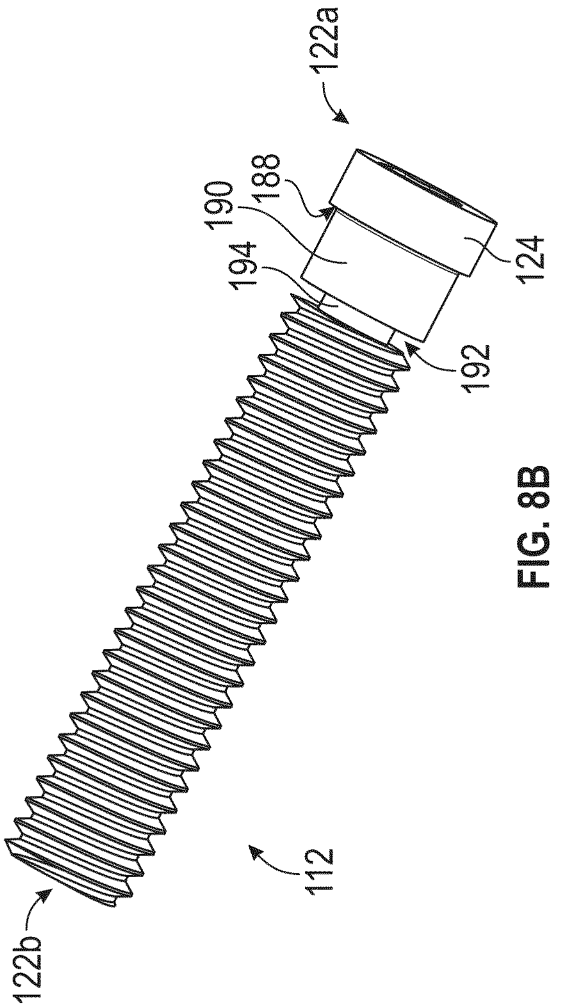
FIG. 8B illustrates a perspective view of some embodiments of a threaded screw of the implant.

FIG. 8A illustrates a perspective view of some embodiments of a threaded screw 112 of the implant 100. FIG. 8B illustrates a perspective view of some embodiments of threaded screw 112 of implant 100. Accordingly, FIGS. 8A-8B are best viewed together. As shown in FIGS. 8A-8B, threaded screw 112 may comprise threads on at least a portion thereof. Threaded screw 112 may have a first end 122*a* comprising a screw head 124 and a second end 122*b*. In some embodiments, second end 122*b* of threaded screw 112 may be proximate distal wings 110*a*, 110*b* (as shown in FIG. 1B) of implant 100 when implant 100 is in the closed configuration. Screw head 124 may comprise an edge 188 configured to contact proximal carrier 144 (as shown in FIG. 1B). In some embodiments, edge 188 may contact at least a portion of proximal carrier 144. As threaded screw 112 is actuated, edge 188 presses against proximal carrier 144 to advance proximal carrier 144 simultaneously with threaded screw 112. In some embodiments, actuation of threaded screw causes edge 188 to press on proximal carrier 144 to thereby translate proximal carrier 144 simultaneously with threaded screw 112. Screw head 124 may comprise a smooth portion 190. Carrier bore 158 may receive smooth portion 190 of screw head 124 to couple proximal carrier 144 to threaded screw 112. Smooth portion may be located proximate edge 188.

In some embodiments, threaded screw 112 may define a slit 192 extending around the circumference of threaded screw 112. Slit 192 may be defined proximate first end 122*a* between smooth portion 190 and the threading of threaded screw 112, as shown in FIG. 8B. Slit 192 may be configured to receive retaining member 156 to thereby secure retaining member 156 between smooth portion 190 and the threading of threaded screw 112. Threaded screw 112 may comprise a retaining portion 194 defining at least part of slit 192. Hole 180 of retaining member 156 may attach to retaining portion 194 to secure retaining member 156 within slit 192, thereby securing retaining member 156 to threaded screw 112.

In some embodiments, retaining member 156 may maintain the position of proximal carrier 144 on threaded screw 112. Retaining member 156 may extend outward from slit 192 when received in slit 192. For example, the outer diameter of retaining member 156 may be greater than the outer diameter of smooth portion 190 and greater than the outer diameter of the threading, such that retaining member 156 extends outward. The portion of retaining member 156 extending outward from slit 192 may contact proximal carrier 144, thereby maintaining the position of proximal carrier 144. For example, retaining member 156 may extend outward from slit 192 such that a portion of retaining member 156 contacts proximal carrier 144 when carrier bore 158 receives smooth portion 190. Retaining member 156 thereby maintains proximal carrier 144 at screw head 124 of threaded screw 112. For example, retaining member 156 may retain proximal carrier 144 at screw head 124 during actuation of threaded screw 112. As edge 188 presses on proximal carrier 144 during actuation of threaded screw 112, proximal carrier 144 may translate simultaneously with threaded screw 112.

Second end 122*b* of threaded screw 112 may be pointed or flat. For example and as shown in FIGS. 8A-8B, second end 122*b* of threaded screw may be flat. Second end 122*b* may be proximate distal wings 110*a*, 110*b* when implant 100 is in a closed position. Actuation of threaded screw 112 may translate second end 122*b* toward distal wings 110*a*, 110*b* such that a portion of threaded screw 112 contacts at least a portion of each distal wing 110*a*, 110*b*. In some embodiments, actuation of threaded screw 112 may distally translate second end 122*b* of threaded screw 112 to contact distal wings 110*a*, 110*b*. When second end 122*b* of threaded screw 112 contacts distal wings 110*a*, 110*b*, distal wings may start to pivot from the closed position to the deployed position, as further discussed herein. Further actuation of threaded screw 112 continues to translate threaded screw 112 toward distal wings 110*a*, 110*b* to pivot distal wings 110*a*, 110*b* from the closed position to the deployed position, as further discussed herein.

Figure 9A:
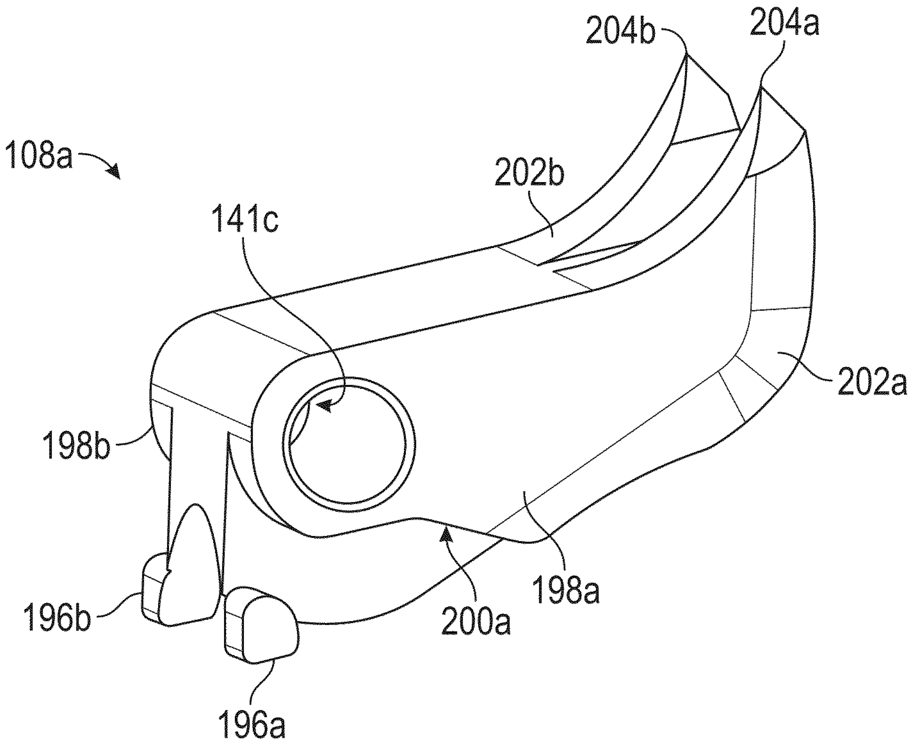
FIG. 9A illustrates a perspective view of some embodiments of a proximal wing of an implant.
Figure 9B:
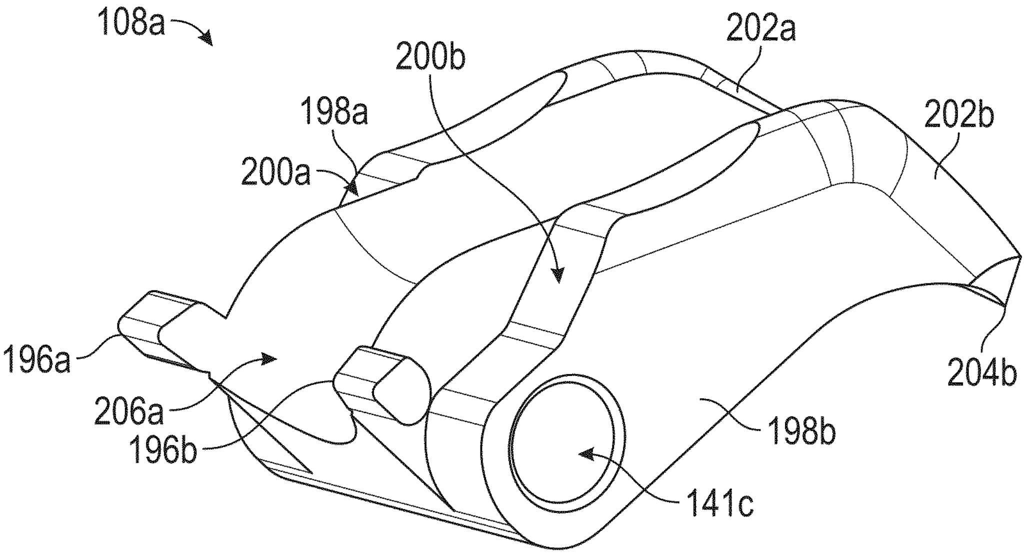
FIG. 9B illustrates a perspective view of some embodiments of a proximal wing of the implant.

FIG. 9A illustrates a perspective view of some embodiments of a proximal wing 108*a*, 108*b* of the implant 100. FIG. 9B illustrates a perspective view of some embodiments of the proximal wing 108*a*, 108*b* of implant 100. Accordingly, FIGS. 9A-9B are best viewed together. Implant 100 may comprise at least one proximal wing 108*a*, 108*b*. In some embodiments, implant 100 may comprise a first proximal wing 108*a* and a second proximal wing 108*b*. Proximal wings 108*a*, 108*b* of implant 100 may be substantially identical in structure. Proximal wings 108*a*, 108*b* may define pivot apertures 141*c*, 141*d* configured to receive pivot pins 142*c*, 142*d*. For example and as shown in FIGS. 9A-9B, first proximal wing 108*a* may define pivot aperture 141*c* configured to receive pivot pin 142*c*. Pivot apertures 141*c*, 141*d* may extend through proximal wings 108*a*, 108*b*. At least a portion of pivot pins 142*c*, 142*d* may be received in outer body apertures 140*e*, 140*f*, 140*g*, 140*h* of outer body pieces 114*a*, 114*b* to thereby pivotally couple proximal wings 108*a*, 108*b* to implant 100 (as shown in FIG. 1A). Outer body apertures 140*e*, 140*f*, 140*g*, 140*h* receiving a portion of each pivot pin 142*c*, 142*d* may pivotally couple proximal wings 108*a*, 108*b* to outer body 102.

In some embodiments, proximal wings 108*a*, 108*b* may each comprise protuberances 196*a*, 196*b*, 196*c*, 196*d*. For example, a first proximal wing 108*a* may comprise protuberances 196*a*, 196*b*, as shown in FIG. 9A. Protuberances 196*a*, 196*b*, 196*c*, 196*d* may interact with inner body grooves 176*a*, 176*b*, 176*c*, 176*d* of inner body pieces 116*a*, 116*b* to facilitate transitioning proximal wings 108*a*, 108*b* between the closed position and deployed position. Actuation of threaded screw 112 may cause protuberances 196*a*, 196*b*, 196*c*, 196*d* to move along at least a portion of each inner body groove 176*a*, 176*b*, 176*c*, 176*d*. For example, actuation of threaded screw 112 may cause protuberances 196*a*, 196*b*, 196*c*, 196*d* to move along interfaces 177*a*, 177*b*, 177*c*, 177*d* of inner body grooves 176*a*, 176*b*, 176*c*, 176*d* to thereby pivot proximal wings 108*a*, 108*b* between the closed position and the deployed position. Protuberances 196*a*, 196*b*, 196*c*, 196*d* may be configured to slide along translation surfaces 172*a*, 172*b*, 172*c*, 172*d* of inner body pieces 116*a*, 116*b* to transition proximal wings 108*a*, 108*b* between the deployed position and the clamped position (also referred to as a clamped configuration), as further discussed herein. Protuberances 196*a*, 196*b*, 196*c*, 196*d* may be rectangularly shaped, square shaped, circular shaped, or any other shape.

In some embodiments, proximal wings 108*a*, 108*b* may comprise juts 198*a*, 198*b*, 198*c*, 198*d* having a proximal surface 200*a*, 200*b*, 200*c*, 200*d* and extending from a side of proximal wings 108*a*, 108*b*. For example, first proximal wing 108*a* may comprise juts 198*a*, 198*b* as shown in FIG. 9A. Proximal surfaces 200*a*, 200*b*, 200*c*, 200*d* of juts 198*a*, 198*b*, 198*c*, 198*d* may contact ramps 174*a*, 174*b* to thereby pivot proximal wings 108*a*, 108*b* from the closed configuration to the deployed configuration. As an example, proximal surface 200*a* of first proximal wing 108*a* may contact at least a portion of ramp 174*a* and proximal surface 200*c* of second proximal wing 108*b* may contact a different portion of ramp 174*a* to thereby pivot proximal wings 108*a*, 108*b* (as shown in FIG. 12A). In some embodiments, proximal surfaces 200*a*, 200*b*, 200*c*, 200*d* may move along ramps 174*a*, 174*b* during actuation of threaded screw 112 to thereby pivot proximal wings 108*a*, 108*b*. Proximal surfaces 200*a*, 200*b*, 200*c*, 200*d* may be at least partially curved or arcuately shaped. In some embodiments, proximal surface 200*a*, 200*b*, 200*c*, 200*d* may have a shape corresponding to the shape of ramps 174*a*, 174*b* to provide a smooth transition of proximal wings 108*a*, 108*b* from the closed configuration to the deployed configuration.

In some embodiments, proximal wings 108*a*, 108*b* may comprise extensions 202*a*, 202*b*, 202*c*, 202*d*. Extensions 202*a*, 202*b*, 202*c*, 202*d* may extend from juts 198*a*, 198*b*, 198*c*, 198*d*. For example and as shown in FIGS. 9A-9B, first proximal wing 108*a* may comprise extensions 202*a*, 202*b* extending from juts 198*a*, 198*b*. At least a portion of extensions 202*a*, 202*b*, 202*c*, 202*d* may be configured to engage with bone or tissue at and/or near the treatment site when proximal wings 108*a*, 108*b* are in the clamped position. In some embodiments, extensions 202*a*, 202*b*, 202*c*, 202*d* may form tips 204*a*, 204*b*, 204*c*, 204*d*. Tips 204*a*, 204*b*, 204*c*, 204*d* may engage bone or tissue at and/or near the treatment site when proximal wings 108*a*, 108*b* are in the clamped position. In some embodiments, Tips 204*a*, 204*b*, 204*c*, 204*d* may be sharp to clamp onto and engage bone or tissue. Tips 204*a*, 204*b*, 204*c*, 204*d* may be shaped like fangs. In some embodiments, tips 204*a*, 204*b*, 204*c*, 204*d* may be spikes with sharp points for engaging with bone or tissue. In some embodiments, tips 204*a*, 204*b*, 204*c*, 204*d* may be arcuately shaped and come to a point. In some embodiments, proximal wings 108*a*, 108*b* may define indentations 206*a*, 206*b* configured to fit around at least a portion of an insertion tool 400 when insertion tool attaches to threaded screw 112. Indentations 206*a*, 206*b* may extend through the length of proximal wings 108*a*, 108*b*.

Figure 10A:
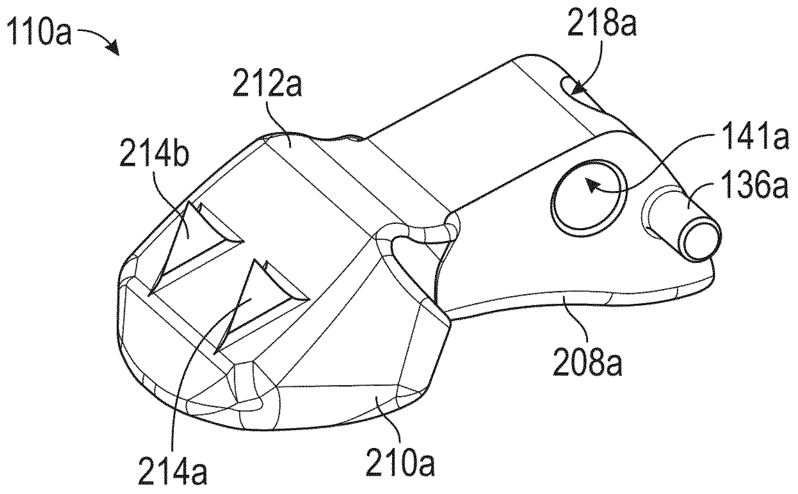
FIG. 10A illustrates a perspective view of some embodiments of a distal wing of the implant.
Figure 10B:
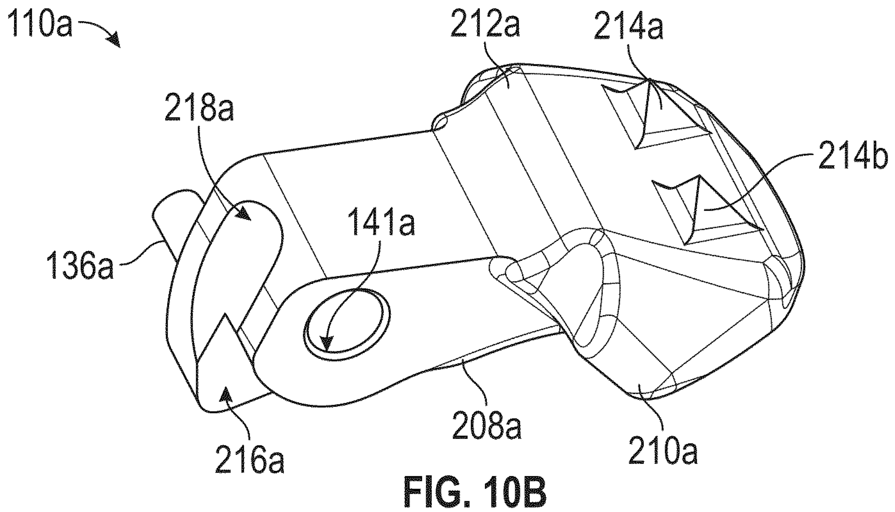
FIG. 10B illustrates a perspective view of some embodiments of a distal wing of the implant.
Figure 10C:
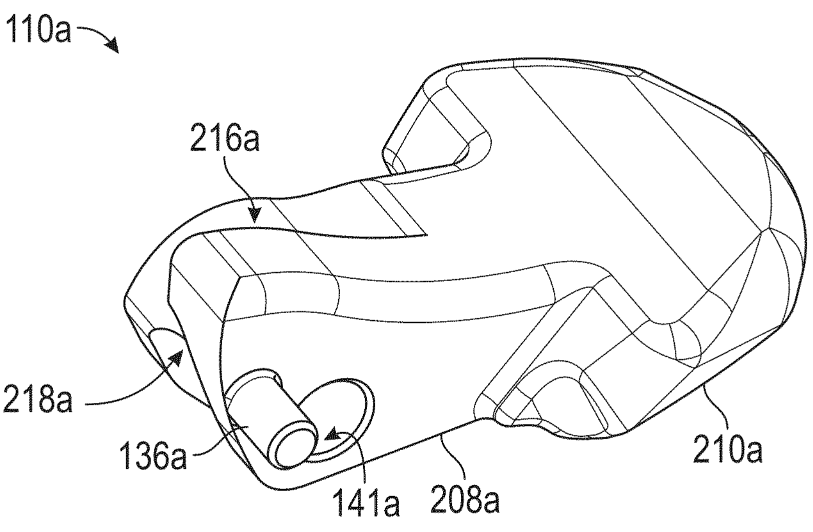
FIG. 10C illustrates a perspective view of some embodiments of a distal wing of the implant.

FIG. 10A illustrates a perspective view of some embodiments of a distal wing 110*a*, 110*b* of the implant 100. FIG. 10B illustrates a perspective view of some embodiments of the distal wing 110*a*, 110*b* of implant 100. FIG. 10C illustrates a perspective view of some embodiments of the distal wing 110*a*, 110*b* of implant 100. Accordingly, FIGS. 10A-10C are best viewed together. Implant 100 may comprise at least one distal wing 110*a*, 110*b*. In some embodiments, implant 100 may comprise a first distal wing 110*a* and a second distal wing 110*b*. Distal wings 110*a*, 110*b* of implant 100 may be identical in structure. In some embodiments, distal wings 110*a*, 110*b* may each comprise an arm 208*a*, 208*b*. Distal wings 110*a*, 110*b* may define pivot apertures 141*a*, 141*b* configured to receive pivot pins 142*a*, 142*b*. In some embodiments, arms 208*a*, 208*b* of distal wings 110*a*, 110*b* define pivot apertures 141*a*, 141*b*. For example and as shown in FIGS. 10A-10C, arm 208*a* of first distal wing 110*a* may define pivot aperture 141*a* configured to receive pivot pin 142*a*. Pivot apertures 141*a*, 141*b* may extend through distal wings 110*a*, 110*b*. At least a portion of pivot pins 142*a*, 142*b* may be received in inner body apertures 140*a*, 140*b*, 140*c*, 140*d* of inner body pieces 116*a*, 116*b* to thereby pivotally couple distal wings 110*a*, 110*b* to implant 100 (as shown in FIG. 1A). Inner body apertures 140*a*, 140*b*, 140*c*, 140*d* receiving at least a portion of each pivot pin 142*a*, 142*b* may pivotally couple distal wings 110*a*, 110*b* to inner body 106.

In some embodiments, distal wings 110*a*, 110*b* may comprise wing pins 136*a*, 136*b*. For example and as shown in FIGS. 10A-10C, wing pin 136*a* may extend from first distal wing 110*a*. Rotation slots 120*a*, 120*b* of inner body pieces 116*a*, 116*b* are configured to receive wing pins 136*a*, 136*b* (as shown in FIG. 11). Wing pins 136*a*, 136*b* may move within rotation slots 120*a*, 120*b* during actuation of threaded screw 112 to thereby pivot distal wings 110*a*, 110*b* between the closed configuration, the deployed configuration, and the clamped configuration. For example, wing pins 136*a*, 136*b* may move between a first end 138*a*, 138*b* and a second end 138*c*, 138*d* of rotation slots 120*a*, 120*b* to transition distal wings 110*a*, 110*b* between the closed position and deployed position. Wing pins 136*a*, 136*b* may extend from ends of arms 208*a*, 208*b* of distal wings 110*a*, 110*b*.

In some embodiments, distal wings 110*a*, 110*b* may comprise clamps 210*a*, 210*b* extending from arms 208*a*, 208*b*. A width of clamp 210*a*, 210*b* may be greater than a width of arm 208*a*, 208*b* to provide additional support when distal wings 110*a*, 110*b* pull at least a portion of the implant 100 through the treatment site, such as through an interspinous process space. For example, clamps 210*a*, 210*b* may pull at least a portion of implant 100 into the treatment site as distal wings 110*a*, 110*b* pivot from the closed position to the deployed position. Clamps 210*a*, 210*b* may comprise ridges 212*a*, 212*b* configured to grip bone or tissue at treatment site to pull inner body 106 and outer body 102 of implant 100 into the treatment site. In some embodiments, ridges 212*a*, 212*b* may be configured to grip bone or tissue at treatment site to pull implant 100 further into treatment site such that distal wings 110*a*, 110*b* move to a distal side of bone (e.g., spinous processes). Ridges 212*a*, 212*b* may form an inclined surface such that ridges 212*a*, 212*b* raise above at least a portion of a surface of arms 208*a*, 208*b*. Ridges 212*a*, 212*b* may provide additional torque to pull implant 100 into treatment site as distal wings 110*a*, 110*b* transition from a closed position to the deployed position, as discussed further herein. Ridges 212*a*, 212*b* may provide additional torque by increasing the surface area contacting bone or tissue proximate the treatment site or at the treatment site.

In some embodiments, clamps 210*a*, 210*b* may be configured to engage bone or tissue at and/or near the treatment site when distal wings 110*a*, 110*b* are in the deployed position. For example and similar to proximal wings 108*a*, 108*b*, distal wings 110*a*, 110*b* may comprise spikes 214*a*, 214*b*, 214*c*, 214*d*. For example and as shown in FIGS. 10A-10B, clamp 210*a* of a first distal wing 110*a* may comprise spikes 214*a*, 214*b*. Spikes 214*a*, 214*b*, 214*c*, 214*d* may be configured to engage with bone or tissue at and/or near the treatment site when proximal wings 108*a*, 108*b* are in the deployed position. Spikes 214*a*, 214*b*, 214*c*, 214*d* may be configured to engage with bone or tissue at and/or near the treatment site when distal wings 110*a*, 110*b* are in the deployed position. In some embodiments, the distal wings 110*a*, 110*b* may be in a substantially identical position when in the deployed position and when in the clamped position. In some embodiments, spikes 214*a*, 214*b*, 214*c*, 214*d* may be sharp to pierce and/or engage bone tissue. Spikes 214*a*, 214*b*, 214*c*, 214*d* may be shaped like fangs. In some embodiments, spikes 214*a*, 214*b*, 214*c*, 214*d* may form sharp pointed tips for engaging with bone or tissue. In some embodiments, spikes 214*a*, 214*b*, 214*c*, 214*d* may be generally triangular in shape and come to a sharp point to pierce bone or tissue at treatment site.

In some embodiments, arms 208*a*, 208*b* of distal wings 110*a*, 110*b* define cutouts 216*a*, 216*b*. For example and as shown in FIGS. 10B-10C, arm 208*a* of first distal wing 110*a* may define cutout 216*a*. In some embodiments, at least a portion of second distal wing 110*b* may fit within cutout 216*a* of first distal wing 110*a* when distal wings 110*a*, 110*b* are in the closed position. Cutouts 216*a*, 216*b* provide space for portions of distal wings 110*a*, 110*b* to fit therein, such that distal wings 110*a*, 110*b* may overlap one another when in the closed position. The overlap of distal wings 110*a*, 110*b* may decrease the overall profile of implant 100 as implant 100 is partially inserted into the treatment site.

In some embodiments, distal wings 110*a*, 110*b* may define contacting surfaces 218*a*, 218*b* configured to contact threaded screw 112 when threaded screw 112 is actuated, as further discussed herein. Contacting surfaces 218*a*, 218*b* may be arcuately shaped to fit around threaded screw 112. In some embodiments, contacting surfaces 218*a*, 218*b* may curve inward to form grooves that may receive threaded screw 112 during actuation of threaded screw 112.

FIG. 11 illustrates a top perspective view of some embodiments of implant 100 in a closed configuration with a portion of the outer body 102 removed. In some embodiments, first ends 138*a*, 138*b* of rotation slots 120*a*, 120*b* of inner body 106 may receive wing pins 136*a*, 136*b* of distal wings 110*a*, 110*b* when implant 100 is in the closed position. For example and as shown in FIG. 11, wing pin 136*a* may be received in first end 138*a* of rotation slot 120*a* of inner body piece 116*a*. Each distal wing 110*a*, 110*b* may define a pivot axis $P_1$ extending from the longitudinal axis $L_1$, through the center of pivot pins 142*a*, 142*b*, and through arms 208*a*, 208*b* of distal wings 110*a*, 110*b*. In some embodiments, pivot axis $P_1$ of each distal wing 110*a*, 110*b* may extend from the longitudinal axis $L_1$ at a center of spacer pins 128*a*, 128*b* through the center of inner body apertures 140*a*, 140*b* and through at least a portion of arms 208*a*, 208*b* when implant 100 is in the closed configuration. As shown in FIG. 11, pivot axis $P_1$ of first distal wing 110*a* may extend from the longitudinal axis $L_1$ at a center of spacer pin 128*a* through the center of inner body aperture 140*a* and through at least a portion of arm 208*a* when implant 100 is in the closed position. A first pivot axis angle $\theta_1$ may be defined between a respective pivot axis $P_1$ and longitudinal axis $L_1$ when implant 100 is in the closed configuration. The first pivot axis angle $\theta_1$ may be acute. The first pivot axis angle $\theta_1$ may be within a range of 20 degrees to 45 degrees, such as between 30 and 40 degrees. In some embodiments, wing pins 136*a*, 136*b* may be located proximally relative to pivot pins 142*a*, 142*b* when implant 100 is in the closed configuration. For example and as shown in FIG. 11, wing pin 136*a* may be located proximally with respect to pivot pin 142*a*. In the closed configuration, distal wings 110*a*, 110*b* may align with longitudinal axis $L_1$ of outer body 102. In some embodiments, distal wings 110*a*, 110*b* may be substantially parallel to outer body 102 in the closed configuration. In some embodiments, contacting surfaces 218*a*, 218*b* of distal wings 110*a*, 110*b* may be located internal to inner body 106 and be located proximally relative to clamps 210*a*, 210*b* in the closed position. The closed configuration may be defined by second end 122*b* of threaded screw 112 being positioned within inner body 106.

In some embodiments, inner body grooves 176*a*, 176*b*, 176*c*, 176*d* may receive protuberances 196*a*, 196*b*, 196*c*, 196*d* when implant 100 is in the closed position, as shown in FIG. 11. In some embodiments, in the closed configuration, protuberances 196*a*, 196*b*, 196*c*, 196*d* may be located distally with respect to extensions 202*a*, 202*b*, 202*c*, 202*d*, as shown in FIG. 11. In some embodiments, first ends 220*a*, 220*b* of translation slots 148*a*, 148*b* may receive carrier pins 146*a*, 146*b* when implant 100 is in the closed configuration. For example and as shown in FIG. 11, first end 220*a* of translation slot 148*a* may receive carrier pin 146*a* when implant 100 is in the closed configuration. Each proximal wing 108*a*, 108*b* may define a wing axis $W_1$ extending from the longitudinal axis $L_1$ through extensions 202*a*, 202*b*, 202*c*, 202*d*. In some embodiments, wing axis $W_1$ of each proximal wing 108*a*, 108*b* may extend from longitudinal axis $L_1$ at a point between inner body grooves 176*a*, 176*b*, 176*c*, 176*d* of each inner body piece 116*a*, 116*b* and through extensions 202*a*, 202*b*, 202*d*, 202*d*. For example and as shown in FIG. 11, wing axis $W_1$ of first proximal wing 108*a* may extend from longitudinal axis $L_1$ at a point between inner body grooves 176*a*, 176*b* and through extensions 202*a*, 202*b*. A first wing axis angle θ2 may be defined between a respective wing axis $W_1$ and longitudinal axis $L_1$ of outer body 102 when implant 100 is in the closed configuration. The first wing axis angle $\theta_2$ may be acute. The first wing axis angle $\theta_2$ may be within a range of 10 degrees to 30 degrees, such as between 15 and 25 degrees. In some embodiments, the closed position may be defined by extensions 202*a*, 202*b*, 202*c*, 202*d* being located proximally relative to pivot pins 142*c*, 142*d* received in pivot apertures 141*c*, 141*d* of proximal wings 108*a*, 108*b*. In the closed configuration, proximal wings 108*a*, 108*b* may align with longitudinal axis $L_1$ of outer body 102. In some embodiments, proximal wings 108*a*, 108*b* may be substantially parallel to longitudinal axis $L_1$. In some embodiments and as shown in FIG. 1A, outer body pieces 114*a*, 114*b* forming outer body 102 may be located at a position proximal to wing pins 136*a*, 136*b* of distal wings 110*a*, 110*b* when implant 100 is in the closed configuration.

Figure 13B:
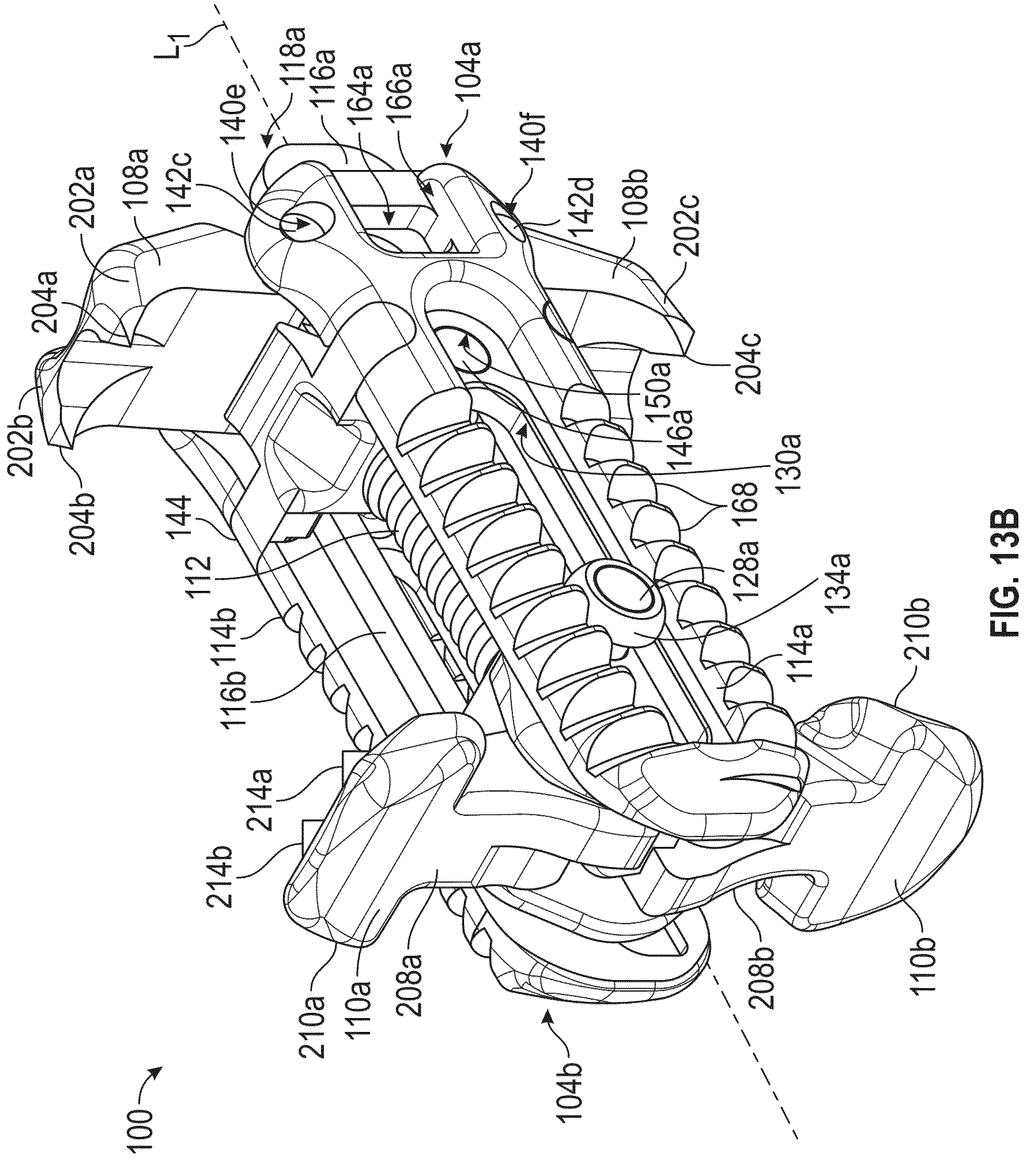
FIG. 13B illustrates a perspective view of some embodiments of the implant in an intermediate position.

FIG. 12A illustrates a top perspective view of some embodiments of implant 100 in an intermediate position with a portion of the outer body 102 removed. FIG. 12B illustrates a perspective view of some embodiments of implant 100 in an intermediate position. FIG. 13A illustrates a top perspective view of some embodiments of implant 100 in an intermediate position with a portion of the outer body 102 removed. FIG. 13B illustrates a perspective view of some embodiments of implant 100 in an intermediate position. Accordingly, FIGS. 12A-13B are best viewed together.

FIGS. 12A-13B show various intermediate positions of implant 100. Implant 100 may transition to intermediate positions when transitioning between the closed configuration and the deployed configuration. The implant 100 may transition from the closed position (as shown in FIG. 11) to intermediate positions (as shown in FIGS. 12A-13B) via actuation of threaded screw 112. In some embodiments, Actuation of threaded screw 112 may include rotation of threaded screw 112 in a first direction. Rotation of threaded screw 112 in a first direction may distally translate threaded screw 112 toward distal wings 110*a*, 110*b*. For example and in some embodiments, rotation of threaded screw 112 in a first direction may distally translate second end 122*b* of threaded screw 112 toward distal wings 110*a*, 110*b*. Distal translation of second end 122*b* may cause second end 122*b* to contact contacting surfaces 218*a*, 218*b* of distal wings 110*a*, 110*b* to initiate pivoting of distal wings 110*a*, 110*b* from the closed configuration to an intermediate position. In some embodiments, second end 122*b* of threaded screw 112 may touch contacting surfaces 218*a*, 218*b* in an intermediate position. Further rotation of threaded screw 112 in a first direction distally translates threaded screw 112 such that a portion of threaded screw 112 contacts contacting surfaces 218*a*, 218*b*. For example, a portion of threading of threaded screw 112 may contact contacting surface 218*a* of first distal wing 110*a* when implant 100 is in an intermediate position, as shown in FIG. 13A.

In the intermediate positions, proximal carrier 144 may be distally located with respect to the position of proximal carrier 144 in the closed configuration. Proximal carrier 144 may distally translate as threaded screw 112 is rotated in the first direction. For example and as shown in FIGS. 12A and 13A, proximal carrier 144 is positioned distally in intermediate positions relative to the position of proximal carrier 144 in the closed configuration (as shown in FIG. 11). Distal translation of proximal carrier 144 may cause carrier pins 146*a*, 146*b* to slide along translation slots 148*a*, 148*b* of inner body 106 such that proximal carrier 144 distally translates relative to inner body 106. In the intermediate positions, wing pins 136*a*, 136*b* may be located between the first ends 138*a*, 138*b* and second ends 138*c*, 138*d* of rotation slots 120*a*, 120*b*, as shown in FIG. 12A. Rotation of threaded screw 112 in a first direction distally translates threaded screw 112 to push contacting surfaces 218*a*, 218*b* of distal wings 110*a*, 110*b*, thereby causing wing pins 136*a*, 136*b* to move within rotation slots 120*a*, 120*b*. Movement of wing pins 136*a*, 136*b* within rotation slots 120*a*, 120*b* pivots distal wings 110*a*, 110*b* about distal end 118*b* of inner body 106. In some embodiments, distal wings 110*a*, 110*b* may pivot proximally outward toward outer body 102 when transitioning from the closed configuration to intermediate positions. In some embodiments, distal wings 110*a*, 110*b* may pivot proximally outward toward proximal end 104*a* of outer body 102 when transitioning from the closed configuration to intermediate positions.

In intermediate positions, a second pivot axis angle $\theta_1$ may be defined between the pivot axis $P_1$ and the longitudinal axis $L_1$. The pivot axis $P_1$ may pivot with the distal wings 110*a*, 110*b*, such that pivot axis $P_1$ is defined extending from the longitudinal axis $L_1$ through the center of pivot pins 142*a*, 142*b* and through arms 208*a*, 208*b*, as shown in FIGS. 12A and 13A. The second pivot axis angle $\theta_1$ may be greater than the first pivot axis angle $\theta_1$ defined in the closed configuration. For example, the second pivot axis angle $\theta_1$ may be within a range of 40 degrees to 125 degrees, such as between 60 degrees and 120 degrees. In some embodiments, the second pivot axis angle $\theta_1$ may be obtuse, as shown in FIG. 13A. A second wing axis angle $\theta_2$ may be defined between the wing axis $W_1$ and the longitudinal axis $L_1$ when the implant 100 is in intermediate positions. The second wing axis angle $\theta_2$ may be greater than the first wing axis angle $\theta_1$. For example, the second wing axis angle $\theta_2$ may be within a range of 30 degrees to 120 degrees, such as between 40° and 100°. In some embodiments, the second wing axis angle $\theta_2$ may be obtuse, as shown in FIG. 13A.

In intermediate positions, proximal wing protuberances 196*a*, 196*b*, 196*c*, 196*d* may contact and move along interfaces 177*a*, 177*b*, 177*c*, 177*d* to facilitate pivoting of proximal wings 108*a*, 108*b* between the closed configuration and the deployed configuration. For example and as shown in FIGS. 12A and 13A, protuberances 196*a*, 196*c* may contact interfaces 177*a*, 177*b* of inner body grooves 176*a*, 176*b* when implant 100 is in intermediate positions. Rotation of threaded screw 112 in a first direction causes threaded screw 112 and proximal carrier 144 to distally translate. Because proximal carrier 144 and threaded screw 112 are coupled to outer body 102, distal translation of threaded screw 112 and proximal carrier 144 causes outer body 102 to distally translate. Distal translation of outer body 102 causes outer body slots 130*a*, 130*b* to slide along spacer pins 128*a*, 128*b*. Because proximal wings 108*a*, 108*b* are pivotally coupled to outer body 102, rotation of threaded screw 112 in a first direction causes proximal wings 108*a*, 108*b* to distally translate. Distal translation of proximal wings 108*a*, 108*b* causes protuberances 196*a*, 196*b*, 196*c*, 196*d* to contact interfaces 177*a*, 177*b*, 177*c*, 177*d* and move along interfaces 177*a*, 177*b*, 177*c*, 177*d* to thereby pivot proximal wings 108*a*, 108*b*. In some embodiments, proximal wings 108*a*, 108*b* may pivot distally outward toward outer body 102 when transitioning from the closed configuration to intermediate positions. In some embodiments, proximal wings 108*a*, 108*b* may pivot distally outward toward distal end 104*b* of outer body 102 when transitioning from the closed configuration to intermediate positions. In intermediate positions, proximal surfaces 200*a*, 200*b*, 200*c*, 200*d* of juts 198*a*, 198*b*, 198*c*, 198*d* of proximal wings 108*a*, 108*b* may contact ramps 174*a*, 174*b* to facilitate pivoting of proximal wings 108*a*, 108*b*. For example and as shown in FIG. 12A, a portion of proximal surface 200*a* of first proximal wing 108*a* and a portion of proximal surface 200*c* of second proximal wing 108*b* may contact ramp 174*a* to thereby initiate pivoting of proximal wings 108*a*, 108*b* from the closed position to the deployed position.

In the intermediate positions and as shown in FIGS. 12B and 13B, outer body pieces 114*a*, 114*b* forming outer body 102 may be located distally relative to a position of outer body pieces 114*a*, 114*b* forming outer body 102 in the closed configuration (as shown in FIG. 1A). For example and as shown in FIG. 13B, a portion of outer body 102 may cover wing pins 136*a*, 136*b* and rotation slots 120*a*, 120*b* in the intermediate positions. In some embodiments, in the intermediate positions, proximal end 118*a* of inner body 106 may extend past proximal end 104*a* of outer body 102, as shown in FIG. 13B. In intermediate positions, distal wings 110*a*, 110*b* and proximal wings 108*a*, 108*b* may be generally orthogonal to longitudinal axis $L_1$ of outer body 102, as shown in FIG. 13A. Outer body 102 may distally translate relative to inner body 106, such that inner body 106 extends outward from outer body 102 when implant 100 is in intermediate positions, as shown in FIGS. 13A-13B.

FIG. 14A illustrates a top perspective view of some embodiments of implant 100 in a deployed configuration position with a portion of the outer body 102 removed. FIG. 14B illustrates a perspective view of some embodiments of implant 100 in a deployed configuration. Accordingly, FIGS. 14A-14B are best viewed together. The deployed configuration may be defined by proximal wing protuberances 196*a*, 196*b*, 196*c*, 196*d* contacting translation surfaces 172*a*, 172*b*, 172*c*, 172*d*. For example and as shown in FIG. 14A, protuberances 196*a*, 196*c* may contact translation surfaces 172*a*, 172*b* when implant 100 is in the deployed position. In some embodiments, in the deployed configuration, protuberances 196*a*, 196*b*, 196*c*, 196*d* of proximal wings 108*a*, 108*b* may be positioned at the intersection of translation surfaces 172*a*, 172*b*, 172*c*, 172*d* and interfaces 177*a*, 177*b*, 177*c*, 177*d*, as shown in FIG. 14A. In the deployed configuration, proximal wings 108*a*, 108*b* may be adjacent to inner body grooves 176*a*, 176*b*, 176*c*, 176*d*. Translation surfaces 172*a*, 172*b*, 172*c*, 172*d* are configured to maintain proximal wings 108*a*, 108*b* in a deployed position by contacting protuberances 196*a*, 196*b*, 196*c*, 196*d*.

During rotation of threaded screw 112 in a first direction, protuberances 196*a*, 196*b*, 196*c*, 196*d* may move along interfaces 177*a*, 177*b*, 177*c*, 177*d* and onto translation surfaces 172*a*, 172*b*, 172*c*, 172*d* to thereby transition the implant 100 from an intermediate position or closed configuration to the deployed configuration. In some embodiments, rotation of threaded screw 112 in the first direction causes protuberances 196*a*, 196*b*, 196*c*, 196*d* to move along interfaces 177*a*, 177*b*, 177*c*, 177*d* and onto translation surfaces 172*a*, 172*b*, 172*c*, 172*d* to thereby pivot proximal wings 108*a*, 108*b* about outer body 102. In some embodiments, proximal wings 108*a*, 108*b* may pivot distally outward toward outer body 102 to transition from the closed configuration or intermediate positions to the deployed configuration. In some embodiments, proximal wings 108*a*, 108*b* may pivot distally outward toward distal end 104*b* of outer body 102 to transition from the closed configuration or intermediate positions to the deployed configuration. In some embodiments, extensions 202*a*, 202*b*, 202*c*, 202*d* of proximal wings 108*a*, 108*b* may be positioned proximal with respect to proximal end 104*a* of outer body 102 when implant 100 is in the closed configuration. When proximal wings 108*a*, 108*b* pivot distally outward to transition to the deployed position, extensions 202*a*, 202*b*, 202*c*, 202*d* may be positioned distal with respect to proximal end 104*a* of outer body 102. In some embodiments, in the deployed position, protuberances 196*a*, 196*b*, 196*c*, 196*d* may be located at a position proximal to extensions 202*a*, 202*b*, 202*c*, 202*d* of proximal wings 108*a*, 108*b*. In the deployed position, second ends 138*c*, 138*d* of rotation slots 120*a*, 120*b* may receive wing pins 136*a*, 136*b* of distal wings 110*a*, 110*b*. For example and as shown in FIG. 14A, wing pin 136*a* may be received in second end 138*c* of rotation slot 120*a* of inner body piece 116*a*.

Implant 100 may transition from the closed position (as shown in FIG. 11) to the deployed position (as shown in FIGS. 14A-14B). In some embodiments, Implant 100 may transition from the closed position (as shown in FIG. 11) to an intermediate position (as shown in FIGS. 12A-13B) and transition from an intermediate position to a deployed position (as shown in FIGS. 14A-14B). Implant 100 may transition from the closed position (or intermediate position) to the deployed position via continued rotation of threaded screw 112 in a first direction, allowing a surgeon or operator to perform one actuation step to transition the implant 100 from the closed position to the deployed position. Rotation of threaded screw 112 in a first direction may distally translate threaded screw 112, outer body 102, proximal carrier 144, and proximal wings 108*a*, 108*b*. Distal translation of threaded screw 112 causes threaded screw 112 to contact distal wings 110*a*, 110*b* to thereby pivot distal wings 110*a*, 110*b* from the closed configuration to the deployed configuration. In some embodiments, distal wings 110*a*, 110*b* may pivot proximally outward toward outer body 102 when transitioning from the closed configuration or intermediate positions to the deployed configuration. In some embodiments, distal wings 110*a*, 110*b* may pivot proximally outward toward a proximal end 104*a* of outer body 102 when transitioning from the closed configuration or intermediate positions to the deployed configuration. In some embodiments, distal wings 110*a*, 110*b* may pivot proximally outward toward a proximal end 118*a* of inner body 106 when transitioning from the closed configuration or intermediate positions to the deployed configuration. In some embodiments, clamps 210*a*, 210*b* may be positioned distal with respect to distal end 118*b* of inner body 106 when implant 100 is in the closed configuration. When distal wings 110*a*, 110*b* pivot proximally outward to transition to the deployed position, clamps 210*a*, 210*b* may be positioned proximal with respect to distal end 118*b* of inner body 106. In some embodiments, threaded screw 112 may press contacting surfaces 218*a*, 218*b* of distal wings 110*a*, 110*b* to move wing pins 136*a*, 136*b* within rotation slots 120*a*, 120*b* from a first end 138*a*, 138*b* to a second end 138*c*, 138*d*. Moving wing pins 136*a*, 136*b* within rotation slots 120*a*, 120*b* causes distal wings 110*a*, 110*b* to pivot about distal end 118*b* of inner body 106. Contacting surfaces 218*a*, 218*b* may receive a portion of threaded screw 112 to maintain distal wings 110*a*, 110*b* in a deployed configuration.

In some embodiments and as shown in FIGS. 14A-14B, the deployed configuration may be defined by second end 122*b* of threaded screw 112 passing between first distal wing 110*a* and second distal wing 110*b*, such that second end 122*b* aligns with distal end 118*b* of inner body 106. In the deployed configuration, proximal carrier 144 may be distally located relative to the position of proximal carrier 144 in the closed configuration and intermediate positions. For example and as shown in FIG. 14A, proximal carrier 144 is positioned distally in the deployed configuration relative to the position of proximal carrier 144 in the closed configuration (as shown in FIG. 11) and relative to the position of proximal carrier 144 in the intermediate positions (as shown in FIGS. 12A-13B). Rotation of threaded screw 112 in the first direction causes proximal carrier 144 to translate distally, such that further rotation of threaded screw in the first direction further distally translates proximal carrier 144 when transitioning implant 100 from the closed position or intermediate positions to the deployed position.

In some embodiments, inner body grooves 176*a*, 176*b*, 176*c*, 176*d* of inner body 106 may extend past proximal end 104*a* of outer body 102 when implant 100 is in the deployed configuration, as shown in FIG. 14B. The overall length of implant 100 may be greater in the deployed configuration than the overall length of implant 100 in intermediate positions or in the closed configuration. Outer body 102 may distally translate relative to inner body 106 when transitioning from the closed position or intermediate positions to the deployed configuration, such that the outer body 102 distally extends past distal end 118*b* of inner body 106.

In the deployed configuration, a third pivot axis angle $\theta_1$ may be defined between the pivot axis $P_1$ and the longitudinal axis $L_1$. The pivot axis $P_1$ may be extend from the longitudinal axis $L_1$, through the center of wing pins 136*a*, 136*b*, through the center of pivot pins 142*a*, 142*b*, and through arms 208*a*, 208*b* when implant 100 is in the deployed configuration. For example and as shown in FIG. 14A, pivot axis $P_1$ of first distal wings 110*a* may be extend from longitudinal axis $L_1$, through the center of wing pin 136*a*, through the center of pivot pin 142*a*, and through arm 208*a* when implant 100 is in the deployed configuration. The third pivot axis angle $\theta_1$ may be greater than the first pivot axis angle $\theta_1$ defined in the closed configuration and the second pivot axis angle $\theta_1$ defined in an intermediate position. For example, the third pivot axis angle $\theta_1$ may be within a range of 121 degrees to 150 degrees, such as between 140 degrees and 150 degrees. In some embodiments, the third pivot axis angle $\theta_1$ may be obtuse, as shown in FIG. 14A. A third wing axis angle $\theta_2$ may be defined between the wing axis $W_1$ and the longitudinal axis $L_1$ when the implant 100 is the deployed configuration. The third wing axis angle $\theta_2$ may be greater than the first wing axis angle $\theta_1$ defined in the closed configuration and the second wing axis angle $\theta_2$ defined by an intermediate position. For example, the third wing axis angle $\theta_2$ may be within a range of 120 degrees to 130 degrees, such as between 125 degrees and 130 degrees. In some embodiments, the third wing axis angle $\theta_1$ may be obtuse, as shown in FIG. 14A. In the deployed configuration, spikes 214*a*, 214*b*, 214*c*, 214*d* of distal wings 110*a*, 110*b* may engage bone or tissue at or near the treatment site, as further discussed herein. In some embodiments, the deployed configuration may be defined by at least a portion of arms 208*a*, 208*b* being located distally with respect to clamps 210*a*, 210*b*, as shown in FIG. 14A. As shown in FIG. 14A, distal wings 110*a*, 110*b* and proximal wings 108*a*, 108*b* may be a distance $D_1$ away from one another when in the deployed configuration.

FIG. 15A illustrates a top perspective view of some embodiments of implant 100 in a clamped configuration with a portion of outer body 102 removed. FIG. 15B illustrates a perspective view of some embodiments of implant 100 in a clamped configuration. Accordingly, FIGS. 15A-15B are best viewed together. In some embodiments, implant 100 may transition from a deployed configuration to a clamped configuration. For example, continued rotation of threaded screw 112 in a first direction may distally translate threaded screw 112 and outer body 102 through the treatment site (e.g., interspinous process space). Rotation of threaded screw 112 in a first direction may distally translate proximal wings 108*a*, 108*b* toward bone or tissue at treatment site to engage proximal wings 108*a*, 108*b* with bone or tissue at treatment site and thereby transition the implant 100 from the deployed configuration to the clamped configuration. As shown in FIG. 15A, proximal carrier 144, second end 122*b* of threaded screw 112, and outer body 102 may be located distally relative to the position of proximal carrier 144, second end 122*b* of threaded screw 112, and outer body 102 when implant 100 is in a deployed configuration (as shown in FIG. 14A). For example, second end 122*b* of threaded screw 112 may extend past distal end 118*b* of inner body 106 when implant 100 is in the clamped configuration.

In the deployed configuration, implant 100 may define a first distance $D_1$ between distal wings 110*a*, 110*b* and proximal wings 108*a*, 108*b* (as shown in FIG. 14A). In the clamped configuration, implant 100 may define a second distance $D_2$ between distal wings 110*a*, 110*b* and proximal wings 108*a*, 108*b*. The second distance $D_2$ may be less than the first distance $D_1$. The distance between distal wings 110*a*, 110*b* and proximal wings 108*a*, 108*b* may be greater in intermediate positions than the distance defined by implant 100 in the clamped configuration. In the clamped configuration, proximal wings 108*a*, 108*b* are distally translated toward distal wings 110*a*, 110*b* such that proximal wings 108*a*, 108*b* are closer to distal wings 110*a*, 110*b*.

Rotation of threaded screw 112 in a first direction may cause proximal wing protuberances 196*a*, 196*b*, 196*c*, 196*b* to move along translation surfaces 172*a*, 172*b*, 172*c*, 172*d* to transition the implant 100 from a deployed configuration to a clamped configuration. For example, protuberances 196*a*, 196*b*, 196*c*, 196*d* may distally translate along translation surfaces 172*a*, 172*b*, 172*c*, 172*d* to distally translate proximal wings 108*a*, 108*b* toward the treatment site, thereby transitioning implant 100 from a deployed configuration to a clamped configuration. In the clamped configuration, protuberances 196*a*, 196*b*, 196*c*, 196*d* may be offset from the intersection of translation surfaces 172*a*, 172*b*, 172*c*, 172*d* and interfaces 177*a*, 177*b*, 177*c*, 177*d*. In some embodiments, proximal wings 108*a*, 108*b* may be offset from interfaces 177*a*, 177*b*, 177*c*, 177*d* in the clamped configuration. In some embodiments, proximal wings 108*a*, 108*b* may be offset from inner body grooves 176*a*, 176*b*, 176*c*, 176*d* when implant 100 is in the clamped configuration.

In some embodiments, the overall length of implant 100 may be greater in the clamped configuration than the overall length of implant 100 in the deployed configuration, intermediate positions, or in the closed configuration. Outer body 102 and threaded screw 112 may further distally translate relative to inner body 106 when transitioning from the deployed configuration, such that the outer body 102 and threaded screw 112 distally extend past distal end 118*b* of inner body 106 to thereby increase the overall length of implant 100 when transitioning from the deployed configuration to the clamped configuration.

Figure 16:
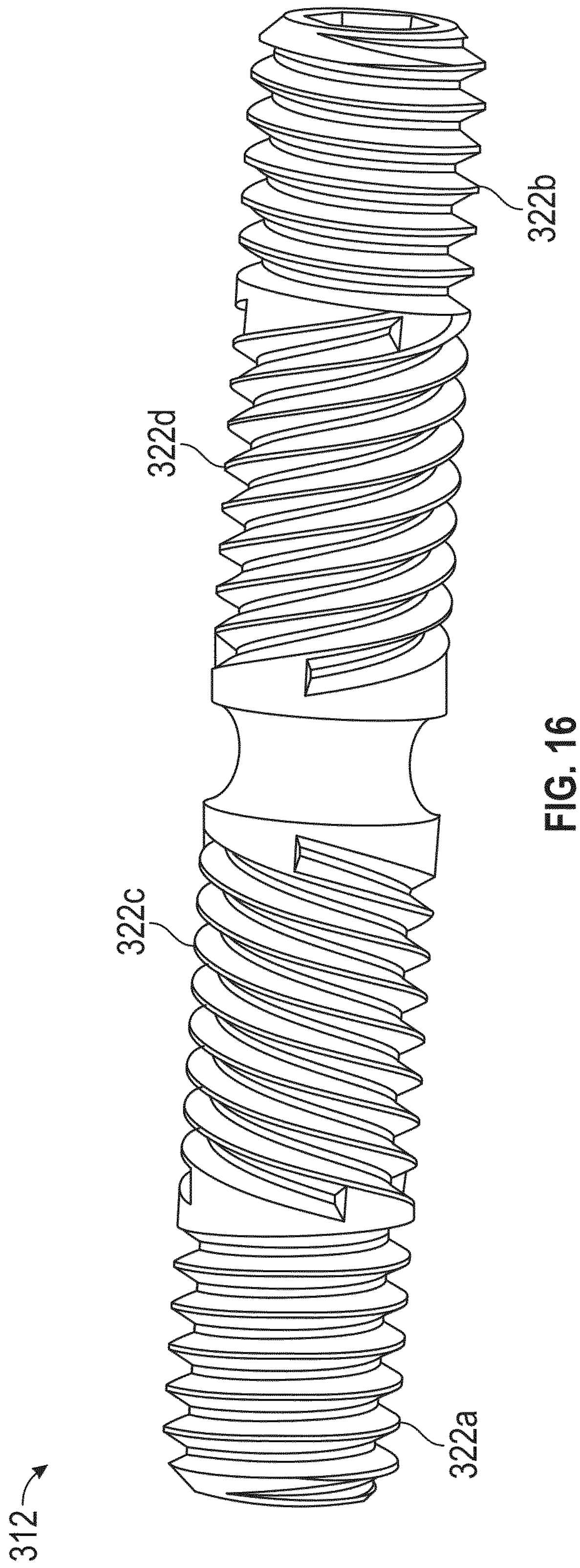
FIG. 16 illustrates some embodiments of a threaded screw of the implant.

FIG. 16 illustrates some alternative embodiments of threaded screw 312 of the implant 100. In some embodiments, threaded screw 312 may comprise a first threading 322*a*, 322*b* and a second threading 322*c*, 322*d*. First threading 322*a*, 322*b* may thread in an opposite direction relative to second threading 322*c*, 322*d*. In some embodiments, first threading 322*a*, 322*b* may thread in a same direction as second threading 322*c*, 322*d* In some embodiments, the spacing between threads on first threading 322*a*, 322*b* may be greater than the spacing between threads on second threading 322*c*, 322*d* such that first threading creates faster motion than second threading 322*c*, 322*d*. First threading 322*a*, 322*b* may be located at ends of threaded screw 312 and second threading 322*c*, 322*d* may be located between first threading 322*a*, 322*b*. Actuating first threading 322*a*, 322*b* located at ends of threaded screw 312 may simultaneously pivot distal wings 110*a*, 110*b* and proximal wings 108*a*, 108*b* of implant 100 between a closed configuration and deployed configuration. Actuation of second threading 322*c*, 322*d* may distally translate proximal wings 108*a*, 108*b*. First threading 322*a*, 322*b* and second threading 322*c*, 322*d* may thereby facilitate multiple simultaneous movements of components of implant 100 to increase the speed of the procedure.

In some embodiments, implant 100 may transition from the clamped configuration to the deployed position, back to intermediate positions, and back to the closed configuration via rotation of threaded screw 112 in a second direction. The second direction may be opposite the first direction. Implant 100 may transition from the deployed configuration or clamped configuration to the closed configuration to allow surgeon to reposition the implant 100 within the treatment site or remove the implant 100. In some embodiments, rotation of threaded screw 112 in a second direction may proximally translate threaded screw, proximal carrier 144, outer body 102, and proximal wings 108*a*, 108*b*, such that proximal wings 108*a*, 108*b* pivot to the closed configuration. In some embodiments, proximal wings 108*a*, 108*b* may pivot proximally inward toward proximal end 104*a* of outer body 102 and distal wings 110*a*, 110*b* may pivot distally inward toward distal end 118*b* of inner body 106 to pivot from the deployed configuration or the clamped configuration to the closed configuration. For example, proximal translation of proximal wings 108*a*, 108*b* may cause protuberances 196*a*, 196*b*, 196*c*, 196*d* to be received in inner body grooves 176*a*, 176*b*, 176*c*, 176*d*. Inner body grooves 176*a*, 176*b*, 176*c*, 176*d* may each comprise a side that may interact with protuberances 196*a*, 196*b*, 196*c*, 196*d* to cause proximal wings 108*a*, 108*b* to pivot about outer body 102 from a deployed configuration to a closed configuration. In some embodiments, proximal wings 108*a*, 108*b* may pivot proximally inward toward proximal end 104*a* when transitioning from the deployed configuration or clamped configuration to the closed configuration. Proximal translation of threaded screw 112 may cause threaded screw 112 to move away from distal wings 110*a*, 110*b* such that distal wings 110*a*, 110*b* pivot about inner body 106 from the deployed configuration to the closed configuration. In some embodiments, distal wings 110*a*, 110*b* may pivot distally inward toward distal end 104*b* of outer body 102 when transitioning from the deployed or clamped configuration to the closed configuration.

First Insertion Tool Embodiment

Figure 17A:
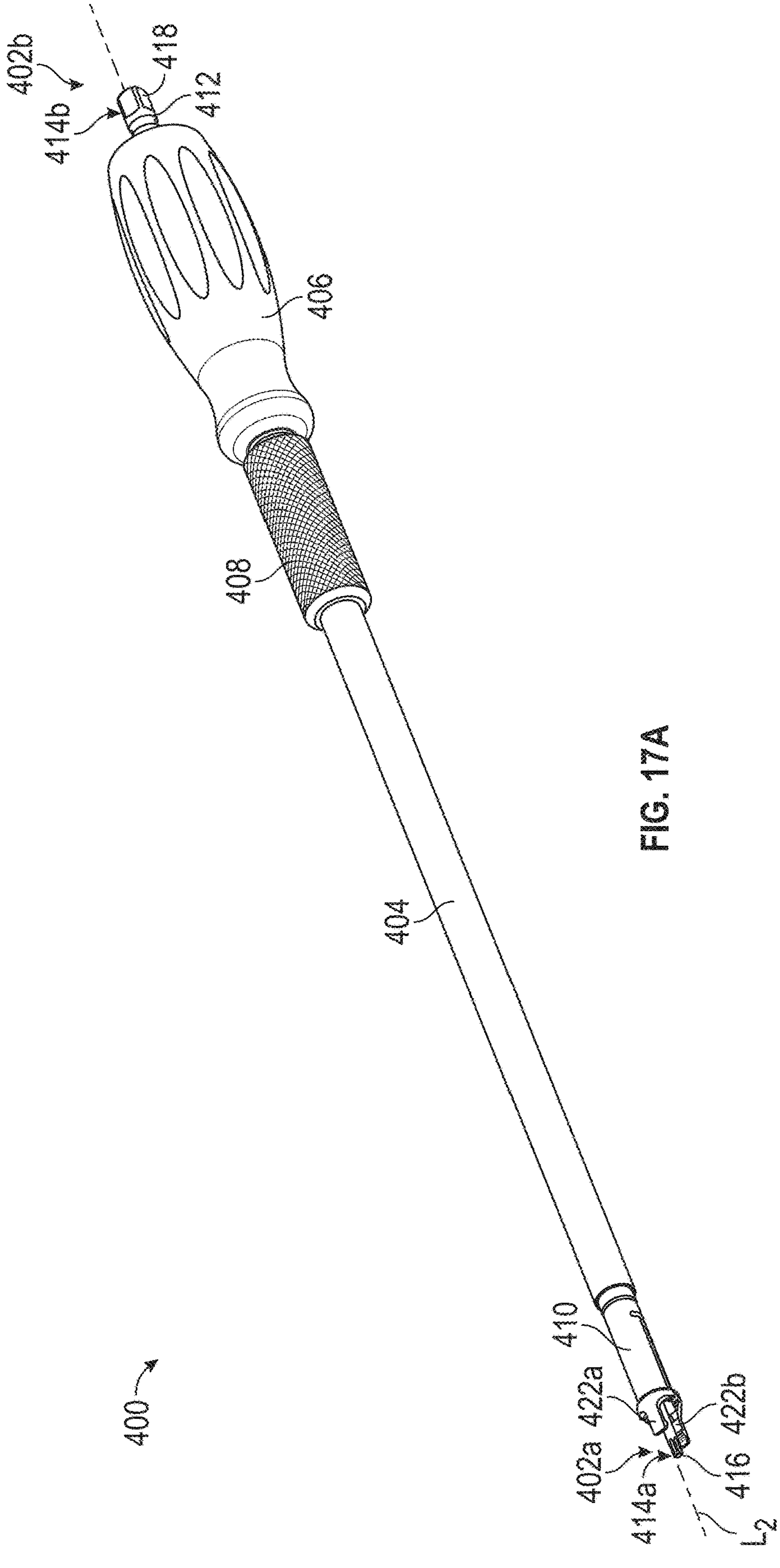
FIG. 17A illustrates a perspective view of some embodiments of an insertion tool.
Figure 17B:
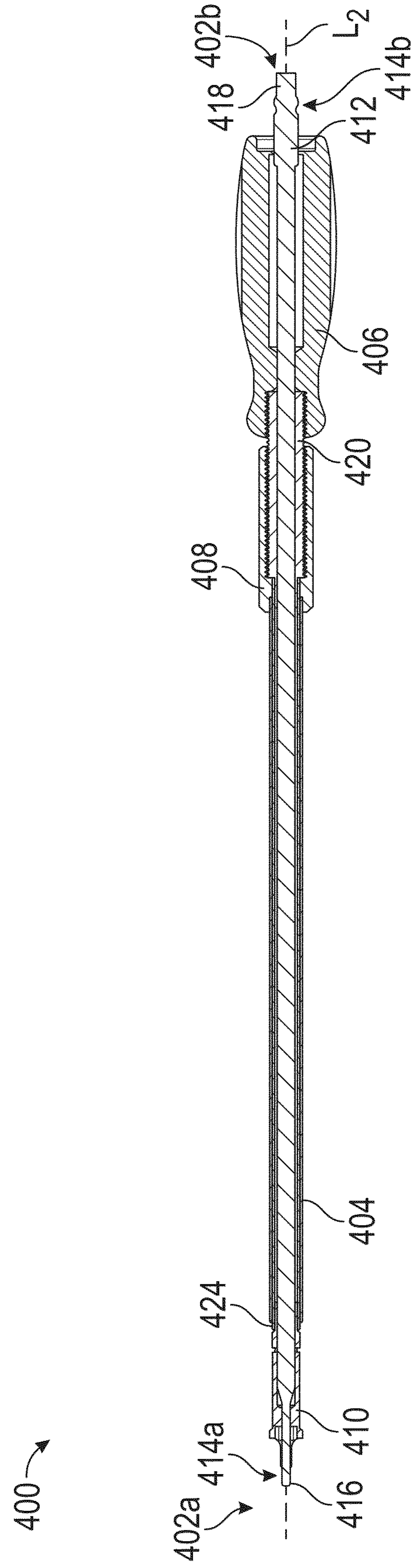
FIG. 17B illustrates a cross-sectional view of some embodiments of the insertion tool.
Figure 18:
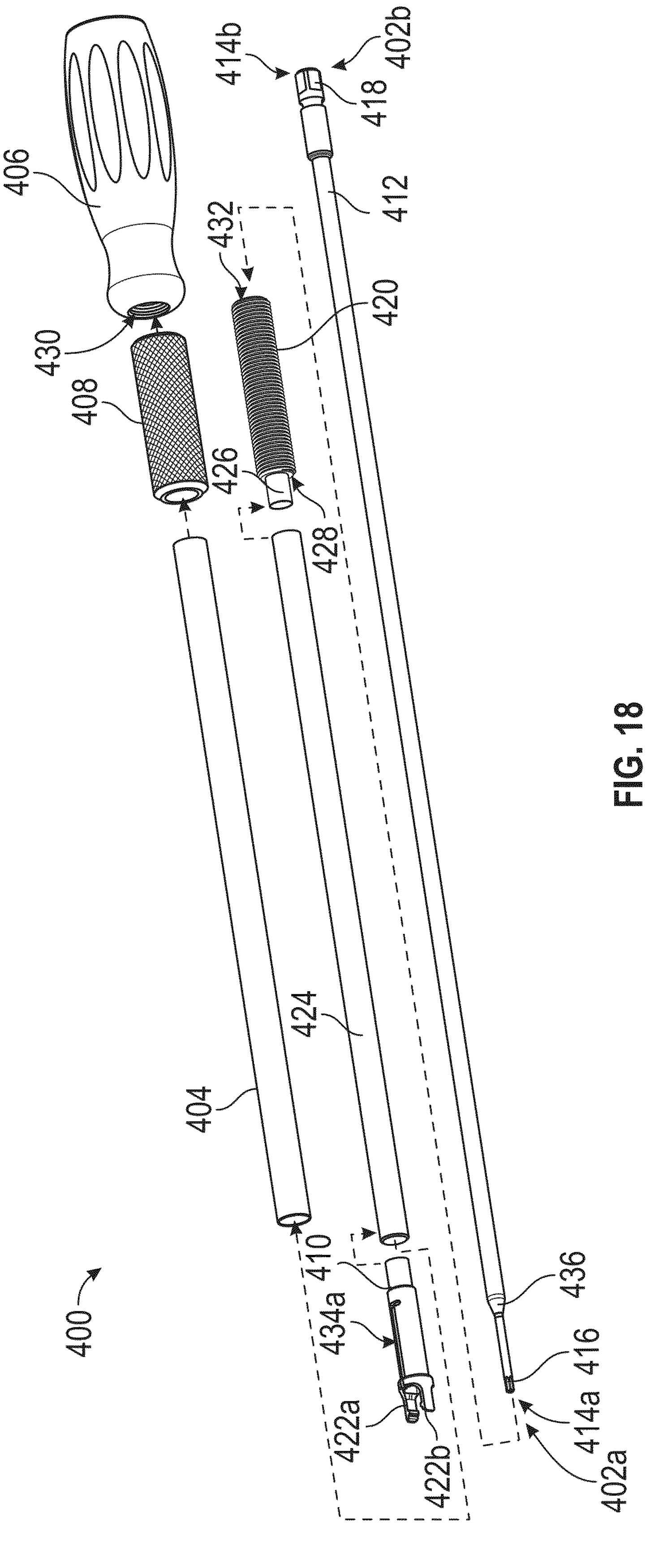
FIG. 18 illustrates an exploded view of some embodiments of the insertion tool.

FIG. 17A illustrates a perspective view of some embodiments of an insertion tool 400. Insertion tool 400 may be configured to insert implant 100 into the treatment site (e.g., interspinous process space). FIG. 17B illustrates a cross-sectional view of some embodiments of an insertion tool 400. FIG. 18 illustrates an exploded view of some embodiments of an insertion tool 400. Accordingly, FIGS. 17A-18 are best viewed together. Insertion tool 400 may be configured to insert implant 100 into treatment site while simultaneously transitioning implant 100 from the closed configuration to the deployed configuration and to the clamped configuration. Insertion tool 400 may define a longitudinal axis $L_2$ extending through a distal end 402*a* and a proximal end 402*b* of insertion tool 400. Insertion tool 400 comprises an outer shaft 404, a handle 406, an outer grip 408, an attachment member 410, and an inner rod 412. Outer shaft 404 may receive inner rod 412. Inner rod 412 may define a distal end 414*a* and a proximal end 414*b*. Inner rod 412 may comprise a driver head 416 at the distal end 414*a* and a control 418 at the proximal end 414*b*. Inner rod 412 may extend through handle 406, such that control 418 is located at a position proximal to handle 406. At least a portion of inner rod 412 may extend through attachment member 410, such that driver head 416 is located at a position distal to attachment member 410. Outer grip 408 may receive at least a portion of outer shaft 404. A connector 420 may operatively couple handle 406 to outer grip 408 and couple outer shaft 404 to handle 406 (as shown in FIG. 17B).

Driver head 416 may be configured to fit within screw head 124 of threaded screw 112 of implant 100, such that threaded screw 112 receives driver head 416. Operation of control 418 may actuate driver head 416 of inner rod 412 to thereby actuate threaded screw 112. For example, a surgeon or operator may turn control 418 to cause driver head 416 to rotate. Rotation of driver head 416 causes threaded screw 112 to rotate when screw head 124 receives driver head 416. Attachment member 410 may be configured to attach insertion tool 400 to implant 100. For example, attachment member 410 may comprise arms 422*a*, 422*b* extending therefrom. In some embodiments, openings 164*a*, 164*b* of outer body 102 may receive at least a portion of each arm 422*a*, 422*b* to thereby attach implant 100 to insertion tool 400 and maintain implant 100 on insertion tool 400. In some embodiments, operation of outer grip 408 may distally translate attachment member 410 to attach implant 100 to attachment member 410. For example, a surgeon or operator may turn outer grip 408 to distally translate attachment member 410 to attach implant 100 to insertion tool 400 and lock arms 422*a*, 422*b* into openings 164*a*, 164*b* to maintain implant 100 on insertion tool 400. A surgeon or operator may hold handle 406 to stabilize insertion tool 400 during operation of insertion tool 400.

As shown in FIGS. 17B-18, insertion tool 400 may comprise inner shaft 424. Inner shaft 424 may receive at least a portion of inner rod 412. Inner shaft 424 may receive at least a portion of attachment member 410, such that attachment member 410 couples to inner shaft 424. In some embodiments, attachment member 410 may couple to inner shaft 424 through an interference fit. In some embodiments, attachment member 410 may couple to inner shaft 424 through a snap fit, threaded fit, or any other coupling mechanism known to a person of skill in the art. In some embodiments, attachment member 410 may fixedly couple to inner shaft 424 through an interference fit, welding, epoxy, or a press fit. Inner shaft 424 may receive at least a portion of connector 420. In some embodiments, connector 420 may comprise a tube 426. Tube 426 may be received within inner shaft 424, thereby coupling inner shaft 424 to connector 420. Tube 426 may have a smooth exterior to provide an interference fit or a press fit between connector 420 and inner shaft 424. In some embodiments, connector 420 may fixedly couple to shaft 424 through welding or epoxy. In some embodiments, tube 426 may couple to inner shaft 424 through a snap fit, threaded fit, or any other coupling mechanism known to one skilled in the art. Abutment 428 of connector 420 (as shown in FIG. 18) may contact an end of inner shaft 424 when inner shaft receives tube 426 or is fixedly connected to connector 420. Once the attachment member 410, inner shaft 424, and connector 420 are coupled, connector 420 may be coupled to handle 406 to thereby couple the attachment member 410 and inner shaft 424 to the handle 406, as discussed further below.

Outer shaft 404 may couple to outer grip 408. In some embodiments, outer grip 408 may receive outer shaft 404. In some embodiments, outer shaft 404 may fixedly couple to outer grip 408 through welding or epoxy. In some embodiments, outer shaft 404 may couple to outer grip 408 through an interference fit, a press fit, or any other coupling mechanism known in the art. Once outer shaft 404 is coupled to outer grip 408, outer shaft 404 and outer grip 408 may receive inner shaft 424, connector 420, and attachment member 410, as shown in FIG. 18. For example, at least a portion of inner shaft 424 may be housed inside outer shaft 404. Outer grip 408 may receive at least a portion of connector 420. Outer grip 408 may threadedly couple to a portion of connector 420, as further discussed herein. Rotation of outer grip 408 may distally translate outer shaft 404 and outer grip 408. Distally translating outer shaft 404 and outer grip 408 may cause outer shaft 404 to interact with attachment member 410 to thereby cause arms 422*a*, 422*b* to to clip into openings 164*a*, 164*b* of outer body 102 of implant 100 to thereby lock implant 100 onto insertion tool 400. Outer shaft 404 may distally translate onto attachment member 410 to cause arms 422*a*, 422*b* to collapse onto implant 100 to thereby lock implant 100 onto insertion tool 400.

Connector 420 may comprise threads on an exterior portion thereof. Handle 406 may define a central bore 430 configured to receive at least a portion of connector 420. Central bore 430 may be threaded. Connector 420 may be configured to threadedly couple to handle 406. Threads on exterior of connector 420 may interact with central bore 430 of handle 406 to thereby fixedly couple connector 420 to handle 406, thereby fixedly coupling attachment member 410 and inner shaft 424 to handle 406. Connector 420 may define a tunnel 432 configured to receive inner rod 412. Attachment member 410 may define inserter slots 434*a*, 434*b* between arms 422*a*, 422*b*.

Inner rod 412 may comprise a taper 436 proximate distal end 414*a*, such that a size of distal end 414*a* of inner rod 412 is smaller than a size of proximal end 414*b* of inner rod 412. In some embodiments, taper 436 may decrease the size of distal end 414*a* relative to proximal end 414*b* to thereby allow distal portion of inner rod 412 to fit within inner body 106 of implant 100 during rotation of inner rod 412. A distal portion of inner rod 412 may be located between inner body pieces 116*a*, 116*b* during insertion of implant 100 into the treatment site. Control 418 may be configured to interact with a T handle. For example and in some embodiments, control 418 may attach to a T handle as otherwise known to a person skilled in the art, to provide a surgeon or operator a handle to use to rotate inner rod 412.

Figure 19A:
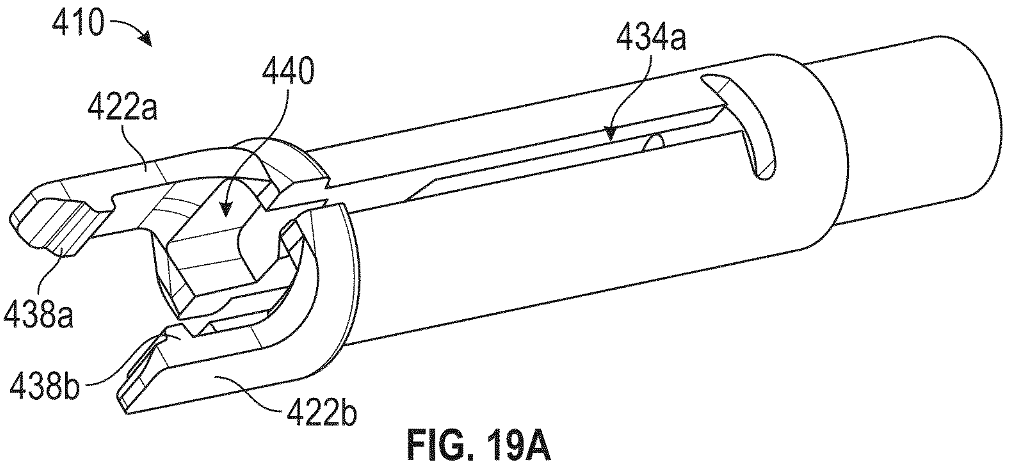
FIG. 19A illustrates a perspective view of some embodiments of an attachment member of the insertion tool.
Figure 19B:
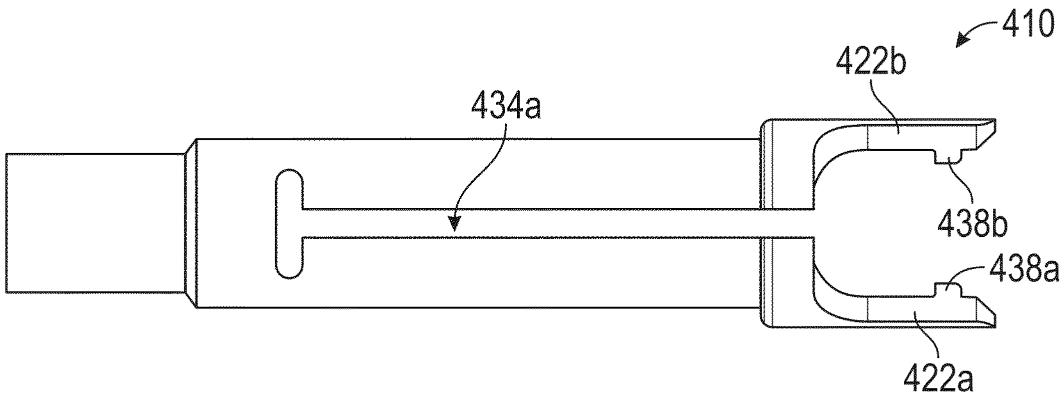
FIG. 19B illustrates a side view of some embodiments of an attachment member of the insertion tool.
Figure 19C:
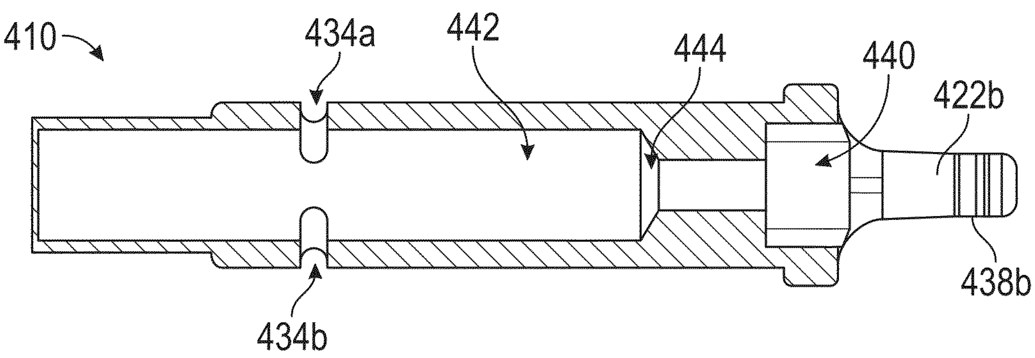
FIG. 19C illustrates a cross-sectional view of some embodiments of an attachment member of the insertion tool.
Figure 20A:
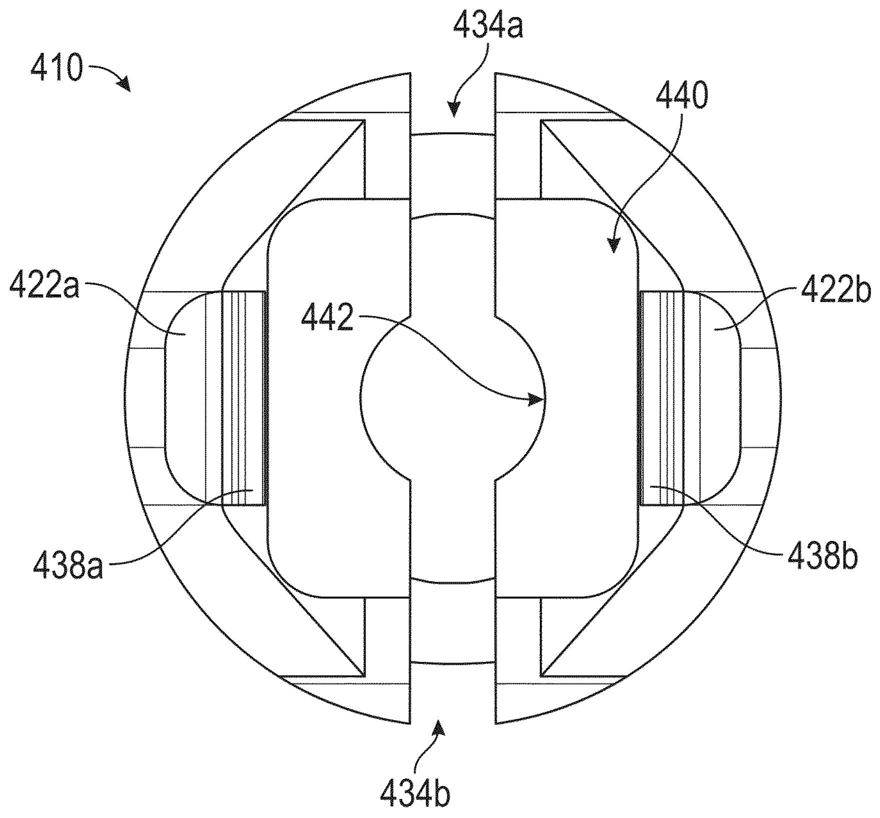
FIG. 20A illustrates a front view of some embodiments of an attachment member of the insertion tool.
Figure 20B:
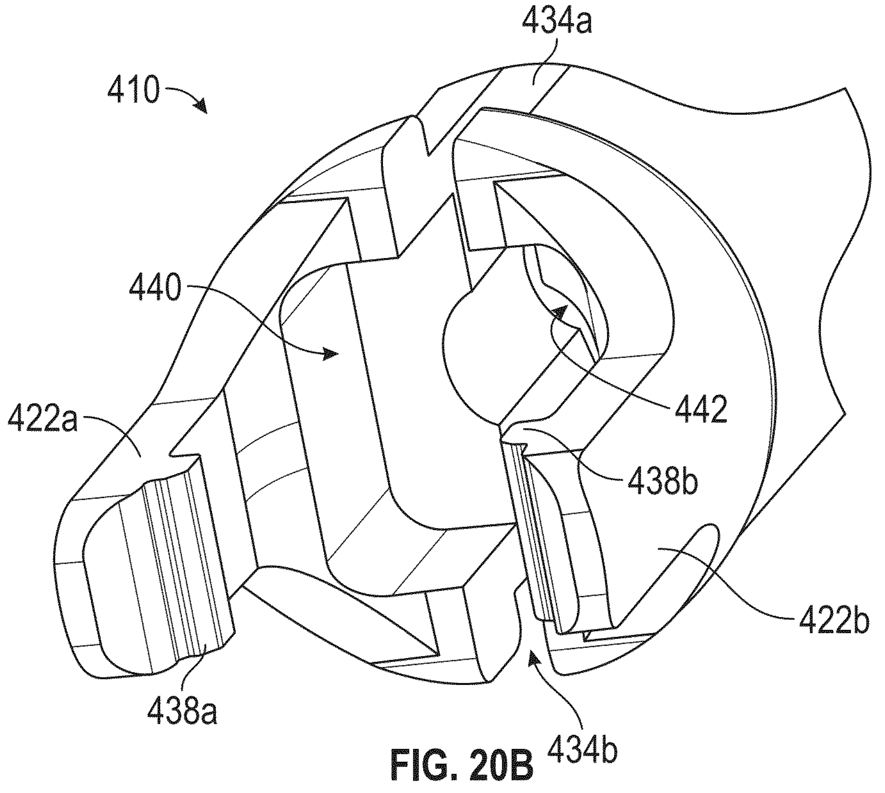
FIG. 20B illustrates a perspective view of some embodiments of an attachment member of the insertion tool.

FIG. 19A illustrates a perspective view of some embodiments of an attachment member 410 of the insertion tool 400. FIG. 19B illustrates a side view of some embodiments of an attachment member 410 of the insertion tool 400. FIG. 19C illustrates a cross-sectional view of some embodiments of an attachment member 410 of the insertion tool 400. FIG. 20A illustrates a front view of some embodiments of an attachment member 410 of the insertion tool 400. FIG. 20B illustrates a perspective view of some embodiments of an attachment member 410 of insertion tool 400. Accordingly, FIGS. 19A-20B are best viewed together. Arms 422*a*, 422*b* of attachment member 410 may comprise clips 438*a*, 438*b* configured to interact with openings 164*a*, 164*b* of outer body pieces 114*a*, 114*b* to lock implant 100 onto insertion tool 400. Clips 438*a*, 438*b* may protrude from arms 422*a*, 422*b*, as shown in FIGS. 19A-19B, 20B. In some embodiments, attachment member 410 may threadedly couple to implant 100 to thereby lock implant 100 to insertion tool 400. Attachment member 410 may define a cavity 440 extending to arms 422*a*, 422*b*, as shown in FIG. 19A. Cavity 440 may be configured to receive inner body 106 during insertion of implant 100 into the treatment site when implant 100 is attached to insertion tool 400. In some embodiments, rotation of inner rod 412 distally translates outer body 102 of implant 100 into the treatment site with respect to inner body 106. As outer body 102 distally translates, inner body 106 may extend outward from proximal end 104*a* of outer body 102. Cavity 440 may receive the portion of inner body 106 extending outward from proximal end 104*a*, such that arms 422*a*, 422*b* of attachment member 410 distally advance with outer body 102 while cavity receives inner body 106. Cavity 440 may have a generally rectangular shape. In some embodiments, cavity 440 may have a hexagonal shape, a cylindrical shape, or any other shape capable of receiving inner body 106. In some embodiments, cavity 440 may be shaped to fit around inner body 106.

Attachment member 410 may define inserter slots 434*a*, 434*b*. Inserter slots may be located between arms 422*a*, 422*b*. Inserter slots 434*a*, 434*b* may extend to arms 422*a*, 422*b*, as shown in FIG. 19B. Inserter slots 434*a*, 434*b* may increase elasticity of a portion of attachment member 410, such that arms 422*a*, 422*b* may flex around outer body 102 and reform to clip into openings 164*a*, 164*b* once outer shaft 404 distally translates onto attachment member 410 to thereby attach implant 100 to insertion tool 400. In some embodiments, openings 164*a*, 164*b* may be defined by depressions 166*a*, 166*b* in outer body pieces 114*a*, 114*b*. Inserter slots 434*a*, 434*b* may allow a portion of attachment member 410 (e.g., arms 422*a*, 422*b*) to flex around outer body 102 to thereby advance arms 422*a*, 422*b* toward depressions 166*a*, 166*b*. Arms 422*a*, 422*b* may then flex back to their original position when outer shaft 404 distally translates onto attachment member 410 to lock clips 438*a*, 438*b* into openings 164*a*, 164*b* in depressions 166*a*, 166*b*, thereby locking implant 100 onto insertion tool 400. Inserter slots 434*a*, 434*b* may be generally T-shaped and extend along a portion of the longitudinal axis $L_2$ (as shown in FIG. 17A).

Attachment member 410 may define a tunnel 442 configured for receiving at least a portion of inner rod 412. Tunnel 442 may connect to cavity 440, as shown in FIG. 19C. Tunnel 442 may be shaped to fit around a distal portion of inner rod 412. In some embodiments, attachment member 410 may define tunnel 442 having a taper 444 matching taper 436 of inner rod 412. Taper 444 may maintain a position of inner rod 412 within attachment member 410. Tunnel 442 may have a generally circular profile, as shown in FIG. 20A. In some embodiments, tunnel 442 may have a generally square profile, rectangular profile, hexagonal profile, or any other profile to fit around inner rod 412. In some embodiments, distal end 414*a* of inner rod 412 may extend from tunnel 442. In some embodiments, distal end 414*a* of inner rod 412 may extend through arms 422*a*, 422*b* of attachment member 410, such that driver head 416 couples to screw head 124 of threaded screw 112 of implant 100 prior to attachment member 410 attaching to implant 100.

Figure 21:
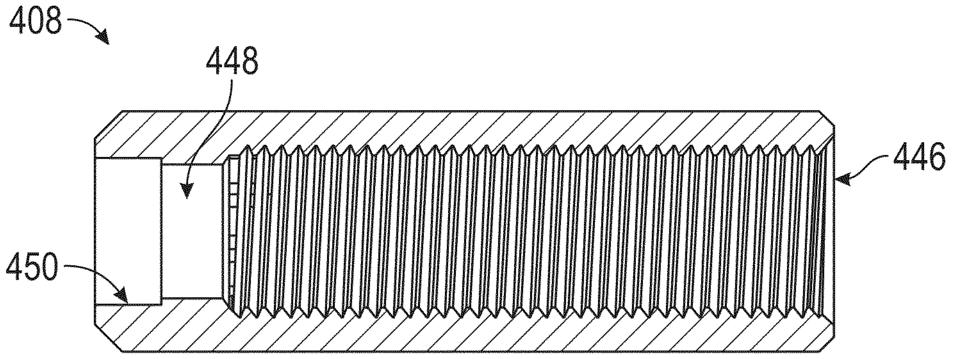
FIG. 21 illustrates a cross-sectional view of some embodiments of an outer grip of the insertion tool.

FIG. 21 illustrates a cross-sectional view of some embodiments of an outer grip 408 of the insertion tool 400. Outer grip 408 may define a threaded bore 446 configured to receive a portion of connector 420, thereby threadedly coupling connector 420 to outer grip 408. In some embodiments, threading on threaded bore 446 may interact with threading on connector 420 as a surgeon or operator rotates outer grip 408 to distally translate outer grip 408 and outer shaft 404 with respect to connector 420, inner shaft 424, and attachment member 410. Outer grip 408 may define an inner through-hole 448 configured to receive a portion of inner shaft 424. Outer grip 408 may define an outer through-hole 450 configured to receive a portion of outer shaft 404. In some embodiments, outer grip 408 may fixedly couple to outer shaft 404 through an interference fit, welding, epoxy, a press fit, or any other coupling mechanism known in the art. In some embodiments, outer shaft 404 may couple to outer grip 408 through a snap fit, threaded fit, or any other coupling mechanism known in the art.

Figure 22:
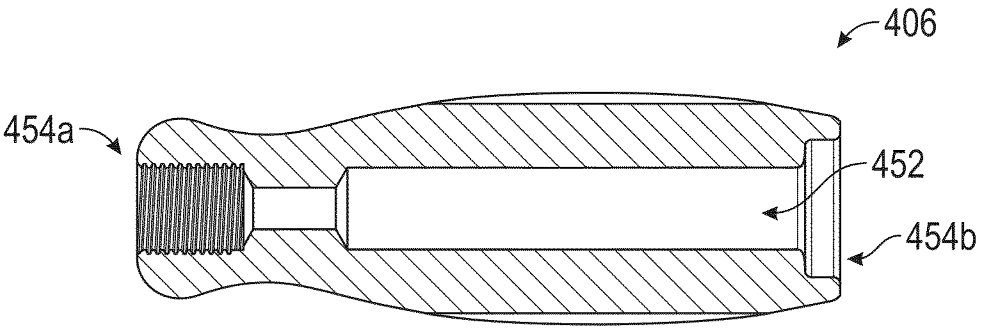
FIG. 22 illustrates a cross-sectional view of some embodiments of a handle of the insertion tool.

FIG. 22 illustrates a cross-sectional view of some embodiments of a handle 406 of insertion tool 400. Handle 406 may define a tunnel 452 configured to receive at least a portion of inner rod 412. Tunnel 452 may extend through handle 406. Handle 406 may define a distal end 454*a* and a proximal end 454*b*. Tunnel 452 may extend from distal end 454*a* to proximal end 454*b*. In some embodiments, tunnel 452 may be threaded at distal end 454*a* and proximate distal end 454*a* of handle 406, such that handle 406 may threadedly couple to connector 420. Outer grip 408 may couple to handle 406 through connector 420. For example, connector 420 may threadedly couple to outer grip 408 and handle 406 to thereby couple outer grip 408 to handle 406.

Figure 23A:
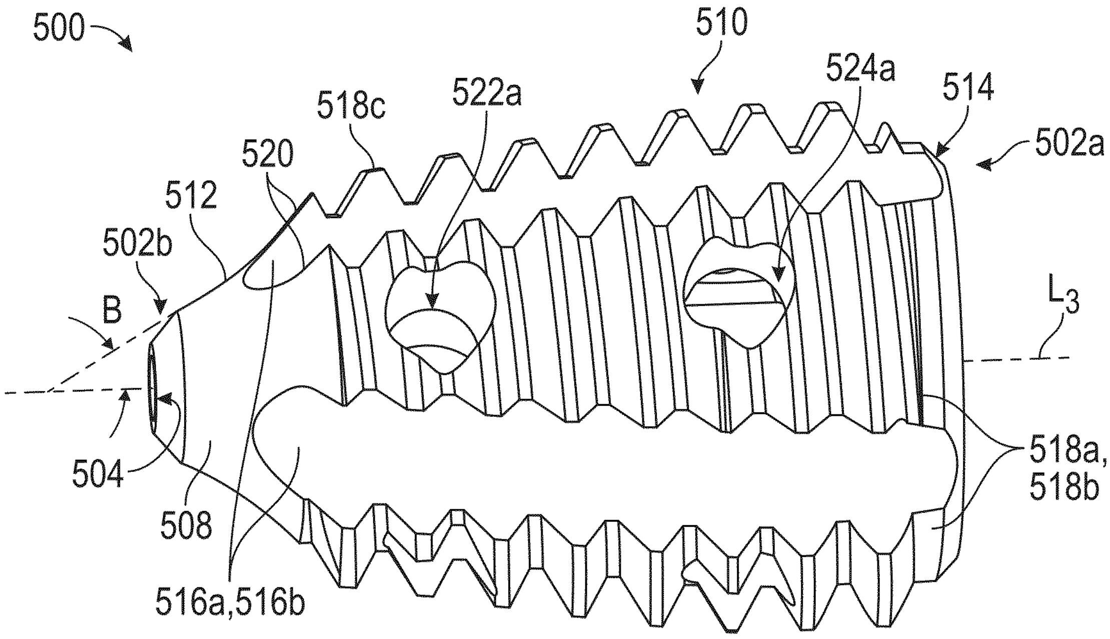
FIG. 23A illustrates a side perspective view of some embodiments of a combined rasp and tap.
Figure 23B:
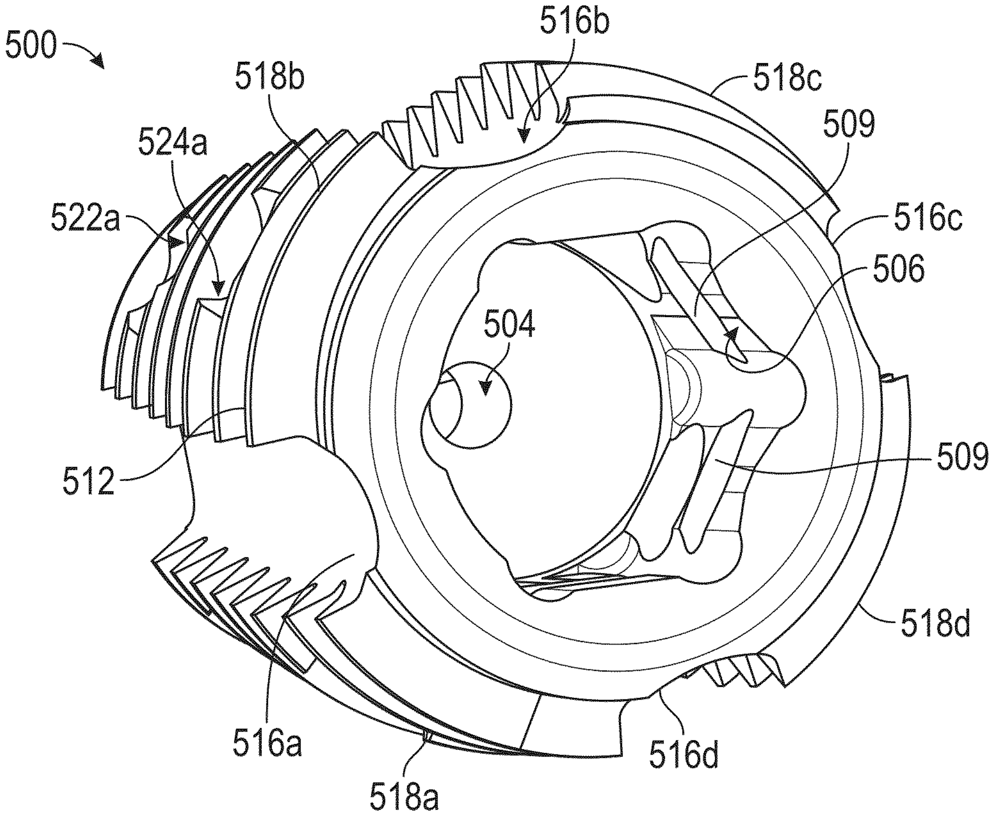
FIG. 23B illustrates a back perspective view of some embodiments of the combined rasp and tap.
Figure 23C:
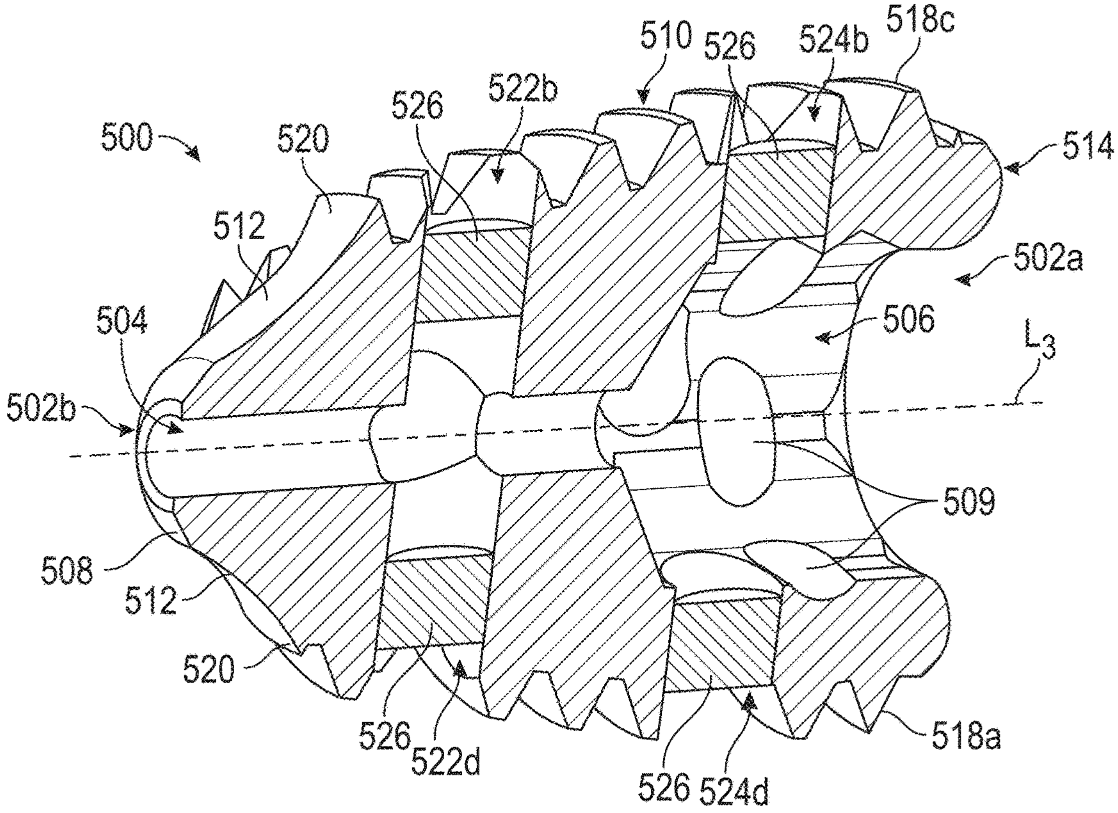
FIG. 23C illustrates a cross-sectional view of some embodiments of the combined rasp and tap.

FIG. 23A illustrates a side perspective view of some embodiments of a combined rasp and tap 500. FIG. 23B illustrates a back perspective view of some embodiments of combined rasp and tap 500. FIG. 23C illustrates a cross-sectional view of some embodiments of combined rasp and tap 500. Accordingly, FIGS. 23A-23C are best viewed together. Combined rasp and tap 500 may be used prior to insertion of implant 100 to both distract and decorticate bone at a joint. Combined rasp and tap 500 may be used prior to insertion of implant 100 to expand the space to receive the implant, remove tissue and/or bone as necessary, and provide sizing information for the implant to the user (e.g., surgeon). Examples of a combined rasp and tap are described in U.S. Pat. No. 11,571,221 and U.S. patent application Ser. No. 18/163,048, which are incorporated by reference in their entirety.

Figure 26:
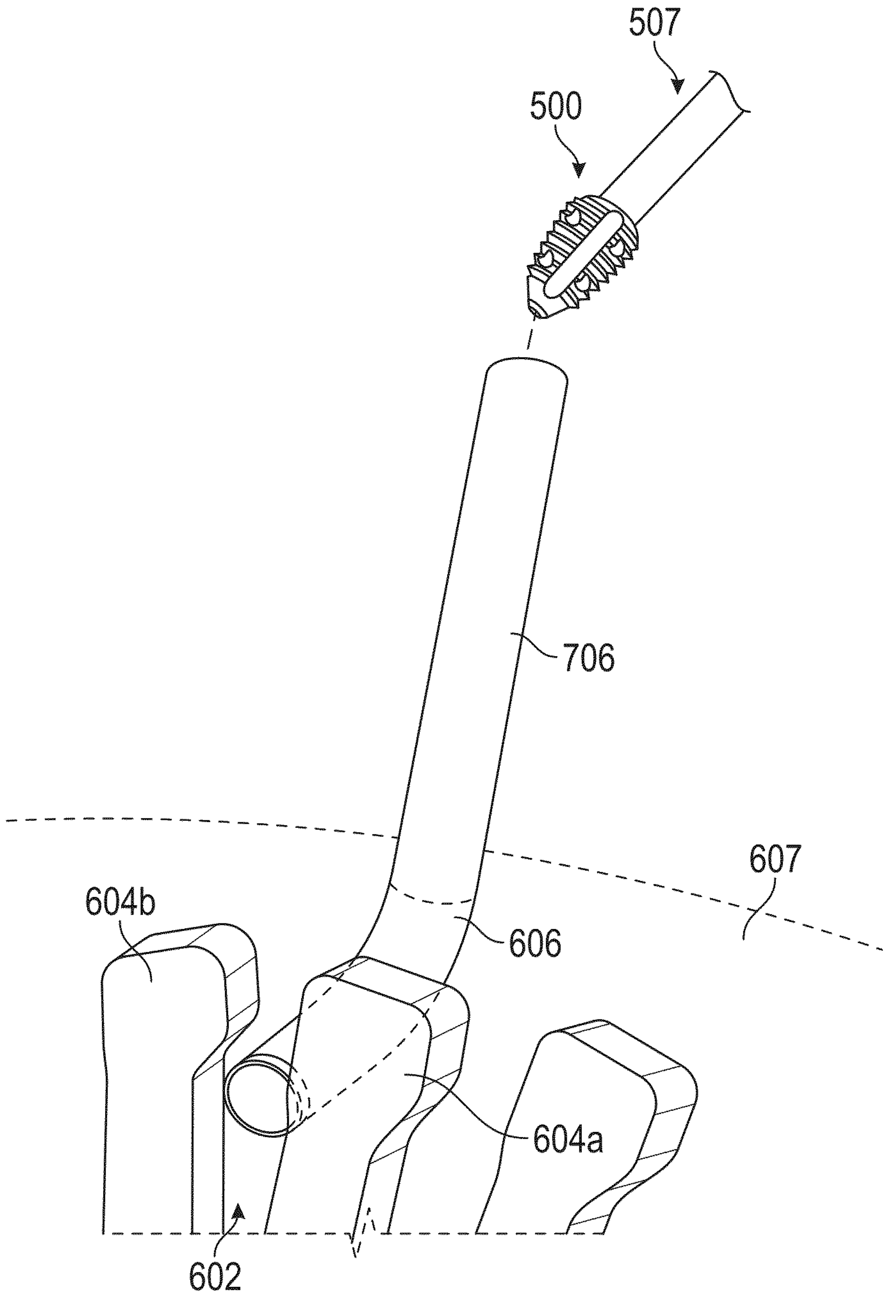
FIG. 26 illustrates insertion of some embodiments of the combined bone rasp and tap up to a target space.

Combined rasp and tap 500 may define central longitudinal axis $L_3$, a proximal end 502*a*, and a distal end 502*b*. Distal end 502*b* may define a lumen 504 extending therefrom. Proximal end 502*a* may define a recess 506 configured to receive an instrument 507 to thereby attach the combined rasp and tap 500 to an instrument 507 (as shown in FIG. 26). Lumen 504 may extend from distal end 502*b* to recess 506, as shown in FIG. 23C. Lumen 504 and recess 506 may be configured to receive a guidewire 702 to guide combined rasp and tap 500 to treatment site, as described further below. Combined rasp and tap 500 may be tapered from the proximal end 502*a* to the distal end 502*b*, such that distal end 502*b* comes to a tip 508. In some embodiments, tip 508 may be sharp, pointed, or substantially rounded. Combined rasp and tap 500 may comprise a proximal section 510 integrated with tip 508. Proximal section 510 may have a sloped wall 512 extending circumferentially from tip 508 and from central longitudinal axis $L_3$ to form an enlarged diameter at proximal section end 514. In some embodiments, sloped wall 512 is sloped at an angle B of about 3 degrees to 25 degrees from the central longitudinal axis $L_3$.

Proximal section 510 may have a diameter of 16 mm to 20 mm at its largest dimension at proximal section end 514. Combined rasp and tap 500 may come in various sizes to accommodate different patients. Combined rasp and tap 500 may have a diameter of 8 mm to 10 mm at its largest dimension at proximal section end 514. Combined rasp and tap 500 may have a diameter of 10 mm to 12 mm at its largest dimension at proximal section end 514. Combined rasp and tap 500 may have a diameter of 12 mm to 16 mm at the largest dimension at proximal section end 514. Combined rasp and tap 500 may be modular and attach to a rod or instrument 507, such that the optimum size of combined rasp and tap 500 may be used for a patient. For example, recess 506 may receive a distal tip of an elongated main body of an insertion instrument, such as insertion instruments described in U.S. Pat. No. 11,766,280; U.S. patent application Ser. No. 17/716,822; U.S. Pat. No. 11,510,710; which are incorporated by reference in their entirety. In some embodiments, recess 506 may receive arms 422*a*, 422*b* of attachment member 410 of insertion tool 400. Recess 506 may define grooves 509 configured to interact with protrusions on a rod or insertion instrument to thereby secure combined rasp and tap 500 on the rod or insertion instrument. In some embodiments, recess 506 may couple to an instrument 507 through a quick-connect connection known in the art to thereby attach combined rasp and tap 500 to instrument 507 for inserting through an introducer sleeve or dilator (as shown in FIG. 26). In some embodiments, instrument 507 may be configured to receive a guidewire 702 when combined rasp and tap 500 and instrument 507 is inserted through an introducer sleeve 706, as further described below. In some embodiments, recess 506 may couple to instrument 507 through an interference fit. In some embodiments, recess 506 may couple to driver head 416 of insertion tool 400, such that insertion tool 400 may be used to insert combined rasp and tap 500 into patient. Combined rasp and tap 500 may be generally conically shaped, with proximal section end 514 forming the base of the conical shape.

Outer surface of sloped wall 512 may include a plurality of longitudinal channels 516*a*, 516*b*, 516*c*, 516*d* and a plurality of threaded sections 518*a*, 518*b*, 518*c*, 518*d*. In some embodiments, the longitudinal channels 516*a*, 516*b*, 516*c*, 516*d* may be evenly spaced between threaded sections 518*a*, 518*b*, 518*c*, 518*d*. In some embodiments, outer surface of sloped wall 512 may include four longitudinal channels 516*a*, 516*b*, 516*c*, 516*d* evenly spaced between four threaded sections 518*a*, 518*b*, 518*c*, 518*d*, such that longitudinal channels 516*a*, 516*b*, 516*c*, 516*d* may be spaced 90 degrees apart circumferentially. In some embodiments, longitudinal channels 516*a*, 516*b*, 516*c*, 516*d* may be straight and align with the central longitudinal axis $L_3$. In some embodiments, each longitudinal channel 516*a*, 516*b*, 516*c*, 516*d* may include a slight turn at the distal end thereof, creating a sharpened distal cutting flute 520. Cutting flutes 520 act as a self-drilling feature to reduce the amount of insertion force needed to start insertion of the combined rasp and tap 500 into the treatment site (e.g., interspinous process space).

In some embodiments, longitudinal channels 516*a*, 516*b*, 516*c*, 516*d* may be curved such that they rotate around the outer surface of sloped wall 512. In some embodiments, edges of the longitudinal channels 516*a*, 516*b*, 516*c*, 516*d* may be sharpened to create flutes for facilitating distracting and/or decorticating of bone or tissue as the combined rasp and tap 500 are inserted into the treatment site.

As shown in FIGS. 23A and 23C, combined rasp and tap 500 may define a first set of lateral hollows 522*a*, 522*b*, 522*c*, 522*d* and a second set of lateral hollows 524*a*, 524*b*, 524*c*, 524*d*, each extending through threaded sections 518*a*, 518*b*, 518*c*, 518*d*. A first set of lateral hollows 522*a*, 522*b*, 522*c*, 522*d* may be located proximate distal end 502*b* of combined rasp and tap 500 and extend into lumen 504. A second set of lateral hollows 524*a*, 524*b*, 524*c*, 524*d* may be located proximate proximal end 502*a* of combined rasp and tap 500 and extend into recess 506. The lateral hollows 522*a*, 522*b*, 522*c*, 522*d*, 524*a*, 524*b*, 524*c*, 524*d* may extend orthogonal to the central longitudinal axis $L_3$. In some embodiments, lateral hollows 522*a*, 522*b*, 522*c*, 522*d*, 524*a*, 524*b*, 524*c*, 524*d* may extend at an angle relative to the longitudinal axis $L_3$ such that they each form a V-shape. In some embodiments, lateral hollows 522*a*, 522*b*, 522*c*, 522*d*, 524*a*, 524*b*, 524*c*, 524*d* may be spaced symmetrically about the combined rasp and tap 500.

Each of the lateral hollows 522*a*, 522*b*, 522*c*, 522*d*, 524*a*, 524*b*, 524*c*, 524*d* are spaced along the combined rasp and tap 500 so as to denote the size of implant 100 to be used. In some embodiments, the outer ends of lateral hollows 522*a*, 522*b*, 522*c*, 522*d*, 524*a*, 524*b*, 524*c*, 524*d* may be located such that they correspond to an 8 mm minor diameter of the combined rasp and tap 500 and thereby correspond to an implant size of 8 mm. The outer ends of lateral hollows 522*a*, 522*b*, 522*c*, 522*d*, 524*a*, 524*b*, 524*c*, 524*d* may be located such that they correspond to a 10 mm minor diameter of the combined rasp and tap 500 and thereby correspond to an implant size of 10 mm. The outer ends of lateral hollows 522*a*, 522*b*, 522*c*, 522*d*, 524*a*, 524*b*, 524*c*, 524*d* may be located such that they correspond to a 12 mm minor diameter of the combined rasp and tap 500 and thereby correspond to an implant size of 12 mm. The outer ends of lateral hollows 522*a*, 522*b*, 522*c*, 522*d*, 524*a*, 524*b*, 524*c*, 524*d* may be located such that they correspond to a 14 mm minor diameter of the combined rasp and tap 500 and thereby correspond to an implant size of 14 mm. The outer ends of lateral hollows 522*a*, 522*b*, 522*c*, 522*d*, 524*a*, 524*b*, 524*c*, 524*d* may be located such that they correspond to a 16 mm minor diameter of the combined rasp and tap 500 and thereby correspond to an implant size of 16 mm.

The lateral hollows 522*a*, 522*b*, 522*c*, 522*d*, 524*a*, 524*b*, 524*c*, 524*d* may be seen under fluoroscopy such that a user (e.g., surgeon) may choose the appropriate size implant. In some embodiments, a fluorescent material or other visible markings may be placed at particular spaced locations along combined rasp and tap 500 to demarcate the implant sizes. In some embodiments, all or part of combined rasp and tap 500 may be composed of titanium or titanium alloy. In some embodiments, all or part of combined rasp and tap 500 may be composed of stainless steel. In some embodiments, all or part of combined rasp and tap 500 may be composed of a polymer or a bioabsorbable material.

In some embodiments, radiopaque or radiolucent material 526 may be inserted into the lateral hollows 522*a*, 522*b*, 522*c*, 522*d*, 524*a*, 524*b*, 524*c*, 524*d* such that the locations of lateral hollows 522*a*, 522*b*, 522*c*, 522*d*, 524*a*, 524*b*, 524*c*, 524*d* may be viewable for sizing. As shown in FIG. 23C, the radiopaque or radiolucent material 526 may form peg-like structures inserted into lateral hollows 522*a*, 522*b*, 522*c*, 522*d*, 524*a*, 524*b*, 524*c*, 524*d*. Radiopaque or radiolucent material 526 may extend partially through lateral hollows 522*a*, 522*b*, 522*c*, 522*d*, 524*a*, 524*b*, 524*c*, 524*d* such that the radiopaque or radiolucent material 526 does not obstruct the lumen 504. In some embodiments, material 526 may be inserted into some or all of the lateral hollows 522*a*, 522*b*, 522*c*, 522*d*, 524*a*, 524*b*, 524*c*, 524*d*.

In some embodiments, combined rasp and tap 500 may be manufactured by an additive manufacturing process. In some embodiments, combined rasp and tap 500 may be manufactured by machining or molding. In some embodiments, all or part of combined rasp and tap 500 may include a coating on at least one surface thereof. In some embodiments, the outer surface of combined rasp and tap 500 may be coated with a friction-reducing coating, such as chrome.

Figure 24:
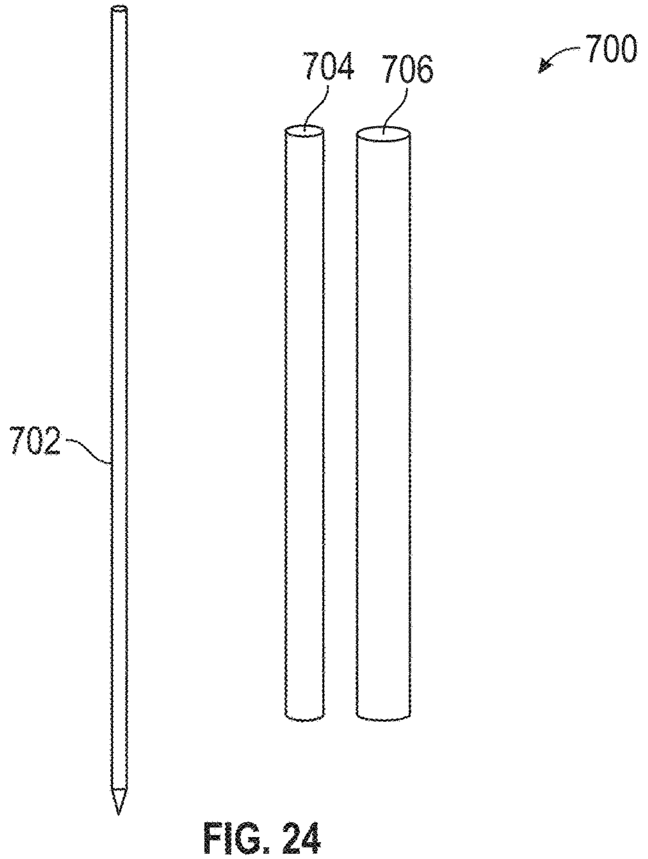
FIG. 24 illustrates exemplary tools for a surgical kit for inserting some embodiments of the implant and preparing a target space for insertion of some embodiments of the implant.

FIG. 24 illustrates exemplary tools for a surgical kit for inserting some embodiments of implant 100 and preparing a target space for insertion of some embodiments of implant 100. An exemplary set of tools 700 is illustrated for preparing a target space (e.g., interspinous process space) for insertion of an implant 100 for some embodiments of the present disclosure. In some embodiments, one or more tools 700 may be provided as part of a surgical kit along with implant 100 and/or insertion tool 400 and/or combined rasp and tap 500 for stabilization of a target space, such as interspinous process space 602 (as shown in FIG. 26).

Figure 28:
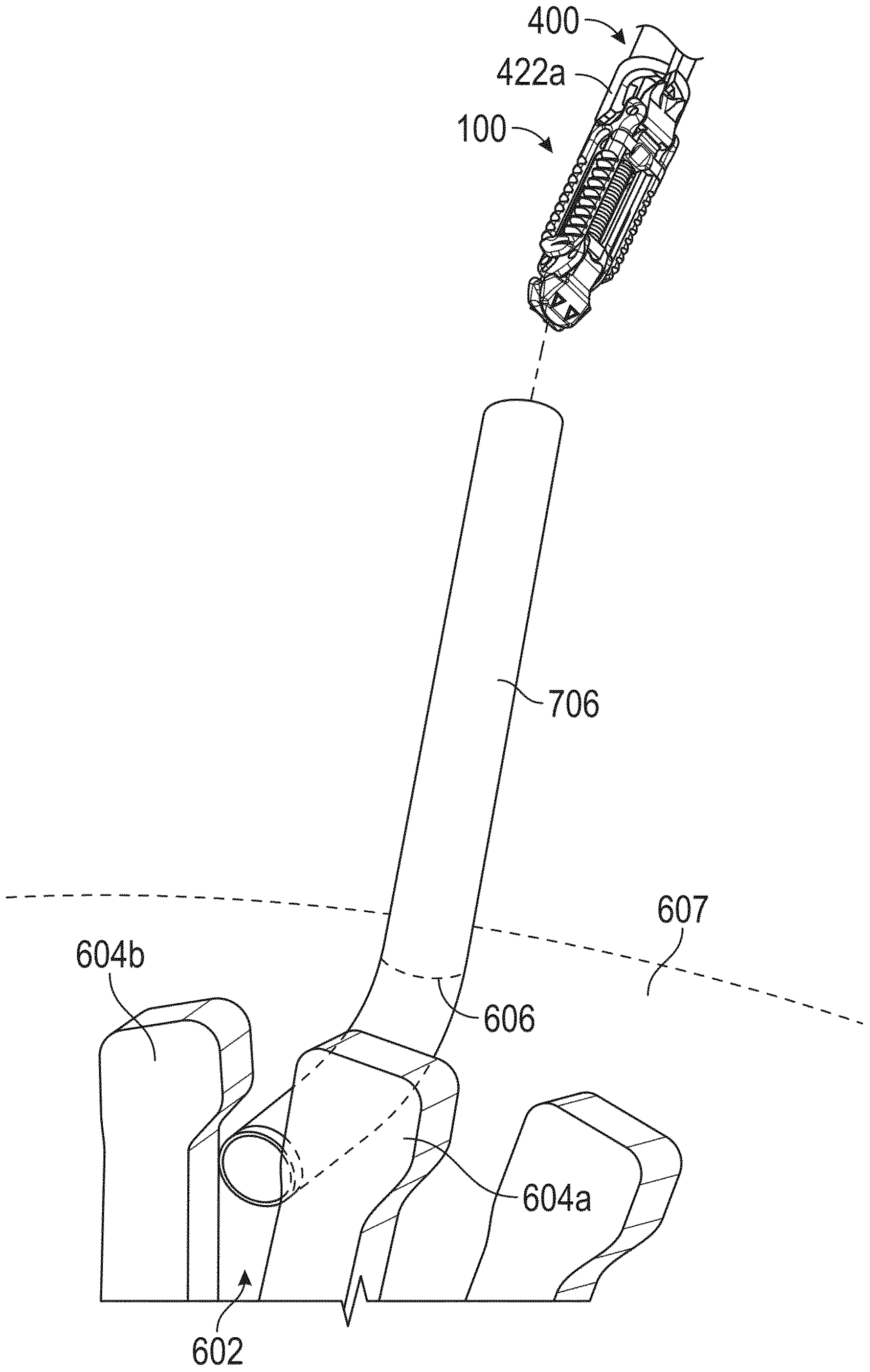
FIG. 28 illustrates insertion of some embodiments of the system through an introducer sleeve, with an outer shaft of the insertion tool removed.

In some embodiments, tools 700 may comprise a guidewire 702. Guidewire 702 may be inserted into a minimally invasive incision and, under fluoroscopy, guidewire 702 may be advanced to locate the target space where it is desired to place implant 100. Combined rasp and tap 500 may be inserted over guidewire 702 to guide the combined rasp and tap 500 up to the treatment site, as further described herein. In some embodiments, tools 700 may comprise one or more dilators 704. Dilators 704 may be hollow tubes that are placed over guidewire 702 to create a working channel for insertion of implant 100 or combined rasp and tap 500. Dilators 704 may be provided in increasing sizes such that a larger sized dilator 704 may be placed over a smaller-sized dilator to dilate soft tissues between the incision and the target space (also referred to as the treatment site), such as interspinous process space 602. Tools 700 may comprise an introducer sleeve 706 used for guiding the combined rasp and tap 500 and/or implant 100 attached to insertion tool 400 up to the target space, such as interspinous process space 602 (as shown in FIGS. 26 and 28). Introducer sleeve 706 may be advanced through the working channel created by dilators 704. As shown in FIGS. 26 and 28, introducer sleeve 706 may be curved to provide an insertion path for a surgical procedure using a posterior percutaneous approach. In some embodiments and as shown in FIGS. 29A, introducer sleeve 706 may be straight to provide an insertion path for a surgical procedure using a lateral percutaneous approach. Combined rasp and tap 500 may be inserted through introducer sleeve 706 and up to the treatment site, such as up to the interspinous process space 602, as shown in FIG. 26. In some embodiments, implant 100 and insertion tool 400 may be inserted through introducer sleeve 706 when inserting implant 100 into the treatment site, as shown in FIG. 28. It will be appreciated that various other tools may be provided with a surgical kit for stabilization of a target space without departing from the scope hereof.

Implant Insertion Method

Figure 25:
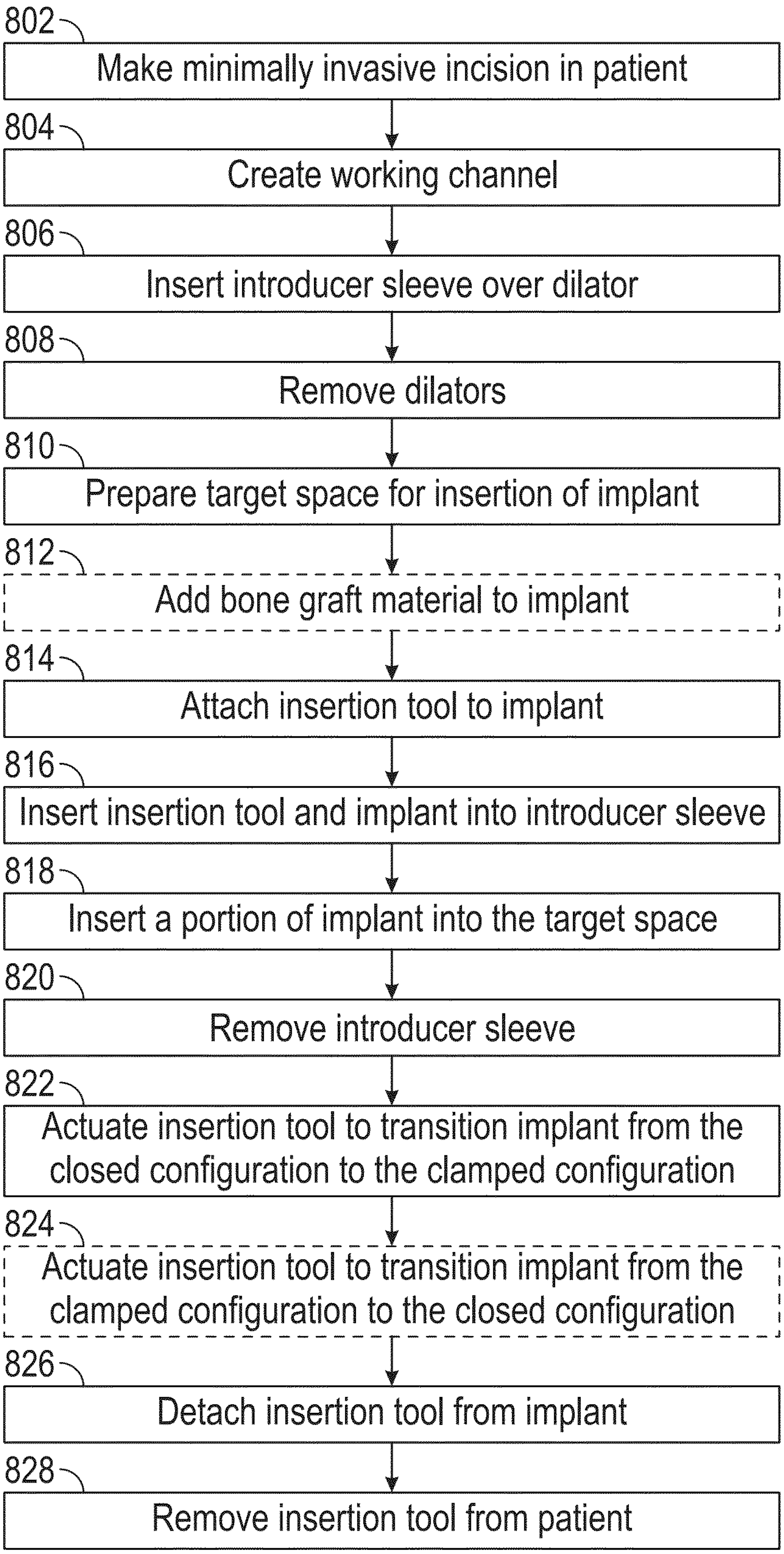
FIG. 25 illustrates a method for inserting the implant into a target space in accordance with embodiments of the present disclosure.
Figure 27:
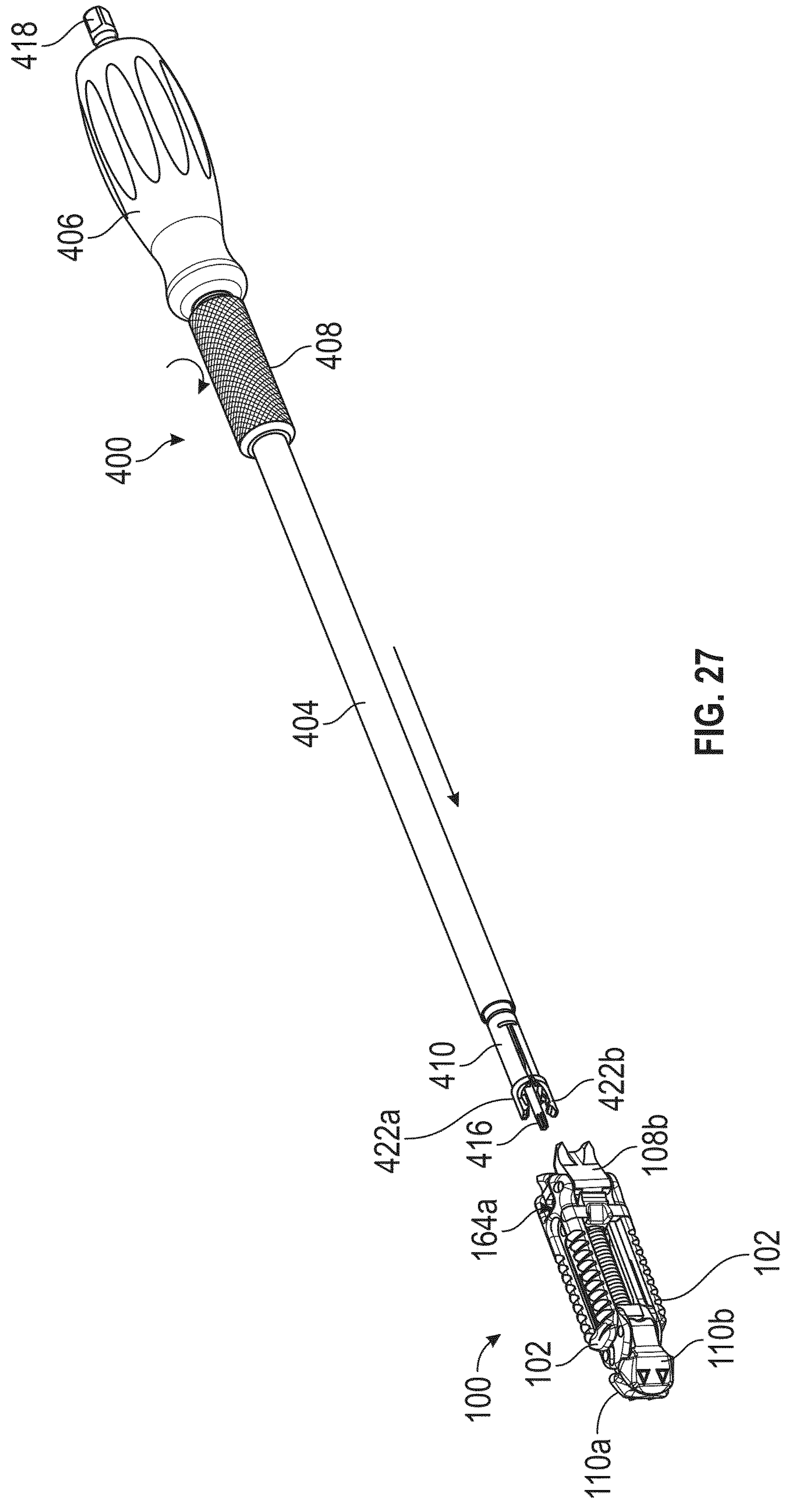
FIG. 27 illustrates some embodiments of components of a system configured to insert the implant into a target space.

FIG. 25 illustrates a method 800 for inserting implant 100 into a target space (also referred to as treatment site) in accordance with embodiments of the present disclosure. Method 800 may be embodied as instructions provided with a surgical kit in some embodiments. The surgical kit may include implant 100, insertion tool 400, combined rasp and tap 500, and tools 700. FIG. 26 illustrates insertion of some embodiments of a combined bone rasp and tap 500 up to a target space. FIG. 27 illustrates some embodiments of components of a system configured to insert implant 100 into a treatment site. The system may comprise insertion tool 400 and implant 100. FIG. 27 illustrates insertion tool 400 prior to attachment to implant 100. FIG. 28 illustrates insertion of some embodiments of the system through an introducer sleeve 706, with outer shaft 404 of insertion tool 400 removed. The system may comprise implant 100 and insertion tool 400. FIG. 29A illustrates a top cross-sectional view of some embodiments of implant 100 partially inserted into a target space in the closed configuration, with the implant 100 attached to the insertion tool 400 and the outer shaft 404 removed. FIG. 29B illustrates a top cross-sectional view of some embodiments of implant 100 partially inserted into a target space in an intermediate position, with the implant 100 attached to the insertion tool 400 and the outer shaft 404 removed. FIG. 29C illustrates a top cross-sectional view of some embodiments of implant 100 inserted in a target space in the clamped configuration with a portion of attachment member 410 removed and outer shaft 404 removed. Accordingly, FIGS. 25-29C are best viewed together.

Method 800 may provide steps for inserting implant 100 into a target space, such as interspinous process space 602. In some embodiments, implant 100 is inserted between adjacent spinous processes 604*a*, 604*b*, as shown in FIGS. 28-29C. Method 800 may begin at a step 802 where a minimally invasive incision 606 may be made on the patient 607. Minimally invasive incisions reduce blood loss, recovery time, and hospital stay, among other benefits, as compared to open surgery. However, it is contemplated that embodiments herein may be practiced in an open surgery without departing from the scope hereof. In some embodiments, the minimally invasive incision is made to provide posterior access to the target space such that implant 100 may be inserted into the target space via a posterior approach. As shown in FIGS. 26 and 28, minimally invasive incision 606 may be made to provide posterior access to the target space, such as to interspinous process space 602. The patient may be placed in a prone position to provide posterior access to the target space. In some embodiments, the minimally invasive incision 606 is made to provide lateral access to the target space such that implant 100 may be inserted into the target space via a lateral approach, such as the lateral approach shown in FIGS. 29A-29C.

Next, at step 804, a working channel for inserting implant 100 may be created. In some embodiments, the working channel is created by successively inserting one or more dilators 704 over a guidewire 702 that is inserted into the target space (e.g., interspinous process space) to dilate soft tissues surrounding the target space. The guidewire 702 may be inserted by tapping or any other method as will be appreciated by one of skill in the art. Thereafter, at step 806, introducer sleeve 706 may be inserted over dilators 704. At step 808, dilators 704 may be removed such that only introducer sleeve 706 remains in the working channel. The dilators 704 and introducer sleeve 706 may be tubes or other hollow bodies that provide a pathway for inserting combined rasp and tap 500, implant 100, and insertion tool 400 therein to access the target space, such as interspinous process space 602.

At step 810, one or more site preparation steps may be taken to prepare the target space for insertion of implant 100. In some embodiments, combined rasp and tap 500 may be inserted into introducer sleeve 706 to advance combined rasp and tap 500 up to the treatment site, such as interspinous process space 602. As shown in FIG. 26, combined bone rasp and tap 500 may couple to instrument 507 such that instrument 507 and combined bone rasp and tap 500 may be inserted into introducer sleeve 706 up to the treatment site. Lumen 504 of combined bone rasp and tap 500 and a lumen of instrument 507 may receive guidewire 702, such that combined bone rasp and tap 500 and instrument 507 may be inserted over a guidewire. During a surgical procedure implementing a posterior approach, instrument 507 may be curved to fit within a curved introducer sleeve 706, such as introducer sleeve 706 illustrated in FIG. 26. During a surgical procedure implementing a lateral approach, instrument 507 may be straight to fit within a straight introducer sleeve, such as introducer sleeve 706 illustrated in FIG. 28.

Once at the treatment site, combined rasp and tap 500 may be rotated to distract bones adjacent to the treatment site, remove ligaments at the treatment site, and partially decorticate the bones for stimulating bone growth. For example, combined rasp and tap 500 may distract spinous processes 604*a*, 604*b*, remove a portion of the interspinous ligament between adjacent spinous processes 604*a*, 604*b*, and partially decorticate spinous processes 604*a*, 604*b* for stimulating bone growth. Instrument 507 may be rotated clockwise to gradually decorticate and/or distract the bones adjacent to the treatment site. Combined rasp and tap 500 may thread into interspinous process space 602 such that threaded sections 518*a*, 518*b*, 518*c*, 518*d* engage with spinous processes 604*a*, 604*b* and tap a path for implant 100 to be inserted along. The degree of distraction may be determined by viewing which lateral hollow 522*a*, 522*b*, 522*c*, 522*d*, 524*a*, 524*b*, 524*c*, 524*d* is positioned between spinous processes 604*a*, 604*b* under fluoroscopy. The degree of distraction may determine the appropriate implant size, which may be 8 mm, 10 mm, 12 mm, 14 mm, or 16 mm. After viewing lateral hollows 522*a*, 522*b*, 522*c*, 522*d*, 524*a*, 524*b*, 524*c*, 524*d* under fluoroscopy to determine the appropriate implant size, combined rasp and tap 500 and instrument 507 may be removed from introducer sleeve 706.

At an optional step 812, bone graft material may be added to implant 100 prior to insertion into the patient. Bone graft material may be applied around the threading 168 of outer body 102. In some embodiments, bone graft material may be added by injecting bone graft material into outer body 102 or inner body 106 of implant 100. At step 814, implant 100 may be attached to insertion tool 400 in the closed configuration, as shown in FIGS. 27-28. Attaching insertion tool 400 to implant 100 may include coupling driver head 416 to screw head 124 of implant 100. Outer grip 408 of insertion tool 400 may be rotated in a first direction to advance outer shaft 404 onto attachment member 410 to cause arms 422*a*, 422*b* to clip into openings 164*a*, 164*b* of outer body 102 to thereby lock implant 100 onto insertion tool 400.

At step 816, implant 100 and insertion tool 400 may be inserted into introducer sleeve 706, as shown in FIGS. 28-29A. Insertion tool 400 may be curved to fit within introducer sleeve 706 during a surgical procedure implementing a posterior approach, as shown in FIG. 28. Insertion tool 400 may be straight to fit within a straight introducer sleeve 706 during a surgical procedure implementing a lateral approach, as shown in FIG. 29A. At step 818, implant 100 may be partially inserted into the treatment site, such as interspinous process space 602. Implant 100 may be partially inserted into the treatment site by distally pushing insertion tool 400 such that a portion of each arm 208*a*, 208*b* of distal wings 110*a*, 110*b* is positioned within the target space, such as within interspinous process space 602, as shown in FIG. 29A. Clamps 210*a*, 210*b* may be pushed through interspinous process space 602 and positioned on a distal side 608*a*, 608*b* of spinous processes 604*a*, 604*b*. At step 820, introducer sleeve 706 may be removed.

At step 822, insertion tool 400 may be actuated to transition the implant 100 from the closed configuration to the clamped configuration. Insertion tool 400 may be actuated to transition the implant 100 from the closed configuration to the deployed configuration, and finally to the clamped configuration. Actuation of insertion tool 400 may include rotating an inner rod 412 to rotate driver head 416 in a first direction to transition proximal wings 108*a*, 108*b* and distal wings 110*a*, 110*b* from a closed configuration to a deployed configuration. Rotating driver head 416 in a first direction may cause threaded screw 112 to rotate in a first direction. Rotating threaded screw 112 in a first direction may cause threaded screw 112 to distally translate toward and push distal wings 110*a*, 110*b* to thereby pivot distal wings 110*a*, 110*b* from the closed configuration, as shown in FIG. 29B. Rotating inner rod 412 in a first direction may cause outer body 102, proximal carrier 144, and proximal wings 108*a*, 108*b* to distally translate. Distal translation of outer body 102 may cause threading 168 to engage with bone and/or soft tissue at the target space to stabilize the implant 100 within the target space. Proximal wings 108*a*, 108*b* may contact ramps 174*a*, 174*b* of inner body 106 when proximal wings 108*a*, 108*b* are distally translated to thereby pivot proximal wings 108*a*, 108*b* from the closed configuration. Proximal wing protuberances 196*a*, 196*b*, 196*c*, 196*d* may interact with inner body grooves 176*a*, 176*b*, 176*c*, 176*d* to pivot proximal wings 108*a*, 108*b* from the closed configuration to the deployed configuration. Proximal wings 108*a*, 108*b* may pivot distally outward toward the distal end 104*b* of the outer body 102 and distal wings 110*a*, 110*b* may pivot proximally outward toward the proximal end 104*a* of the outer body 102 when transitioning from the closed configuration to the deployed configuration. In some embodiments, proximal wings 108*a*, 108*b* may pivot distally outward toward the outer body 102 and distal wings 110*a*, 110*b* may pivot proximally outward toward the outer body 102. Spikes 214*a*, 214*b*, 214*c*, 214*d* of distal wings 110*a*, 110*b* may engage with bone and/or tissue at the treatment site when implant 100 is in the deployed configuration. In some embodiments, spikes 214*a*, 214*b*, 214*c*, 214*d* may engage with distal sides 608*a*, 608*b* of adjacent spinous processes 604*a*, 604*b* in the deployed configuration such that distal wings 110*a*, 110*b* deploy on distal sides 608*a*, 608*b* of adjacent spinous processes.

Ridges 212*a*, 212*b* of clamps 210*a*, 210*b* may grip bone or tissue at the treatment site as distal wings 110*a*, 110*b* transition from the closed configuration to the deployed configuration to facilitate pulling implant 100 into the target space. For example and as shown in FIG. 29B, ridges 212*a*, 212*b* of clamps 210*a*, 210*b* may grip adjacent spinous processes 604*a*, 604*b* as distal wings 110*a*, 110*b* pivot from the closed configuration to the deployed configuration (not shown) to facilitate pulling implant 100 into interspinous process space 602. The implant 100 may be fully inserted into the treatment site (e.g., interspinous process space 602) when the implant 100 is in the deployed configuration. FIG. 29B shows implant 100 in an intermediate position as implant transitions from the closed configuration to the deployed configuration.

Actuating insertion tool 400 may transition the implant 100 from the deployed configuration to the clamped configuration. In some embodiments, once proximal wings 108*a*, 108*b* are in the deployed configuration, continuing to rotate inner rod 412 in the first direction may cause protuberances 196*a*, 196*b*, 196*c*, 196*d* to distally move along translation surfaces 172*a*, 172*b*, 172*c*, 172*d*. Thereby, proximal wings 108*a*, 108*b* distally advance toward bones or tissue at the treatment site to engage with bone and/or tissue at the treatment site. For example and as shown in FIG. 29C, proximal wings 108*a*, 108*b* may distally translate toward bones and/or tissue near the interspinous process space 602 and engage with a proximal side 610*a*, 610*b* of adjacent spinous processes 604*a*, 604*b* when implant 100 is in the clamped configuration. Distal wings 110*a*, 110*b* and proximal wings 108*a*, 108*b* may engage with bone and/or tissue at the treatment site when implant 100 is in the clamped configuration. In some embodiments, proximal wings 108*a*, 108*b* may engage with proximal sides 610*a*, 610*b* of adjacent spinous processes 604*a*, 604*b* when implant 100 is in the clamped configuration, as shown in FIG. 29C. In some embodiments, extensions 202*a*, 202*b*, 202*c*, 202*d* may engage with bone and/or tissue at and/or near the treatment site when implant 100 is in the clamped configuration. In some embodiments, tips 204*a*, 204*b*, 204*c*, 204*d* of extensions may engage with bone and/or tissue at the treatment side when implant 100 is in the clamped configuration. Distal wings 110*a*, 110*b* engaging with bone and/or tissue at the treatment site may form a distal anchor and proximal wings 108*a*, 108*b* engaging with bone and/or tissue at the treatment site may form a proximal anchor to thereby stabilize implant 100 within the target space, such as within the interspinous process space 602.

During rotation of inner rod 412 in a first direction to deploy implant 100, outer body 102 may distally translate with threaded screw 112 relative to inner body 106 such that inner body 106 extends outward from proximal end 104*a* of outer body 102. For example and as shown in FIG. 29C, inner body piece 116*b* extends outward from proximal end of outer body piece 114*b*. As inner rod 412 is rotated in a first direction, inserter slots 434*a*, 434*b* may receive at least part of inner body 106. At least a portion of outer body 102 may be located in the interspinous process space between adjacent spinous processes 604*a*, 604*b* when implant 100 is in the clamped configuration. For example and as shown in FIG. 29C, at least a portion of outer body piece 114*b* may be located in the interspinous process space between adjacent spinous processes 604*a*, 604*b* when implant is in the clamped configuration. Rotation of inner rod 412 of insertion tool 400 in a first direction may distally translate outer body 102 into the treatment site when transitioning implant 100 from the closed configuration to the clamped configuration.

At optional step 824, insertion tool 400 may be actuated to transition the implant 100 from the clamped configuration to the closed configuration. Insertion tool 400 may be actuated to transition the implant 100 from the clamped configuration to the deployed configuration, and finally to the closed configuration. Actuation of insertion tool 400 may include rotating an inner rod 412 in a second direction to transition proximal wings 108*a*, 108*b* and distal wings 110*a*, 110*b* from the deployed position or clamped position to the closed position. Rotating inner rod 412 in a second direction may cause threaded screw 112 to rotate in a second direction and thereby proximally translate away from distal wings 110*a*, 110*b* to thereby cause distal wings 110*a*, 110*b* to pivot from the deployed configuration or clamped configuration to the closed configuration. Rotating inner rod 412 in a second direction may cause outer body 102, proximal carrier 144, and proximal wings 108*a*, 108*b* to proximally translate away from the target space. Proximal translation of proximal wings 108*a*, 108*b* may cause protuberances 196*a*, 196*b*, 196*c*, 196*d* to proximally translate along translation surfaces 172*a*, 172*b*, 172*c*, 172*d* and into inner body grooves 176*a*, 176*b*, 176*c*, 176*d*. Proximal wing protuberances 196*a*, 196*b*, 196*c*, 196*d* may interact with sides of inner body grooves 176*a*, 176*b*, 176*c*, 176*d* to pivot proximal wings 108*a*, 108*b* from the deployed configuration to the closed configuration. Proximal wings 108*a*, 108*b* may pivot proximally inward toward proximal end 104*a* of outer body 102 and distal wings 110*a*, 110*b* may pivot distally inward toward distal end 118*b* of inner body 106 when transitioning from the deployed configuration to the closed configuration.

At step 826, insertion tool 400 may be detached from implant 100. In some embodiments, insertion tool 400 may be detached from implant 100 by rotating outer grip 408 in a second direction to proximally translate outer shaft 404 away from attachment member 410 to thereby allow arms 422*a*, 422*b* to flex away from outer body 102 such that implant 100 detaches from attachment member 410. Proximal translation of outer shaft 404 may cause arms 422*a*, 422*b* to dislodge from openings 164*a*, 164*b* to thereby detach implant 100 from insertion tool 400. At step 828, insertion tool 400 may be removed from the patient.

Figure 30:
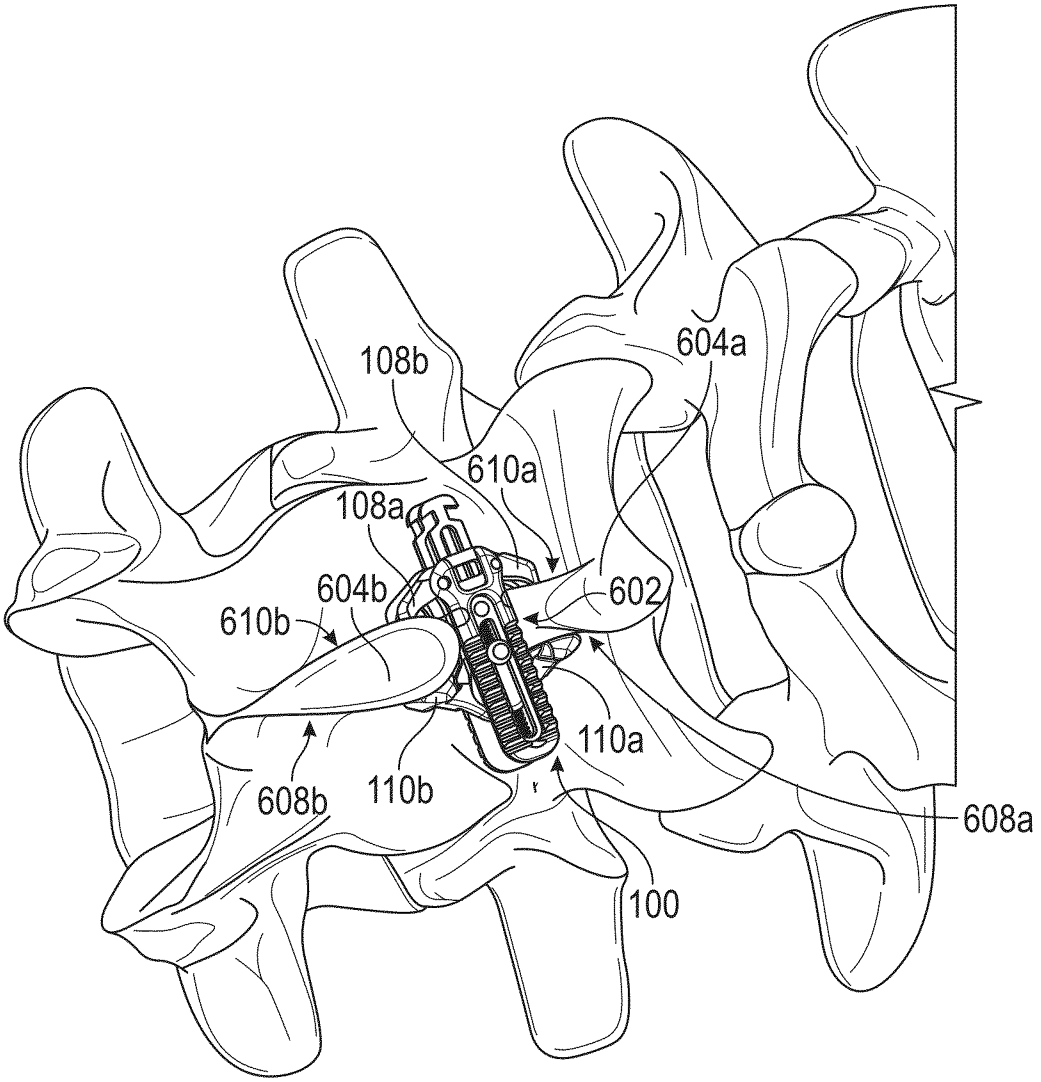
FIG. 30 illustrates a perspective view of some embodiments of the implant in a clamped configuration, inserted in the spine of a patient.

FIG. 30 illustrates a perspective view of some embodiments of the implant 100 in a clamped configuration, inserted in the spine of a patient. As shown in FIG. 30, distal wings 110*a*, 110*b* may anchor to distal sides 608*a*, 608*b* of adjacent spinous processes 604*a*, 604*b* when in a clamped configuration in interspinous process space 602. Proximal wings 108*a*, 108*b* may anchor to proximal sides 610*a*, 610*b* of adjacent spinous processes 604*a*, 604*b* when in a clamped configuration in interspinous process space 602. Distal wings 110*a*, 110*b* and proximal wings 108*a*, 108*b* thereby provide anchors for maintaining implant 100 in place at the treatment site. Implant 100 may be used for stabilization and fusion of other bony structures and/or joints within the body. For example, implant 100 may anchor to any adjacent bony structures and/or soft tissue to stabilize bony structures and/or joints. Implant 100 may be inserted in an SI joint space to fixate bone at the SI joint and/or stabilize the SI joint.

Second Implant Embodiment

Figure 31A:
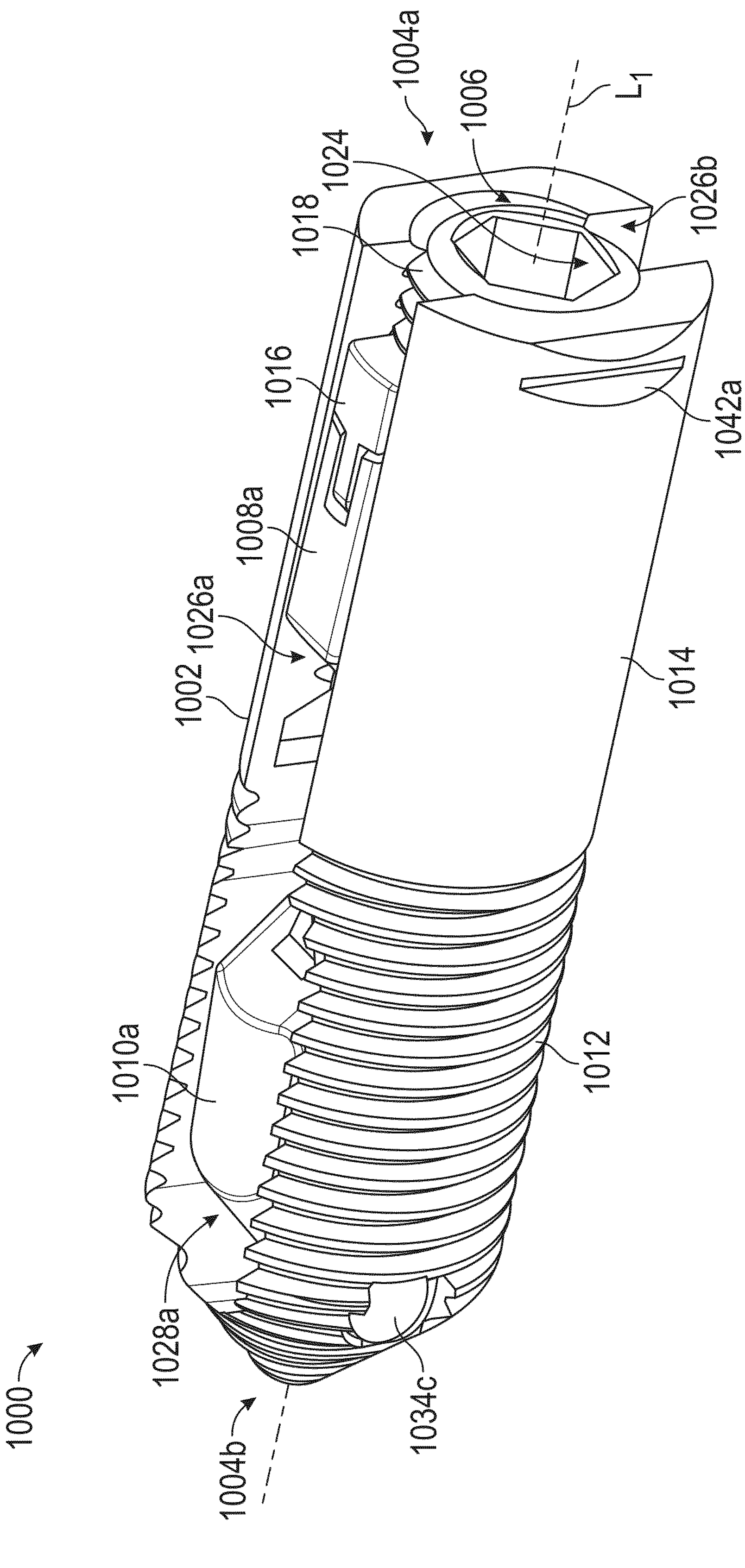
FIG. 31A illustrates a perspective view of a second embodiment of an implant in a closed position.
Figure 31B:
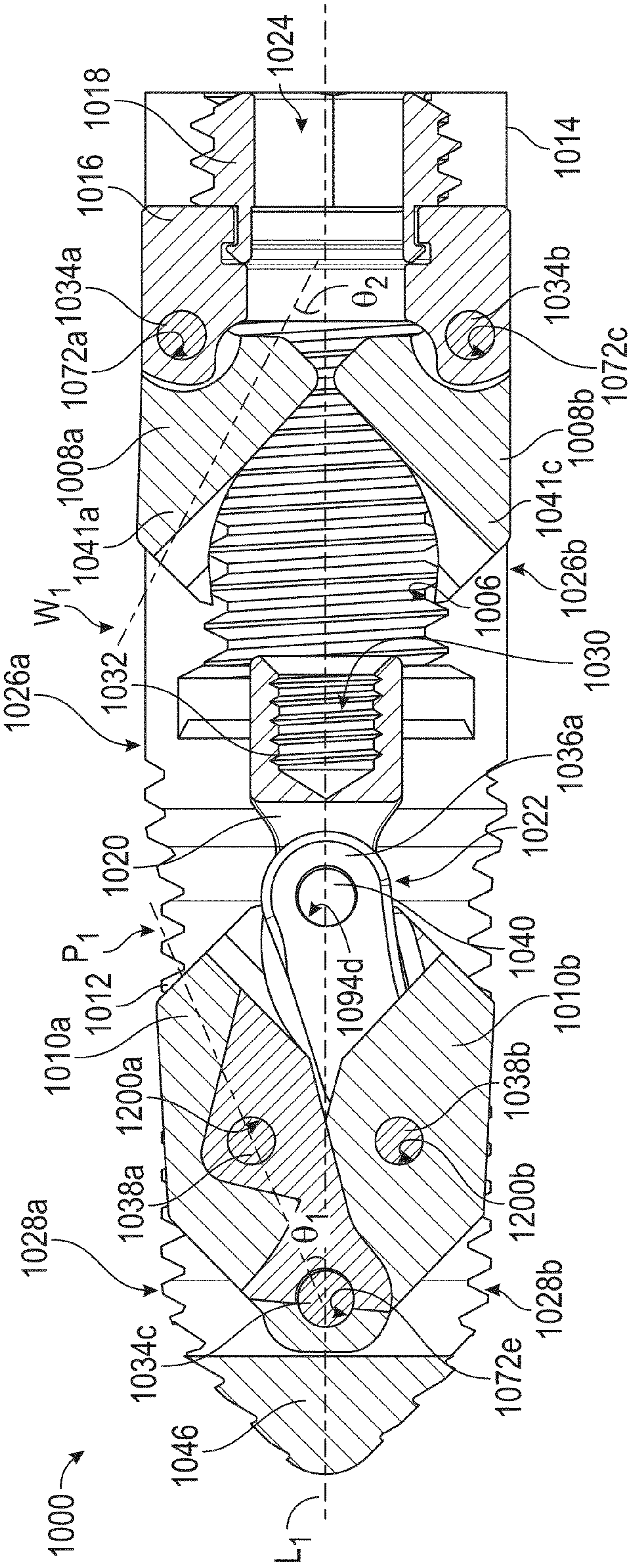
FIG. 31B illustrates a cross-sectional view of the second embodiment of the implant in the closed position.

FIG. 31A illustrates a perspective view of a second embodiment of an implant 1000 in a closed position (also referred to as a closed configuration). FIG. 31B illustrates a cross-sectional view of some embodiments of the second embodiment of the implant 1000 in a closed configuration. Accordingly, FIGS. 31A-31B are best viewed together. Implant 1000 may be configured to be inserted within a target space between bones and/or within a joint for fusion, fixation, and/or stabilization of bones and/or joints. Implant 1000 may be inserted anywhere in a body where there is a need for fixation and/or stabilization of bones, joints, and/or soft tissue. In some embodiments, implant 1000 may be configured to be inserted into an interspinous process space for fusion and stabilization of spinous processes. Implant 1000 may comprise an outer body 1002 defining a longitudinal axis $L_1$ extending through a proximal end 1004*a* and a distal end 1004*b*. Outer body 1002 may define a bore 1006 extending through proximal end 1004*a*. Implant 1000 may include proximal wings 1008*a*, 1008*b* (also referred to as proximal anchors) and distal wings 1010*a*, 1010*b* (also referred to as distal anchors). In some embodiments, implant 1000 may comprise at least one proximal wing 1008*a*, 1008*b* and at least one distal wing 1010*a*, 1010*b*. In some embodiments, implant 1000 may comprise more than one proximal wing 1008*a*, 1008*b* and more than one distal wing 1010*a*, 1010*b*. Distal wings 1010*a*, 1010*b* may pivotally couple to outer body 1002. Proximal wings 1008*a*, 1008*b* may operatively couple to outer body 1002. Distal wings 1010*a*, 1010*b* may pivot about outer body 1002 to transition between a closed configuration and a deployed configuration. Proximal wings 1008*a*, 1008*b* may pivot around outer body 1002 to transition between a closed configuration and a deployed configuration. Proximal wings 1008*a*, 1008*b* may travel along outer body 1002 to transition the implant 1000 between the deployed configuration and a clamped configuration.

In the closed configuration, distal wings 1010*a*, 1010*b* and proximal wings 1008*a*, 1008*b* may substantially align with longitudinal axis $L_1$, as shown in FIG. 31B. In some embodiments, distal wings 1010*a*, 1010*b* and proximal wings 1008*a*, 1008*b* may be substantially parallel to longitudinal axis $L_1$ when implant is in the closed configuration.

At least a portion of outer body 1002 may include external threading, forming a threaded portion 1012. Outer body 1002 may include a cartridge 1014. In some embodiments, cartridge 1014 may be integrally connected to threaded portion 1012. In some embodiments, cartridge 1014 may be operatively coupled to threaded portion 1012. Cartridge 1014 may be threadedly coupled to threaded portion 1012. In some embodiments, cartridge 1014 may be coupled to threaded portion 1012 through an interference fit, snap fit, or any other coupling mechanism known to one of skill in the art. Cartridge 1014 may be removable from threaded portion 1012, as further discussed herein. Threading on threaded portion 1012 may engage muscle, soft tissue, and/or bone at the treatment site to provide fixation of implant 1000 at the treatment site. Threading on threaded portion 1012 may engage muscle, soft tissue, and/or bone during insertion of the implant 1000 up to the treatment site to aid implant insertion and make insertion easier. Threading on threaded portion 1012 may engage muscle, soft tissue, and/or bone at the treatment site to stabilize the implant 1000 at the treatment site.

Proximal wings 1008*a*, 1008*b* may pivotally couple to a proximal carrier 1016, as shown in FIGS. 31A-31B. Proximal carrier 1016 may operatively couple to outer body 1002 through a nut 1018. Proximal wings 1008*a*, 1008*b* may pivot about proximal carrier 1016 to transition between a closed configuration and a deployed configuration. Proximal wings 1008*a*, 1008*b* may translate along outer body 1002 to transition the implant 1000 between the deployed position and the clamped configuration. Actuation of nut 1018 may translate proximal wings 1008*a*, 1008*b* to transition the implant 1000 between the deployed configuration and the clamped configuration.

Distal wings 1010*a*, 1010*b* may pivotally couple to a portion of outer body 1002. Distal wings 1010*a*, 1010*b* may pivotally couple to outer body 1002 proximate the distal end 1004*b* of outer body 1002. Distal wings 1010*a*, 1010*b* may operatively couple to a plunger 1020 of implant 1000 via a linkage assembly 1022, as shown in FIG. 31B. Translation of plunger 1020 may pivot distal wings 1010*a*, 1010*b* between the closed configuration and a deployed configuration, as further described below.

Proximal carrier 1016 may couple to nut 1018. Nut 1018 may threadedly couple to cartridge 1014, thereby operatively coupling proximal wings 1008*a*, 1008*b* to outer body 1002. Cartridge 1014 of outer body 1002 may define bore 1006. As shown in FIG. 31B, cartridge 1014 may include internal threading along bore 1006. Nut 1018 may threadedly couple to cartridge 1014, with bore 1006 receiving nut 1018. At least a portion of bore 1006 may receive proximal carrier 1016 when proximal carrier 1016 is coupled to nut 1018. Actuation of nut 1018 may include rotation of nut 1018 to translate proximal wings 1008*a*, 1008*b* along outer body 1002 to transition the implant 1000 between the deployed configuration and the clamped configuration. Nut 1018 may define a through-hole 1024. Through-hole 1024 may receive a portion of an insertion tool 1400 to actuate nut 1018, as discussed further herein.

Outer body 1002 of implant 1000 may define channels 1026*a*, 1026*b*, as shown in FIG. 31A. In some embodiments, channels 1026*a*, 1026*b* may be defined by cartridge 1014. In the closed configuration, proximal wings 1008*a*, 1008*b* may be received inside channels 1026*a*, 1026*b*, as shown in FIG. 31A. The proximal wings 1008*a*, 1008*b* being received inside channels 1026*a*, 1026*b* decreases the overall profile of the implant 1000 when the implant 1000 is inserted in the closed position, as compared to the proximal wings 1008*a*, 1008*b* extending outward from the channels 1026*a*, 1026*b* during insertion. This decreases the amount of blood loss during insertion, decreases the disruption of soft tissue and/or bone during insertion, and decreases the size of the incision required to insert implant 1000, thereby minimizing recovery time after the surgery and pain felt by the patient.

Figure 41A:
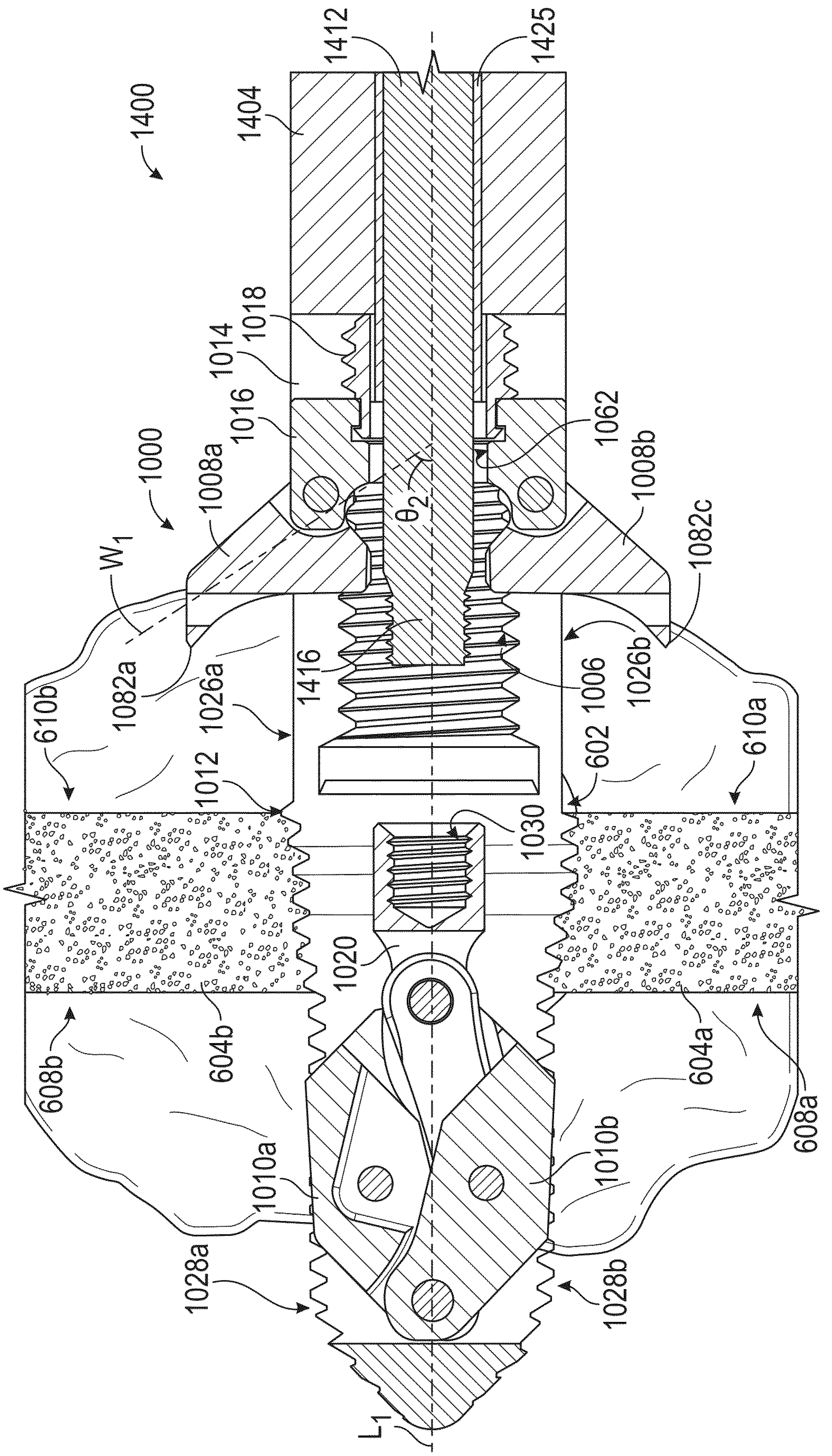
FIG. 41A illustrates a cross-sectional view of the second embodiment of the implant inserted in a target space, with the proximal wings of the second embodiment of the implant in the deployed configuration.
Figure 41B:
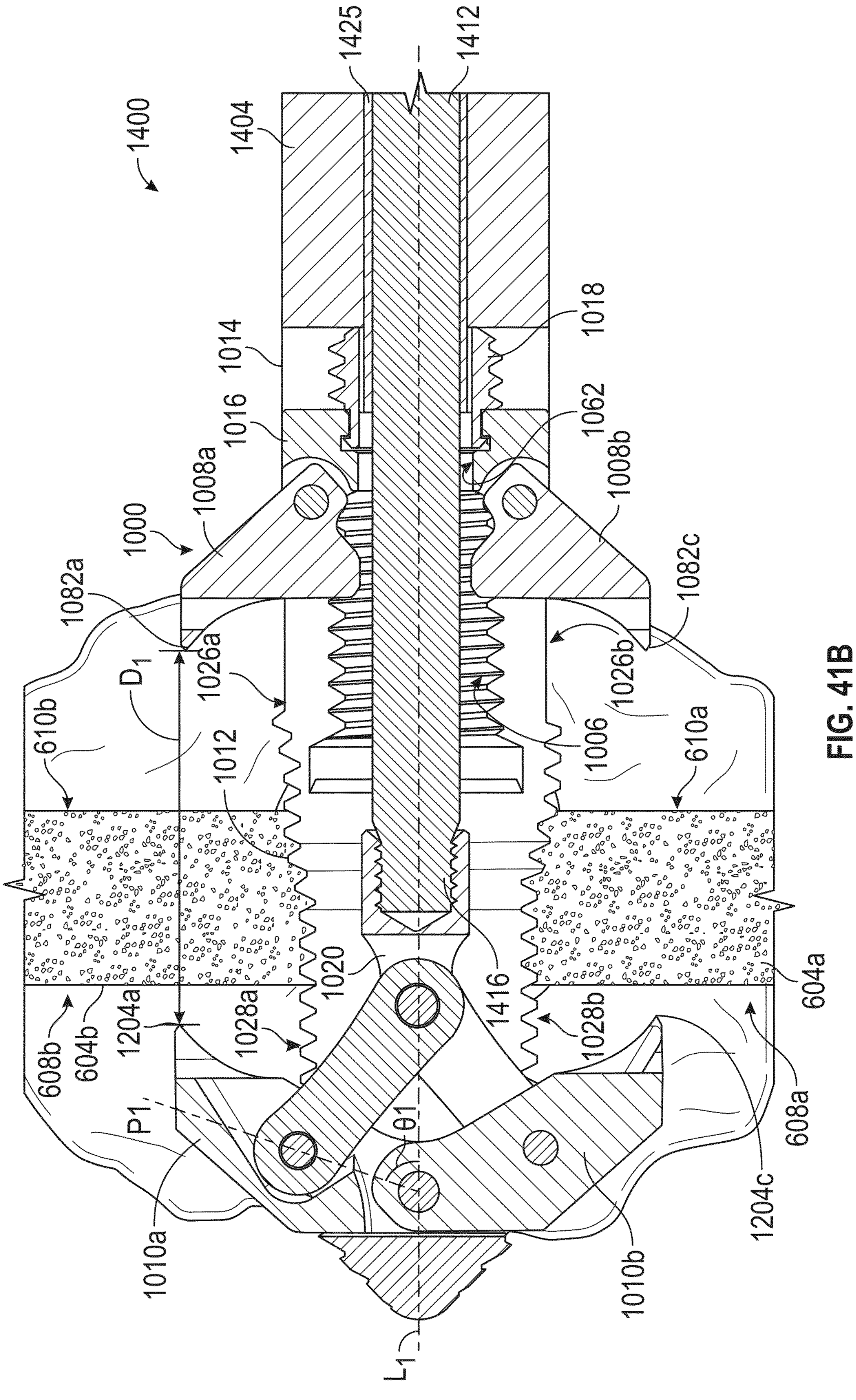
FIG. 41B illustrates a cross-sectional view of the second embodiment of the implant inserted in a target space in the deployed configuration.
Figure 41C:
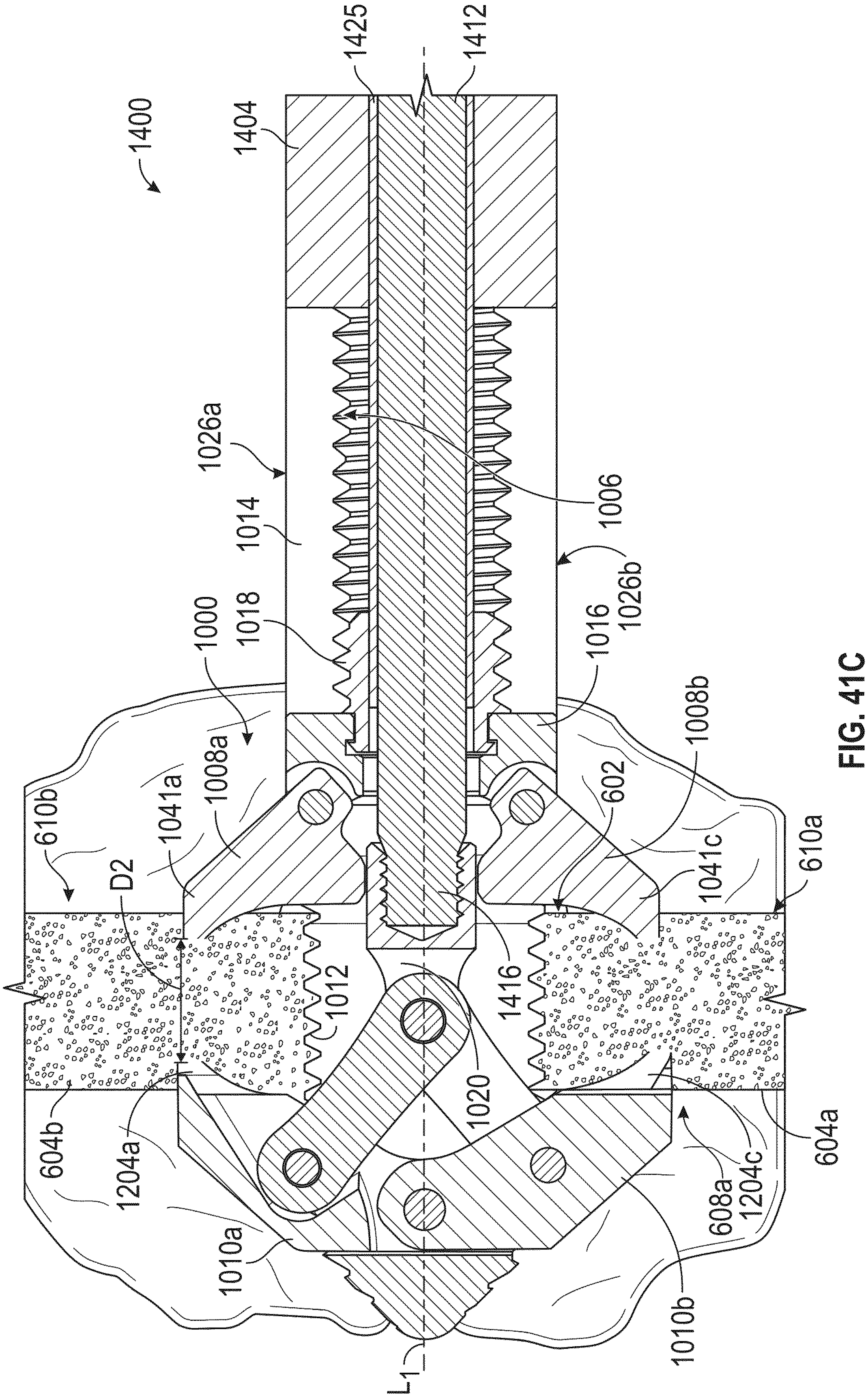
FIG. 41C illustrates a cross-sectional view of the second embodiment of the implant inserted in a target space in the clamped configuration.

Proximal wings 1008*a*, 1008*b* may pivot outward through channels 1026*a*, 1026*b* to transition from the closed position to the deployed position, as further described below. Proximal wings 1008*a*, 1008*b* may then distally translate along channels 1026*a*, 1026*b* to transition implant 1000 from the deployed position to the clamped configuration (as shown in FIGS. 41B-41C). Proximal wings 1008*a*, 1008*b* may interact with a portion of an insertion tool 1400 to pivot proximal wings 1008*a*, 1008*b* between the closed configuration and the deployed configuration, as discussed further herein. In the deployed configuration, a portion of each proximal wing 1008*a*, 1008*b* may extend through channels 1026*a*, 1026*b* (as shown in FIG. 41A), as discussed further herein. In some embodiments, when implant 1000 is in the deployed configuration, distal wings 1010*a*, 1010*b* may be a first distance $D_1$ away from proximal wings 1008*a*, 1008*b* (see FIG. 41B). When implant 1000 is in the clamped configuration, distal wings 1010*a*, 1010*b* may be a second distance $D_2$ away from proximal wings 1008*a*, 1008*b* (see FIG. 41C). Second distance $D_2$ may be less than first distance $D_1$, such that distal wings 1010*a*, 1010*b* and proximal wings 1008*a*, 1008*b* are closer together in the clamped configuration relative to the deployed configuration.

In some embodiments and as shown in FIG. 31A, distal wings 1010*a*, 1010*b* may pivotally couple to threaded portion 1012 of outer body 1002. Outer body 1002 may define windows 1028*a*, 1028*b*. Distal wings 1010*a*, 1010*b* may be seated within windows 1028*a*, 1028*b* when in the closed position, as shown in FIGS. 31A-31B. The distal wings 1010*a*, 1010*b* being received inside windows 1028*a*, 1028*b* decreases the overall profile of the implant 1000 when the implant 1000 is inserted in the closed position, as compared to the distal wings 1010*a*, 1010*b* extending outward from the windows 1028*a*, 1028*b* during insertion. This decreases the amount of blood loss during insertion, decreases the disruption of soft tissue and/or bone during insertion, and decreases the size of the incision required to insert implant 1000, thereby minimizing recovery time after the surgery and pain felt by the patient. Plunger 1020 may define a central bore 1030 configured to receive a portion of an insertion tool 1400, as discussed further herein. In some embodiments, plunger 1020 may comprise internal threads 1032 along interior wall defining central bore 1030, as shown in FIG. 31B. Distally advancing the portion of the insertion tool 1400 received in central bore 1030 may distally advance plunger 1020 to thereby cause distal wings 1010*a*, 1010*b* to pivot from the closed configuration to the deployed configuration, as discussed further herein. In the deployed configuration, a portion of each distal wing 1010*a*, 1010*b* may extend outward through windows 1028*a*, 1028*b* (as shown in FIG. 41B).

Implant 1000 may comprise pivot pins 1034*a*, 1034*b*, 1034*c*. Pivot pins 1034*a*, 1034*b* may pivotally couple proximal wings 1008*a*, 1008*b* to proximal carrier 1016. Linkage assembly 1022 may comprise linkages 1036*a*, 1036*b*. Linkages 1036*a*, 1036*b* may operatively couple plunger 1020 to distal wings 1010*a*, 1010*b*. Linkage pins 1038*a*, 1038*b* may couple distal wings 1010*a*, 1010*b* to linkages 1036*a*, 1036*b*. Plunger pin 1040 may couple linkages 1036*a*, 1036*b* to plunger 1020. Pivot pin 1034*c* may pivotally couple distal wings 1010*a*, 1010*b* to outer body 1002.

Each distal wing 1010*a*, 1010*b* may define a pivot axis $P_1$ extending from the longitudinal axis $L_1$ at the center of pivot pin 1034*c* through the center of linkage pins 1038*a*, 1038*b*, and through distal wings 1010*a*, 1010*b*. For example and as shown in FIG. 31B, a first distal wing 1010*a* may define a pivot axis $P_1$ extending from the longitudinal axis $L_1$ at the center of pivot pin 1034*c* through the center of linkage pin 1038*a*, and through first distal wings 1010*a*. A first pivot axis angle $\theta_1$ may be defined between a respective pivot axis $P_1$ of each distal wing 1010*a*, 1010*b* and longitudinal axis $L_1$ of outer body 1002 when implant 1000 is in the closed configuration. In the closed configuration, the first pivot axis angle $\theta_1$ may be within a range of 10 degrees to 30 degrees, such as between 15 and 25 degrees. Each proximal wing 1008*a*, 1008*b* may define a wing axis $W_1$ extending from the longitudinal axis $L_1$ through a center of ends of proximal wings 1008*a*, 1008*b*. In some embodiments, a wing axis $W_1$ may be defined extending from the longitudinal axis $L_1$ at the center of proximal carrier 1016 through a center of ends of extensions 1041*a*, 1041*b*, 1041*c*, 1041*d* of proximal wings 1008*a*, 1008*b*. For example and as shown in FIG. 31B, a wing axis $W_1$ of a first proximal wing 1008*a* may be defined extending from the longitudinal axis $L_1$ at the center of proximal carrier 1016 through a center of ends of extensions 1041*a*, 1041*b*. A first wing axis angle $\theta_2$ may be defined between a respective wing axis $W_1$ and longitudinal axis $L_1$ of outer body 1002 when implant 1000 is in the closed configuration. In some embodiments, the first wing axis angle $\theta_2$ may be within a range of 15 degrees to 40 degrees, such as between 25 and 35 degrees.

Outer body 1002 may comprise indentations 1042*a*, 1042*b* configured to receive at least a portion of an insertion tool 1400 to thereby attach implant 1000 to an insertion tool 1400, as further discussed herein. Implant 1000 may further define pivot apertures 1072*a*, 1072*b*, 1072*c*, 1072*d*, linkage apertures 1094*a*, 1094*b*, 1094*c*, 1094*d*, wing apertures 1200*a*, 1200*b*, and a tip 1046, as further described below.

Figure 32:
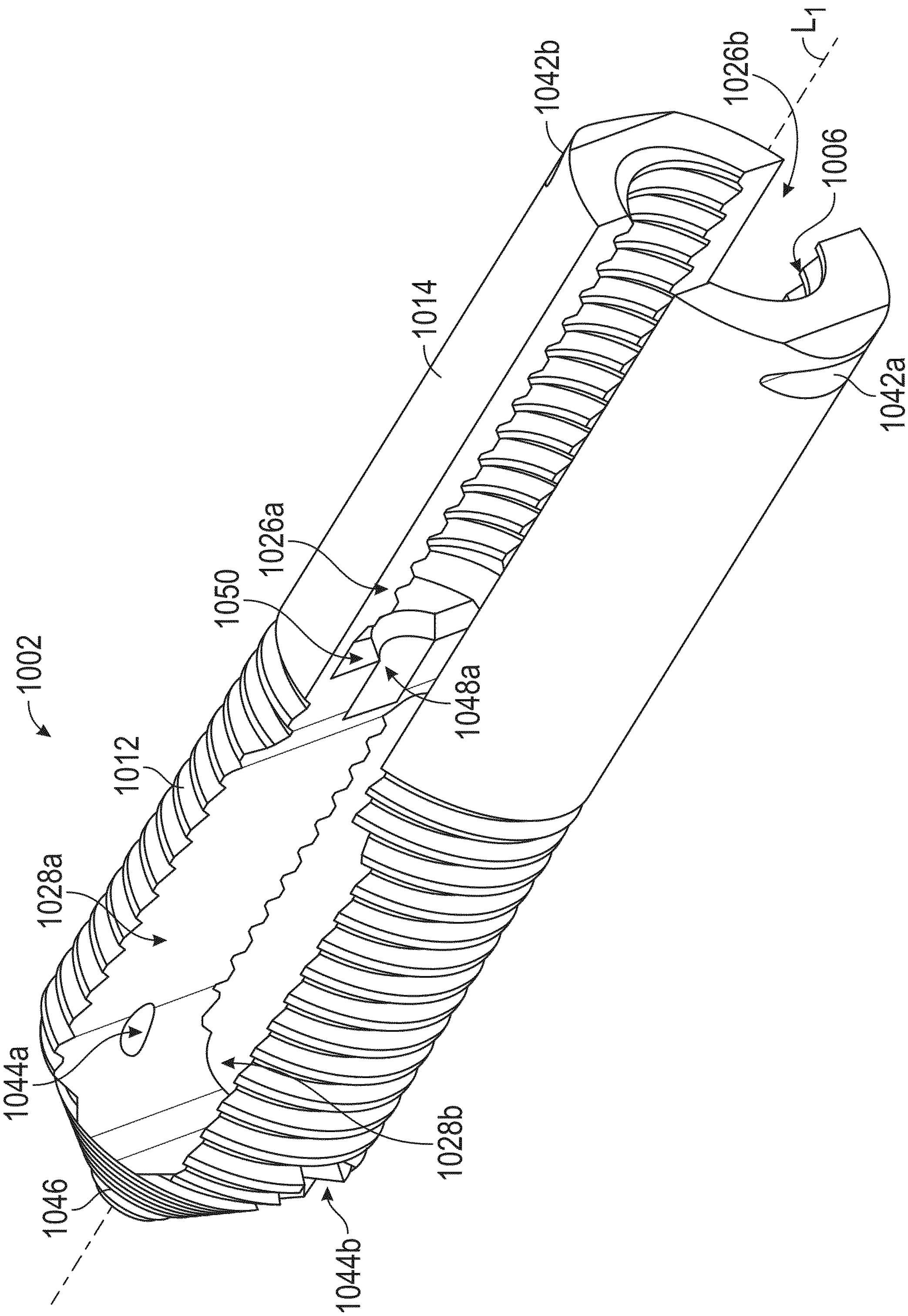
FIG. 32 illustrates a perspective view of some embodiments of an outer body of the second embodiment of the implant.

FIG. 32 illustrates a perspective view of some embodiments of an outer body 1002 of implant 1000. Outer body 1002 may define outer body apertures 1044*a*, 1044*b*. At least a portion of pivot pin 1034*c* may extend through outer body apertures 1044*a*, 1044*b* to thereby pivotally couple distal wings 1010*a*, 1010*b* to outer body 1002. Outer body apertures 1044*a*, 1044*b* may be located proximate distal end 1004*b* of outer body 1002. Outer body 1002 may comprise tip 1046 on distal end 1004*b*. In some embodiments, threaded portion 1012 may comprise tip 1046. Tip 1046 may have a generally conical shape. Tip 1046 may be pointed to aid in inserting the implant 1000 into bone or tissue. In some embodiments, threaded portion 1012 may additionally or alternatively include cutting threads to aid in inserting the implant 1000 into the target space (e.g., interspinous process space). Threaded portion 1012 may decorticate bone and/or tissue to facilitate inserting implant 1000 into the treatment site (also referred to as the target space). Tip 1046 may include cutting threads to aid in inserting the implant 1000 into the target space. In some embodiments, tip 1046 may have a smooth exterior surface without any threads thereon. In some embodiments, tip 1046 is solid (as shown in FIG. 31B) to strengthen implant 1000 during insertion.

Outer body 1002 may define concavities 1048*a*, 1048*b* located on either side of longitudinal axis $L_1$ and configured to receive at least a portion of insertion tool 1400, as discussed further herein. In some embodiments, an interface of threaded portion 1012 and cartridge 1014 may define concavities 1048*a*, 1048*b*. In some embodiments, concavities 1048*a*, 1048*b* may be configured to receive plunger 1020 when distal wings 1010*a*, 1010*b* are in the closed configuration.

In some embodiments, cartridge 1014 of outer body 1002 may define bore 1006. In some embodiments, cartridge 1014 may define a recess 1050 at a distal end of bore 1006 configured to receive proximal carrier 1016. When recess 1050 receives proximal carrier 1016, proximal wings 1008*a*, 1008*b* may be maintained at a position to keep proximal wings 1008*a*, 1008*b* from traveling into windows 1028*a*, 1028*b*. Windows 1028*a*, 1028*b* may be located distally with respect to channels 1026*a*, 1026*b*. Windows 1028*a*, 1028*b* may be located opposite one another, as shown in FIG. 32.

Figure 33:
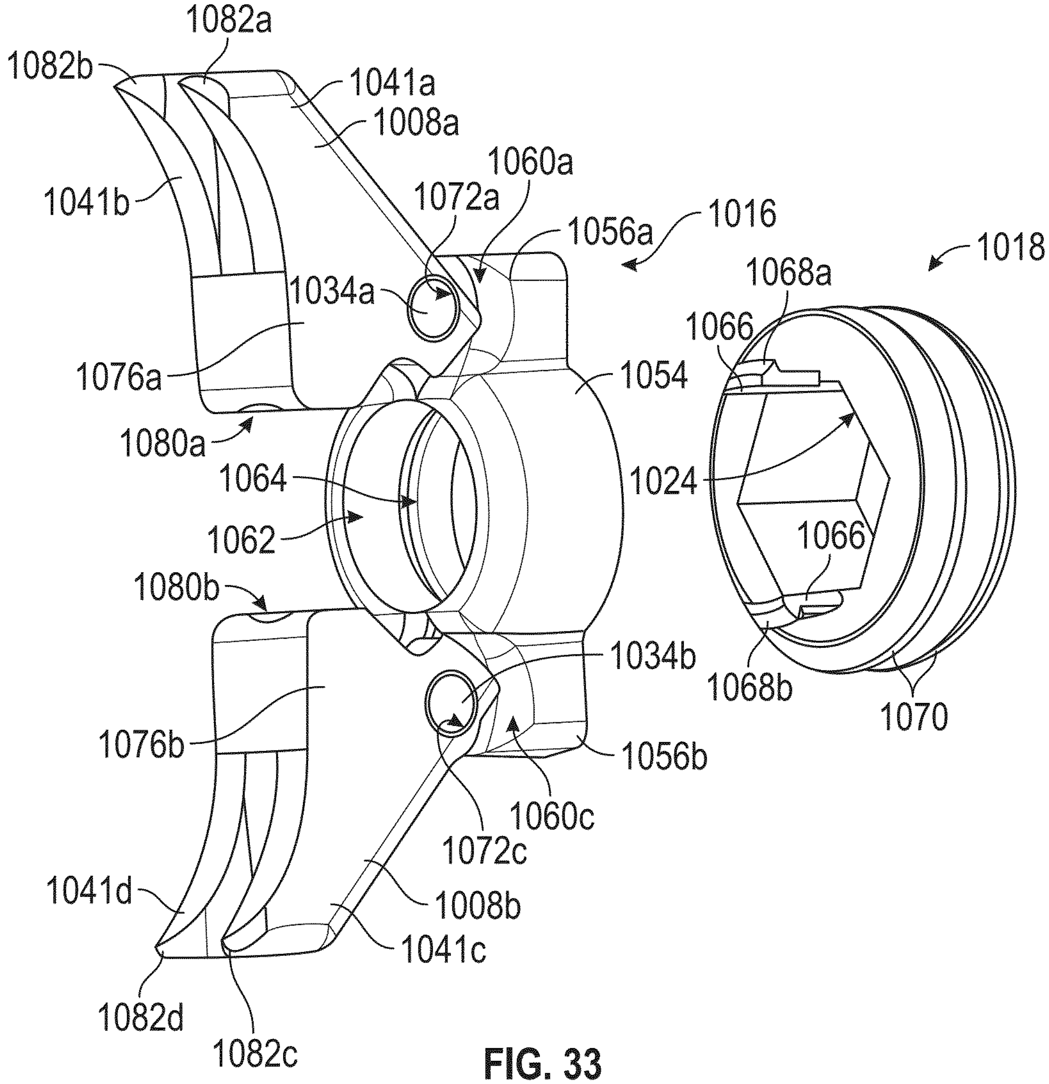
FIG. 33 illustrates a perspective view of some embodiments of a proximal carrier coupled to proximal wings and a nut of the second embodiment of the implant.
Figure 34:
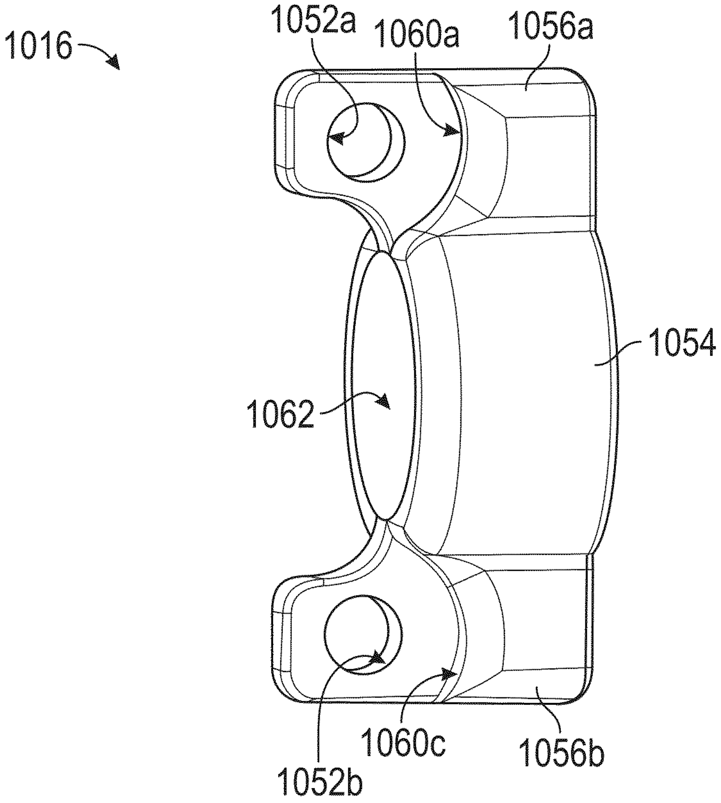
FIG. 34 illustrates a perspective view of some embodiments of the proximal carrier of the second embodiment of the implant.
Figure 35:
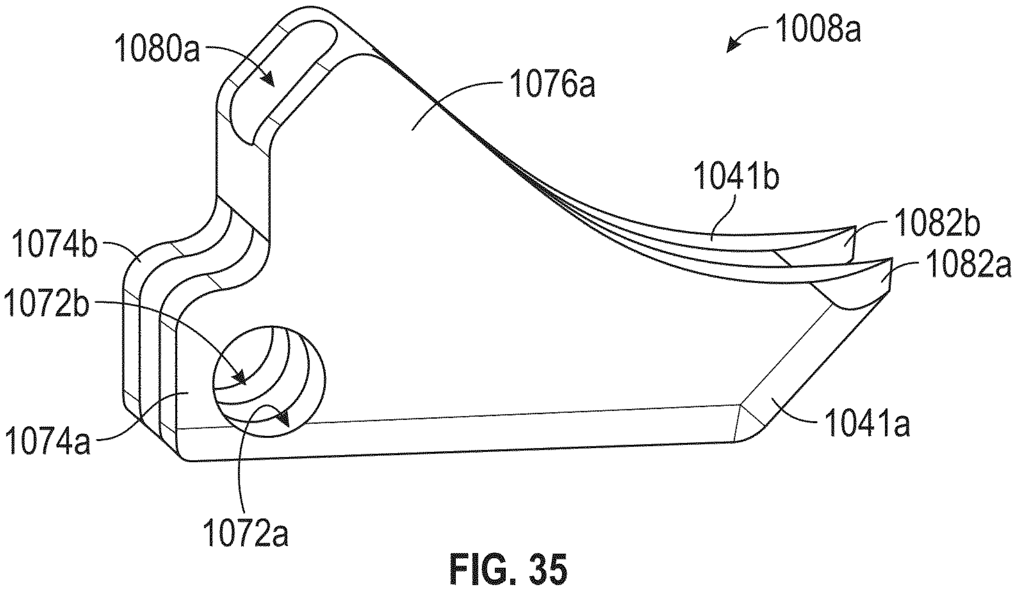
FIG. 35 illustrates a perspective view of some embodiments of proximal wings of the second embodiment of the implant.

FIG. 33 illustrates a perspective view of some embodiments of proximal carrier 1016 coupled to proximal wings 1008*a*, 1008*b* and nut 1018 of implant 1000. FIG. 34 illustrates a perspective view of some embodiments of proximal carrier 1016 of implant 1000. FIG. 35 illustrates a perspective view of some embodiments of proximal wings 1008*a*, 1008*b*. Accordingly, FIGS. 33-35 are best viewed together. Proximal carrier 1016 may include a carrier body 1054. Carrier projections 1056*a*, 1056*b* may extend from carrier body 1054. At least a portion of carrier projections 1056*a*, 1056*b* may be raised so as to act as a stop to keep proximal wings 1008*a*, 1008*b* from over-rotating. The raised surface or structure on carrier projections 1056*a*, 1056*b* may interact with a portion of proximal wings 1008*a*, 1008*b* to maintain a deployed position of proximal wings 1008*a*, 1008*b* and keep proximal wings 1008*a*, 1008*b* from pivoting past the deployed configuration. Carrier projections 1056*a*, 1056*b* may define depressions 1060*a*, 1060*b*, 1060*c*, 1060*d*. Projections 1056*a*, 1056*b* may extend into channels 1026*a*, 1026*b* of outer body 1002 when implant 1000 is in the closed configuration and the deployed configuration. Projections 1056*a*, 1056*b* may move along channels 1026*a*, 1026*b* to translate proximal wings 1008*a*, 1008*b*.

Proximal carrier 1016 may define carrier apertures 1052*a*, 1052*b* configured to receive pivot pins 1034*a*, 1034*b* to thereby pivotally couple proximal wings 1008*a*, 1008*b* to proximal carrier 1016, as shown in FIGS. 33-34. Depressions 1060*a*, 1060*b*, 1060*c*, 1060*d* may define carrier apertures 1052*a*, 1052*b*. Carrier apertures 1052*a*, 1052*b* may be located distally with respect to carrier body 1054. Carrier body 1054 may define a central bore 1062. Carrier body 1054 may be cylindrical in shape or any other shape configured to fit within bore 1006 of outer body 102. A groove 1064 may be defined within central bore 1062. Groove 1064 may extend around the surface of carrier body 1054 defining central bore 1062. In some embodiments, more than one groove 1064 may be defined within central bore 1062.

Nut 1018 may include protrusions 1066 that interact with groove 1064 to secure nut 1018 to proximal carrier 1016, thereby coupling proximal wings 1008*a*, 1008*b* to nut 1018. In some embodiments, nut 1018 may include a single protrusion 1066 configured to interact with groove 1064. In some embodiments, nut 1018 may include more than one protrusion 1066, each interacting with grooves 1064 defined by proximal carrier 1016. Protrusions 1066 may include clips 1068*a*, 1068*b*. Groove 1064 may receive clips 1068*a*, 1068*b* to thereby couple nut 1018 to proximal carrier 1016. Clips 1068*a*, 1068*b* may rotate within groove 1064 such that as nut 1018 is rotated in a first direction and engages threads on bore 1006, proximal carrier 1016 translates along bore 1006.

Nut 1018 may be cylindrically shaped. In some embodiments, nut 1018 may be any shape that fits within bore 1006 of outer body 1002 to thereby couple nut 1018 to outer body 1002. In some embodiments, nut 1018 may include threading 1070 along an exterior surface thereof. Threading 1070 may interact with internal threading of bore 1006 to thereby threadedly couple nut 1018 to outer body 1002. Rotation of nut 1018 may cause threading 1070 to interact with threading of bore 1006 to thereby cause proximal carrier 1016 to translate along bore 1006. In some embodiments, bore 1006 may be defined by cartridge 1014 of outer body 1002, such that nut 1018 threadedly couples to cartridge 1014. In embodiments where cartridge 1014 is removable from threaded portion 1012 of outer body 1002, nut 1018 may then be removed with cartridge 1014, as discussed further herein.

Nut 1018 may define a through-hole 1024. In some embodiments, through-hole 1024 may be hexagonal shaped. In some embodiments, nut 1018 may define a square-shaped, rectangular-shaped, circular-shaped, or any other shape of through-hole 1024. The shape of through-hole 1024 may match with a portion of insertion tool 1400, such that the portion of insertion tool 1400 interacts with nut 1018 to actuate nut 1018. Actuating nut 1018 may include rotating nut 1018 to move proximal wings 1008*a*, 1008*b* along outer body 1002 to transition implant 1000 between a deployed configuration and a clamped configuration. Rotating nut 1018 in a first direction may cause proximal carrier 1016 to distally translate along bore 1006. Proximal carrier 1016 distally translating may cause proximal wings 1008*a*, 1008*b* to distally translate along channels 1026*a*, 1026*b* to transition from a deployed configuration to a clamped configuration. Rotating nut 1018 in a second direction may cause proximal wings 1008*a*, 1008*b* to proximally translate along channels 1026*a*, 1026*b* to transition from a clamped configuration back to a deployed configuration.

Proximal wings 1008*a*, 1008*b* may define pivot apertures 1072*a*, 1072*b*, 1072*c*, 1072*d*. For example and as shown in FIG. 35, a first proximal wing 1008*a* may define pivot apertures 1072*a*, 1072*b*. Proximal wings 1008*a*, 1008*b* may include arms 1074*a*, 1074*b*, 1074*c*, 1074*d* extending from a proximal body 1076*a*, 1076*b*. Arms 1074*a*, 1074*b*, 1074*c*, 1074*d* may define pivot apertures 1072*a*, 1072*b*, 1072*c*, 1072*d*. At least a portion of carrier projections 1056*a*, 1056*b* may fit within a space between arms 1074*a*, 1074*b*, 1074*c*, 1074*d* such that carrier apertures 1052*a*, 1052*b* align with pivot apertures 1072*a*, 1072*b*, 1072*c*, 1072*d*. In some embodiments, depressions 1060*a*, 1060*b*, 1060*c*, 1060*d* may fit within a space between arms 1074*a*, 1074*b*, 1074*c*, 1074*d*. Pivot apertures 1072*a*, 1072*b*, 1072*c*, 1072*d* may receive pivot pins 1034*a*, 1034*b* and carrier apertures 1052*a*, 1052*b* may receive pivot pins 1034*a*, 1034*b* to thereby pivotally couple proximal wings 1008*a*, 1008*b* to proximal carrier 1016. Arms 1074*a*, 1074*b*, 1074*c*, 1074*d* may be shaped to fit within depressions 1060*a*, 1060*b*, 1060*c*, 1060*d*.

Proximal wings 1008*a*, 1008*b* may include extensions 1041*a*, 1041*b*, 1041*c*, 1041*d* extending from proximal bodies 1076*a*, 1076*b* such that proximal bodies 1076*a*, 1076*b* are located between extensions 1041*a*, 1041*b*, 1041*c*, 1041*d* and arms 1074*a*, 1074*b*, 1074*c*, 1047*d*. Proximal bodies 1076*a*, 1076*b* may define contacting surfaces 1080*a*, 1080*b* configured to contact a portion of an insertion tool 1400, as further discussed herein. Contacting surfaces 1080*a*, 1080*b* may be concave to fit around a portion of insertion tool 1400. Proximal body 1076*a*, 1076*b* may have a width greater than extensions 1041*a*, 1041*b*, 1041*c*, 1041*d* such that a portion of proximal body 1067*a*, 1076*b* is located in front of central bore 1062 of proximal carrier 1016 when proximal wings 1008*a*, 1008*b* are in the closed configuration. Contacting surfaces 1080*a*, 1080*b* may be located in front of central bore 1062 of proximal carrier 1016 when proximal wings 1008*a*, 1008*b* are in the closed configuration. A portion of insertion tool 1400 may be inserted through central bore and push contacting surfaces 1080*a*, 1080*b* to thereby pivot proximal wings 1008*a*, 1008*b* from the closed configuration to the deployed configuration, as discussed further herein. In some embodiments, a portion of proximal body 1076*a*, 1067*b* rests in front of central bore 1062 such that proximal body 1076*a*, 1076*b* blocks central bore 1062 when proximal wings 1008*a*, 1008*b* are in the closed configuration. When proximal wings 1008*a*, 1008*b* pivot about proximal carrier 1016 to transition from the closed configuration to the deployed configuration, proximal bodies 1076*a*, 1076*b* pivot away from central bore 1062.

At least a portion of each extension 1041*a*, 1041*b*, 1041*c*, 1041*d* may be configured to engage with bone or tissue at the treatment site when proximal wings 1008*a*, 1008*b* are in the clamped configuration. In some embodiments, extensions 1041*a*, 1041*b*, 1041*c*, 1041*d* may form tips 1082*a*, 1082*b*, 1082*c*, 1082*d*. Tips 1082*a*, 1082*b*, 1082*c*, 1082*d* may engage bone or tissue at and/or near the treatment site when proximal wings 1008*a*, 1008*b* are in the clamped position. In some embodiments, tips 1082*a*, 1082*b*, 1082*c*, 1082*d* may be sharp to clamp onto and engage bone or tissue. Tips 1082*a*, 1082*b*, 1082*c*, 1082*d* may be shaped like fangs. In some embodiments, tips 1082*a*, 1082*b*, 1082*c*, 1082*d* may be spikes with sharp points for engaging with bone or tissue. In some embodiments, tips 1082*a*, 1082*b*, 1082*c*, 1082*d* may be arcuately shaped and come to a point.

Figure 36:
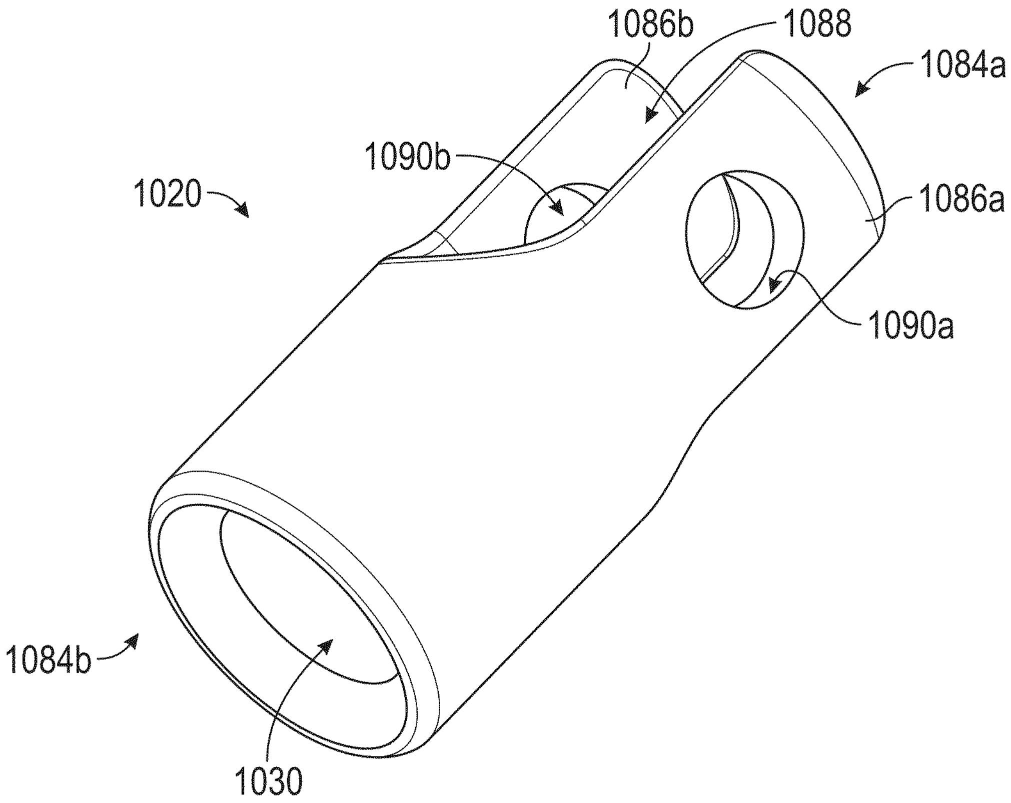
FIG. 36 illustrates a perspective view of some embodiments of a plunger of the second embodiment of the implant.

FIG. 36 illustrates a perspective view of some embodiments of a plunger 1020 of implant 1000. Plunger 1020 has a distal end 1084*a* and a proximal end 1084*b*. Distal end 1084*a* is configured to be located proximate the windows 1028*a*, 1028*b* of outer body 1002. Plunger 1020 may be moved longitudinally to transition distal wings 1010*a*, 1010*b* between the closed configuration and the deployed configuration, as discussed further herein. Proximal end 1084*b* of plunger 1020 defines central bore 1030. In some embodiments, central bore 1030 may be threaded to cooperate with threading on a portion of an insertion tool 1400, as discussed further herein. Plunger 1020 may have a Y-shaped construction, having a first arm 1086*a* and a second arm 1086*b* extending distally to distal end 1084*a*, as shown in FIG. 36. Arms 1086*a*, 1086*b* have a space 1088 therebetween. Space 1088 may be configured to receive a portion of linkages 1036*a*, 1036*b*. Linkages 1036*a*, 1036*b* may be mounted within space 1088 and coupled to plunger 1020 via plunger pin 1040 to thereby operatively couple distal wings 1010*a*, 1010*b* to plunger 1020. Each arm 1086*a*, 1086*b* defines a hole 1090*a*, 1090*b* extending therethrough and configured to receive plunger pin 1040.

Figure 37:
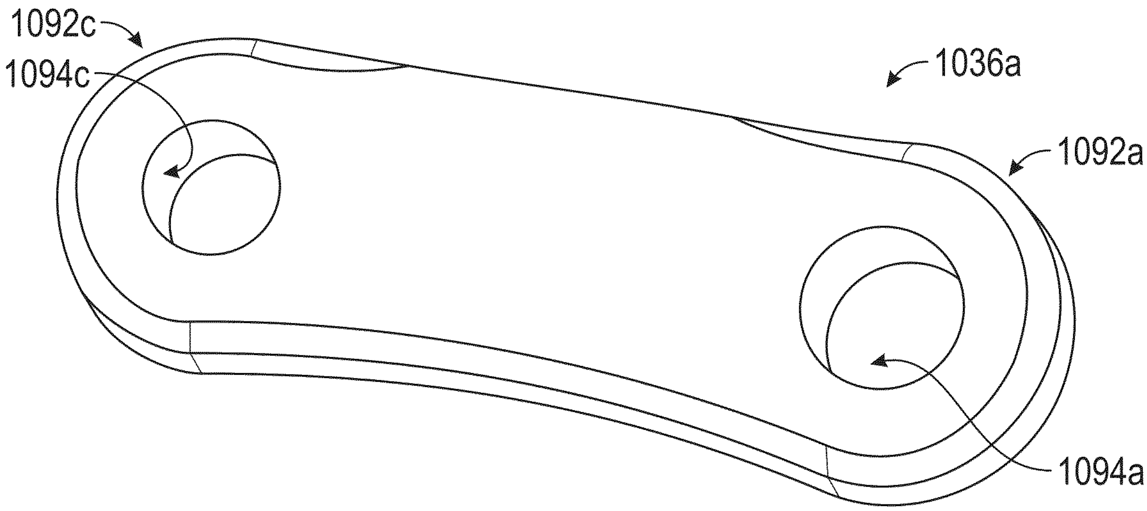
FIG. 37 illustrates a perspective view of some embodiments of a linkage of the second embodiment of the implant.
Figure 39:
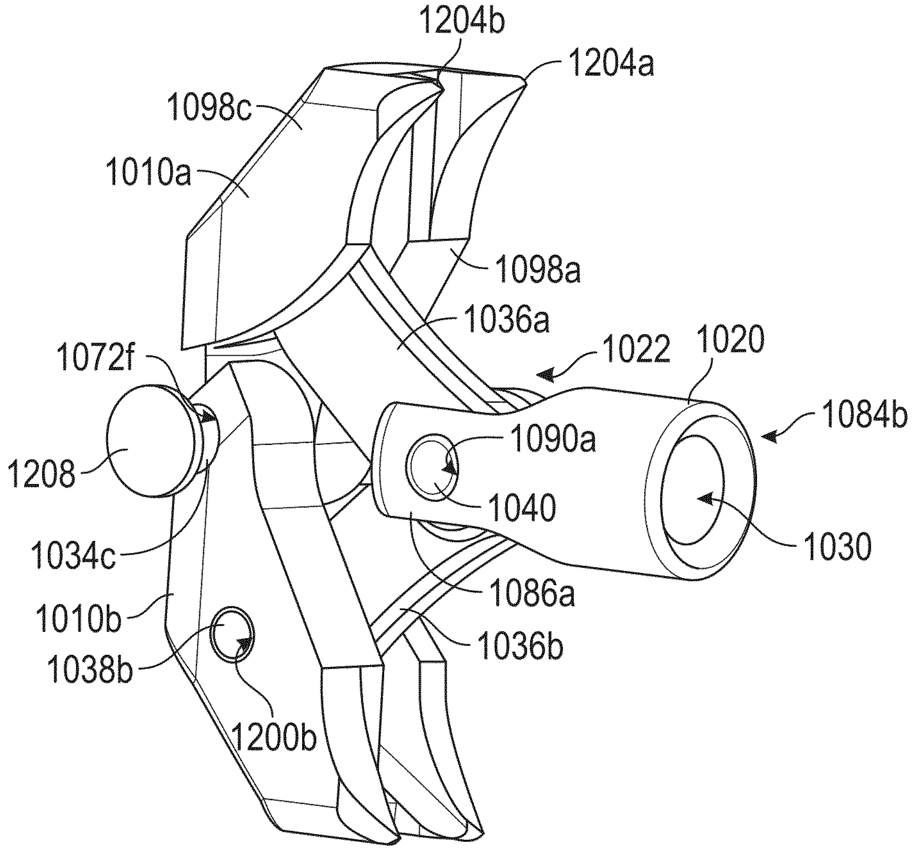
FIG. 39 illustrates a perspective view of some embodiments of distal wings coupled to a linkage assembly and plunger of the second embodiment of the implant.

FIG. 37 illustrates a perspective view of some embodiments of a linkage 1036*a*, 1036*b* of implant 1000. For example, FIG. 37 illustrates a perspective view of linkage 1036*a*. Each linkage 1036*a*, 1035*b* may be substantially identical to one another. Implant 1000 may comprise more than one linkage 1036*a*, 1036*b*, with each linkage 1036*a*, 1036*b* operatively connecting each distal wing 1010*a*, 1010*b* to plunger 1020. Linkages 1036*a*, 1036*b* each define a first end 1092*a*, 1092*b* and a second end 1092*c*, 1092*d*. Each end 1092*a*, 1092*b*, 1092*c*, 1092*d* defines a linkage aperture 1094*a*, 1094*b*, 1094*c*, 1094*d*. Linkage apertures 1094*a*, 1094*b* at first ends 1092*a*, 1092*b* are configured to receive linkage pins 1038*a*, 1038*b* to thereby couple linkages 1036*a*, 1036*b* to distal wings 1010*a*, 1010*b*. Linkage apertures 1094*c*, 1094*d* at second ends 1092*c*, 1092*d* are configured to receive plunger pin 1040 to thereby couple linkages 1036*a*, 1036*b* to plunger 1020 (as shown in FIG. 39).

Linkages 1036*a*, 1036*b* may be substantially oval shaped, having ends 1092*a*, 1092*b*, 1092*c*, 1092*d* that are round. In some embodiments, linkages 1036*a*, 1036*b* may be substantially rectangular shaped. Linkages 1036*a*, 1036*b* may be substantially flat such that a portion of each linkage 1036*a*, 1036*b* fits within cavities 1202*a*, 1202*b* of distal wings 1010*a*, 1010*b* (as shown in FIG. 39).

Figure 38:
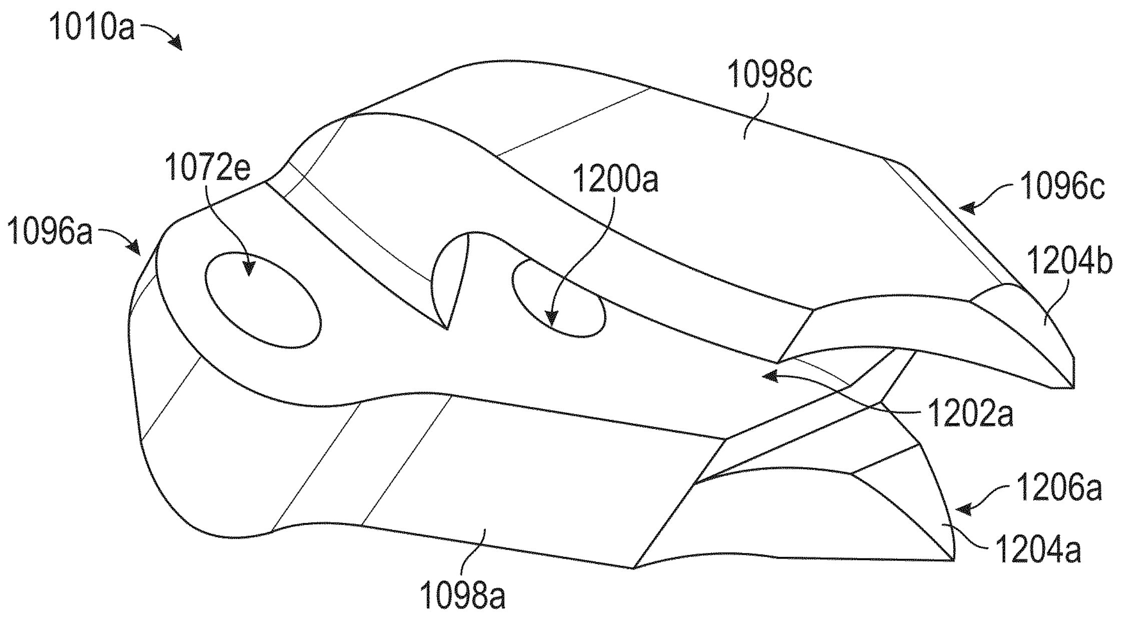
FIG. 38 illustrates a perspective view of some embodiments of a distal wing of the second embodiment of the implant.

FIG. 38 illustrates a perspective view of some embodiments of a distal wing 1010*a*, 1010*b* of implant 1000. Distal wings 1010*a*, 1010*b* may each have a first end 1096*a*, 1096*b* and a second end 1096*c*, 1096*d*. First ends 1096*a*, 1096*b* of distal wings 1010*a*, 1010*b* may define pivot apertures 1072*e*, 1072*f* configured to receive pivot pin 1034*c* to thereby pivotally couple distal wings 1010*a*, 1010*b* to outer body 1002. For example, first distal wing 1010*a* may define pivot aperture 1072*e* at first end 1096*a*. First extensions 1098*a*, 1098*b* may extend from first ends 1096*a*, 1096*b* of distal wings 1010*a*, 1010*b*. First extensions 1098*a*, 1098*b* may define wing apertures 1200*a*, 1200*b* configured to receive linkage pins 1038*a*, 1038*b* to thereby operatively couple distal wings 1010*a*, 1010*b* to the linkage assembly 1022. Second extensions 1098*c*, 1098*d* may protrude from a side of first extensions 1098*a*, 1098*b*. For example and as shown in FIG. 38, a first distal wing 1010*a* may include a first extension 1098*a* defining a wing aperture 1200*a*. First distal wing 1010*a* may include a second extension 1098*c* protruding from a side of first extension 1098*a*.

In some embodiments, a cavity 1202*a*, 1202*b* may be defined between a first extension 1098*a*, 1098*b* and a second extension 1098*c*, 1098*d* of each distal wing 1010*a*, 1010*b*. Cavity 1202*a*, 1202*b* may be configured to receive at least a portion of a linkage 1036*a*, 1036*b*. Second extensions 1098*c*, 1098*d* may extend substantially parallel to first extensions 1098*a*, 1098*b*. Wing apertures 1200*a*, 1200*b* may extend through first extensions 1098*a*, 1098*b*, but not through second extensions 1098*c*, 1098*d* such that each linkage 1036*a*, 1036*b* is only coupled to a first extension 1098*a*, 1098*b*.

In some embodiments, second ends 1096*c*, 1096*d* may include tips 1204*a*, 1204*b*, 1204*c*, 1204*d* extending therefrom. Tips 1204*a*, 1204*b*, 1204*c*, 1204*d* may extend from extensions 1098*a*, 1098*b*, 1098*c*, 1098*d*. For example and as shown in FIG. 38, tip 1204*a* may extend from first extension 1098*a* and tip 1204*b* may extend from second extension 1098*c* of first distal wing 1010*a*. Tips 1204*a*, 1204*b*, 1204*c*, 1204*d* may be adapted for engaging bone and/or tissue at the treatment site when distal wings 1010*a*, 1010*b* are in a clamped configuration, as discussed further herein. Tips 1204*a*, 1204*b*, 1204*c*, 1204*d* of each distal wing 1010*a*, 1010*b* may have a gap 1206*a*, 1206*b* therebetween. Tips 1204*a*, 1204*b*, 1204*c*, 1204*d* may be sharp or pointed such that tips 1204*a*, 1204*b*, 1204*c*, 1204*d* may clamp onto and/or pierce bone or tissue at and/or near the treatment site to secure implant 1000 to treatment site. In some embodiments, tips 1204*a*, 1204*b*, 1204*c*, 1204*d* may be shaped like fangs. In some embodiments, tips 1204*a*, 1204*b*, 1204*c*, 1204*d* may be spiked to engage bone or tissue. In some embodiments, tips 1204*a*, 1204*b*, 1204*c*, 1204*d* may be arcuately shaped and come to a point.

FIG. 39 illustrates a perspective view of some embodiments of distal wings 1010*a*, 1010*b* coupled to linkage assembly 1022 and plunger 1020 of implant 1000. Linkage apertures 1094*a*, 1094*b* at first ends 1092*a*, 1092*b* of linkages 1036*a*, 1036*b* and wing apertures 1200*a*, 1200*b* receive linkage pins 1038*a*, 1083*b* to thereby couple linkages 1036*a*, 1036*b* to distal wings 1010*a*, 1010*b*. Linkage apertures 1094*c*, 1094*d* at second ends 1092*c*, 1092*d* of linkages 1036*a*, 1036*b* and holes 1090*a*, 1090*b* of plunger receive plunger pin 1040 to thereby couple the linkages 1036*a*, 1036*b* to plunger 1020. Because linkages 1036*a*, 1036*b* are coupled to both plunger 1020 and distal wings 1010*a*,

1010*b*, linkages 1036*a*, 1036*b* thereby operatively couple distal wings 1010*a*, 1010*b* to plunger 1020. Space 1088 between arms 1086*a*, 1086*b* of plunger 1020 where linkages 1036*a*, 1036*b* are mounted may provide linkages 1036*a*, 1036*b* with room to rotate about plunger pin 1040. Rotation of linkages 1036*a*, 1036*b* about plunger pin 1040 may cause distal wings 1010*a*, 1010*b* to pivot about pivot pin 1034*c* to thereby transition between the closed configuration and the deployed configuration. A cap 1208 may receive an end of pivot pin 1034*c* to secure pivot pin 1034*c* within linkage apertures 1094*a*, 1094*b* and wing apertures 1200*a*, 1200*b*.

Second Insertion Tool Embodiment

Figure 40A:
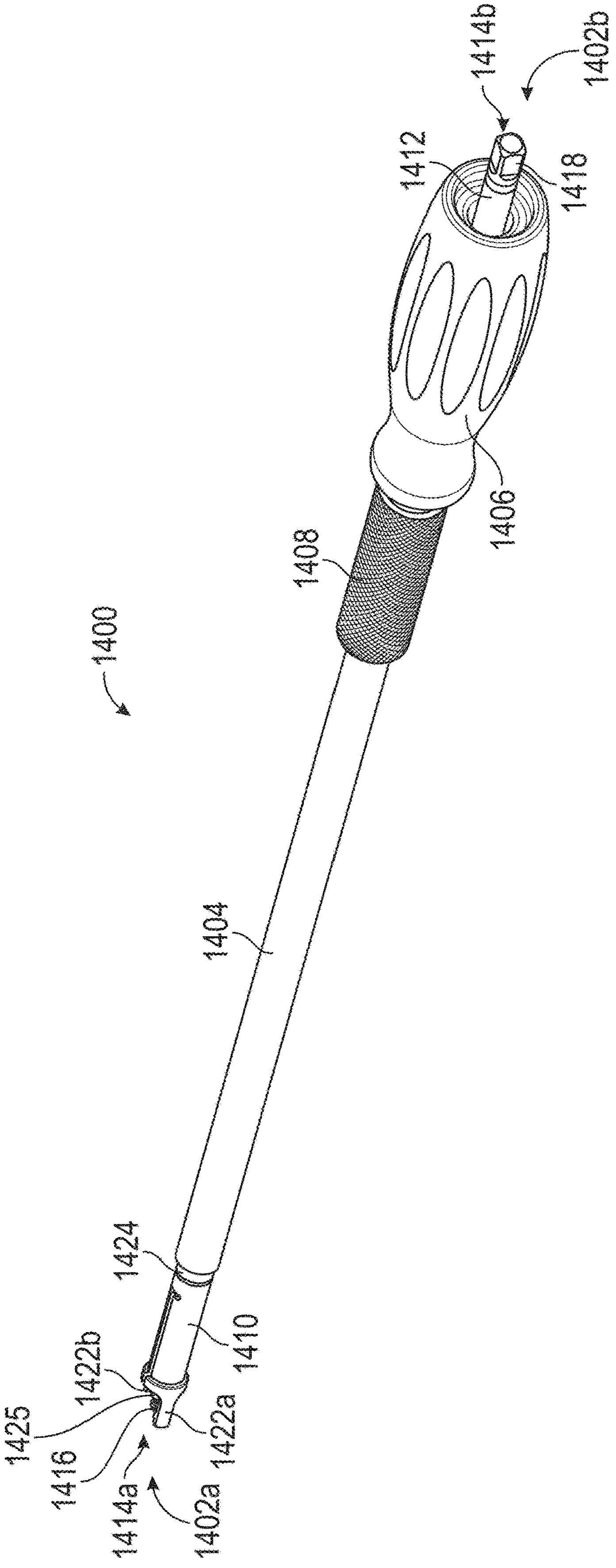
FIG. 40A illustrates a perspective view of a second embodiment an insertion.
Figure 40B:
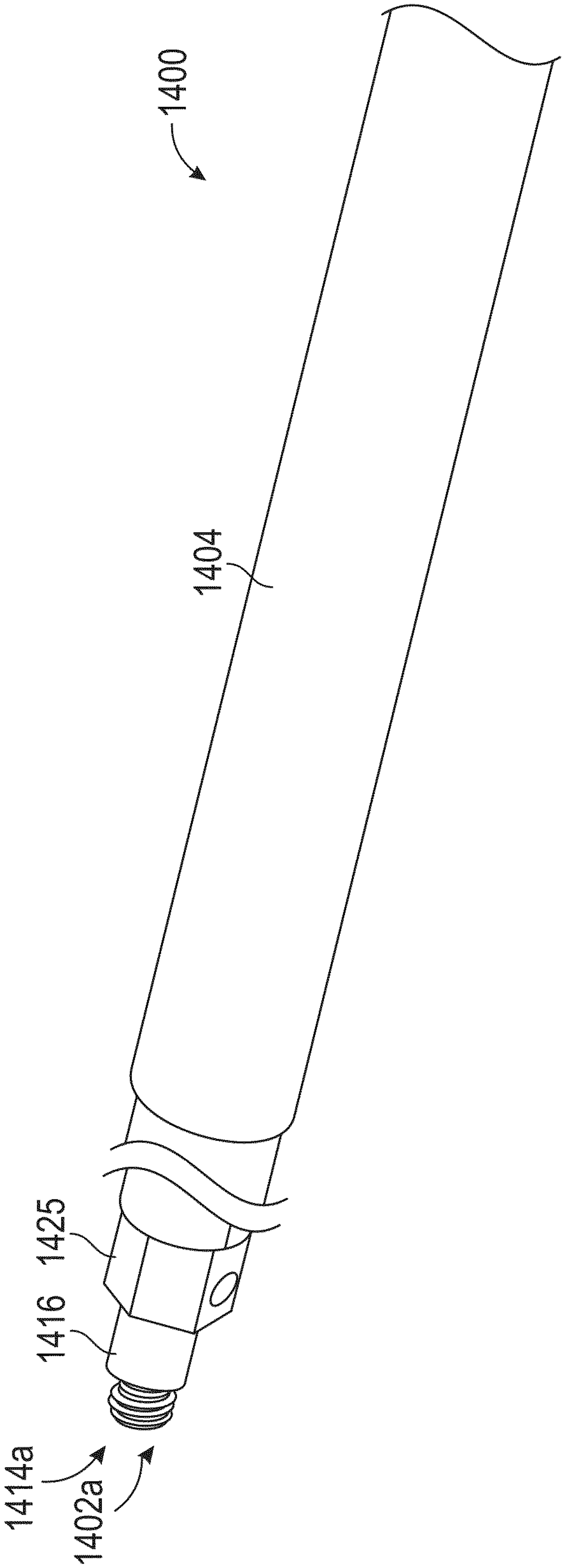
FIG. 40B illustrates a perspective of the second embodiment of the insertion tool with a portion of insertion tool removed.

FIG. 40A illustrates a perspective view of a second embodiment of an insertion tool 1400. FIG. 40B illustrates a perspective view of the second embodiment of the insertion tool 1400 with a portion of insertion tool 1400 removed. Accordingly, FIGS. 40A-40B are best viewed together. Insertion tool 1400 may be substantially similar to insertion tool 400. For example and as shown in FIG. 40A, insertion tool 1400 may define a distal end 1402*a* and a proximal end 1402*b*. Insertion tool 1400 may include an outer shaft 1404, a handle 1406, an outer grip 1408, an attachment member 1410, and an inner rod 1412. Inner rod 1412 may define a distal end 1414*a* and a proximal end 1414*b*. Inner rod 1412 may comprise a driver head 1416 at distal end 1414*a* thereof and a control 1418 at the proximal end 1414*b* thereof. Driver head 1416 of inner rod 1412 may include threads such that driver head 1416 may threadedly couple to central bore 1030 of plunger 1020. Driver head 1416 of inner rod 1412 may extend through attachment member 1410, as shown in FIG. 40A. Inner rod 1412 may extend through handle 1406 such that control 1418 extends past handle 1406.

Operation of control 1418 may translate plunger 1020. In some embodiments, distally pushing control 1418 causes driver head 1416 to distally translate plunger 1020. Distal translation of plunger 1020 may pivot distal wings 1010*a*, 1010*b* about outer body 1002 to transition from the closed configuration to the deployed configuration. Proximally translating control 1418 may cause driver head 1416 to proximally translate plunger 1020. Proximal translation of plunger 1020 may pivot distal wings 1010*a*, 1010*b* about outer body 1002 to transition from the deployed configuration back to the closed configuration. Attachment member 1410 may be configured to attach insertion tool 1400 to implant 1000. Insertion tool 1400 may include a connector for coupling handle 1406 to outer grip 1408. The connector of insertion tool 400 may be substantially similar to connector 420 of insertion tool 400. Attachment member 1410 may be substantially similar to attachment member 410, comprising arms 1422*a*, 1422*b* that may be received in indentations 1042*a*, 1042*b* of outer body 1002 of implant 1000 to thereby attach implant 1000 to insertion tool 1400 and maintain implant 1000 on insertion tool 1400 during insertion.

Similar to embodiments of insertion tool 400, insertion tool 1400 may include inner shaft 1424 received in outer shaft 1404. Inner shaft 1424 may receive inner rod 1412. Inner shaft 1424 may receive a portion of attachment member 1410 such that inner shaft 1424 couples to attachment member 1410. Inner shaft 1424 may couple to the connector. Similar to embodiments of insertion tool 400, outer shaft 1404 may couple to outer grip 1408 and outer grip 1408 may threadedly couple to the connector such that operation of outer grip 1408 distally translates outer shaft 1404 onto attachment member 1410 to cause arms 1422*a*, 1422*b* to clip into indentations 1042*a*, 1042*b* of outer body 1002 of implant 1000 to thereby lock implant 1000 onto insertion tool 1400.

Insertion tool 1400 may include a rotating shaft 1425. A portion of rotating shaft 1425 may be received in through-hole 1024 of nut 1018. Rotating shaft 1425 may extend from handle 1406 such that a surgeon or operator may interact with rotating shaft 1425. For example, a surgeon or operator may turn rotating shaft 1425 to cause nut 1018 to rotate within bore 1006. Rotation of nut 1018 causes proximal wings 1008*a*, 1008*b* to move along outer body 1002 to thereby transition proximal wings 1008*a*, 1008*b* between the deployed configuration and the clamped configuration. Turning rotating shaft 1425 in a first direction may cause nut 1018 to rotate in a first direction to thereby distally translate proximal wings 1008*a*, 1008*b* within channels 1026*a*, 1026*b* to transition proximal wings 1008*a*, 1008*b* from a deployed configuration to a clamped configuration. Turning rotating shaft 1425 in a second direction may cause nut 1018 to rotate in a second direction to thereby proximally translate proximal wings 1008*a*, 1008*b* from a clamped configuration back to a deployed configuration. Rotating shaft 1425 may receive inner rod 1412 and control 1418 of inner rod 1412 may extend from rotating shaft 1425, such that a surgeon or operator may reach control 1418 of inner rod 1412.

Arms 1422*a*, 1422*b* of attachment member 1410 may include clips substantially similar to clips 438*a*, 438*b* disposed on arms 422*a*, 422*b* of insertion tool 400. Indentations 1042*a*, 1042*b* may receive the clips of insertion tool 1400 to attach implant 1000 to insertion tool 1400. Operation of outer grip 1408 may distally translate outer shaft 1404 onto attachment member 1410 such that clips of arms 1422*a*, 1422*b* are received in indentations 1042*a*, 1042*b* to attach implant 1000 to insertion tool 1400. In some embodiments, a surgeon or operator may rotate outer grip 1408 to distally translate outer shaft 1404 onto attachment member 1410 such that arms 1422*a*, 1422*b* are received in indentations 1042*a*, 1042*b* to thereby attach insertion tool 1400 to implant 1000.

Rotating shaft 1425 may be substantially hexagonal in shape, as shown in FIG. 40B. In some embodiments, rotating shaft 1425 may be any shape known to a person skilled in the art such that the shape fits within through-hole 1024 of nut 1018 to thereby couple rotating shaft 1425 to nut 1018.

Insertion tool 1400 and implant 1000 may form part of tools 700 used during insertion of implant 1000 into a target space. Combined rasp and tap 500 may also form part of tools 700 used during insertion of implant 1000.

Second Implant Insertion Method

A method 1800 for inserting implant 1000 into a target space in accordance with embodiments of the present disclosure may be substantially similar to method 800. For example, method 1800 may provide steps for inserting implant 1000 into a target space, such as interspinous process space 602. In some embodiments, implant 1000 is inserted between adjacent spinous processes 604*a*, 604*b*, as shown in FIGS. 41A-41C. Similar to method 800, method 1800 may begin with a step 1802 where a minimally invasive incision, such as incision 606, is made in a patient, such as a patient 607. At step 1804, a working channel for inserting implant 1000 may be created, similar to step 804 of method 800. At step 1806, an introducer sleeve, such as introducer sleeve 706, may be inserted over dilators 704 that created the working channel, similar to step 806 of method 800. At step 1808, dilators 704 may be removed, similar to step 808 of method 800. Method 1800 may be embodied as instructions provided with a surgical kit in some embodiments. The surgical kit may include implant 1000, insertion tool 1400, combined rasp and tap 500, and tools 700.

Step 1810 may be substantially similar to step 810 of method 800. For example, at step 1810, one or more site preparation steps may be taken, such as inserting combined rasp and tap 500 into introducer sleeve 706. Rotating combined rasp and tap 500 may then distract bones adjacent the treatment side, remove ligaments at the treatment site, and partially decorticate the bones for stimulating bone growth. A degree of distraction may be determined by viewing lateral hollows 522*a*, 522*b*, 522*c*, 522*d*, 524*a*, 524*b*, 524*c*, 524*d* under fluoroscopy to determine the appropriate implant size. Combined rasp and tap 500 may then be removed.

Step 1812 may be substantially similar to step 812 of method 800. For example, at an optional step 1812, bone graft material may be added to implant 100 prior to insertion into the patient, as further discussed herein. Bone graft material may be applied around the threaded portion 1012 of outer body 1002 of implant 1000. At step 1814, implant 1000 may be attached to insertion tool 1400 in the closed configuration through a similar mechanism for attaching implant 100 to insertion tool 400. For example, outer grip 1408 of insertion tool 1400 may be rotated in a first direction to advance attachment member 1410 toward implant 1000 to clip arms 1422*a*, 1422*b* into indentations 1042*a*, 1042*b* of outer body 1002 to thereby lock implant 1000 onto insertion tool 1400. Rotating shaft 1425 may be coupled to nut 1018 prior to rotating outer grip 1408 to attach attachment member 1410 to outer body 1002 of implant 1000. Driver head 1416 of inner rod 1412 may be threadedly coupled to central bore 1030 of plunger 1020 prior to rotating outer grip 1408 to attach attachment member 1410 to outer body 1002 of implant 1000.

Step 1816 may be substantially similar to step 816 of method 800. For example, at step 1816, insertion tool 1400 and implant 1000 may be inserted into introducer sleeve 706. At step 1818, instead of partially inserting implant 1000 into the target space, implant 1000 may be fully inserted into the target space such that distal wings 1010*a*, 1010*b* are located proximate distal sides 608*a*, 608*b* of spinous processes 604*a*, 604*b* and proximal wings 1008*a*, 1008*b* are located proximate proximal sides 610*a*, 610*b* of spinous processes 604*a*, 604*b*. At step 1820, an introducer sleeve, such as introducer sleeve 706, may be removed.

Fully inserting implant 1000 into the target space may include inserting distal wings 1010*a*, 1010*b* through the target space, such as an interspinous process space 602, as shown in FIG. 41A. A surgeon or operator may rotate insertion tool 1400 to insert implant 1000 into the target space, such that threads of threaded portion 1012 of outer body 1002 decorticate bones and/or tissue at the treatment site to facilitate inserting implant 1000 into treatment site. Threading on threaded portion 1012 may engage muscle, soft tissue, and/or bone at the treatment site to provide fixation of implant 1000 at the treatment site. During insertion of implant 1000 into the target space, the distal wings 1010*a*, 1010*b* and proximal wings 1008*a*, 1008*b* may be in the closed configuration, as shown in FIG. 31B. In the closed configuration, the pivot axis $P_1$ of each distal wing 1010*a*, 1010*b* and longitudinal axis $L_1$ may define a first pivot axis angle $\theta_1$ (as shown in FIG. 31B). In some embodiments, driver head 1416 may be coupled to central bore 1030 of plunger 1020 prior to fully inserting implant 1000 into the target space. In these embodiments, proximal wings 1008*a*, 1008*b* may be in a deployed configuration and distal wings 1010*a*, 1010*b* may be in the closed configuration during full insertion of implant 1000 into the target space.

Step 1822 may be substantially similar to step 822 of method 800. At step 1822, insertion tool 1400 may be actuated to transition implant 1000 from the closed configuration to the clamped configuration. Actuating insertion tool 1400 may include distally advancing inner rod 1412 to advance inner rod 1412 through central bore 1062 of proximal carrier 1016. Inner rod 1412 may then contact contacting surfaces 1080*a*, 1080*b* of proximal wings 1008*a*, 1008*b* located in front of central bore 1062 to pivot proximal wings 1008*a*, 1008*b* about proximal carrier 1016 from the closed configuration to the deployed configuration, as shown in FIG. 41A.

In embodiments where driver head 1416 is coupled to central bore 1030 of plunger 1020 prior to fully inserting implant 1000 into the target space, distally advancing inner rod 1412 to advance inner rod 1412 through central bore 1062 of proximal carrier 1016 may occur during attachment of implant 1000 to insertion tool 1400 (e.g., during step 1814). In these embodiments, inner rod 1412 may contact contacting surfaces 1080*a*, 1080*b* of proximal wings 1008*a*, 1008*b* located in front of central bore 1062 to pivot proximal wings 1008*a*, 1008*b* about proximal carrier 1016 from the closed configuration to the deployed configuration prior to implant 1000 being fully inserted into the target space.

FIG. 41A illustrates a cross-sectional view of some embodiments of implant 1000 inserted in a target space, with proximal wings 1008*a*, 1008*b* of implant 1000 in the deployed configuration. When proximal wings 1008*a*, 1008*b* are in the deployed configuration, a second wing axis angle $\theta_2$ may be defined between each respective wing axis $W_1$ and the longitudinal axis $L_1$, as shown in FIG. 41A. The second wing axis angle $\theta_2$ of the deployed configuration may be greater than the first wing axis angle $\theta_2$ of the closed configuration. In some embodiments, the second wing axis angle $\theta_2$ may be within a range of 45 degrees to 65 degrees, such as between 50 and 60 degrees. In some embodiments, distally translating inner rod 1412 may cause inner rod 1412 to push on contacting surfaces 1080*a*, 1080*b* to thereby pivot proximal wings 1008*a*, 1008*b* from the closed position to the deployed position. Once proximal wings 1008*a*, 1008*b* pivot to the deployed configuration, contacting surfaces 1080*a*, 1080*b* may touch inner rod 1412 while inner rod 1412 is inserted through central bore 1062 of proximal carrier 1016. Inner rod 1412 may maintain proximal wings 1008*a*, 1008*b* in the deployed configuration and act as a stop to keep proximal wings 1008*a*, 1008*b* from pivoting back to the closed configuration.

Actuating the insertion tool 1400 may further include distally advancing inner rod 1412 to central bore 1030 of plunger 1020 and coupling driver head 1416 to central bore 1030. Driver head 1416 may threadedly couple to central bore 1030 by rotating inner rod 1412. Distal advancement of insertion tool 1400, once coupled to central bore 1030, may distally translate plunger 1020. Distal translation of plunger 1020 may cause distal wings 1010*a*, 1010*b* to pivot about outer body 1002 from the closed configuration to the deployed configuration.

FIG. 41B illustrates a cross-sectional view of some embodiments of implant 1000 inserted in a target space in the deployed configuration. Implant 1000 may be in the deployed configuration when both distal wings 1010*a*, 1010*b* and proximal wings 1008*a*, 1008*b* are in the deployed position. When distal wings 1010*a*, 1010*b* are in the deployed configuration, a second pivot axis angle $\theta_1$ may be defined between each respective pivot axis $P_1$ and the longitudinal axis $L_1$. For example and as shown in FIG. 41B, a second pivot axis angle $\theta_1$ may be defined between a pivot axis $P_1$ of first distal wing 1010*a* and the longitudinal axis $L_1$. The second pivot axis angle $\theta_1$ of the deployed configuration may be greater than the first pivot axis angle $\theta_1$ of the closed configuration. In some embodiments, the second pivot axis angle $\theta_1$ may be within a range of 50 degrees to 80 degrees, such as between 65 and 75 degrees. Additionally, when implant 1000 is in the deployed configuration, a first distance $D_1$ may be defined between distal wings 1010*a*, 1010*b* and proximal wings 1008*a*, 1008*b*, as shown in FIG. 41B.

Next, implant 1000 and insertion tool 1400 may be moved proximally to engage distal wings 1010*a*, 1010*b* with bone or tissue at and/or near the treatment site to thereby transition distal wings 1010*a*, 1010*b* from the deployed configuration to the clamped configuration. FIG. 41C illustrates a cross-sectional view of some embodiments of implant 1000 inserted in a target space in the clamped configuration. At least a part of extensions 1098*a*, 1098*b*, 1098*c*, 1098*d* of distal wings 1010*a*, 1010*b* may engage bone or tissue at and/or near the treatment site when distal wings 1010*a*, 1010*b* are in the clamped configuration. In some embodiments, tips 1204*a*, 1204*b*, 1204*c*, 1204*d* of extensions 1098*a*, 1098*b*, 1098*c*, 1098*d* may engage bone or tissue at and/or near the treatment site, such as spinous processes 604*a*, 604*b* adjacent interspinous process space 602, as shown in FIG. 41C. When implant 1000 is in the clamped configuration, a second distance $D_2$ may be defined between distal wings 1010*a*, 1010*b* and proximal wings 1008*a*, 1008*b*, as shown in FIG. 41C. Second distance $D_2$ may be less than first distance $D_1$, such that proximal wings 1008*a*, 1008*b* are closer to distal wings 1010*a*, 1010*b* in the clamped configuration relative to the deployed configuration.

Actuation of insertion tool 1400 may further include turning rotating shaft 1425 in a first direction to rotate nut 1018 in a first direction to thereby distally advance proximal carrier 1016 and proximal wings 1008*a*, 1008*b* toward the treatment site to transition proximal wings 1008*a*, 1008*b* from the deployed configuration to the clamped configuration. In the clamped configuration, proximal wings 1008*a*, 1008*b* may engage bone or tissue at and/or near the treatment site to secure implant 1000 within treatment site. For example and as shown in FIG. 41C, extensions 1041*a*, 1041*b*, 1041*c*, 1041*d* of proximal wings 1008*a*, 1008*b* may engage spinous processes 604*a*, 604*b* adjacent the interspinous process space 602 to maintain implant 1000 within interspinous process space 602. In some embodiments, tips 1082*a*, 1082*b*, 1082*c*, 1082*d* of extensions 1041*a*, 1041*b*, 1041*c*, 1041*d* may engage bone or tissue at and/or near the target space.

Optional step 1824 may be substantially similar to optional step 824. At an optional step 1824, insertion tool 1400 may be actuated to transition implant 1000 from the clamped configuration to the closed configuration. Insertion tool 1400 may be actuated to transition implant 1000 from the clamped configuration to the deployed configuration, and finally to the closed configuration. Optional step 1824 may allow surgeons or operators to reposition or remove implant 1000 from the target space. Actuation of insertion tool 1400 may include turning rotating shaft 1425 in a second direction to rotate nut 1018 in a second direction to thereby proximally translate proximal wings 1008*a*, 1008*b* away from the treatment site to transition proximal wings 1008*a*, 1008*b* from the clamped configuration to the deployed configuration. Moving insertion tool 1400 distally may move implant 1000 distally to disengage distal wings 1010*a*, 1010*b* from bone or tissue near the treatment site, thereby transitioning distal wings 1010*a*, 1010*b* from the clamped configuration to the deployed configuration. Proximally translating inner rod 1412 may proximally translate plunger 1020, thereby pivoting distal wings 1010*a*, 1010*b* from the deployed configuration to the closed configuration. Proximally translating inner rod 1412 out of central bore 1062 may cause proximal wings 1008*a*, 1008*b* to collapse from the deployed configuration to the closed configuration.

Step 1826 may be substantially similar to step 826 of method 800. For example, at step 1826, insertion tool 1400 may be detached from implant 1000. In some embodiments, insertion tool 1400 may be detached from implant 1000 by rotating outer grip 1408 in a second direction to proximally translate attachment member 1410 away from outer body 1002. Proximal translation of attachment member 1410 may cause arms 1422*a*, 1422*b* to dislodge from indentations 1042*a*, 1042*b* to thereby detach implant 1000 from insertion tool 1400. Detaching insertion tool 1400 from implant 1000 may also include decoupling inner rod 1412 from central bore 1030 of plunger 1020. In some embodiments, inner rod 1412 may be decoupled from plunger 1020 by rotating inner rod 1412 such that threads on driver head 1416 decouple from threads in central bore 1030. Detaching insertion tool 1400 from implant 1000 may also include decoupling rotating shaft 1425 from nut 1018 in some embodiments. At step 1828, insertion tool 1400 may be removed from the patient.

Figure 42:
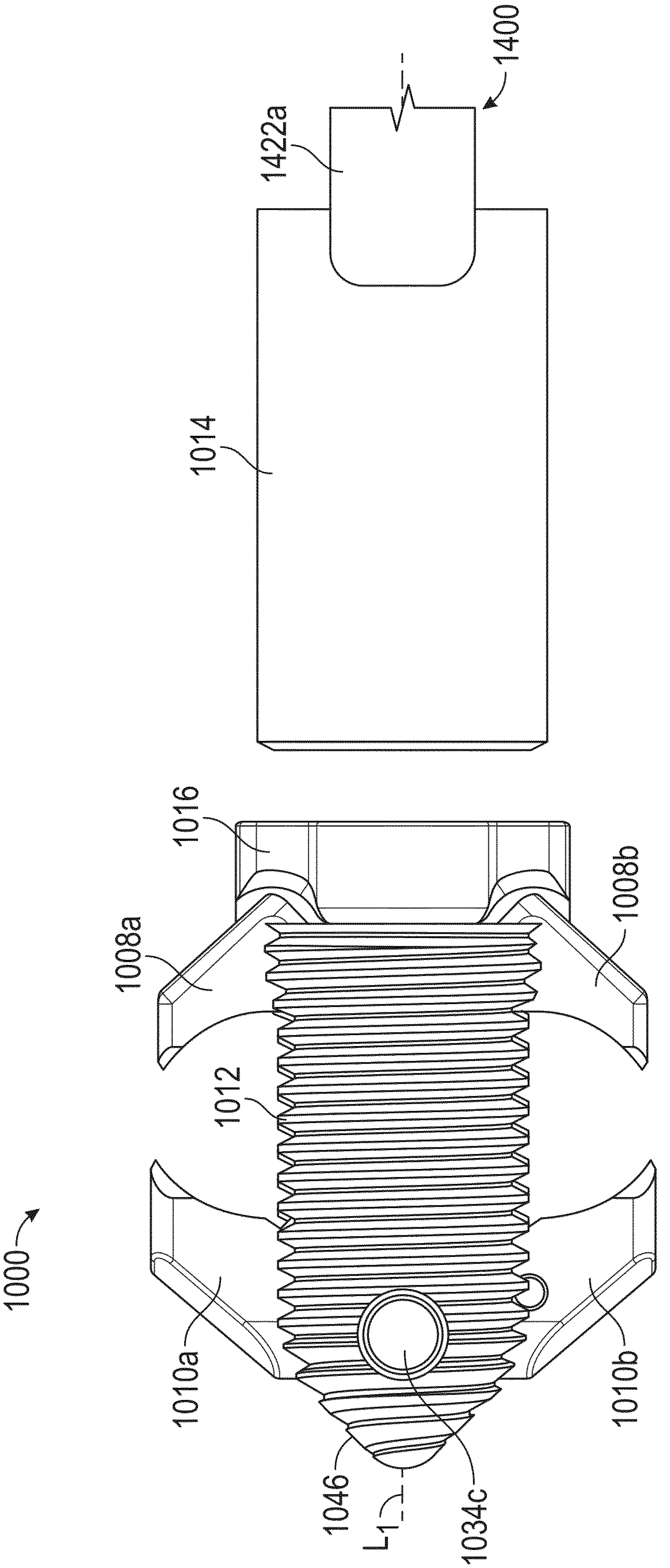
FIG. 42 illustrates some embodiments of a cartridge of the outer body of the second embodiment of the implant being removed.

In some embodiments, step 1826 may include detaching cartridge 1014 from implant 1000. FIG. 42 illustrates some embodiments of cartridge 1014 of outer body 1002 being removed from implant 1000. In some embodiments, cartridge 1014 may be removable from threaded portion 1012 of outer body 1002. Cartridge 1014 may couple to threaded portion 1012. In some embodiments, cartridge 1014 may connect to threaded portion 1012 through a preformed frangible or separable connection known to one skilled in the art. Detaching of insertion tool 1400 may simultaneously break the frangible connection and thereby remove cartridge 1014 from threaded portion 1012. The frangible connection may be a snap fit that may be un-snapped through movement of insertion tool 1400. In embodiments where cartridge 1014 detaches from threaded portion 1012, proximal carrier 1016 may distally translate onto a portion of plunger 1020 and thereby couple to plunger 1020, such that proximal wings 1008*a*, 1008*b* remain on implant 1000 when cartridge is removed. In embodiments where cartridge 1014 detaches from threaded portion 1012, nut 1018 may detach from proximal carrier 1016 such that nut 1018 stays within bore 1006 of cartridge 1014 when cartridge 1014 is removed.

Figure 43:
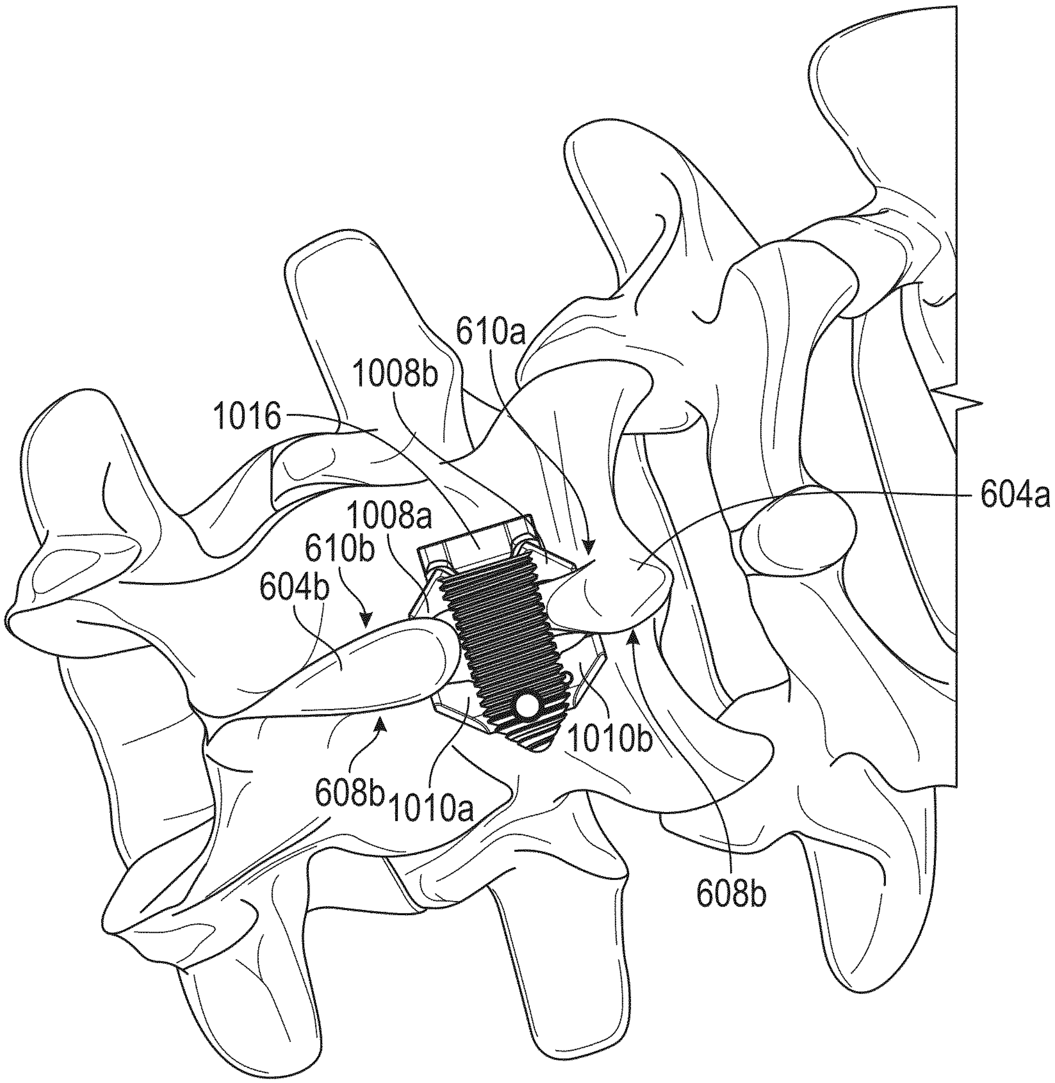
FIG. 43 illustrates a perspective view of the second embodiment of the implant in a clamped configuration, inserted in the spine of a patient.

FIG. 43 illustrates a perspective view of some embodiments of implant 1000 in a clamped configuration inserted in the spine of a patient. As shown in FIG. 30, distal wings 1010*a*, 1010*b* may anchor to distal sides 608*a*, 608*b* of adjacent spinous processes 604*a*, 604*b* when in the clamped configuration in an interspinous process space, such as interspinous process space 602 shown in FIGS. 41A and 41C. Proximal wings 1008*a*, 1008*b* may anchor to proximal sides 610*a*, 610*b* of adjacent spinous processes 604*a*, 604*b* when in the clamped configuration in an interspinous process space, such as interspinous process space 602 shown in FIGS. 41A and 41C. Distal wings 1010*a*, 1010*b* and proximal wings 1008*a*, 1008*b* thereby provide anchors for maintaining implant 1000 in place at the treatment site. Implant 1000 may be used for stabilization and fusion of other bony structures and/or joints within the body. For example, implant 1000 may anchor to any adjacent bony structures and/or soft tissue to stabilize bony structures and/or joints. Implant 1000 may be inserted in an SI joint space to fixate bone at the SI joint and/or stabilize the SI joint.

Third Implant Embodiment

Figure 44A:
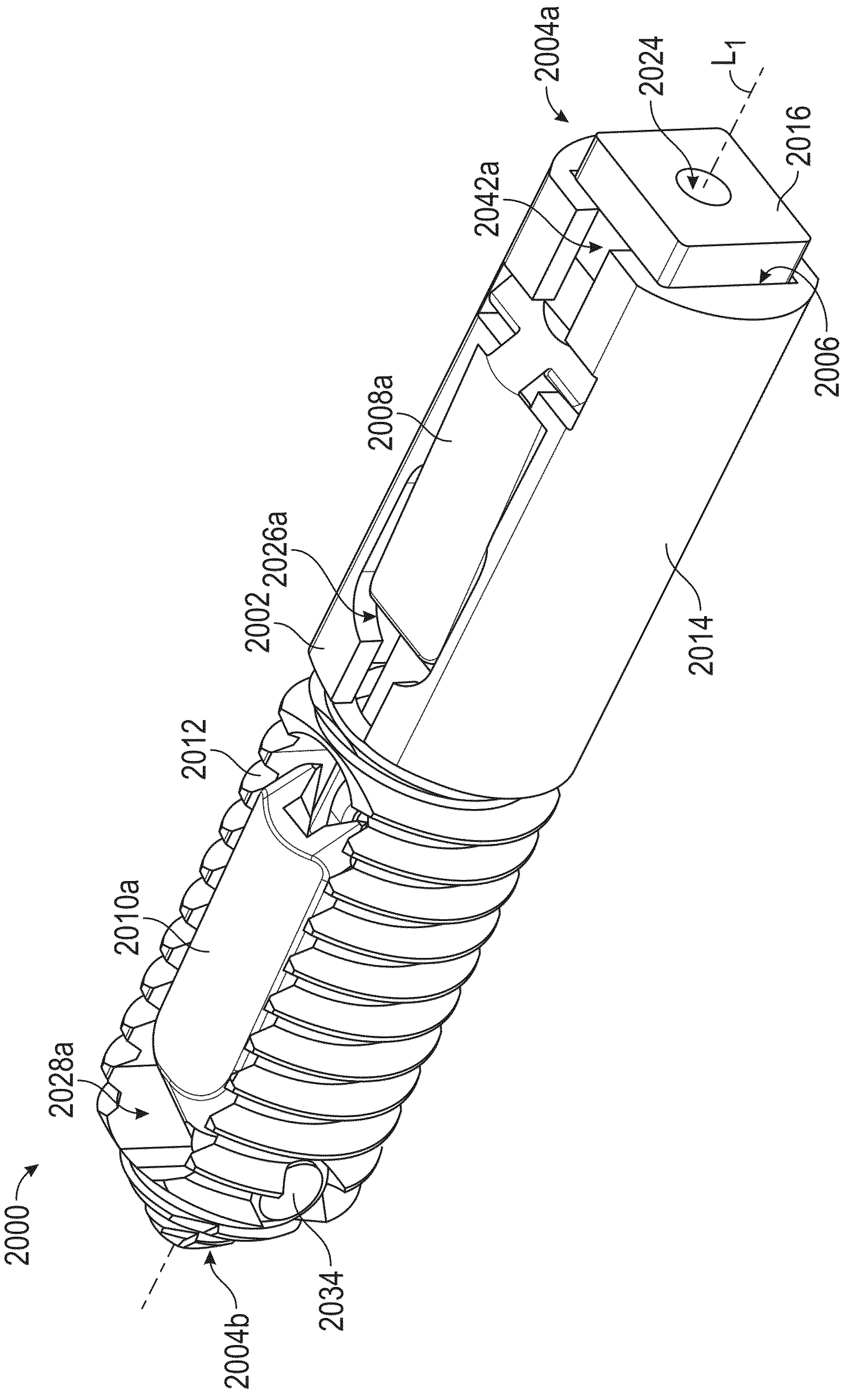
FIG. 44A illustrates a perspective view of a third embodiment of an implant in a closed position.
Figure 44B:
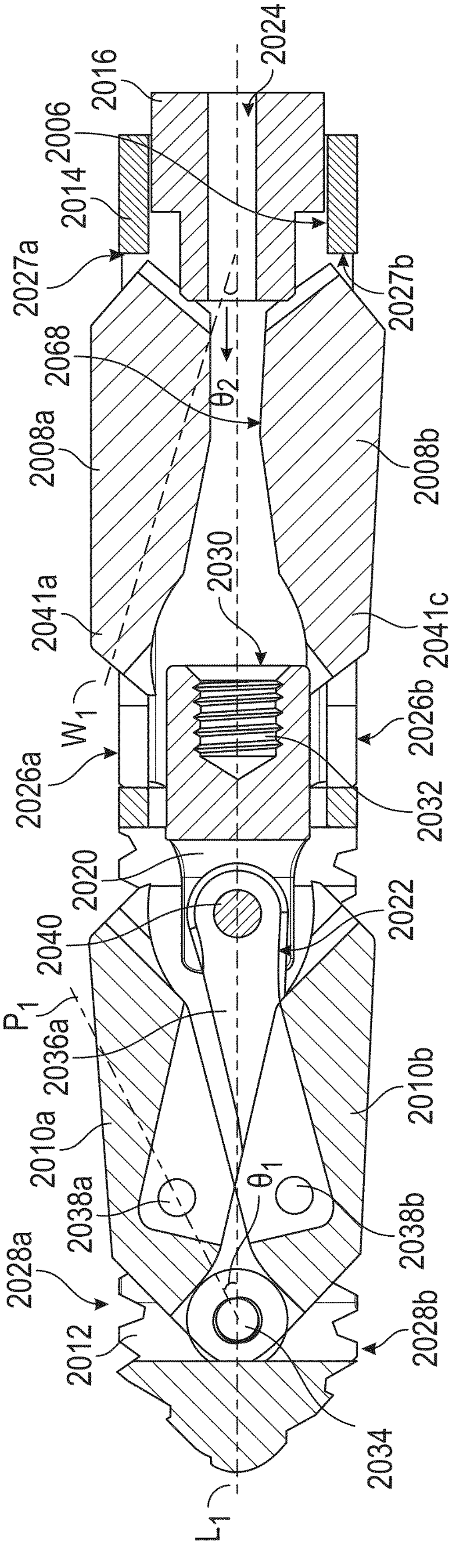
FIG. 44B illustrates a cross-sectional view of the third embodiment of the implant in the closed position.

FIG. 44A illustrates a perspective view of a third embodiment of an implant 2000 in a closed position (also referred to as a closed configuration). FIG. 44B illustrates a cross-sectional view of the third embodiment of the implant 2000 in a closed configuration. Accordingly, FIGS. 44A-44B are best viewed together. Implant 2000 may be configured to be inserted within a target space between bones and/or within a joint for fusion, fixation, and/or stabilization of bones and/or joints. Implant 2000 may be inserted anywhere in a body where there is a need for fixation and/or stabilization of bones, joints, and/or soft tissue. In some embodiments, implant 2000 may be configured to be inserted into an interspinous process space for fusion and stabilization of spinous processes. Implant 2000 may comprise an outer body 2002 defining a longitudinal axis $L_1$ extending through a proximal end 2004*a* and a distal end 2004*b*. Outer body 2002 may define a bore 2006 extending through proximal end 2004*a*. Implant 2000 may include proximal wings 2008*a*, 2008*b* (as referred to as proximal anchors) and distal wings 2010*a*, 2010*b* (also referred to as distal anchors). In some embodiments, implant 2000 may comprise at least one proximal wing 2008*a*, 2008*b* and at least one distal wing 2010*a*, 2010*b*. In some embodiments, implant 2000 may comprise more than one proximal wing 2008*a*, 2008*b* and more than one distal wing 2010*a*, 2010*b*. Distal wings 2010*a*, 2010*b* may pivotally couple to outer body 2002. Proximal wings 2008*a*, 2008*b* may operatively couple to outer body 2002. Distal wings 2010*a*, 2010*b* may pivot about outer body 2002 to transition between a closed configuration and a deployed configuration. Proximal wings 2008*a*, 2008*b* may pivot around outer body 2002 to transition between a closed configuration and a deployed configuration. Proximal wings 2008*a*, 2008*b* may travel along outer body 2002 to transition implant 2000 between the deployed configuration and a clamped configuration.

In the closed configuration, distal wings 2010*a*, 2010*b* and proximal wings 2008*a*, 2008*b* may substantially align with longitudinal axis $L_1$, as shown in FIG. 44B. In some embodiments, distal wings 2010*a*, 2010*b* and proximal wings 2008*a*, 2008*b* may be substantially parallel to longitudinal axis $L_1$ when implant is in the closed configuration.

Outer body 2002 may be substantially similar to outer body 1002. At least a portion of outer body 2002 may include external threading, forming a threaded portion 2012. Threading on threaded portion 2012 may engage muscle, soft tissue, and/or bone at the treatment site to provide fixation of implant 2000 at the treatment site. Threading on threaded portion 2012 may engage muscle, soft tissue, and/or bone during insertion of the implant 2000 up to the treatment site to aid implant insertion and make insertion easier. Threading on threaded portion 2012 may engage muscle, soft tissue, and/or bone at the treatment site to stabilize the implant 2000 at the treatment site. Outer body 2002 may include a cartridge 2014. In some embodiments, cartridge 2014 may be integrally connected to threaded portion 2012. In some embodiments, cartridge 2014 may be operatively coupled to threaded portion 2012. Cartridge 2014 may be threadedly coupled to threaded portion 2012. In some embodiments, cartridge 2014 may be coupled to threaded portion 2012 through an interference fit, snap fit, or any other coupling mechanism known to those of skill in the art. Cartridge 2014 may be removable from threaded portion 2012, as further discussed herein. In embodiments where cartridge 2014 is removable from threaded portion 2012, cartridge 1014 may couple to threaded portion 1012 through a preformed frangible or separable connection known to one skilled in the art.

Proximal wings 2008*a*, 2008*b* may pivotally couple to outer body 2002. In some embodiments, proximal wings 2008*a*, 2008*b* may pivotally couple to outer body 2002 similarly to proximal wings 108*a*, 108*b* pivotally coupling to outer body 102. For example, proximal wings 2008*a*, 2008*b* may pivotally couple to outer body 2002 through a pin received in apertures defined by outer body 2002 and proximal wings 2008*a*, 2008*b*. In some embodiments where cartridge 2014 is integrally connected to threaded portion 2012 and is not removable, proximal wings 2008*a*, 2008*b* may pivotally couple to cartridge 2014 of outer body 2002. In some embodiments, proximal wings 2008*a*, 2008*b* may pivotally couple to a proximal carrier 2016, similarly to proximal wings 1008*a*, 1008*b* pivotally coupling to proximal carrier 1016. For example, proximal wings 2008*a*, 2008*b* may pivotally couple to proximal carrier 2016 through a pin received in apertures defined by outer body 2002 and proximal wings 2008*a*, 2008*b*. In some embodiments, proximal wings 2008*a*, 2008*b* may pivotally couple to proximal carrier 2016 via any coupling mechanism known to a person of skill in the art. In embodiments where cartridge 2014 is removable from threaded portion 2012 of outer body 2002, proximal wings 2008*a*, 2008*b* may be pivotally coupled to proximal carrier 2016.

Distal wings 2010*a*, 2010*b* may pivotally couple to a portion of outer body 2002. Distal wings 2010*a*, 2010*b* may pivotally couple to outer body 2002 proximate the distal end 2004*b* of outer body 2002. Distal wings 2010*a*, 2010*b* may operatively couple to a plunger 2020 of implant 2000 via a linkage assembly 2022 (as shown in FIG. 44B), as discussed further herein. Translation of plunger 2020 may pivot distal wings 2010*a*, 2010*b* between the closed configuration and a deployed configuration.

In some embodiments, proximal carrier 2016 may operatively couple to outer body 2002. Proximal carrier 2016 may operatively couple to cartridge 2014 of outer body. In embodiments where cartridge 2014 is integrally connected to threaded portion 2012, proximal carrier 2016 may operatively couple to cartridge 2014. Proximal carrier 2016 may operatively couple to cartridge 2014 via a pin and slot mechanism, such that proximal carrier 2016 may move along cartridge 2014. In some embodiments, proximal carrier may move within bore 2006. In some embodiments, proximal carrier 2016 may not be connected to outer body 2002 and may instead slide within bore 2006 of cartridge 2014. Proximal carrier 2016 may attach to an insertion tool 2400 and move within bore 2006 of cartridge 2014, as discussed further herein. In embodiments where proximal wings 2008*a*, 2008*b* are pivotally coupled to proximal carrier 2016, proximal wings 2008*a*, 2008*b* may pivot about proximal carrier 2016 to transition between a closed configuration and a deployed configuration. In embodiments where proximal wings 2008*a*, 2008*b* are pivotally coupled to outer body 2002, proximal wings 2008*a*, 2008*b* may pivot about outer body 2002 to transition between the closed configuration and the deployed configuration. Proximal wings 2008*a*, 2008*b* may translate along outer body 2002 to transition implant 2000 between the deployed position and a clamped configuration.

Proximal carrier 2016 may be received in bore 2006 and may move within bore 2006. Translation of proximal carrier 2016 within bore 2006 may cause proximal carrier 2016 to contact proximal wings 2008*a*, 2008*b* to thereby pivot proximal wings 2008*a*, 2008*b* from the closed configuration to the deployed configuration. Translation of proximal carrier 2016 along outer body 2002 may further cause proximal wings 2008*a*, 2008*b* to translate along outer body 2002 to thereby transition implant 2000 between the deployed configuration and the clamped configuration, as discussed further herein. In some embodiments, translation of proximal carrier 2016 along bore 2006 may cause proximal wings 2008*a*, 2008*b* to translate along outer body 2002 to thereby transition implant 2000 between the deployed configuration and the clamped configuration.

In some embodiments, a portion of proximal carrier 2016 may be received in bore 2006 when implant is in the closed configuration, as shown in FIGS. 44A-44B. In some embodiments, proximal carrier 2016 may be separate from implant 2000 when implant 2000 is in the closed configuration. Instead, proximal carrier 2016 may be attached to an insertion tool 2400, as discussed further herein. Translation of proximal carrier 2016 may include a portion of insertion tool 2400 pushing or pressing proximal carrier 2016. Pushing or pressing proximal carrier 2016 may cause proximal carrier 2016 to push proximal wings 2008*a*, 2008*b* to thereby transition proximal wings 2008*a*, 2008*b* from the closed configuration to the deployed configuration. Continuing to push or press proximal carrier 2016 may cause proximal wings 2008*a*, 2008*b* to distally translate along outer body 2002 to thereby transition proximal wings 2008*a*, 2008*b* from the deployed configuration to the clamped configuration. Proximal carrier 2016 may define a through-hole 2024. Through-hole 2024 may receive a portion of an insertion tool 2400, as discussed further herein.

Figure 50A:
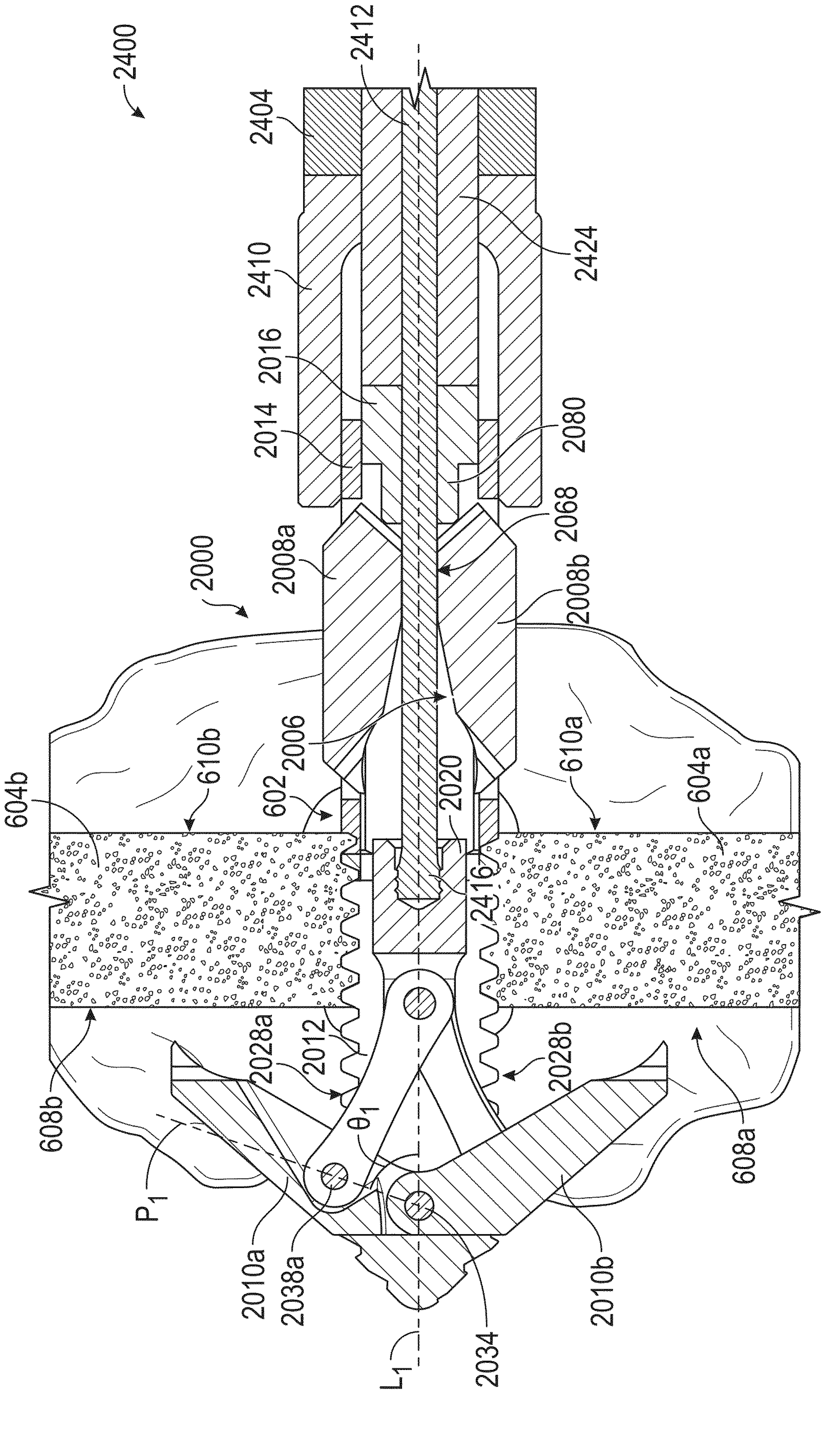
FIG. 50A illustrates a cross-sectional view of the third embodiment of the implant inserted in a target space, with the distal wings of the third embodiment of the implant in the deployed configuration.
Figure 50B:
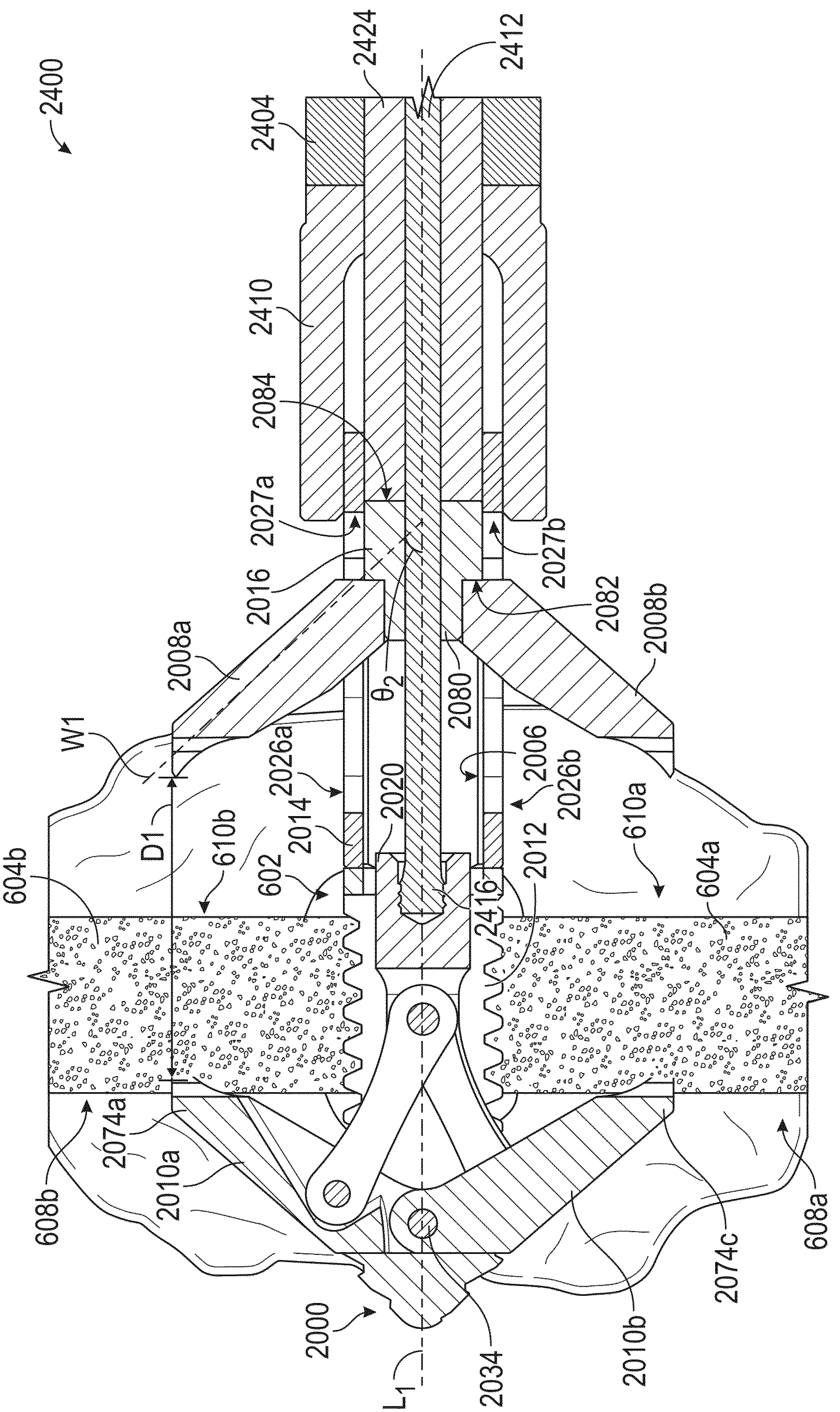
FIG. 50B illustrates a cross-sectional view of the third embodiment of the implant inserted in a target space in the deployed configuration.
Figure 50C:
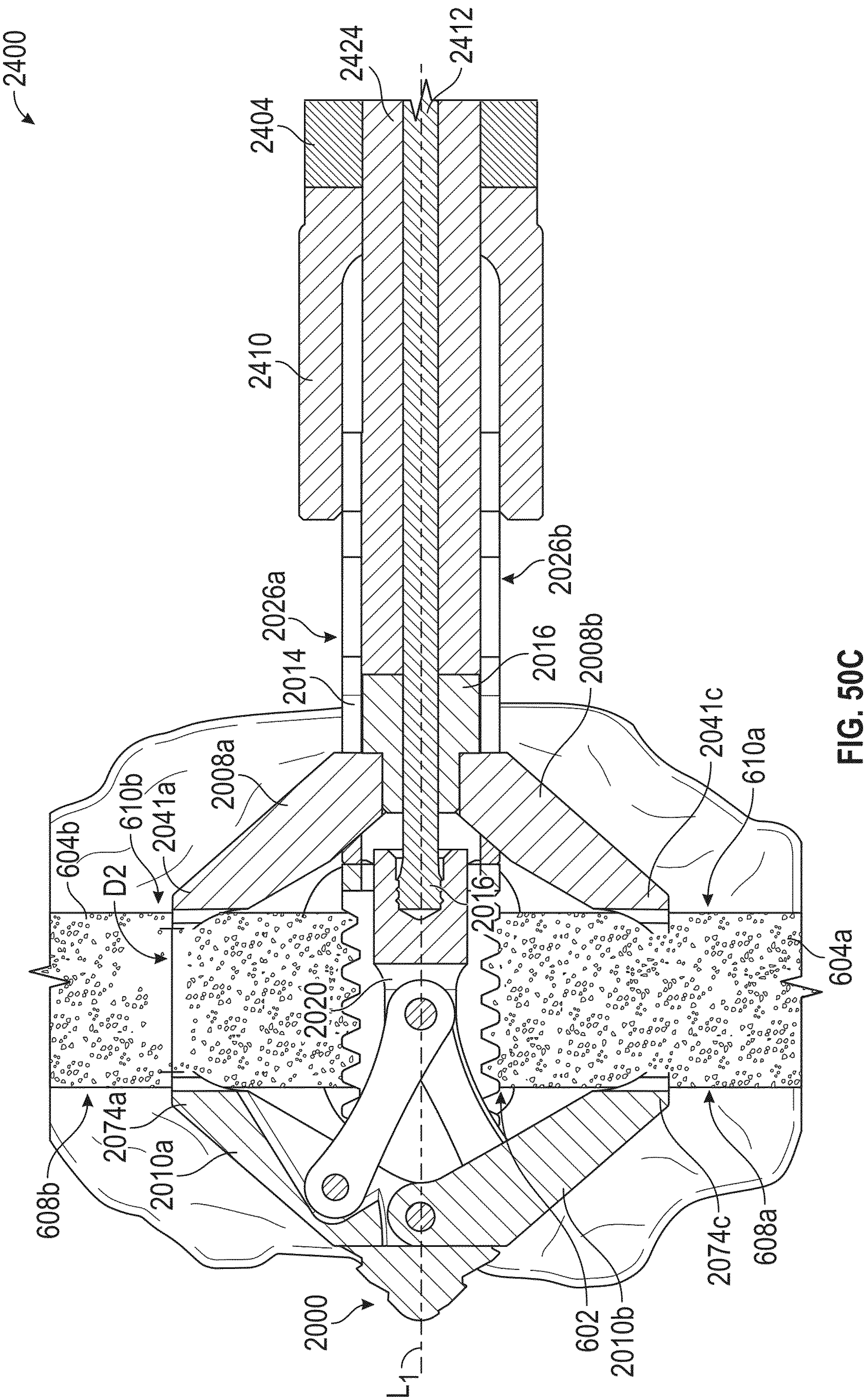
FIG. 50C illustrates a cross-sectional view of the third embodiment of the implant inserted in a target space in the clamped configuration.

Outer body 2002 of implant 2000 may define channels 2026*a*, 2026*b*, as shown in FIG. 44A. In some embodiments, channels 2026*a*, 2026*b* may be defined by cartridge 2014. In the closed configuration, proximal wings 2008*a*, 2008*b* may be received inside channels 2026*a*, 2026*b*, as shown in FIGS. 44A-44B. The proximal wings 2008*a*, 2008*b* being received inside channels 2026*a*, 2026*b* decreases the overall profile of the implant 2000 when the implant 2000 is inserted in the closed position, as compared to the proximal wings 2008*a*, 2008*b* extending outward from the channels 2026*a*, 2026*b* during insertion. This decreases the amount of blood loss during insertion, decreases the disruption of soft tissue and/or bone during insertion, and decreases the size of the incision required to insert implant 2000, thereby minimizing recovery time after the surgery and pain felt by the patient. Proximal wings 2008*a*, 2008*b* may pivot outward through channels 2026*a*, 2026*b* to transition from the closed position to the deployed position. Proximal wings 2008*a*, 2008*b* may then distally translate along channels 2026*a*, 2026*b* to transition implant 2000 from the deployed position to the clamped configuration (as shown in FIG. 50C). Proximal wings 2008*a*, 2008*b* may interact with proximal carrier 2016 to pivot proximal wings 2008*a*, 2008*b* between the closed configuration and the deployed configuration. In the deployed configuration, a portion of each proximal wing 2008*a*, 2008*b* may extend through channels 2026*a*, 2026*b* (as shown in FIG. 50B). In some embodiments, when proximal wings 2008*a*, 2008*b* are in the deployed configuration, distal wings 2010*a*, 2010*b* may be a first distance $D_1$ away from proximal wings 2008*a*, 2008*b* (see FIG. 50B). When implant 2000 is in the clamped configuration, distal wings 2010*a*, 2010*b* may be a second distance $D_2$ away from proximal wings 2008*a*, 2008*b* (see FIG. 50C). Second distance $D_2$ may be less than the first distance $D_1$, such that distal wings 2010*a*, 2010*b* and proximal wings 2008*a*, 2008*b* are closer together in the clamped configuration relative to the deployed configuration.

In some embodiments and as shown in FIG. 44A, distal wings 2010*a*, 2010*b* may pivotally couple to threaded portion 2012 of outer body 2002. Outer body 2002 may define windows 2028*a*, 2028*b*. Distal wings 2010*a*, 2010*b* may be seated within windows 2028*a*, 2028*b* when in the closed position, as shown in FIG. 44A. The distal wings 2010*a*, 2010*b* being received inside windows 2028*a*, 2028*b* decreases the overall profile of the implant 2000 when the implant 2000 is inserted in the closed position, as compared to the distal wings 2010*a*, 2010*b* extending outward from the windows 2028*a*, 2028*b* during insertion. This decreases the amount of blood loss during insertion, decreases the disruption of soft tissue and/or bone during insertion, and decreases the size of the incision required to insert implant 2000, thereby minimizing recovery time after the surgery and pain felt by the patient. Plunger 2020 may define a central bore 2030 configured to receive a portion of an insertion tool 2400, as discussed further herein. In some embodiments, plunger 2020 may comprise threads 2032 along the interior wall defining central bore 2030, as shown in FIG. 44B. Distally advancing the portion of the insertion tool 2400 received in central bore 2030 may distally advance plunger 2020 to thereby cause distal wings 2010*a*, 2010*b* to pivot from the closed configuration to the deployed configuration, as discussed further herein. In the deployed configuration, a portion of each distal wing 2010*a*, 2010*b* may extend outward through windows 2028*a*, 2028*b* (as shown in FIG. 50A).

Implant 2000 may comprise pivot pins 2034. Pivot pins 2034 may pivotally couple proximal wings 2008*a*, 2008*b* to proximal carrier 2016 and pivotally couple distal wings 2010*a*, 2010*b* to outer body 2002. In embodiments where cartridge is removable, pivot pins 2034 may pivotally couple proximal wings 2008*a*, 2008*b* to proximal carrier 2016. In embodiments where cartridge is integrally connected to threaded portion 2012, pivot pins 2034 may pivotally couple proximal wings 2008*a*, 2008*b* to cartridge 2014 of outer body 2002. Linkage assembly 2022 may be substantially similar to linkage assembly 1022 and comprise linkages 2036*a*, 2036*b*. Linkages 2036*a*, 2036*b* may operatively couple plunger 2020 to distal wings 2010*a*, 2010*b*. Linkage pins 2038*a*, 2038*b* may couple distal wings 2010*a*, 2010*b* to linkages 2036*a*, 2036*b*. Plunger pin 2040 may couple linkages 2036*a*, 2036*b* to plunger 2020.

Each distal wing 2010*a*, 2010*b* may define a pivot axis $P_1$ extending from the longitudinal axis $L_1$ at the center of pivot pin 2034 through the center of linkage pins 2038*a*, 2038*b*, and through distal wings 2010*a*, 2010*b*. For example and as shown in FIG. 44B, a pivot axis $P_1$ may be defined extending from the longitudinal axis $L_1$ at the center of pivot pin 2034 through the center of linkage pin 2038*a* and through a first distal wing 2010*a*. A first pivot axis angle $\theta_1$ may be defined between a respective pivot axis $P_1$ and longitudinal axis $L_1$ of outer body 2002 when implant 2000 is in the closed configuration. In the closed configuration, the first pivot axis angle $\theta_1$ may be within a range of 10 degrees to 30 degrees, such as between 15 and 25 degrees. Each proximal wing 2008*a*, 2008*b* may define a wing axis $W_1$ extending from the longitudinal axis $L_1$ through a center of ends of proximal wings 2008*a*, 2008*b*. For example and as shown in FIG. 44B, a wing axis $W_1$ may be defined extending from the longitudinal axis $L_1$ through a center of an end of a first proximal wing 2008*a*. In some embodiments, a wing axis $W_1$ may be defined extending from a point on longitudinal axis $L_1$ aligned with an edge 2027*a*, 2027*b* of channels 2026*a*, 2026*b* through a center of ends of extensions 2041*a*, 2041*b*, 2041*c*, 2041*d* of proximal wings 2008*a*, 2008*b*, as shown in FIG. 44B. A first wing axis angle $\theta_2$ may be defined between a respective wing axis $W_1$ and longitudinal axis $L_1$ of outer body 2002 when implant 2000 is in the closed configuration. In some embodiments, the first wing axis angle $\theta_2$ may be within a range of 10 degrees to 30 degrees, such as between 15 and 25 degrees.

In some embodiments, outer body 2002 may comprise openings 2042*a*, 2042*b* configured to receive at least a portion of an insertion tool 2400 to thereby attach implant 2000 to an insertion tool 2400, as further discussed herein. Implant 2000 may further comprise a space 2068 between proximal wings 2008*a*, 2008*b* when proximal wings 2008*a*, 2008*b* are in the closed configuration (see FIG. 44B), as further described below.

Figure 45:
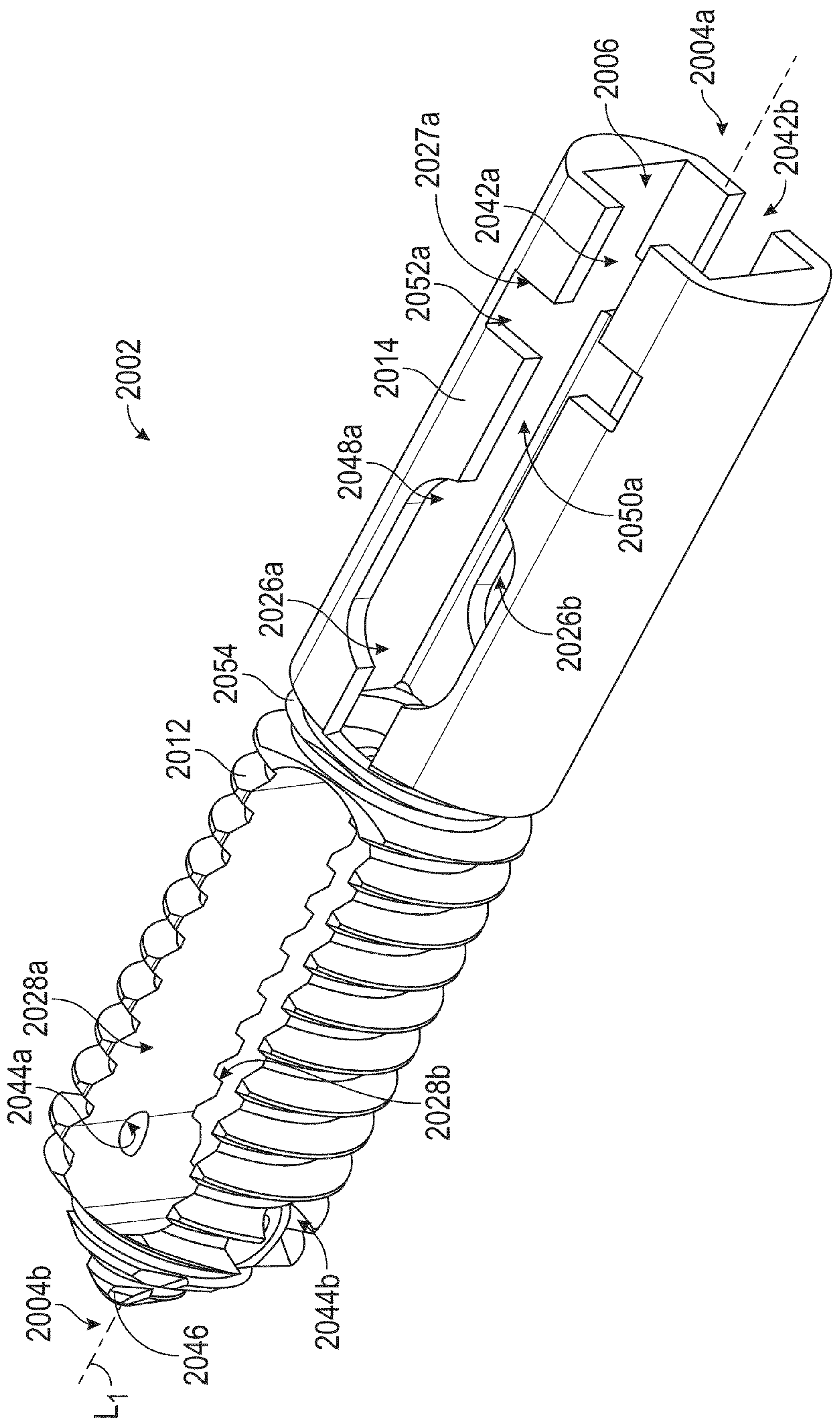
FIG. 45 illustrates a perspective view of some embodiments of an outer body of the third embodiment of the implant.

FIG. 45 illustrates a perspective view of some embodiments of outer body 2002 of implant 2000. Outer body 2002 may define outer body apertures 2044*a*, 2044*b*. At least a portion of a pivot pin 2034 may extend through outer body apertures 2044*a*, 2044*b* to thereby pivotally couple distal wings 2010*a*, 2010*b* to outer body 2002. Outer body apertures 2044*a*, 2044*b* may be located proximate distal end 2004*b* of outer body 2002. Outer body 2002 may comprise tip 2046 on distal end 2004*b*. In some embodiments, threaded portion 2012 may comprise tip 2046. Tip 2046 may have a generally conical shape. Tip 2046 may be pointed to aid in inserting the implant 2000 into bone or tissue. In some embodiments, threaded portion 2012 may additionally or alternatively include cutting threads to aid in inserting the implant 2000 into the target space (e.g., interspinous process space). Threaded portion 2012 may decorticate bone and/or tissue to facilitate inserting implant 2000 into the treatment site (also referred to as the target space). Tip 2046 may include cutting threads to aid in inserting the implant 2000 into the target space. In some embodiments, tip 2046 may have a smooth exterior surface without any threads thereon. In some embodiments, tip 2046 is solid (as shown in FIG. 44B) to strengthen implant 2000 during insertion.

At least a portion of each channels 2026*a*, 2026*b* may be shaped to receive ends of extensions 2041*a*, 2041*b*, 2041*c*, 2041*d* when proximal wings 2008*a*, 2008*b* are in the closed configuration. Channels 2026*a*, 2026*b* may have a first section 2048*a*, 2048*b* configured to receive ends of extensions 2041*a*, 2041*b*, 2041*c*, 2041*d* when proximal wings 2008*a*, 2008*b* are in the closed configuration. Channels 2026*a*, 2026*b* may have a second section 2050*a*, 2050*b*. The width of second section 2050*a*, 2050*b* may be less than the width of first section 2048*a*, 2048*b*. A portion of each channel 2026*a*, 2026*b* may form a T shape with edges 2027*a*, 2027*b*. Distal ends 2052*a*, 2052*b* of second sections 2050*a*, 2050*b* may form a T shape. Distal ends 2052*a*, 2052*b* may form edges 2027*a*, 2027*b*, as shown in FIG. 45.

In some embodiments, cartridge 2014 of outer body 2002 may define bore 2006. Bore 2006 may be square shaped. In some embodiments, bore 2006 may have any shape configured to receive proximal carrier 2016. Outer body 2002 may include a divider 2054 located between threaded portion 2012 and cartridge 2014. Divider may extend around an exterior of outer body 2002. Divider 2054 may be removable with cartridge 2014. Outer body 2002 may be substantially cylindrically shaped to facilitate insertion of implant 2000 into the target space. In some embodiments, outer body 2002 may be substantially hexagonally shaped, rectangularly shaped, or any other shape. In embodiments where cartridge 2014 is removable, divider 2054 may form the coupling mechanism that couples cartridge 2014 to threaded portion 2012.

Windows 2028*a*, 2028*b* of outer body 2002 may extend through an exterior of threaded portion 2012, such that windows 2028*a*, 2028*b* form a space for distal wings 1010*a*, 1010*b* to be seated in when distal wings 1010*a*, 1010*b* are in the closed configuration. Outer body 2002 may define openings 2042*a*, 2042*b* that receive a portion of an insertion tool 2400 to thereby attach implant 2000 to insertion tool 2400, as discussed further herein. In some embodiments, cartridge 2014 may define openings 2042*a*, 2042*b*.

Figure 46A:
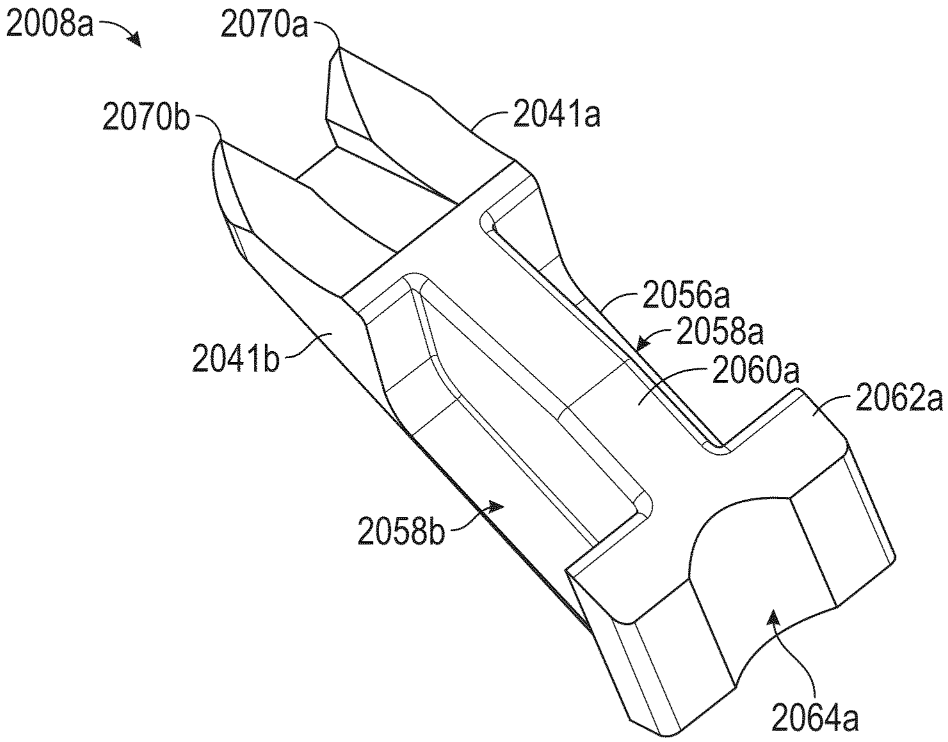
FIG. 46A illustrates a perspective bottom view of some embodiments of a proximal wing of the third embodiment of the of implant.
Figure 46B:
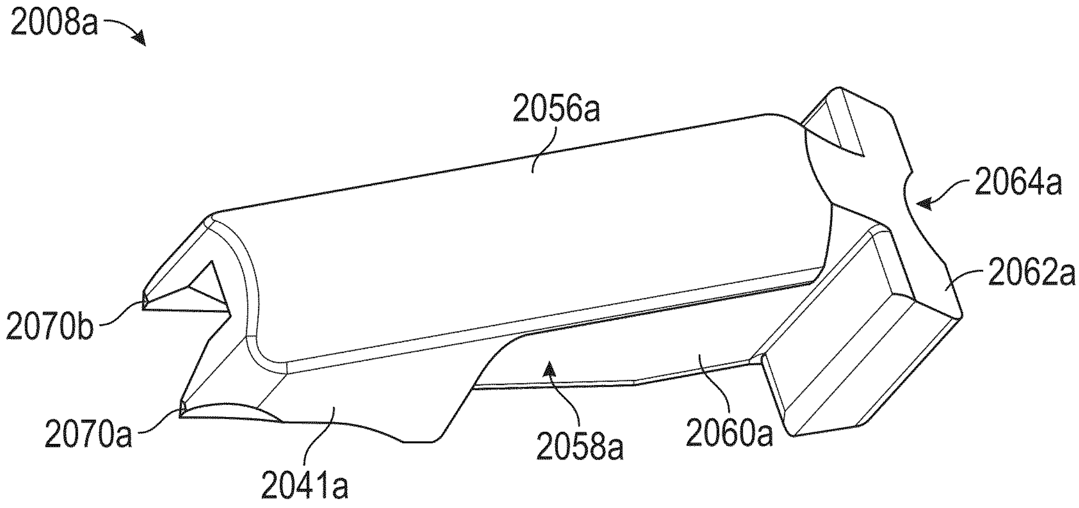
FIG. 46B illustrates a perspective top view of some embodiments of the proximal wing of the third embodiment of the implant.

FIG. 46A illustrates a perspective bottom view of some embodiments of a proximal wing 2008*a*, 2008*b* of implant 2000. FIG. 46B illustrates a perspective top view of some embodiments of a proximal wing 2008*a*, 2008*b* of implant 2000. Accordingly, FIGS. 46A-46B are best viewed together. Each proximal wing 2008*a*, 2008*b* may include extensions 2041*a*, 2041*b*, 2041*c*, 2041*d* extending from a proximal body 2056*a*, 2056*b*. For example and as shown in FIGS. 46A-46B, a first proximal wing 2008*a* may include extensions 2041*a*, 2041*b* extending from a proximal body 2056*a*. Proximal body 2056*a*, 2056*b* may define indentations 2058*a*, 2058*b*, 2058*c*, 2058*c*. A wall 2060*a*, 2060*b* may be located between indentations 2058*a*, 2058*b*, 2058*c*, 2058*d*. For example and as shown in FIG. 46A, a first proximal wing 2008*a* may define indentations 2058*a*, 2058*b* having a wall 2060*a* therebetween. Walls 2060*a*, 2060*b* may be received within second sections 2050*a*, 2050*b* of channels 2026*a*, 2026*b* when proximal wings 2008*a*, 2008*b* are in the closed configuration. Indentations 2058*a*, 2058*b*, 2058*c*, 2058*d* may provide space for walls 2060*a*, 2060*b* to be seated in second sections 2050*a*, 2050*b*.

Proximal wings 2008*a*, 2008*b* may comprise arms 2062*a*, 2062*b* extending from proximal body 2056*a*, 2056*b* such that proximal bodies 2056*a*, 2056*b* are located between arms 2062*a*, 2062*b* and extensions 2041*a*, 2041*b*, 2041*c*, 2041*d*. Arms 2062*a*, 2062*b* may be received by distal ends 2052*a*, 2052*b* of channels 2026*a*, 2026*b*. In some embodiments, arms 2062*a*, 2062*b* of proximal wings 2008*a*, 2008*b* may pivotally couple proximal wings 2008*a*, 2008*b* to proximal carrier 2016 to thereby pivotally couple proximal wings 2008*a*, 2008*b* to proximal carrier 2016. In some embodiments, arms 2062*a*, 2062*b* may pivotally couple to outer body 2002 to thereby pivotally couple proximal wings 2008*a*, 2008*b* to outer body 2002. In embodiments where cartridge 2014 is integrally connected to threaded portion 2012, arms 2062*a*, 2062*b* may pivotally couple to cartridge 2014. In some embodiments, arms 2062*a*, 2062*b* may comprise pivot apertures for receiving a pivot pin, similar to pivot apertures 1072*a*, 1072*b*, 1027*c*, 1027*d* of proximal wings 1008*a*, 1008*b*. A pivot pin, such as pivot pin 1034*a*, 1034*b* of implant 1000, may be received in pivot apertures defined by arms 2062*a*, 2062*b* and in apertures defined by cartridge 2014 to thereby pivotally couple proximal wings 2008*a*, 2008*b* to outer body 2002. In some embodiments, a pivot pin may be received in pivot apertures defined by arms 2062*a*, 2062*b* and in carrier apertures defined by proximal carrier 2016 to thereby pivotally couple proximal wings 2008*a*, 2008*b* to proximal carrier 2016. Proximal wings 2008*a*, 2008*b* may pivot about distal ends 2052*a*, 2052*b* of channels 2026*a*, 2026*b* to transition proximal wings 2008*a*, 2008*b* between the closed configuration and the deployed configuration.

Arms 2062*a*, 2062*b* may include contacting surfaces 2064*a*, 2064*b*. Contacting surfaces 2064*a*, 2064*b* may be configured to contact a portion of proximal carrier 2016 during translation of proximal carrier 2016. Contacting surfaces 2064*a*, 2064*b* may define grooves 2066*a*, 2066*b* configured to receive a portion of proximal carrier 2016 during translation of proximal carrier 2016, as discussed further herein. At least a portion of each contacting surface 2064*a*, 2064*b* may be located within bore 2006, such that proximal carrier 2016 contacts contacting surfaces 2064*a*, 2064*b* when proximal carrier translates in bore 2006. Grooves 2066*a*, 2066*b* may be concave to receive a portion of proximal carrier 2016. When proximal carrier 2016 contacts contacting surfaces 2064*a*, 2064*b*, proximal wings 2008*a*, 2008*b* may pivot from the closed configuration to the deployed configuration. Once grooves 2066*a*, 2066*b* receive proximal carrier 2016, proximal wings 2008*a*, 2008*b* may distally translate with proximal carrier 2016 to transition from the deployed configuration to the clamped configuration. Arms 2062*a*, 2062*b* may move along channels 2026*a*, 2026*b* to thereby translate proximal wings 2008*a*, 2008*b* between the deployed configuration and the clamped configuration. A space 2068 may be defined between walls 2060*a*, 2060*b* of proximal wings 2008*a*, 2008*b* when proximal wings 2008*a*, 2008*b* are in the closed configuration (see FIG. 44B). Space 2068 may receive a portion of insertion tool 2400, as discussed further herein (as shown in FIG. 50A).

Proximal wings 2008*a*, 2008*b* may include extensions 2041*a*, 2041*b*, 2041*c*, 2041*d* extending from proximal bodies 2056*a*, 2056*b* such that proximal bodies 2056*a*, 2056*b* are located between extensions 2041*a*, 2041*b*, 2041*c*, 2041*d* and arms 2062*a*, 2062*b*. At least a portion of each extension 2041*a*, 2041*b*, 2041*c*, 2041*d* may be configured to engage with bone or tissue at and/or near the treatment site when proximal wings 2008*a*, 2008*b* are in the clamped configuration. In some embodiments, extensions 2041*a*, 2041*b*, 2041*c*, 2041*d* may form tips 2070*a*, 2070*b*, 2070*c*, 2070*d*. Tips 2070*a*, 2070*b*, 2070*c*, 2070*d* may engage bone or tissue at and/or near the treatment site when proximal wings 2008*a*, 2008*b* are in the clamped position. In some embodiments, tips 2070*a*, 2070*b*, 2070*c*, 2070*d* may be sharp to clamp onto and engage bone or tissue. Tips 2070*a*, 2070*b*, 2070*c*, 2070*d* may be shaped like fangs. In some embodiments, tips 2070*a*, 2070*b*, 2070*c*, 2070*d* may be spikes with sharp points for engaging with bone or tissue. In some embodiments, tips 2070*a*, 2070*b*, 2070*c*, 2070*d* may be arcuately shaped and come to a point.

Figure 47:
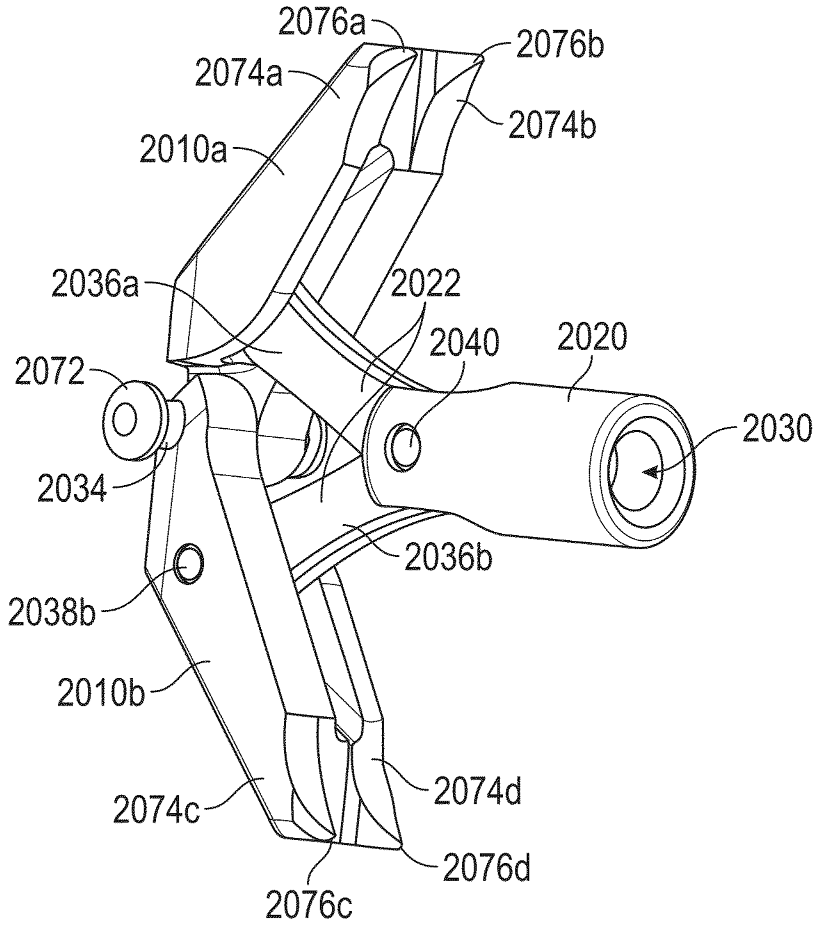
FIG. 47 illustrates a perspective view of some embodiments of distal wings coupled to a linkage assembly and a plunger of the third embodiment of the implant.

FIG. 47 illustrates a perspective view of some embodiments of distal wings 2010*a*, 2010*b* coupled to linkage assembly 2022 and plunger 2020 of implant 2000. Linkages 2036*a*, 2036*b*, distal wings 2010*a*, 2010*b*, plunger 2020, linkage pins 2038*a*, 2038*b*, plunger pin 2040, pivot pin 2034, and cap 2072 may be substantially similar to linkages 1036*a*, 1036*b*, distal wings 1010*a*, 1010*b*, plunger 1020, linkage pins 1038*a*, 1038*b*, plunger pin 1040, pivot pin 1034*c*, and cap 1208. Because linkages 2036*a*, 2036*b* are coupled to both plunger 2020 and distal wings 2010*a*, 2010*b*, linkages 2036*a*, 2036*b* operatively couple distal wings 2010*a*, 2010*b* to plunger 2020. Linkages 2036*a*, 2036*b* may rotate about plunger pin 2040 when plunger 2020 is distally advanced to pivot distal wings 2010*a*, 2010*b* from the closed configuration to the deployed configuration. Distal wings 2010*a*, 2010*b* may include extensions 2074*a*, 2074*b*, 2074*c*, 2074*d* having tips 2076*a*, 2076*b*, 2076*c*, 2076*d* extending therefrom for engaging tissue or bone at the treatment site when implant 2000 is in the clamped configuration. Extensions 2074*a*, 2074*b*, 2074*c*, 2074*d* and tips 2076*a*, 2076*b*, 2076*c*, 2076*d* may be substantially similar to extensions 1098*a*, 1098*b*, 1098*c*, 1098*d* and tips 1204*a*, 1204*b*, 1204*c*, 1204*d* of distal wings 1010*a*, 1010*b* of implant 1000.

Figure 48:
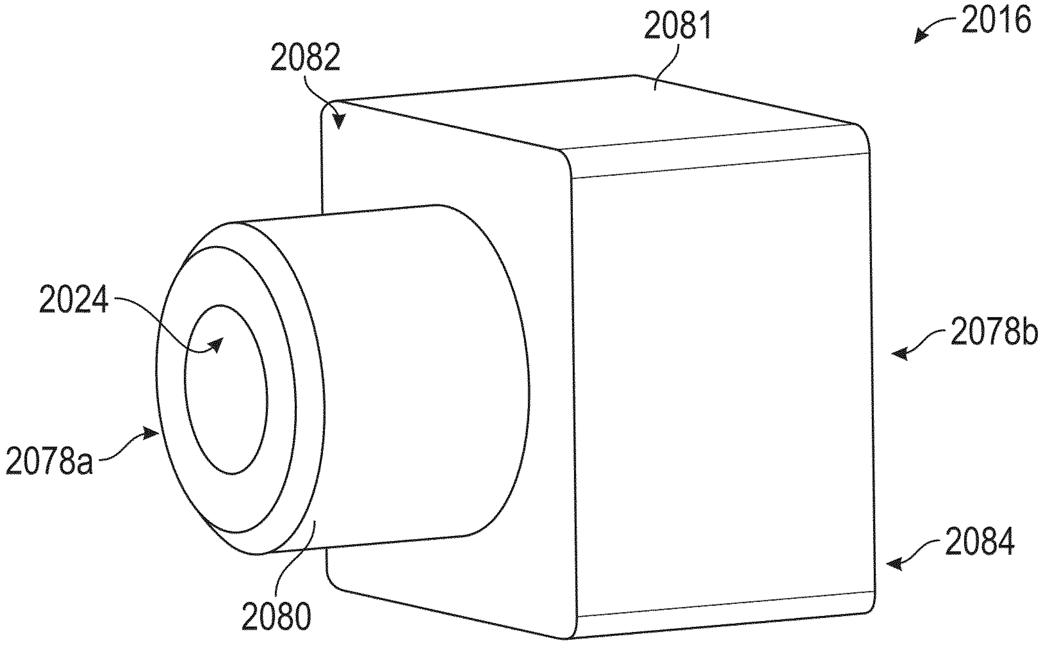
FIG. 48 illustrates a perspective view of some embodiments of a proximal carrier of the third embodiment of the implant.

FIG. 48 illustrates a perspective view of some embodiments of a proximal carrier 2016 of implant 2000. Proximal carrier 2016 may have a distal end 2078*a* and a proximal end 2078*b*. A protrusion 2080 may define distal end 2078*a* of proximal carrier 2016. Protrusion 2080 may contact proximal wings 2008*a*, 2008*b* as proximal carrier 2016 distally translates to pivot proximal wings 2008*a*, 2008*b* from the closed configuration to the deployed configuration. The exterior of protrusion 2080 may contact grooves 2066*a*, 2066*b* of proximal wings 2008*a*, 2008*b* to pivot proximal wings 2008*a*, 2008*b* from the closed position to the deployed position. Proximal carrier 2016 may comprise a carrier body 2081 proximal to protrusion 2080. Protrusion 2080 may extend from carrier body 2081. Protrusion 2080 may extend from a side 2082 of carrier body 2081 facing distal end 2078*a* of proximal carrier 2016. Side 2082 of carrier body 2081 may receive a portion of arms 2062*a*, 2062*b* to distally push proximal wings 2008*a*, 2008*b* from the deployed configuration to the clamped configuration. Carrier body 2081 may define an interface 2084. Interface 2084 may define proximal end 2078*b* of proximal carrier 2016. Interface 2084 may interact with a portion of an insertion tool 2400 to push or press proximal carrier 2016 distally such that proximal carrier 2016 distally translates within bore 2006 of outer body 2002, as discussed further herein.

Protrusion 2080 may be cylindrical so as to be received in grooves 2066*a*, 2066*b*. In some embodiments, protrusion 2080 may be any shape configured to fit within grooves 2066*a*, 2066*b* of proximal wings 2008*a*, 2008*b* when proximal wings 2008*a*, 2008*b* are in the deployed configuration. Carrier body 2081 may be rectangular shaped and have a square profile, such that carrier body 2081 may be received in bore 2006. In some embodiments, carrier body 2081 may be any shape configured to fit within bore 2006 of outer body 2002. Proximal carrier 2016 may define through-hole 2024 extending from distal end 2078*a* to proximal end 2078*b*. Through-hole 2024 may receive a portion of an insertion tool 2400, as discussed further herein.

In some embodiments, proximal carrier 2016 may include grooves configured to interact with protrusions on an insertion tool 2400 to attach proximal carrier 2016 to insertion tool. In some embodiments, proximal carrier 2016 may attach to insertion tool 2400 through a snap fit, an interference fit, or any other coupling mechanism to secure proximal carrier 2016 to insertion tool 2400.

Third Insertion Tool Embodiment

Figure 49A:
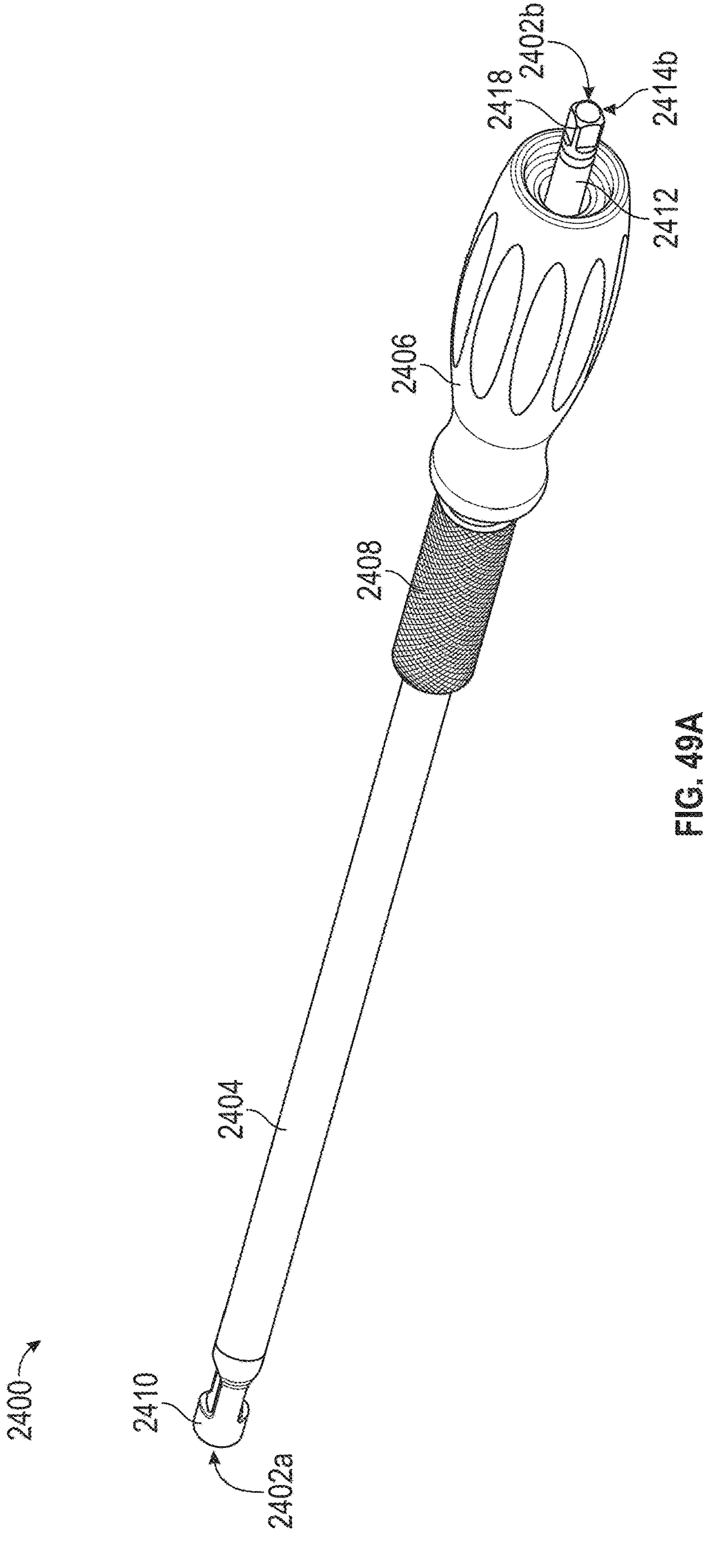
FIG. 49A illustrates a perspective view of a third embodiment of an insertion tool.
Figure 49B:
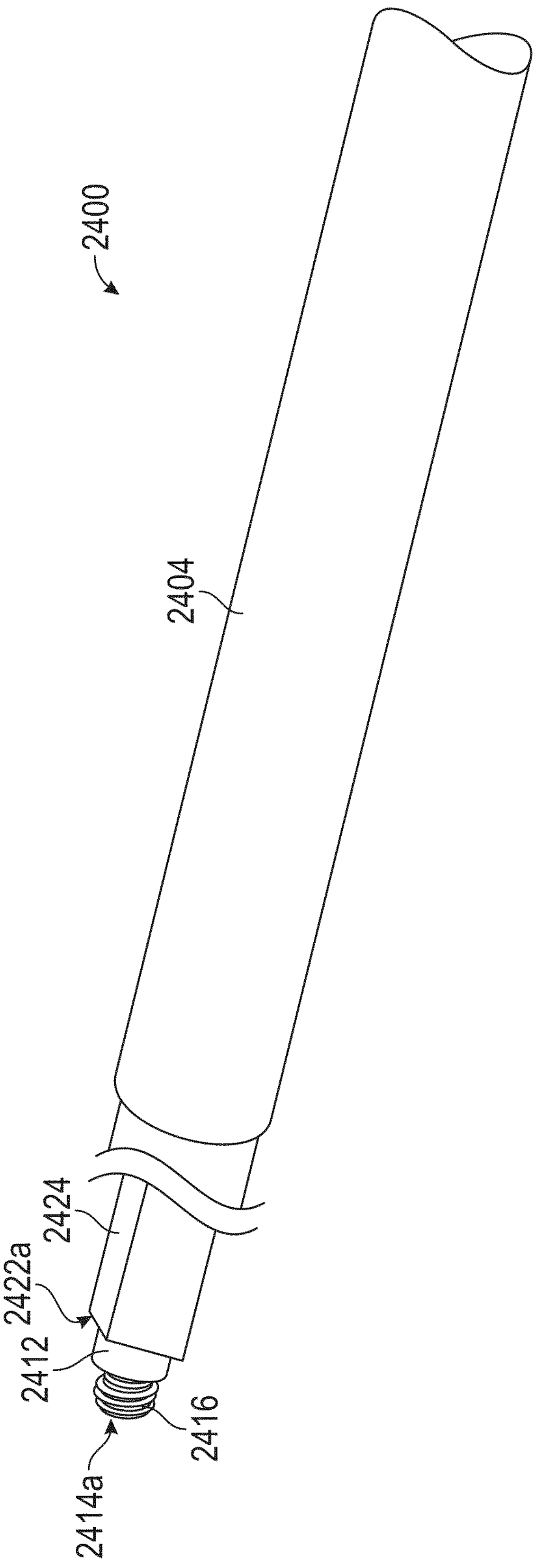
FIG. 49B illustrates a perspective view of the third embodiment of the insertion tool with a portion of the insertion tool removed.

FIG. 49A illustrates a perspective view of a third embodiment of an insertion tool 2400. FIG. 49B illustrates a perspective view of the third embodiment of insertion tool 2400 with a portion of insertion tool 2400 removed. Accordingly, FIGS. 49A-49B are best viewed together. Insertion tool 2400 may be substantially similar to insertion tool 1400 or insertion tool 400. For example and as shown in FIG. 49A, insertion tool 2400 may define a distal end 2402*a* and a proximal end 2402*b*. Insertion tool 2400 may include an outer shaft 2404, a handle 2406, an outer grip 2408, an attachment member 2410, and an inner rod 2412. Inner rod 2412 may define a distal end 2414*a* and a proximal end 2414*b*. Inner rod 2412 may comprise a driver head 2416 at distal end 2414*a* (as shown in FIG. 49B) thereof and a control 2418 at the proximal end 2414*b* thereof (as shown in FIG. 49A). Driver head 2416 of inner rod 2412 may include threads such that driver head 2416 may threadedly couple to central bore 2030 of plunger 2020, as shown in FIG. 49B. Driver head 2416 of inner rod 2412 may extend into attachment member 2410. Inner rod 2412 may extend through handle 2406 such that control 2418 extends past handle 2406. Outer grip 2408 may couple to handle 2406 through a connector substantially similar to connector 420 that couples handle 406 to outer grip 408. The connector may couple outer shaft 2404 to handle 2406. In some embodiments, the connector may couple to outer shaft 2404 through an interference fit, a threaded coupling, a snap fit, or any other coupling mechanism known to a person of skill in the art.

Operation of control 2418 may translate plunger 2020. In some embodiments, distally pushing control 2418 causes driver head 2416 to distally translate plunger 2020. Distal translation of plunger 2020 may pivot distal wings 2010*a*, 2010*b* about outer body 2002 to transition from the closed configuration to the deployed configuration. Attachment member 2410 may be configured to attach insertion tool 2400 to implant 2000. Attachment member 2410 may be substantially similar to attachment member 1410 or 410, comprising arms that may be received in openings 2042*a*, 2042*b* of outer body 2002 of implant 2000 to thereby attach implant 2000 to insertion tool 2400 and maintain implant 2000 on insertion tool 2400 during insertion.

In some embodiments, attachment member 2410 may form an adapter that comprises clips (not shown). Clips may be received in openings 2042*a*, 2042*b* of outer body 2002 to thereby attach insertion tool 2400 to implant 2000. Attachment member 2410 may couple to outer body 2002 of implant 2000 through a snap fit, threaded fit, or any other coupling mechanism known to a person of skill in the art to attach implant to insertion tool 2400. Attachment member 2410 may be substantially similar to an adapter described in U.S. Pat. Nos. 10,420,591; 11,766,280; U.S. patent application Ser. Nos. 17/944,101; 17/716,822; U.S. Pat. Nos. 11,510,710; 11,298,161; U.S. patent application Ser. No. 18/212,946; U.S. Pat. Nos. 1,042,059; 10,285,739; 9,603,648; 11,234,740; 11,801,075; 11,672,572; U.S. patent application Ser. No. 17/949,648, which are incorporated by reference. Attachment member 2410 may couple to outer shaft 2404 and form the distal end 2402*a* of insertion tool 2400, as shown in FIG. 49A.

Similar to embodiments of insertion tool 1400 or 400, insertion tool 2400 may include inner shaft 2424 received in outer shaft 2404 (see FIG. 49B). Inner shaft 2424 may receive inner rod 2412, as shown in FIG. 49B. Inner shaft 2424 may define a distal end 2422*a* and a proximal end opposite distal end 2422*a*. A portion of inner shaft 2424 may extend from handle 2406 such that a surgeon or operator may interact with inner shaft 2424. In some embodiments, proximal end (not shown) of inner shaft 2424 may extend from handle 2406. Proximal end 2414*b* of inner rod 2412 may extend from proximal end 2422*b* of inner shaft 2424 such that a surgeon or operator may reach inner rod 2412. Distal end 2422*a* of inner shaft may interact with interface 2084 of proximal carrier 2016. In some embodiments, distal end 2422*a* of inner shaft 2424 may contact interface 2084 of proximal carrier 2016 when attachment member 2410 is attached to implant 2000. In some embodiments, distal end 2422*a* of inner shaft 2424 may couple to proximal carrier 2016 such that distal end 2422*a* remains in contact with interface 2084.

Distally pushing inner shaft 2424 may distally push proximal carrier 2016 to distally translate proximal carrier 2016 within bore 2006 of outer body 2002. Distally pushing proximal carrier 2016 may cause protrusion 2080 to contact arms 2062*a*, 2062*b* of proximal wings 2008*a*, 2008*b* to thereby pivot proximal wings 2008*a*, 2008*b* from the closed configuration to the deployed configuration. In some embodiments, protrusion 2080 may push arms 2062*a*, 2062*b* to thereby pivot proximal wings 2008*a*, 2008*b*. Distally pushing proximal carrier 2016 may cause side 2082 of proximal carrier 2016 to push arms 2062*a*, 2062*b* of proximal wings 2008*a*, 2008*b* once proximal wings 2008*a*, 2008*b* are in the deployed configuration, to thereby transition proximal wings 2008*a*, 2008*b* from the deployed configuration to the clamped configuration. In some embodiments, inner shaft 2424 may include protrusions on a distal end 2422*a* configured to be received in grooves on proximal carrier 2016 to thereby attach proximal carrier 2016 to insertion tool 2400. In some embodiments, distal end 2422*a* of inner shaft 2424 may couple to proximal carrier 2016 through a snap fit, threaded fit, or any other coupling mechanism known to one skilled in the art.

Inner shaft 2424 may be rectangular and have a square profile such that inner shaft 2424 fits within bore 2006 of outer body 2002. In some embodiments, inner shaft 2424 may be any shape and have any profile shape to configure inner shaft 2424 to be received within bore 2006.

Insertion tool 2400 and implant 2000 may form part of tools 700 used during insertion of implant 2000 into a target space. Combined rasp and tap 500 may also form part of tools 700 used during insertion of implant 2000.

Third Implant Insertion Method

A method 2800 for inserting implant 2000 into a target space in accordance with embodiments of the present disclosure may be substantially similar to method 800 or method 1800. For example, method 2800 may provide steps for inserting implant 2000 into a target space, such as interspinous process space 602. In some embodiments, implant 2000 is inserted between adjacent spinous processes 604*a*, 604*b*, as shown in FIGS. 50A-50C. Method 2800 may be embodied as instructions provided with a surgical kit in some embodiments. The surgical kit may include implant 2000, insertion tool 2400, combined rasp and tap 500, and tools 700. Similar to method 800 or method 1800, method 2800 may begin with a step 2802 where a minimally invasive incision, such as incision 606, is made in a patient, such as patient 607. At step 2804, a working channel for inserting implant 2000 may be created. At step 2806, an introducer sleeve, such as introducer sleeve 706, may be inserted over dilators 704 used for creating the working channel. At step 2808, dilators 704 may be removed.

Step 2810 may be substantially similar to step 810 or step 1810 of method 800 or 1800, respectively. For example, at step 2810, one or more site preparation steps may be taken, such as inserting combined rasp and tap 500 into introducer sleeve 706. Rotating combined rasp and tap 500 may then distract bones adjacent the treatment side, remove ligaments at the treatment site, and partially decorticate the bones for stimulating bone growth. A degree of distraction may be determined by viewing lateral hollows 522*a*, 522*b*, 522*c*, 522*d*, 524*a*, 524*b*, 524*c*, 524*d* under fluoroscopy to determine the appropriate implant size. Combined rasp and tap 500 may then be removed.

Step 2812 may be substantially similar to step 812 or step 1812 of method 800 or method 1800, respectively. For example, at an optional step 2812, bone graft material may be added to implant 2000 prior to insertion into the patient. Bone graft material may be applied around the threaded portion 2012 of outer body 2002 of implant 2000. At step 2814, implant 2000 may be attached to insertion tool 2400 in the closed configuration through a similar mechanism for attaching implant 100 to insertion tool 400 or attaching implant 1000 to insertion tool 1400. For example, outer grip 2408 of insertion tool 2400 may be rotated in a first direction to advance attachment member 2410 toward implant 2000 to clip arms and/or clips of attachment member 2410 into openings 2042*a*, 2042*b* of outer body 2002 to thereby lock implant 2000 onto insertion tool 2400. In some embodiments, inner shaft 2424 may be coupled to proximal carrier 2016 prior to rotating outer grip 2408 to attach attachment member 2410 to outer body 2002 of implant 2000. To attach implant 2000 to insertion tool 2400, a surgeon or operator may clip clips of attachment member 2410 into openings 2042*a*, 2042*b* of outer body 2002 to thereby lock implant 2000 onto insertion tool 2400 during insertion. In some embodiments, inner rod 2412 may be threadedly coupled to central bore 2030 of plunger 2020 prior to attaching attachment member 2410 to outer body 2002 of implant 2000.

Step 2816 may be substantially similar to step 816 or step 1816. For example, at step 2816, insertion tool 2400 and implant 2000 may be inserted into introducer sleeve 706. At step 2818, instead of partially inserting implant 2000 into the target space, implant 2000 may be fully inserted into the target space such that distal wings 2010*a*, 2010*b* are located proximate distal sides 608*a*, 608*b* of spinous processes 604*a*, 604*b* and proximal wings 2008*a*, 2008*b* are located proximate proximal sides 610*a*, 610*b* of spinous processes 604*a*, 604*b*. At step 2820, an introducer sleeve, such as introducer sleeve 706, may be removed.

Distal wings 2010*a*, 2010*b* may be inserted through the target space, such as an interspinous process space 602. A surgeon or operator may rotate insertion tool 2400 to insert implant 2000 into the target space, such that threads of threaded portion 2012 of outer body 2002 decorticate bones and/or tissue at the treatment site to facilitate inserting implant 2000 into treatment site. Threading on threaded portion 2012 may engage muscle, soft tissue, and/or bone at the treatment site to provide fixation of implant 2000 in the target space. During insertion of implant 2000 into the target space, the distal wings 2010*a*, 2010*b* and proximal wings 2008*a*, 2008*b* may be in the closed configuration, as shown in FIGS. 44A-44B. In the closed configuration, the pivot axis $P_1$ of each distal wing 2010*a*, 2010*b* and longitudinal axis $L_1$ may define a first pivot axis angle $\theta_1$, respectively. The wing axis $W_1$ of each proximal wings 2008*a*, 2008*b* and longitudinal axis $L_1$ may define a first wing axis angle $\theta_2$.

Step 2822 may be substantially similar to step 822 or step 1822 of method 800 or method 1800, respectively. At step 2822, insertion tool 2400 may be actuated to transition the implant 2000 from the closed configuration to the clamped configuration. Actuating insertion tool 2400 may include distally advancing inner rod 2412 to distally advance plunger 2020 of implant 2000. Distally advancing plunger 2020 of implant 2000 may pivot distal wings 2010*a*, 2010*b* from the closed configuration to the deployed configuration. Distal translation of plunger 1020 may cause distal wings 1010*a*, 1010*b* to pivot about outer body 1002 from the closed configuration to the deployed configuration.

FIG. 50A illustrates a cross-sectional view of some embodiments of implant 2000 inserted in a target space, with distal wings 2010*a*, 2010*b* of implant 2000 in the deployed configuration. When distal wings 2010*a*, 2010*b* are in the deployed configuration, a second pivot axis angle $\theta_1$ may be defined between each respective pivot axis $P_1$ and the longitudinal axis $L_1$, as shown in FIG. 50A. The second pivot axis angle $\theta_1$ of the deployed configuration may be greater than the first pivot axis angle $\theta_1$ of the closed configuration. In some embodiments, the second pivot axis angle $\theta_1$ may be within a range of 50 degrees to 80 degrees, such as between 60 degrees and 70 degrees.

Actuating the insertion tool 2400 may further include distally advancing inner shaft 2424 of insertion tool 2400. Distally advancing inner shaft 2424 may push interface 2084 of proximal carrier 2016 to thereby distally advance proximal carrier 2016. Distally advancing inner shaft 2424 may distally advance proximal carrier 2016 within bore 2006. Distally advancing proximal carrier 2016 may cause protrusion 2080 to contact proximal wings 2008*a*, 2008*b* to thereby pivot proximal wings 2008*a*, 2008*b* from the closed configuration to the deployed configuration. In some embodiments, distally pushing proximal carrier 2016 may cause protrusion 2080 to push arms 2062*a*, 2062*b* such that proximal wings 2008*a*, 2008*b* pivot about distal ends 2052*a*, 2052*b* of channels 2026*a*, 2026*b* from the closed configuration to the deployed configuration.

FIG. 50B illustrates a cross-sectional view of some embodiments of implant 2000 inserted in a target space in the deployed configuration. Implant 2000 may be in the deployed configuration when both distal wings 2010*a*, 2010*b* and proximal wings 2008*a*, 2008*b* are in the deployed position. When distal wings 2010*a*, 2010*b* are in the deployed configuration, a second wing axis angle $\theta_2$ may be defined between each respective wing axis $W_1$ and the longitudinal axis $L_1$, as shown in FIG. 50B. The second wing axis angle $\theta_2$ of the deployed configuration may be greater than the first wing axis angle $\theta_2$ of the closed configuration. In some embodiments, the second wing axis angle $\theta_2$ may be within a range of 40 degrees to 70 degrees, such as between 50 degrees and 60 degrees. Additionally, when implant 2000 is in the deployed configuration, a first distance $D_1$ may be defined between distal wings 2010*a*, 2010*b* and proximal wings 2008*a*, 2008*b*, as shown in FIG. 50B.

Next, implant 2000 and insertion tool 2400 may be moved proximally to engage distal wings 2010*a*, 2010*b* with bone or tissue at and/or around the treatment site to thereby transition distal wings 2010*a*, 2010*b* from the deployed configuration to the clamped configuration. FIG. 50C illustrates a cross-sectional view of some embodiments of implant 2000 inserted in a target space in the clamped configuration. At least a part of extensions 2074*a*, 2074*b*, 2074*c*, 2074*d* of distal wings 2010*a*, 2010*b* may engage bone or tissue at and/or near the treatment site when distal wings 2010*a*, 2010*b* are in the clamped configuration. In some embodiments, tips 2076*a*, 2076*b*, 2076*c*, 2076*d* of extensions 2074*a*, 2074*b*, 2074*c*, 2074*d* may engage bone or tissue at treatment site, such as spinous processes 604*a*, 604*b* adjacent interspinous process space 602, as shown in FIG. 50C.

Actuation of insertion tool 2400 may further include distally advancing inner shaft 2424 to distally advance proximal carrier 2016. Because arms 2062*a*, 2062*b* contact side 2082 of proximal carrier 2016 when proximal wings 2008*a*, 2008*b* are in the deployed configuration, distally advancing proximal carrier 2016 distally advances proximal wings 2008*a*, 2008*b* toward the treatment site to transition proximal wings 2008*a*, 2008*b* from the deployed configuration to the clamped configuration. In the clamped configuration, proximal wings 2008*a*, 2008*b* may engage bone or tissue at and/or near the treatment site to secure implant 2000 within treatment site. For example and as shown in FIG. 50C, extensions 2041*a*, 2041*b*, 2041*c*, 2041*d* of proximal wings 2008*a*, 2008*b* may engage spinous processes 604*a*, 604*b* adjacent the interspinous process space 602 to maintain implant 2000 within interspinous process space 602. In some embodiments, tips 2070*a*, 2070*b*, 2070*c*, 2070*d* of extensions 2041*a*, 2041*b*, 2041*c*, 2041*d* may engage bone or tissue at or near the target space. When implant 2000 is in the clamped configuration, a second distance $D_2$ may be defined between distal wings 2010*a*, 2010*b* and proximal wings 2008*a*, 2008*b*, as shown in FIG. 50C. Second distance $D_2$ may be less than first distance $D_1$, such that proximal wings 2008*a*, 2008*b* are closer to distal wings 2010*a*, 2010*b* in the clamped configuration relative to the deployed configuration.

Step 2824 may be substantially similar to step 826 of method 800 or to step 1826 or method 1800. For example, at step 2824, insertion tool 2400 may be detached from implant 2000. In some embodiments, insertion tool 2400 may be detached from implant 2000 by rotating outer grip 2408 in a second direction to proximally translate attachment member 2410 away from outer body 2002 to thereby detach attachment member 2410 from outer body 2002. Proximal translation of attachment member 2410 may cause arms and/or clips of attachment member 2410 to dislodge from openings 2042*a*, 2042*b* to thereby detach implant 2000 from insertion tool 2400. Detaching insertion tool 2400 from implant 2000 may also include decoupling inner rod 2412 from central bore 2030 of plunger 2020. In some embodiments, inner rod 2412 may be decoupled from plunger 2020 by rotating inner rod 2412 such that threads on driver head 2416 decouple from threads in central bore 2030. In some embodiments, detaching implant 2000 from insertion tool 2400 may include removing protrusions on inner shaft 2424 from grooves on proximal carrier 2016 to thereby detach insertion tool 2400 from proximal carrier 2016. Step 2826 may be substantially similar to step 828 of method 800 or step 1828 of method 1800. At step 2826, insertion tool 2400 may be removed from the patient.

Figure 51:
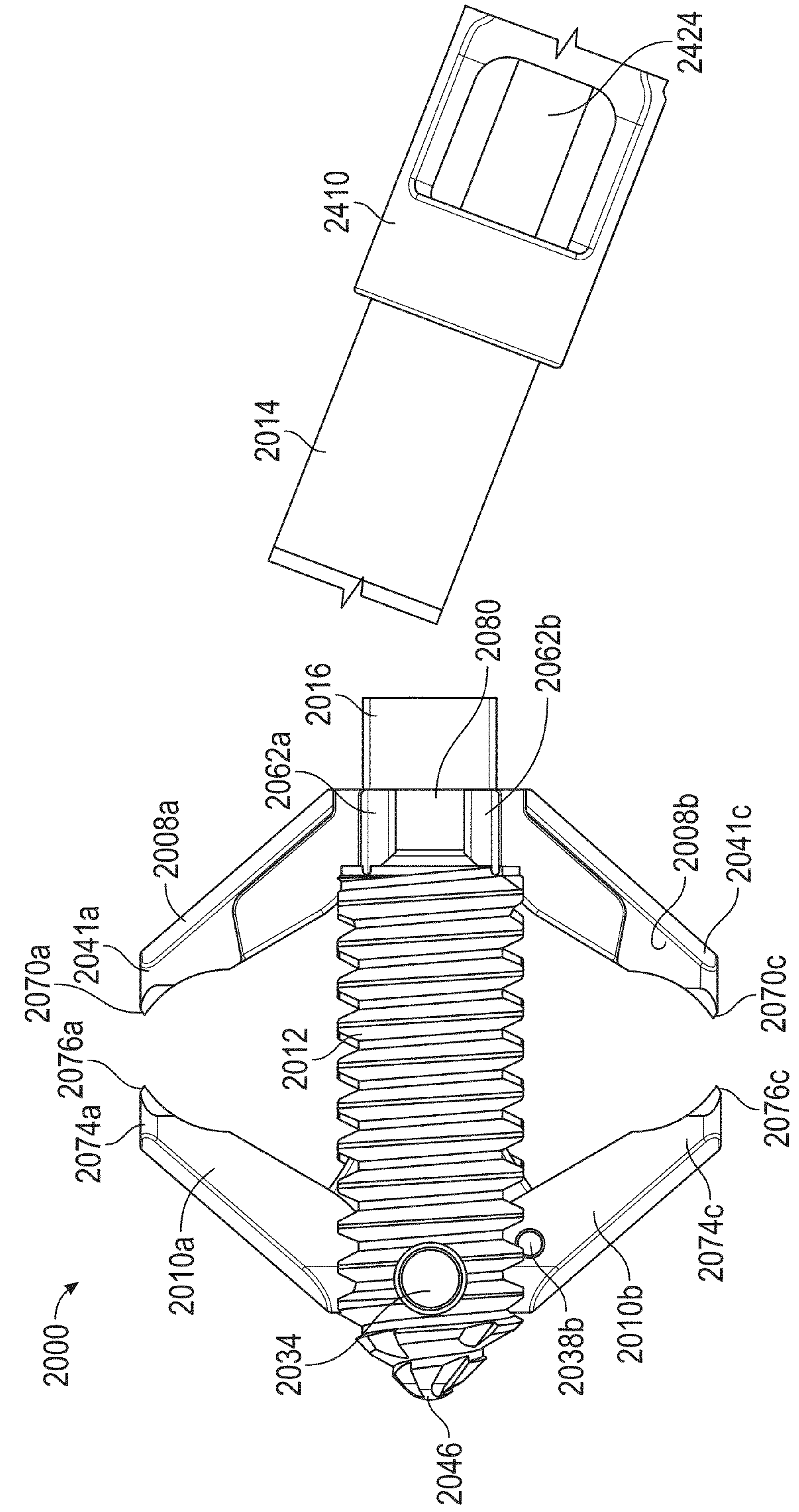
FIG. 51 illustrates some embodiments of a cartridge of the outer body of the third embodiment of the implant being removed.

In some embodiments, step 2824 may include detaching cartridge 2014 from implant 2000. FIG. 51 illustrates some embodiments of cartridge 2014 of outer body 2002 being removed from implant 2000. In some embodiments, cartridge 2014 may be removable from threaded portion 2012 of outer body 2002. Cartridge 2014 may couple to threaded portion 2012. Detaching of insertion tool 2400 from implant 2000 may simultaneously remove cartridge 2014 from threaded portion 2012. In some embodiments, cartridge 2014 may connect to threaded portion 2012 through a preformed frangible or separable connection known to one skilled in the art. Detaching of insertion tool 2400 may simultaneously break the frangible connection and thereby remove cartridge 2014 from threaded portion 2012. The frangible connection may be a snap fit that may be unsnapped through movement of insertion tool 2400. In embodiments where cartridge 2014 detaches from threaded portion 2012, proximal carrier 2016 may distally translate onto a portion of plunger 2020 and thereby couple to plunger 2020 when implant 2000 is in the clamped configuration, such that proximal wings 2008*a*, 2008*b* remain on implant 2000 when cartridge 2014 is removed. In some embodiments, protrusion 2080 may distally translate into a portion of plunger 2020 and thereby couple proximal carrier 2016 to plunger 2020. In embodiments where cartridge is removable, proximal wings 2008*a*, 2008*b* may pivotally couple to proximal carrier 2016 such that when proximal carrier 2016 couples to plunger 2020, proximal wings 2008*a*, 2008*b* remain on implant 2000 when cartridge 2014 is removed. Inner shaft 2424 may simultaneously decouple from proximal carrier 2016 when cartridge 2014 is removed. For example, projections on inner shaft may be removed from grooves on proximal carrier 2016 such that inner shaft 2424 decouples from proximal carrier 2016 as cartridge 2014 is removed.

Figure 52:
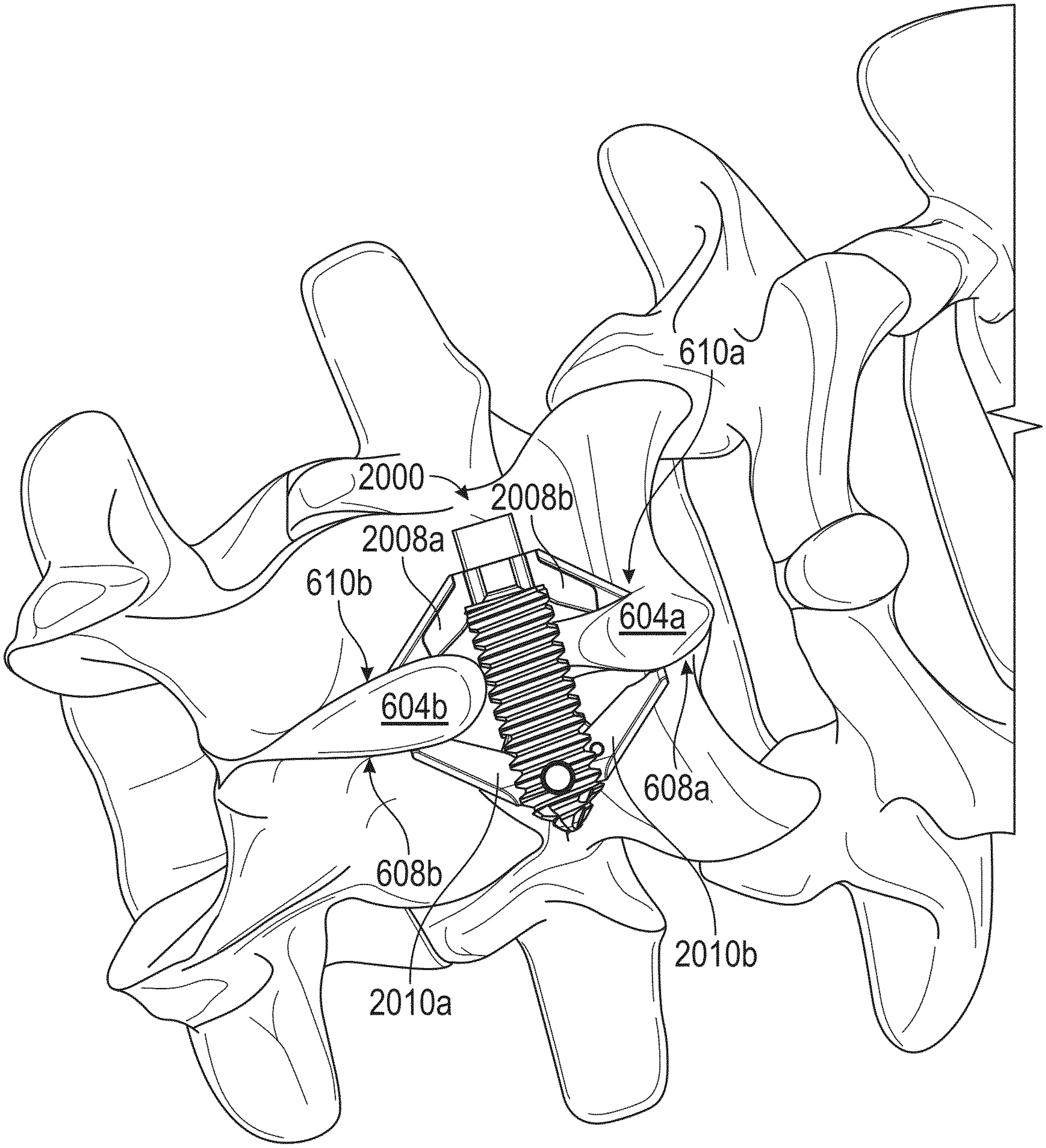
FIG. 52 illustrates a perspective view of the third embodiment of the implant in a clamped configuration, inserted in the spine of a patient.

FIG. 52 illustrates a perspective view of some embodiments of implant 2000 in a clamped configuration, inserted in the spine of a patient. As shown in FIG. 52, distal wings 2010*a*, 2010*b* may anchor to distal sides 608*a*, 608*b* of adjacent spinous processes 604*a*, 604*b* when in the clamped configuration in an interspinous process space, such as interspinous process space 602 shown in FIGS. 50A-50C. Proximal wings 2008*a*, 2008*b* may anchor to proximal sides 610*a*, 610*b* of adjacent spinous processes 604*a*, 604*b* when in the clamped configuration in an interspinous process space, such as interspinous process space 602 shown in FIGS. 50A-50C. Distal wings 2010*a*, 2010*b* and proximal wings 2008*a*, 2008*b* thereby provide anchors for maintaining implant 2000 in place at the treatment site. Implant 2000 may be used for stabilization and fusion of other bony structures and/or joints within the body. For example, implant 2000 may anchor to any adjacent bony structures and/or soft tissue to stabilize bony structures and/or joints. Implant 2000 may be inserted in an SI joint space to fixate bone at the SI joint and/or stabilize the SI joint.

In some embodiments, at least a portion of implant 100, 1000, 2000 may be adapted to contain bone graft material therein. For example, inner body 106 or outer body 102 of implant 100 may be adapted to contain bone graft material therein. The bone graft material may be added to implant 100 by injecting bone graft material into outer body 102 or inner body 106. Outer body 1002 of implant 1000 and outer body 2002 of implant 2000 may be adapted to contain bone graft material therein. The bone graft material may be added to implant 1000, 2000 by injecting bone graft material into outer body 1002, 2002. Bone graft material may also be applied around threading 168 of outer body 102 before insertion of implant 100 into the body of a patient. Bone graft material may also be applied around threaded portion 1012, 2012 of implant 1000, 2000 before insertion of implant 1000, 2000 into the body of a patient. In some embodiments, the bone graft material may be viscous to avoid any interference with the proper functioning of distal wings 110*a*, 110*b*, 1010*a*, 1010*b*, 2010*a*, 2010*b* and proximal wings 108*a*, 108*b*, 1008*a*, 1008*b*, 2008*a*, 2008*b*. The volume of the bone graft material may range from about 0.5 cc to about 3.0 cc, or from about 1.2 cc to about 2.5 cc, depending on the size of implant 100, 1000, 2000.

In some embodiments, all or part of implant 100, 1000, 2000 may be composed of titanium or a titanium alloy. In some embodiments, all or part of the implant may be composed of stainless steel. In some embodiments, all or part of the implant may be composed of a polymer or a bioabsorbable material. In some embodiments, the implant may be manufactured by an additive manufacturing process. In some embodiments, the implant may be manufactured by machining or molding. In some embodiments, all or part of the implant may include a coating on at least one surface thereof. In some embodiments, at least one outer surface of the implant may be coated with hydroxyapatite (HA). In some embodiments, multiple surfaces may be coated with HA.

In some embodiments, all or part of insertion tool 400, 1400, 2400 may be composed of titanium or titanium alloy. In some embodiments, all or part of insertion tool 400, 1400, 2400 may be composed of stainless steel. In some embodiments, all or part of insertion tool 400, 1400, 2400 may be composed of a polymer or a bioabsorbable material.

Features described above as well as those claimed below may be combined in various ways without departing from the scope hereof. The following examples illustrates some possible, non-limiting combinations:

(A1) A medical implant for insertion at a treatment site, comprising: an outer body defining a longitudinal axis extending through a proximal end of the outer body and a distal end of the outer body; an inner body operatively coupled to the outer body; one or more proximal wings pivotally coupled to the outer body proximate the proximal end; one or more distal wings pivotally coupled to the inner body; and a threaded screw operatively coupled to the outer body and the inner body, wherein actuation of the threaded screw pivots the one or more proximal wings between a closed position and a deployed position and pivots the one or more distal wings between a closed position and a deployed position.

(A2) For the medical implant denoted as (A1), wherein the inner body comprises ramps, wherein actuation of the threaded screw causes at least a portion of each proximal wing of the one or more proximal wings to contact the ramps to thereby pivot the one or more proximal wings.

(A3) For the medical implant denoted as (A1) or (A2), wherein actuation of the threaded screw distally translates the threaded screw to contact the one or more distal wings to thereby pivot the one or more distal wings.

(A4) For the medical implant denoted as (A1) through (A3), wherein the one or more proximal wings pivot distally outward toward the distal end of the outer body to transition the one or more proximal wings from the closed position to the deployed position, wherein the one or more distal wings pivot proximally outward toward the proximal end of the outer body to transition the one or more distal wings from the closed position to the deployed position.

(A5) For the medical implant denoted as (A1) through (A4), wherein one or more inner body pieces form the inner body, wherein each inner body piece of the one or more inner body pieces comprises a groove and a rotation slot, the rotation slot having a first end and second end.

(A6) For the medical implant denoted as (A1) through (A5), wherein each distal wing of the one or more distal wings comprises a wing pin and the rotation slot of each inner body piece of the one or more inner body pieces receives the wing pin of each distal wing of the one or more distal wings, wherein distal translation of the threaded screw to contact the one or more distal wings causes each wing pin of each distal wing of the one or more distal wings to move between the first end and the second end of the rotation slot of each inner body piece of the one or more inner body pieces to thereby transition the one or more distal wings between the closed position and the deployed position.

(A7) For the medical implant denoted as (A1) through (A6), wherein each proximal wing of the one or more proximal wings comprises a protuberance, wherein the groove of each inner body piece of the one or more inner body pieces receives the protuberance of each proximal wing of the one or more proximal wings, wherein actuation of the threaded screw moves the protuberance of each proximal wing of the one or more proximal wings along a least a portion of the groove of each inner body piece of the one or more inner body pieces.

(A8) For the medical implant denoted as (A1) through (A7), wherein the inner body comprises translations surfaces, wherein, in the deployed position, the protuberance of each proximal wing of the one or more proximal wings contacts translations surfaces of the inner body to maintain each proximal wing of the one or more proximal wings in the deployed position.

(A9) For the medical implant denoted as (A1) through (A8), further comprising: a proximal carrier coupled to the outer body and comprising a carrier bore, wherein the carrier bore receives the threaded screw.

(B1) A system configured to insert a medical implant into a treatment site, the system comprising: the medical implant, comprising: an outer body having a proximal end and a distal end; an inner body operatively coupled to the outer body; one or more proximal wings pivotally coupled to the outer body; one or more distal wings pivotally coupled to the inner body; and a threaded screw operatively coupled to the outer body and the inner body, and an insertion tool, comprising: an outer shaft coupled to an outer grip; a handle operatively coupled to the outer grip such that the outer shaft couples to the handle; an inner shaft, the outer shaft receiving at least a portion of the inner shaft; and an inner rod having a distal end and a proximal end, wherein the inner shaft receives at least a portion of the inner rod, wherein the distal end of the inner rod comprises a driver head and the proximal end of the inner rod comprises a control, wherein the threaded screw is configured to receive the driver head, wherein operation of the control rotates the driver head to actuate the threaded screw, wherein actuation of the threaded screw transitions the one or more proximal wings and the one or more distal wings between a closed position and a deployed position.

(B2) For the system denoted as (B1), wherein the threaded screw comprises a screw head and the screw head receives the driver head, wherein rotation of the driver head rotates the threaded screw to transition the one or more proximal wings and the one or more distal wings between the closed position and the deployed position.

(B3) For the system denoted as (B1) or (B2), the insertion tool further comprising: an attachment member coupled to the inner shaft, wherein the attachment member comprises a plurality of arms configured to attach the medical implant to the insertion tool.

(B4) For the system denoted as (B1) through (B3), the medical implant further comprising: openings defined by the outer body, wherein the openings receive at least a portion of each arm of the plurality of arms to thereby attach the medical implant to the insertion tool and maintain the medical implant on the insertion tool.

(B5) For the system denoted as (B1) through (B4), wherein rotation of the outer grip translates the plurality of arms of the attachment member such that the openings receive the plurality of arms to thereby maintain the medical implant on the insertion tool.

(B6) For the system denoted as (B1) through (B5), the insertion tool further comprising: a connector coupled to the inner shaft, wherein an exterior portion of the connector comprises threads, wherein a threaded bore defined by the outer grip receives the connector to threadedly couple the connector to the outer grip, wherein the connector operatively couples the outer grip to the handle.

(B7) For the system denoted as (B1) through (B6), wherein the handle defines a tunnel extending from a distal end of the handle to a proximal end of the handle, wherein the tunnel receives at least a portion of the inner rod, wherein a portion of the tunnel located at the distal end of the handle is threaded to thereby threadedly couple the handle to the connector.

(C1) A method of inserting a medical implant into a treatment site, the method comprising: providing a medical implant, the medical implant comprising: an outer body having a proximal end and a distal end; an inner body operatively coupled to the outer body; one or more proximal wings pivotally coupled to the outer body; one or more distal wings pivotally coupled to the inner body; and a threaded screw operatively coupled to the outer body and the inner body, wherein the one or more proximal wings and the one or more distal wings are in a closed position, providing instructions comprising: attaching an insertion tool to the medical implant; inserting a portion of the medical implant into the treatment site; and actuating the insertion tool in a first direction to transition the medical implant from a closed configuration to a deployed configuration, wherein actuating the insertion tool in a first direction comprises rotating a portion of the insertion tool in a first direction to pivot the one or more distal wings and the one or more proximal wings from the closed configuration to the deployed configuration.

(C2) For the method denoted as (C1), wherein rotating a portion of the insertion tool in a first direction rotates the threaded screw in a first direction to thereby pivot the one or more distal wings and the one or more proximal wings from the closed configuration to the deployed configuration, wherein the one or more distal wings are configured to grip bone or tissue at the treatment site when the medical implant is transitioning from the closed configuration to the deployed configuration to pull the medical implant into the treatment site, such that the medical implant is fully inserted into the treatment site when in the deployed configuration.

(C3) For the method denoted as (C1) or (C2), wherein actuating the insertion tool transitions the medical implant from the deployed configuration to a clamped configuration, wherein, in the clamped configuration, the one or more proximal wings and the one or more distal wings engage bone or tissue at and/or near the treatment site to stabilize the medical implant within the treatment site, wherein the method further comprises: detaching the insertion tool from the medical implant when the medical implant is in the clamped configuration.

(C4) For the method denoted as (C1) through (C3), further comprising: actuating the insertion tool in a second direction to transition the medical implant from the deployed configuration to the closed configuration, wherein actuating the insertion tool in a second direction comprises rotating a portion of the insertion tool in a second direction to pivot the one or more distal wings and the one or more proximal wings from the deployed configuration to the closed configuration.

Although the present disclosure has been described with reference to the embodiments illustrated in the attached drawing figures, it is noted that equivalents may be employed, and substitutions made herein without departing from the scope of the present disclosure as recited in the claims.

Having thus described various embodiments of the present disclosure, what is claimed as new and desired to be protected by Letters Patent includes the following:

1. A medical implant for insertion at a treatment site, comprising:

an outer body defining a longitudinal axis extending through a proximal end of the outer body and a distal end of the outer body;

an inner body a threaded screw operatively coupled to the outer body and having a first threading and a second threading, wherein the first threading threads in an opposite direction relative to the second threading;

a carrier coupled to the threaded screw;

ramps defined by the medical implant, wherein the inner body comprises the ramps;

one or more proximal wings operatively coupled to the carrier; and one or more distal wings, wherein actuation of the threaded screw simultaneously pivots the one or more proximal wings between a closed position and a deployed position and pivots the one or more distal wings between a closed position and a deployed position, wherein continued actuation of the threaded screw distally translates the one or more proximal wings from the deployed position to a clamped position to engage the one or more proximal wings with bone or tissue at the treatment site.

2. The medical implant of claim 1, wherein each proximal wing of the one or more proximal wings comprises a jut having a proximal surface and extending from a side of each proximal wing of the one or more proximal wings, wherein the proximal surface of each jut of each proximal wing contacts the ramps to thereby pivot the one or more proximal wings.

3. The medical implant of claim 1, wherein the outer body comprises a first outer body piece and a second outer body piece, and wherein the first outer body piece and the second outer body piece define openings.

4. The medical implant of claim 3, wherein the openings of the first outer body piece and the second outer body piece are configured to receive at least a portion of an insertion tool to attach and maintain the medical implant to the insertion tool.

5. The medical implant of claim 1, wherein the one or more proximal wings pivot distally outward toward the distal end of the outer body to transition the one or more proximal wings from the closed position to the deployed position, wherein the one or more distal wings pivot proximally outward toward the proximal end of the outer body to transition the one or more distal wings from the closed position to the deployed position.

6. The medical implant of claim 1, wherein the carrier defines a carrier bore and the carrier bore receives the threaded screw to thereby couple the carrier to the threaded screw.

7. The medical implant of claim 1, wherein the one or more distal wings comprise one or more arms, and wherein the one or more distal wings comprise one or more clamps extending from the one or more arms.

8. The medical implant of claim 7, wherein the one or more clamps pull at least a portion of the medical implant into the treatment site when the one or more distal wings pivot from the closed position to the deployed position.

9. The medical implant of claim 1, wherein the inner body comprises a first inner body piece and a second inner body piece.

10. A system configured to insert a medical implant into a treatment site, the system comprising:

the medical implant, comprising:

an outer body defining a longitudinal axis extending through a proximal end of the outer body and a distal end of the outer body;

an inner body, wherein the inner body comprises ramps;

a threaded screw operatively coupled to the outer body and having a first threading and a second threading, wherein the first threading threads in an opposite direction relative to the second threading;

one or more proximal wings; and one or more distal wings;

an insertion tool, comprising:

an outer shaft coupled to an outer grip;

a handle operatively coupled to the outer grip such that the outer shaft couples to the handle;

an inner shaft, the outer shaft receiving at least a portion of the inner shaft;

an attachment member coupled to the inner shaft, wherein the attachment member removably couples to the outer body of the medical implant to attach the medical implant to the insertion tool; and an inner rod having a distal end and a proximal end, wherein the inner shaft receives at least a portion of the inner rod, wherein the distal end of the inner rod comprises a driver head and the proximal end of the inner rod comprises a control, wherein the threaded screw is configured to receive the driver head, wherein operation of the control rotates the driver head to actuate the threaded screw, wherein rotation of the driver head rotates the threaded screw to transition the one or more proximal wings and the one or more distal wings between a closed position and a deployed position.

11. The system of claim 10, wherein the threaded screw comprises a screw head and the screw head receives the driver head, wherein the inner rod comprises a taper proximate the distal end of the inner rod such that a size of the distal end of the inner rod is smaller than a size of the proximal end of the inner rod.

12. The system of claim 10, wherein the attachment member comprises a plurality of arms configured to attach the medical implant to the insertion tool.

13. The system of claim 12, the medical implant further comprising:

openings defined by the outer body, wherein the openings receive at least a portion of each arm of the plurality of arms to thereby attach the medical implant to the insertion tool and maintain the medical implant on the insertion tool.

14. The system of claim 13, wherein rotation of the outer grip translates the plurality of arms of the attachment member such that the openings receive the plurality of arms to thereby maintain the medical implant on the insertion tool.

15. The system of claim 12, the insertion tool further comprising:

a connector operatively coupling the handle to the outer grip and the outer shaft to the handle.

16. The system of claim 15, wherein the handle defines a tunnel configured to receive at least a portion of the inner rod.

17. A method of inserting a medical implant into a treatment site, the method comprising:

providing the medical implant, the medical implant comprising:

an outer body defining a longitudinal axis extending through a proximal end of the outer body and a distal end of the outer body;

a threaded screw operatively coupled to the outer body and having a first threading and a second threading, wherein the first threading threads in an opposite direction relative to the second threading;

a proximal carrier coupled to the threaded screw;

ramps defined by the medical implant;

one or more proximal wings operatively coupled to the proximal carrier; and one or more distal wings, wherein the one or more proximal wings and the one or more distal wings are in a closed position;

attaching an insertion tool to the medical implant, inserting a portion of the medical implant into the treatment site; and actuating the insertion tool in a first direction to transition the medical implant from a closed configuration to a deployed configuration, wherein actuating the insertion tool in a first direction comprises rotating a portion of the insertion tool in the first direction to pivot the one or more distal wings and the one or more proximal wings from the closed configuration to the deployed configuration, wherein rotating the portion of the insertion tool in the first direction rotates the threaded screw to thereby pivot the one or more distal wings and the one or more proximal wings from the closed configuration to the deployed configuration, the rotation of the threaded screw causing at least a portion of each proximal wing of the one or more proximal wings to contact the ramps to thereby pivot the one or more proximal wings from the closed configuration to the deployed configuration.

18. The method of claim 17, wherein a working channel for inserting the medical implant is created by inserting one or more dilators over a guidewire inserted into the treatment site to dilate soft tissues surrounding the treatment site.

19. The method of claim 17, wherein the one or more distal wings are configured to grip bone or tissue at the treatment site when the medical implant is transitioning from the closed configuration to the deployed configuration to pull the medical implant into the treatment site, such that the medical implant is fully inserted into the treatment site when in the deployed configuration.

20. The method of claim 17, further comprising:

actuating the insertion tool in a second direction to transition the medical implant from the deployed configuration to the closed configuration, wherein actuating the insertion tool in a second direction comprises rotating a portion of the insertion tool in the second direction to pivot the one or more distal wings and the one or more proximal wings from the deployed configuration to the closed configuration.

* * * * *